(12) United States Patent
Blake et al.

(10) Patent No.: US 11,029,303 B2
(45) Date of Patent: Jun. 8, 2021

(54) PAH ANTIBODIES AND USES THEREOF

(71) Applicant: The Administrators of the Tulane Educational Fund, New Orleans, LA (US)

(72) Inventors: Diane Blake, Mandeville, LA (US); Yue Sun, San Diego, CA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 226 days.

(21) Appl. No.: 15/827,241

(22) Filed: Nov. 30, 2017

(65) Prior Publication Data

US 2018/0231517 A1 Aug. 16, 2018

Related U.S. Application Data

(63) Continuation-in-part of application No. PCT/US2016/035275, filed on Jun. 1, 2016.

(60) Provisional application No. 62/169,427, filed on Jun. 1, 2015.

(51) Int. Cl.
*G01N 33/28* (2006.01)
*C07K 16/44* (2006.01)
*C07K 16/00* (2006.01)
*G01N 33/53* (2006.01)

(52) U.S. Cl.
CPC ....... *G01N 33/2835* (2013.01); *C07K 16/005* (2013.01); *C07K 16/44* (2013.01); *G01N 33/5308* (2013.01); *C07K 2317/33* (2013.01); *C07K 2317/622* (2013.01); *C07K 2317/92* (2013.01)

(58) Field of Classification Search
CPC .. C07K 16/005; C07K 16/44; C07K 2317/33; C07K 2317/622; C07K 2317/92; G01N 33/2835; G01N 33/5308
See application file for complete search history.

(56) References Cited

U.S. PATENT DOCUMENTS

| 5,618,681 | A | 4/1997 | Friedman et al. | |
|---|---|---|---|---|
| 2009/0123921 | A1 | 5/2009 | Georgiou et al. | |
| 2010/0015665 | A1* | 1/2010 | Latham | C07K 16/22 435/69.6 |
| 2010/0061933 | A1 | 3/2010 | Kimura | |
| 2010/0273988 | A1* | 10/2010 | Kimura | C07K 16/22 530/387.3 |

OTHER PUBLICATIONS

Rudikoff et al., "Single amino acid substitution altering antigen-binding specificity," PNAS USA, 1982, vol. 79, pp. 1979-1983.*
Spier et al., "The development and evaluation of monoclonal antibodies for the detection of polycyclic aromatic hydrocarbons," Anal. Biochem., 2009, vol. 387, pp. 287-293.*
International Search Report dated Dec. 7, 2016 for PCT/US2016/035275.
Written Opinion of the International Searching Authority dated Dec. 7, 2016 for PCT/US2016/035275.
Lynge, Elsebeth, et al. "Risk of cancer and exposure to gasoline vapors." American journal of epidemiology 145.5 (1997): 449-458.
Martin, Holger, et al. "Field trial of contaminant groundwater monitoring: comparing time-integrating ceramic dosimeters and conventional water sampling." Environmental science & technology 37.7 (2003): 1360-1364.
Melton, Scott J. Transitioning from the bench to the real world: Adaptation of uranyl specific antibodies for use in field-based environmental analysis. Diss. Tulane University, 2010.
Melton, Scott J., et al. "Field-based detection and monitoring of uranium in contaminated groundwater using two immunosensors." Environmental science & technology 43.17 (2009): 6703-6709.
Mimura, Junsei, et al. "Loss of teratogenic response to 2, 3, 7, 8-tetrachlorodibenzo-p-dioxin (TCDD) in mice lacking the Ah (dioxin) receptor." Genes to cells 2.10 (1997): 645-654.
Patel, Ami S., et al. "Risk of cancer as a result of community exposure to gasoline vapors." (2004): 497-503.
Peipp, Matthias, et al. "An improved procedure for the generation of recombinant single-chain Fv antibody fragments reacting with human CD13 on intact cells." Journal of immunological methods 251.1-2 (2001): 161-176.
Pepper, Lauren R et al. "A decade of yeast surface display technology: where are we now?." Combinatorial chemistry & high throughput screening vol. 11,2 (2008): 127-34. doi:10.2174/138620708783744516.
Pfeifer, Gerd P., et al. "Tobacco smoke carcinogens, DNA damage and p53 mutations in smoking-associated cancers." Oncogene 21.48 (2002): 7435-7451.
Plaza, G., K. Ulfig, and A. J. Tien. "Immunoassays and environmental studies." Pol. J. Environ. Studies 9 (2000): 231-236.
Rajpal, Arvind, et al. "A general method for greatly improving the affinity of antibodies by using combinatorial libraries." Proceedings of the National Academy of Sciences 102.24 (2005): 8466-8471.
Saha, Mahua, et al. "Sources of sedimentary PAHs in tropical Asian waters: differentiation between pyrogenic and petrogenic sources by alkyl homolog abundance." Marine pollution bulletin 58.2 (2009): 189-200.
Sblattero, Daniele, and Andrew Bradbury. "Exploiting recombination in single bacteria to make large phage antibody libraries." Nature biotechnology 18.1 (2000): 75-80.
Schaefer, Jonas V., Annemarie Honegger, and Andreas Plückthun. "Construction of scFv fragments from hybridoma or spleen cells by PCR assembly." Antibody engineering. Springer, Berlin, Heidelberg, 2010. 21-44.
Schwacke, Lori H., et al. "Health of common bottlenose dolphins (*Tursiops truncatus*) in Barataria Bay, Louisiana, following the Deepwater Horizon oil spill." Environmental science & technology 48.1 (2014): 93-103.
Schwemmlein, Michael, et al. "A CD33-specific single-chain immunotoxin mediates potent apoptosis of cultured human myeloid leukaemia cells." British journal of haematology 133.2 (2006): 141-151.

(Continued)

*Primary Examiner* — Galina M. Yakovleva
(74) *Attorney, Agent, or Firm* — Baker Donelson

(57) ABSTRACT

The invention is directed to antibody compositions that specifically bind to polycyclic aromatic hydrocarbons (PAHs) and kits encompassing the same.

12 Claims, 92 Drawing Sheets
Specification includes a Sequence Listing.

(56) References Cited

OTHER PUBLICATIONS

Shimada, Tsutomu. "Xenobiotic-metabolizing enzymes involved in activation and detoxification of carcinogenic polycyclic aromatic hydrocarbons." Drug metabolism and pharmacokinetics 21.4 (2006): 257-276.

Shimizu, Yasuhito, et al. "Benzo [a] pyrene carcinogenicity is lost in mice lacking the aryl hydrocarbon receptor." Proceedings of the National Academy of Sciences 97.2 (2000): 779-782.

Sidhu, Sachdev S. "Engineering M13 for phage display." Biomolecular engineering 18.2 (2001): 57-63.

Su, Feng-yi, et al. "Simple and sensitive bacterial quantification by a flow-based kinetic exclusion fluorescence immunoassay." Biosensors and Bioelectronics 22.11 (2007): 2500-2507.

Sun, Yue, et al. "Methylated phenanthrenes are more potent than phenanthrene in a bioassay of human aryl hydrocarbon receptor (AhR) signaling." Environmental toxicology and chemistry 33.10 (2014): 2363-2367 . . . .

Szurdoki, F., et al. "Rapid assays for environmental and biological monitoring." Journal of Environmental Science & Health Part B 31.3 (1996): 451-458.

Veglia, Fabrizio, Giuseppe Matullo, and Paolo Vineis. "Bulky DNA adducts and risk of cancer: a meta-analysis." Cancer Epidemiology and Prevention Biomarkers 12.2 (2003): 157-160.

Volkering, F., et al. "Microbial degradation of polycyclic aromatic hydrocarbons: effect of substrate availability on bacterial growth kinetics." Applied Microbiology and Biotechnology 36.4 (1992): 548-552.

Vondráček, Jan, et al. "Concentrations of methylated naphthalenes, anthracenes, and phenanthrenes occurring in Czech river sediments and their effects on toxic events associated with carcinogenesis in rat liver cell lines." Environmental Toxicology and Chemistry: An International Journal 26.11 (2007): 2308-2316.

Wandinger, Sebastian Karl, Klaus Richter, and Johannes Buchner. "The Hsp90 chaperone machinery." Journal of Biological Chemistry 283.27 (2008): 18473-18477.

Watson, John D., et al. "TCDD dysregulation of 13 AHR-target genes in rat liver." Toxicology and applied pharmacology 274.3 (2014): 445-454.

Weaver-Feldhaus, Jane M., et al. "Directed evolution for the development of conformation-specific affinity reagents using yeast display." Protein Engineering Design and Selection 18.11 (2005): 527-536.

Wise, Stephen A., Lane C. Sander, and Michele M. Schantz. "Analytical methods for determination of polycyclic aromatic hydrocarbons (PAHs)—a historical perspective on the 16 US EPA priority pollutant PAHs." Polycyclic Aromatic Compounds 35.2-4 (2015): 187-247.

Yang, Wei-Ping, et al. "CDR walking mutagenesis for the affinity maturation of a potent human anti-HIV-1 antibody into the picomolar range." Journal of molecular biology 254.3 (1995): 392-403.

Zhang, Nan. "The role of endogenous aryl hydrocarbon receptor signaling in cardiovascular physiology." (2011): 91-95.

Alnafisi, Abeer, et al. "Evaluating polycyclic aromatic hydrocarbons using a yeast bioassay." Environmental Toxicology and Chemistry: An International Journal 26.7 (2007): 1333-1339.

Beloglazova, Natalia V., et al. "New approach to quantitative analysis of benzo [a] pyrene in food supplements by an immunochemical column test." Talanta 85.1 (2011): 151-156.

Boutros, Paul C., et al. "Hepatic transcriptomic responses to TCDD in dioxin-sensitive and dioxin-resistant rats during the onset of toxicity." Toxicology and applied pharmacology 251.2 (2011): 119-129.

Cerniglia, Carl E. "Biodegradation of polycyclic aromatic hydrocarbons." Current opinion in biotechnology 4.3 (1993): 331-338.

Chernova, T. G., et al. "The composition and the source of hydrocarbons in sediments taken from the tectonically active Andaman Backarc Basin, Indian Ocean." Marine chemistry 75.1-2 (2001): 1-15.

Darling, Ryan J., and Pierre-Alexandre Brault. "Kinetic exclusion assay technology: characterization of molecular interactions." Assay and drug development technologies 2.6 (2004): 647-657.

Darwish, Ibrahim A., and Diane A. Blake. "One-step competitive immunoassay for cadmium ions: development and validation for environmental water samples." Analytical chemistry 73.8 (2001): 1889-1895.

De Nobel, J. G., and J. A. Barnett. "Passage of molecules through yeast cell walls: A brief essay-review." Yeast 7.4 (1991): 313-323.

Dinis-Oliveira, Ricardo Jorge. "Heterogeneous and homogeneous immunoassays for drug analysis." Bioanalysis 6.21 (2014): 2877-2896.

Feng, Shaolong, Zhaohui Cao, and Xinming Wang. "Role of aryl hydrocarbon receptor in cancer." Biochimica et Biophysica Acta (BBA)—Reviews on Cancer 1836.2 (2013): 197-210.

Fernandez-Salguero, Pedro M., et al. "Aryl-hydrocarbon receptor-deficient mice are resistant to 2, 3, 7, 8-tetrachlorodibenzo-p-dioxin-induced toxicity." Toxicology and applied pharmacology 140.1 (1996): 173-179.

Gendloff, E. H., et al. "Hapten-protein conjugates prepared by the mixed anhydride method: Cross-reactive antibodies in heterologous antisera." Journal of immunological methods 92.1 (1986): 15-20.

Haritash, A. K., and C. P. Kaushik. "Biodegradation aspects of polycyclic aromatic hydrocarbons (PAHs): a review." Journal of hazardous materials 169.1-3 (2009): 1-15.

Hua, Shao-bing, et al. "Minimum Length of Sequence Homology Required for in Vivo Cloning by Homologous Recombination in Yeast." Plasmid 38.2 (1997): 91-96.

Jenner, W. N., and B. Law. "Immunogen preparation and purification." Immunoassay: a practical guide, B. Law, ed. (London; Bristol, Pa.: Taylor & Francis) (1996): 11-31.

Keith, Lawrence H. "The source of US EPA's sixteen PAH priority pollutants." Polycyclic Aromatic Compounds 35.2-4 (2015): 147-160.

Li, Nanqin, and Hian Kee Lee. "Solid-phase extraction of polycyclic aromatic hydrocarbons in surface water: negative effect of humic acid." Journal of Chromatography A 921.2 (2001): 255-263.

Mallet, M. J., N. J. Grandy, and R. F. Lacey. "Interlaboratory comparison of a method to evaluate the effects of chemicals on fish growth." Environmental Toxicology and Chemistry: An International Journal 16.3 (1997): 528-533.

Matschulat, Diana, et al. "Development of a highly sensitive monoclonal antibody based ELISA for detection of benzo [a] pyrene in potable water." Analyst 130.7 (2005): 1078-1086.

Mu, Jingli, et al. "Comparative embryotoxicity of phenanthrene and alkyl-phenanthrene to marine medaka (*Oryzias melastigma*)." Marine pollution bulletin 85.2 (2014): 505-515.

Phillips, David H., Philip L. Grover, and Peter Sims. "A quantitative determination of the covalent binding of a series of polycylic hydrocarbons to DNA in mouse skin." International Journal of Cancer 23.2 (1979): 201-208.

Ronkainen, Niina J., and Stanley L. Okon. "The Role of Immunoassays in Urine Drug Screening." Advanced Healthcare Materials (2014): 493-524.

Scharnweber, T., et al. "Monoclonal antibody to polycyclic aromatic hydrocarbons based on a new benzo [a] pyrene immunogen." Fresenius' journal of analytical chemistry 371.5 (2001): 578-585.

Sherry, James. "Environmental immunoassays and other bioanalytical methods: overview and update." Chemosphere 34.5-7 (1997): 1011-1025.

Spier, Candace R., et al. "Near real-time, on-site, quantitative analysis of PAHs in the aqueous environment using an antibody-based biosensor." Environmental Toxicology and Chemistry 30.7 (2011): 1557-1563.

Uno, Shigeyuki, et al. "Benzo [a] pyrene-induced toxicity: paradoxical protection in Cyp1a1 (−/−) knockout mice having increased hepatic BaP-DNA adduct levels." Biochemical and biophysical research communications 289.5 (2001): 1049-1056.

Vendrame, Rosana, et al. "Structure-activity relationship studies of carcinogenic activity of polycyclic aromatic hydrocarbons using calculated molecular descriptors with principal component analysis and neural network methods." Journal of chemical information and computer sciences 39.6 (1999): 1094-1104.

(56) References Cited

OTHER PUBLICATIONS

Wang, Cuiping, et al. "PAHs distribution in sediments associated with gas hydrate and oil seepage from the Gulf of Mexico." Marine pollution bulletin 62.12 (2011): 2714-2723.
Wang, Wentao, et al. "Extraction of polycyclic aromatic hydrocarbons and organochlorine pesticides from soils: A comparison between Soxhlet extraction, microwave-assisted extraction and accelerated solvent extraction techniques." analytica chimica acta 602.2 (2007): 211-222.
Yalow, Rosalyn S., and Solomon A. Berson. "Assay of plasma insulin in human subjects by immunological methods." Nature 184.4699 (1959): 1648-1649.
Blake II, Robert C., Andrey R. Pavlov, and Diane A. Blake. "Automated kinetic exclusion assays to quantify protein binding interactions in homogeneous solution." Analytical biochemistry 272.2 (1999): 123-134.
Blumer, Max. "Polycyclic aromatic compounds in nature." Scientific American 234.3 (1976): 34-45.
Boder, Eric T., and K. Dane Wittrup. "[25] Yeast surface display for directed evolution of protein expression, affinity, and stability." Methods in enzymology. vol. 328. Academic Press, 2000. 430-444.
Machala, M., et al. "Effects of methylated chrysenes on AhR-dependent and-independent toxic events in rat liver epithelial cells." Toxicology 247.2-3 (2008): 93-101.
Moghaddam, Amir, et al. "Identification of scFv antibody fragments that specifically recognise the heroin metabolite 6-monoacetylmorphine but not morphine." Journal of immunological methods 280.1-2 (2003): 139-155.
National Research Council. Oil in the sea III: inputs, fates, and effects. National Academies Press (US), 2003.
Reardan, Dayton T., et al. "Antibodies against metal chelates." Nature 316 (6025) (1985): 265-268.
Salerno, Judith A., and Margaret A. McCoy, eds. Assessing the effects of the Gulf of Mexico oil spill on human health: A summary of the Jun. 2010 workshop. National Academies Press, 2010.
Samarajeewa, U., et al. "Application of immunoassay in the food industry." Critical Reviews in Food Science & Nutrition 29.6 (1991): 403-434.
Tijet, Nathalie, et al. "Aryl hydrocarbon receptor regulates distinct dioxin-dependent and dioxin-independent gene batteries." Molecular pharmacology 69.1 (2006): 140-153.
Zhu, Xiaoxia, et al. "Single-chain variable fragment (scFv) antibodies optimized for environmental analysis of uranium." Analytical chemistry 83.10 (2011): 3717-3724.
Abel, Josef, and Thomas Haarmann-Stemmann. "An introduction to the molecular basics of aryl hydrocarbon receptor biology." Biological chemistry 391.11 (2010): 1235-1248.
AC't Hoen, Peter, et al. "Phage display screening without repetitious selection rounds." Analytical biochemistry 421.2 (2012): 622-631.
Aga, Diana S., and E. M. Thurman. "Environmental immunoassays: alternative techniques for soil and water analysis." 1997. 1-20.
Ahmad, Azrilawani, and Eric J. Moore. "Comparison of cell-based biosensors with traditional analytical techniques for cytotoxicity monitoring and screening of polycyclic aromatic hydrocarbons in the environment." Analytical letters 42.1 (2009): 1-28.
Allan, Sarah E., Brian W. Smith, and Kim A. Anderson. "Impact of the Deepwater Horizon oil spill on bioavailable polycyclic aromatic hydrocarbons in Gulf of Mexico coastal waters." Environmental science & technology 46.4 (2012): 2033-2039.
Amorim, Mónica JB, et al. "Toxicity and bioaccumulation of phenanthrene in *Enchytraeus albidus* (Oligochaeta: Enchytraeidae)." Environmental toxicology and chemistry 30.4 (2011): 967-972.
Ayriss, Joanne, et al. "High-throughput screening of single-chain antibodies using multiplexed flow cytometry." Journal of proteome research 6.3 (2007): 1072-1082.
Baba, Takashi, et al. "Intrinsic function of the aryl hydrocarbon (dioxin) receptor as a key factor in female reproduction." Molecular and cellular biology 25.22 (2005): 10040-10051.

Baker, Monya. "Blame it on the antibodies." Nature 521.7552 (2015): 274.
Barron, Mace G., and Eric Holder. "Are exposure and ecological risks of PAHs underestimated at petroleum contaminated sites?." Human and Ecological Risk Assessment: An International Journal 9.6 (2003): 1533-1545.
Batrla, Richard, and Bruce WM Jordan. "Personalized health care beyond oncology: new indications for immunoassay-based companion diagnostics." Annals of the New York Academy of Sciences 1346.1 (2015): 71.
Bednar, Anthony J., et al. Field-portable gas chromatograph mass spectrometer (GC-MS) unit for semi-volatile compound analysis in groundwater. No. ERDC-TR-11-11. Engineer Research and Development Center Vicksburg MS Environmental Lab, 2011.
Begley, C. Glenn, and Lee M. Ellis. "Raise standards for preclinical cancer research." Nature 483.7391 (2012): 531-533.
Beloglazova, Natalia V., et al. "New immunochemically-based field test for monitoring benzo [a] pyrene in aqueous samples." Analytical Sciences 24.12 (2008): 1613-1617.
Blake, Diane A., et al. "Antibodies to heavy metals: Isolation, characterization, and incorporation into microplate-based assays and immunosensors." Immunoassay and other Bioanalytical Techniques (2007): 93-111.
Blake, Diane A., et al. "Metal binding properties of a monoclonal antibody directed toward metal-chelate complexes." Journal of Biological Chemistry 271.44 (1996): 27677-27685.
Boder, Eric T., and K. Dane Wittrup. "Yeast surface display for screening combinatorial polypeptide libraries." Nature biotechnology 15.6 (1997): 553-557.
Boder, Eric T., Katarina S. Midelfort, and K. Dane Wittrup. "Directed evolution of antibody fragments with monovalent femtomolar antigen-binding affinity." Proceedings of the National Academy of Sciences 97.20 (2000): 10701-10705.
Boonyatumanond, Ruchaya, et al. "Distribution and origins of polycyclic aromatic hydrocarbons (PAHs) in riverine, estuarine, and marine sediments in Thailand." Marine pollution bulletin 52.8 (2006): 942-956.
Bostrom, Jenny, et al. "Improving antibody binding affinity and specificity for therapeutic development." Therapeutic Antibodies. Humana Press, 2009. 353-376.
Bradbury, Andrew, and Andreas Plückthun. "Reproducibility: Standardize antibodies used in research." Nature 518.7537 (2015): 27-29.
Bunger, Maureen K., et al. "Resistance to 2, 3, 7, 8-tetrachlorodibenzo-p-dioxin toxicity and abnormal liver development in mice carrying a mutation in the nuclear localization sequence of the aryl hydrocarbon receptor." Journal of Biological Chemistry 278.20 (2003): 17767-17774.
Castro-Jiménez, Javier, and Catherine Gonzalez. "Immunoassay-based screening of polychlorinated biphenyls (PCB) in sediments: requirements for a new generation of test kits." Journal of Environmental Monitoring 13.4 (2011): 894-900.
Chames, Patrick, Stéphane Coulon, and Daniel Baty. "Improving the affinity and the fine specificity of an anti-cortisol antibody by parsimonious mutagenesis and phage display." The Journal of Immunology 161.10 (1998): 5421-5429.
Darwish, Ibrahim A. "Immunoassay methods and their applications in pharmaceutical analysis: basic methodology and recent advances." International journal of biomedical science: IJBS 2.3 (2006): 217.
Feldhaus, Michael J., et al. "Flow-cytometric isolation of human antibodies from a nonimmune *Saccharomyces cerevisiae* surface display library." Nature biotechnology 21.2 (2003): 163-170.
Fernando, Himesh, Raphaël Rodriguez, and Shankar Balasubramanian. "Selective recognition of a DNA G-quadruplex by an engineered antibody." Biochemistry 47.36 (2008): 9365-9371.
Ferrara, Fortunato, et al. "Using phage and yeast display to select hundreds of monoclonal antibodies: application to antigen 85, a tuberculosis biomarker." PloS one 7.11 (2012): e49535.
Fox, Jennifer E., et al. "Detecting ligands and dissecting nuclear receptor-signaling pathways using recombinant strains of the yeast *Saccharomyces cerevisiae*." Nature Protocols 3.4 (2008): 637.

(56) References Cited

OTHER PUBLICATIONS

Gai, S. Annie, and K. Dane Wittrup. "Yeast surface display for protein engineering and characterization." Current opinion in structural biology 17.4 (2007): 467-473.

Georgieva, Yuliya, and Zoltán Konthur. "Design and screening of M13 phage display cDNA libraries." Molecules 16.2 (2011): 1667-1681.

Glanville, Jacob, et al. "Precise determination of the diversity of a combinatorial antibody library gives insight into the human immunoglobulin repertoire." Proceedings of the National Academy of Sciences 106.48 (2009): 20216-20221.

Gust, K. A. "Joint toxicity of cadmium and phenanthrene in the freshwater amphipod *Hyalella azteca*." Archives of environmental contamination and toxicology 50.1 (2006): 7-13.

Hecht, Stephen S., William E. Bondinell, and Dietrich Hoffmann. "Chrysene and methylchrysenes: presence in tobacco smoke and carcinogenicity." Journal of the National Cancer Institute 53.4 (1974): 1121-1133.

Heitkamp, Michael A., Wilbur Franklin, and Carl E. Cerniglia. "Microbial metabolism of polycyclic aromatic hydrocarbons: isolation and characterization of a pyrene-degrading bacterium." Applied and Environmental Microbiology 54.10 (1988): 2549-2555.

Hollender, Juliane, et al. "Efficiency of different methods and solvents for the extraction of polycyclic aromatic hydrocarbons from soils." International Journal of Environmental & Analytical Chemistry 83.1 (2003): 21-32.

Inkley, D., S. Gonzalez-Rothi Kronenthal, and L. McCormick. "Restoring a degraded Gulf of Mexico: Wildlife and wetlands three years into the gulf oil disaster." Report of the National Wildlife Federation (2013).

Jin, Guang-Bi, et al. "New insights into the role of the aryl hydrocarbon receptor in the function of CD11c+ cells during respiratory viral infection." European journal of immunology 44.6 (2014): 1685-1698.

Juhascik, Matthew P., and Amanda J. Jenkins. "Comparison of liquid/liquid and solid-phase extraction for alkaline drugs." Journal of chromatographic science 47.7 (2009): 553-557.

Kavanagh, Owen, Christopher T. Elliott, and Katrina Campbell. "Progress in the development of immunoanalytical methods incorporating recombinant antibodies to small molecular weight biotoxins." Analytical and Bioanalytical Chemistry 407.10 (2015): 2749-2770.

Kerley-Hamilton, Joanna S., et al. "Inherent and benzo [a] pyrene-induced differential aryl hydrocarbon receptor signaling greatly affects life span, atherosclerosis, cardiac gene expression, and body and heart growth in mice." Toxicological Sciences 126.2 (2012): 391-404.

Kevin R, Oldenburg, et al. "Recombination-mediated PCR-directed plasmid construction in vivo in yeast." Nucleic acids research 25.2 (1997): 451-452.

Knopp, Dietmar. "Immunoassay development for environmental analysis." Analytical and bioanalytical chemistry 385.3 (2006): 425-427.

Köhler, Georges, and Cesar Milstein. "Continuous cultures of fused cells secreting antibody of predefined specificity." nature 256.5517 (1975): 495-497.

Lau, E. V., S. Gan, and H. K. Ng. "Extraction techniques for polycyclic aromatic hydrocarbons in soils." International Journal of Analytical Chemistry 2010 (2010).

LaVoie, Edmond J., et al. "Mutagenicity, tumor-initiating activity, and metabolism of methylphenanthrenes." Cancer research 41.9 Part 1 (1981): 3441-3447.

LaVoie, Edmond J., et al. "Tumor-initiating activity and metabolism of polymethylated phenanthrenes." Cancer Research 42.10 (1982): 4045-4049.

Lee, Carol MY, et al. "Selection of human antibody fragments by phage display." Nature protocols 2.11 (2007): 3001.

Lesnik, Barry. "Immunoassay techniques in environmental analyses." Encyclopedia of Analytical Chemistry: Applications, Theory and Instrumentation (2006).

Liang, H. C., Navdeep Bilon, and Michael T. Hay. "Analytical methods for pesticide residues in the water environment." Water Environment Research 87.10 (2015): 1923-1937.

\* cited by examiner

Pool 1/Protocol 1

| Rd | Coating | Conditions | Input | Output | Yield | Enrichment |
|---|---|---|---|---|---|---|
| 1 | | Enrichment | $3 \times 10^{12}$ | $10^6$ | $3.3 \times 10^{-7}$ | 1 |
| 2 | Phen-BSA, 5µg/ml | 1%DMSO solvent | $1.5 \times 10^{12}$ | $4.4 \times 10^4$ | $2.9 \times 10^{-8}$ | 0.09 |
| 3 | | Elute with 100µM phen | $2.4 \times 10^{12}$ | $1.4 \times 10^6$ | $5.8 \times 10^{-7}$ | 20 |

Pool 2/Protocol 2

| Rd | Coating | Conditions | Input | Output | Yield | Enrichment |
|---|---|---|---|---|---|---|
| 1 | | Enrichment | $3 \times 10^{12}$ | $10^6$ | $3.3 \times 10^{-7}$ | 1 |
| 2 | 2mp-BSA, 5µg/ml | 1%DMSO solvent | $1.3 \times 10^{12}$ | $3.6 \times 10^4$ | $2.8 \times 10^{-8}$ | 0.08 |
| 3 | | Elute with 100µM phen | $1.4 \times 10^{12}$ | $4.2 \times 10^6$ | $3 \times 10^{-6}$ | 108 |

*FIG. 2*

|  |  |  |
|---|---|---|
| Tested clones | 184 | 48 |
| Positives by Flow | 70 | 8 |
| Positives by cELISA | 65 | 6 |
| Diversity | 7 | 3 |

*FIG. 8*

| Forward primers for heavy chain | | |
|---|---|---|
| Extension-for | GCTACCGTGGCCCAGGCGGCCATGGCCAGAA GCGCGC ATGCC S A (SEQ ID NO: 1) | SEQ ID NO: |
| VH-for 1 | CTAGA GCGCGC ATGCC G A G G T T C D S C T G C A A C A G T Y | 2 |
| VH-for 2 | CTAGA GCGCGC ATGCC C A G G T G C A A M T G M A G S A G T C | 3 |
| VH-for 3 | CTAGA GCGCGC ATGCC G A V G T G M W G C T G G T G G A G T C | 4 |
| VH-for 4 | CTAGA GCGCGC ATGCC C A G G T T A Y T C T G A A A G A G T C | 5 |
| VH-for 5 | CTAGA GCGCGC ATGCC G A K G T G C A G C T T C A G S A G T C | 6 |
| VH-for 6 | CTAGA GCGCGC ATGCC C A G A T C C A G T T S G Y G C A G T C | 7 |
| VH-for 7 | CTAGA GCGCGC ATGCC C A G R T C C A A C T G C A G C A G Y C | 8 |
| VH-for 8 | CTAGA GCGCGC ATGCC G A G G T G M A G C T A S T T G A G W C | 9 |
| VH-for 9 | CTAGA GCGCGC ATGCC G A A G T G A A G M T T G A G G A G T C | 10 |
| VH-for 10 | CTAGA GCGCGC ATGCC G A T G T G A A C C T G G A A G T G T C | 11 |
| VH-for 11 | CTAGA GCGCGC ATGCC C A G A T K C A G C T T M A G G A G T C | 12 |
| VH-for 12 | CTAGA GCGCGC ATGCC C A G G C T T A T C T G C A G C A G T C | 13 |
| VH-for 13 | CTAGA GCGCGC ATGCC C A G G T T C A C C T A C A A C A G T C | 14 |
| VH-for 14 | CTAGA GCGCGC ATGCC C A G G T G C A G C T T G T A G A G A C | 15 |
| VH-for 15 | CTAGA GCGCGC ATGCC G A R G T G M A G C T G K T G G A G A C | 16 |
| Reverse primers for heavy chain | | |
| VH-rev 1 | CCGCCTCGAGCACCTCCGCCGGAGCCGCCGCCGCCAGAACCACCACCACC C G A G G A G A C G G T G A C M G T G G | 17 |
| VH-rev 2 | CCGCCTCGAGCACCTCCGCCGGAGCCGCCGCCGCCAGAACCACCACCACC C G C A G A G A C A G T G A C C A G A G | 18 |
| VH-rev 3 | CCGCCTCGAGCACCTCCGCCGGAGCCGCCGCCGCCAGAACCACCACCACC C G A G G A G A C T G T G A G A S T G G | 19 |

*FIG. 11*

| Forward primers for light chain | | SEQ ID NO: |
|---|---|---|
| VLk-for 1 | GGCGGAGGTGCTCGAGGCGGTGGCGGATCG GACAWTGTTCTCA CCCAGTC | 20 |
| VLk-for 2 | GGCGGAGGTGCTCGAGGCGGTGGCGGATCG GACATCCAGATGA CACAGWC | 21 |
| VLk-for 3 | GGCGGAGGTGCTCGAGGCGGTGGCGGATCG GATRTTGTGATGA CCCAGWC | 22 |
| VLk-for 4 | GGCGGAGGTGCTCGAGGCGGTGGCGGATCG GACATTSTGMTGA CCCAGTC | 23 |
| VLk-for 5 | GGCGGAGGTGCTCGAGGCGGTGGCGGATCG GATGTTGTGVTGA CCCAAAC | 24 |
| VLk-for 6 | GGCGGAGGTGCTCGAGGCGGTGGCGGATCG GACACAACTGTGA CCCAGTC | 25 |
| VLk-for 7 | GGCGGAGGTGCTCGAGGCGGTGGCGGATCG GAYATTKTGCTCA CTCAGTC | 26 |
| VLk-for 8 | GGCGGAGGTGCTCGAGGCGGTGGCGGATCG GATATTGTGATRA CCCAGGM | 27 |
| VLk-for 9 | GGCGGAGGTGCTCGAGGCGGTGGCGGATCG GACATTGTAATGA CCCAATC | 28 |
| VLk-for 10 | GGCGGAGGTGCTCGAGGCGGTGGCGGATCG GACATTGTGATG WCACAGTC | 29 |
| VLk-for 11 | GGCGGAGGTGCTCGAGGCGGTGGCGGATCG GATRCCAGATGA MCCAGTC | 30 |
| VLk-for 12 | GGCGGAGGTGCTCGAGGCGGTGGCGGATCG GATGGAGAAACA ACACAGGC | 31 |
| Reverse primers for light chain | | |
| Extension-Rev | GTGATGGTGCTGGCCGGCCTGGCC TGAGCTAGC GCGTTT | 32 |
| VLk-rev 1 | GG TGAGCTAGC GCGTTT8ATTTCCAGCTTGG | 33 |
| VLk-rev 2 | GG TGAGCTAGC GCGTTTTATTTCCAATTTTG | 34 |

*FIG. 12*

| Transfer primer | | SEQ ID NO: |
|---|---|---|
| phageTOyeast-for | TCT GGT GGT GGT GGT TCT GGT GGT GGT GGT TCT GCT AGAA GCGCGCATGCC | 35 |
| phageTOyeast-rev | CGTTCAGGTC TTC TTC AGA GAT CAG TTT CTG TTC AGC ACC TGA GCTAGCGCGTTT | 36 |

*FIG. 13*

FIG. 14 A and B

FIG. 14 C and D

| Spill | Location | Date | Gallon (x1000) |
|---|---|---|---|
| Lakeview Gusher | Kern County, California, United States | March 14, 1910 – September 1911 | 378,000 |
| Gulf War Oil Spill | Kuwait | January 19, 1991 – January 28, 1991 | 252,000–336,000 |
| Deepwater Horizon | Gulf of Mexico, United States | April 20, 2010 – July 15, 2010 | 172,000–180,800 |
| Ixtoc I Oil Well | Gulf of Mexico, Mexico | June 3, 1979 – March 23, 1980 | 139,818–147,840 |
| Atlantic Empress | Trinidad and Tobago, West Indies | July 19, 1979 | 88,396 |
| Fergana Valley | Uzbekistan | March 2, 1992 | 87,780 |
| Nowruz Field Platform | Persian Gulf, Iran | February 4, 1983 | 80,080 |
| ABT Summer | Angola, 700 nmi offshore | May 28, 1991 | 80,080 |
| Castillo de Bellver | Saldanha Bay, South Africa | August 6, 1983 | 77,616 |
| Amoco Cadiz | Brittany, France | March 16, 1978 | 68,684 |

*FIG. 15*

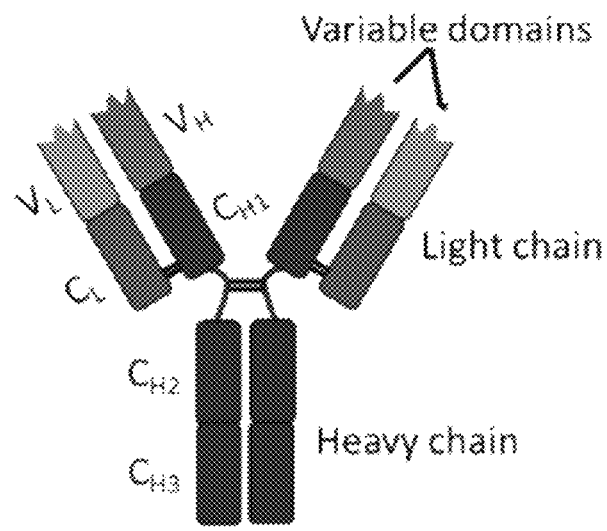
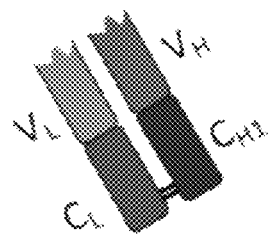
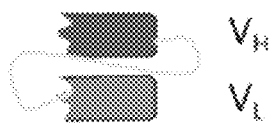
FIG. 19

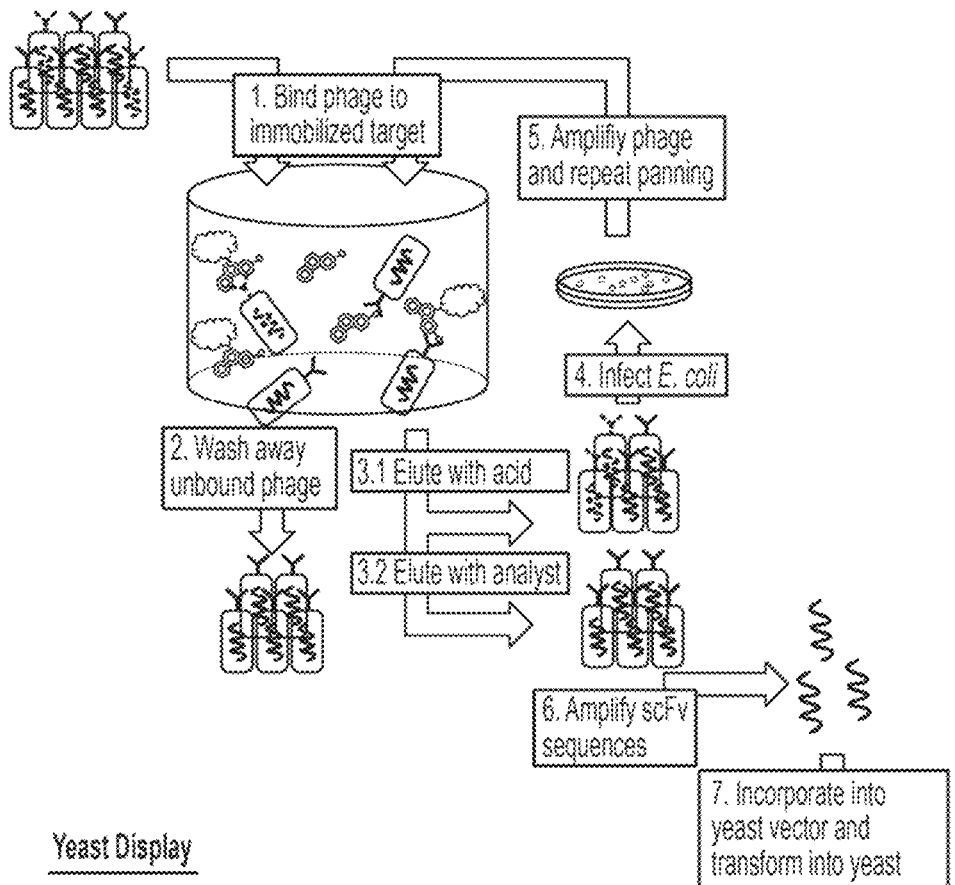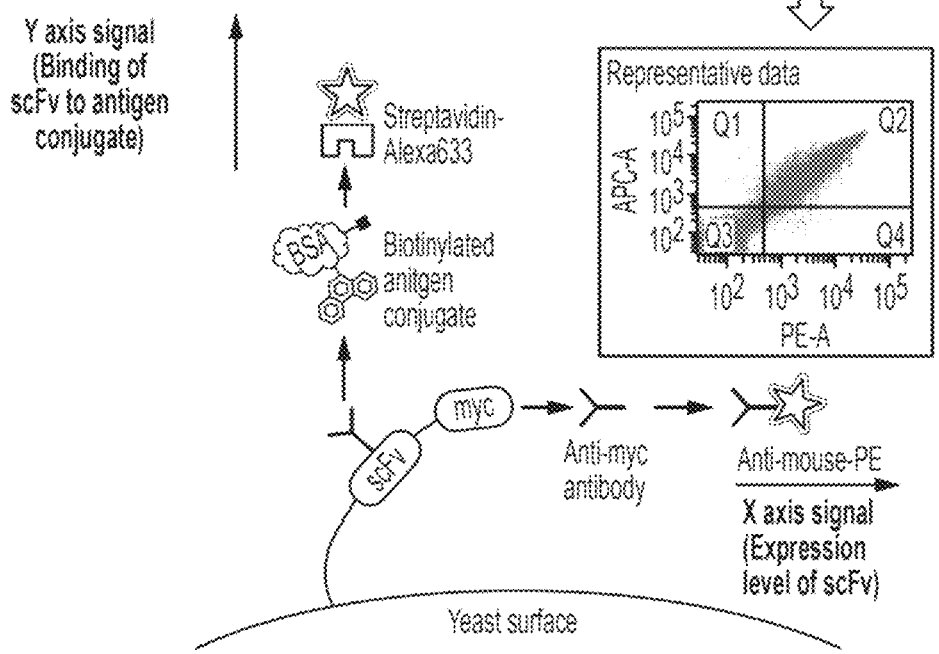
FIG. 21

| Compound | $r^2$ | a0 (Maximum Response, LacZ Units) | a1 (Half-Maximum Response, μM) |
|---|---|---|---|
| Phenanthrene | 0.993212 | 110.99859 | 43.90682 |
| 1-methylphenanthrene | 0.971649 | 120.300398 | 11.112638 |
| 2-methylphenanthrene | 0.997768 | 199.033005 | 24.364655 |
| 3-methylphenanthrene | 0.996653 | 173.761311 | 19.230946 |
| 4-methylphenanthrene | 0.994801 | 142.457146 | 29.769956 |
| 9-methylphenanthrene | 0.994671 | 126.461 | 15.846446 |
| 3,6-dimethylphenanthrene | 0.962489 | 47.887954 | 1.780058 |

*FIG. 26*

| Compound | rEC$_{50}$, μM (±SEM) | rEC$_{25}$, μM (±SEM) |
|---|---|---|
| Phenanthrene | 22.4380±1.0924 | 8.9357±0.6268 |
| 1-methylphenanthrene | 3.9815±0.7119 | 1.6883±0.3200 |
| 2-methylphenanthrene | 4.6214±0.1727 | 2.1105±0.0875 |
| 3-methylphenanthrene | 5.7875±0.2805 | 2.5152±0.1405 |
| 4-methylphenanthrene | 11.7017±0.6118 | 4.8898±0.3430 |
| 9-methylphenanthrene | 7.8321±0.4586 | 1.6883±0.2153 |
| 3,6-dimethylphenanthrene | 6.4576±2.6137 | 1.1475±0.1927 |

*FIG. 27*

| rEC$_{50}$ \ rEC$_{25}$ | Phen | 1-MP | 2-MP | 3-MP | 4-MP | 9-MP | 3,6-DMP |
|---|---|---|---|---|---|---|---|
| Phen |  | <0.001 | <0.001 | <0.001 | <0.001 | <0.001 | <0.001 |
| 1-MP | <0.001 |  | >0.05 | >0.05 | <0.001 | >0.05 | >0.05 |
| 2-MP | <0.001 | >0.05 |  | >0.05 | <0.001 | >0.05 | >0.05 |
| 3-MP | <0.001 | >0.05 | >0.05 |  | <0.001 | >0.05 | >0.05 |
| 4-MP | <0.001 | <0.001 | <0.001 | <0.01 |  | <0.001 | <0.001 |
| 9-MP | <0.001 | >0.05 | >0.05 | >0.05 | <0.01 |  | <0.001 |
| 3,6-DMP | <0.001 | >0.05 | >0.05 | >0.05 | <0.01 | >0.05 |  |

FIG. 28

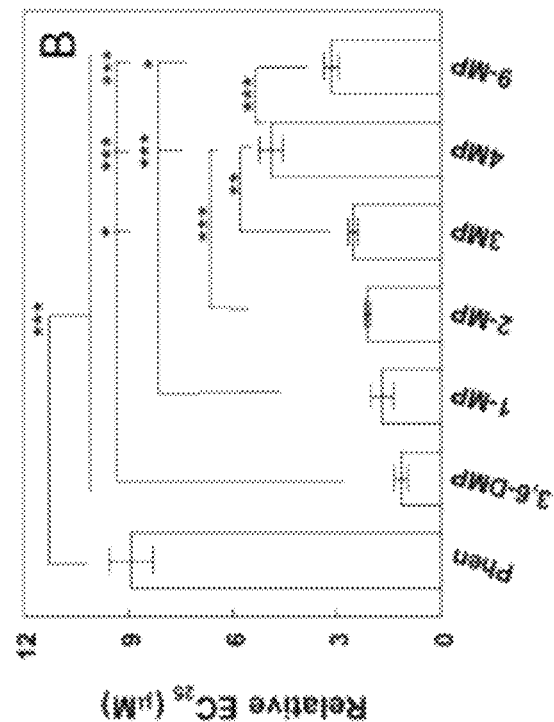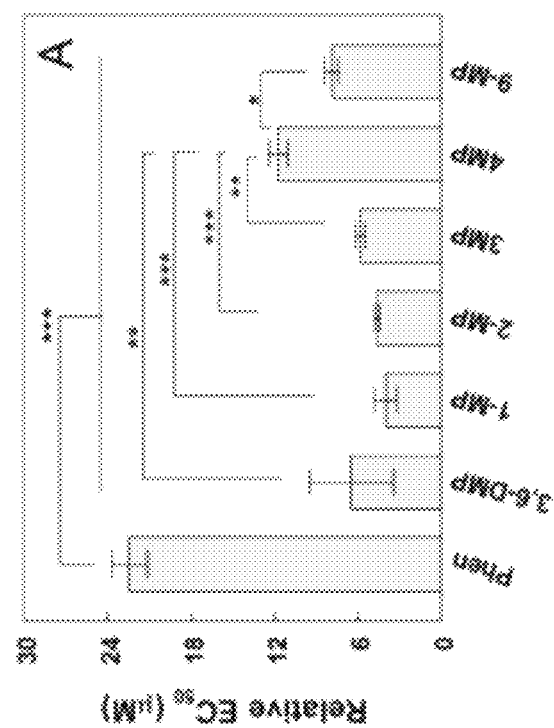
FIG. 29

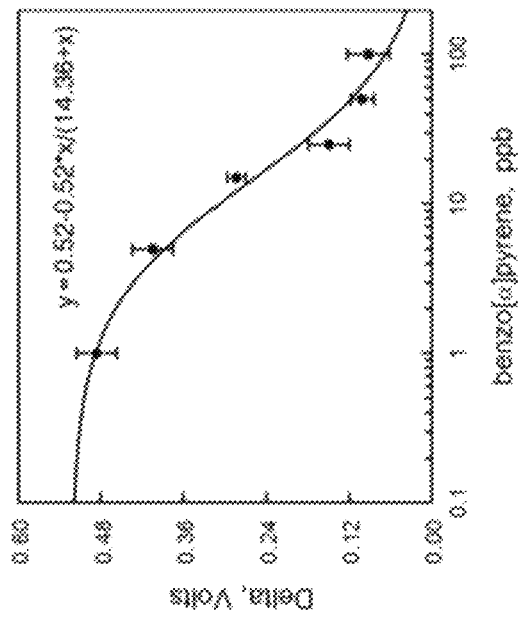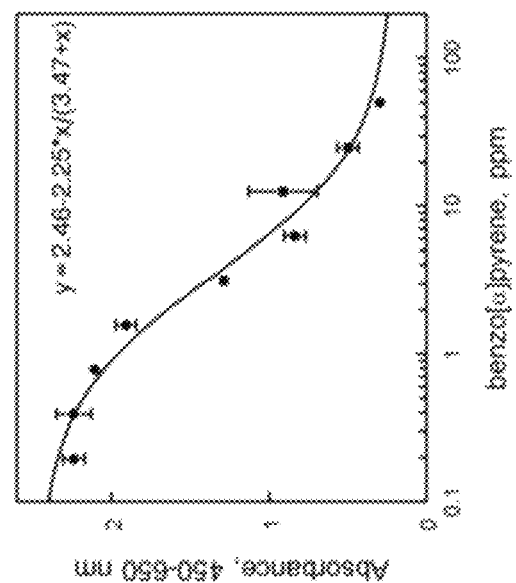
FIG. 34

| Models | R² coefficiency | IC₅₀ |
|---|---|---|
| cELISA | 0.962408 | 3.47 ppm or 13.88 µM |
| KinExA | 0.980636 | 14.36 ppb or 57.44 nM |

*FIG. 35*

| Injection | Immunogen | Adjuvant | Intervals | Serum samples |
|---|---|---|---|---|
| 1 | PAH*-KLH | Sigma adjuvant system (Sigma Aldrich, MO) ** | - | - |
| 2 | PAH-KLH | | 19 | - |
| 3 | PAH-BSA | | 14 | 7 days after injection |
| 4 | PAH-KLH | | 21 | 7 days after injection |

*FIG. 36*

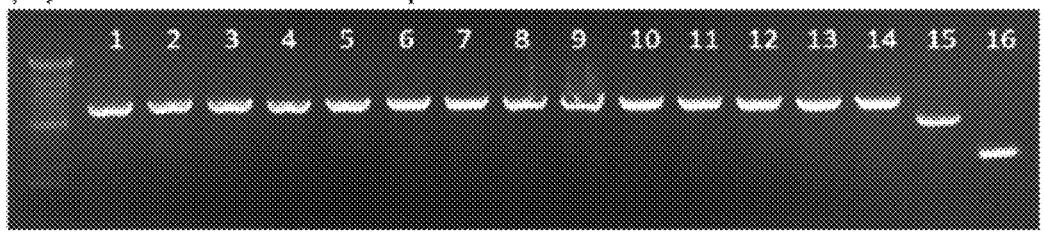
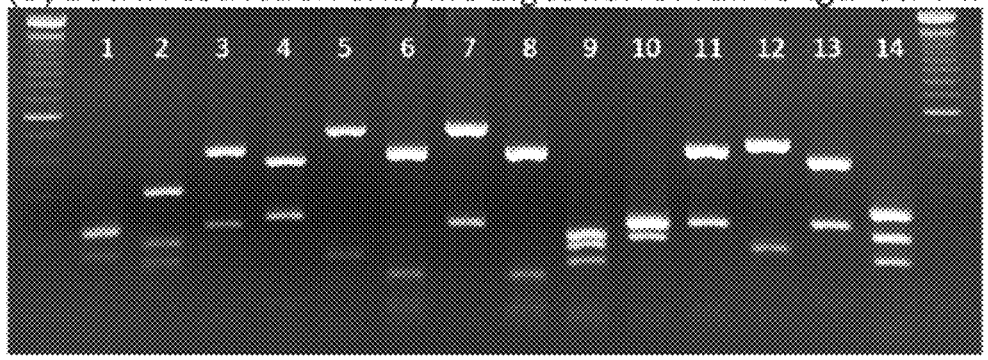
FIG. 39

| Rd | **Coating, 2np-BSA | Incubation time, hour | Number of washes | Solvent/ Competitor | Input | Output | Yield |
|---|---|---|---|---|---|---|---|
| 1 | 100µg/ml | 2 | 5 | - | $1 \times 10^{12}$ | $3 \times 10^{5}$ | $3 \times 10^{-7}$ |
| 2 | 50µg/ml | 2 | 10 | - | $3 \times 10^{12}$ | $1.1 \times 10^{7}$ | $3.7 \times 10^{-6}$ |
| 3 | 25µg/ml | 1 | 10 | 10% MeOH | $3 \times 10^{11}$ | $1 \times 10^{6}$ | $3.3 \times 10^{-6}$ |
| 4 | 10µg/ml | 1 | 15 | benzo[a]pyrene | $1 \times 10^{11}$ | $1.2 \times 10^{6}$ | $1.2 \times 10^{-5}$ |
| 5 | 2.5µg/ml 2-MePhen-KLH | 1 | 20 | 10% MeOH | $6 \times 10^{11}$ | $7 \times 10^{6}$ | $1.2 \times 10^{-5}$ |
| 6 | 5µg/ml | 1 | 20 | 3µM Phen | $1 \times 10^{12}$ | $1.9 \times 10^{8}$ | $1.9 \times 10^{-4}$ |
| 7 | 2.5µg/ml | 1 | 20 | 10µM Phen | $1 \times 10^{12}$ | $1.2 \times 10^{8}$ | $1.9 \times 10^{-5}$ |

FIG. 40

(A) BstNI fingerprint of representative clones from the 7th output pool
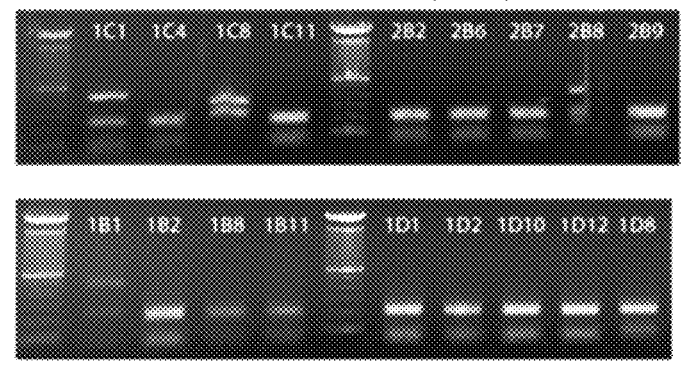
(B) Indirect phage ELISA of selected full-length clones
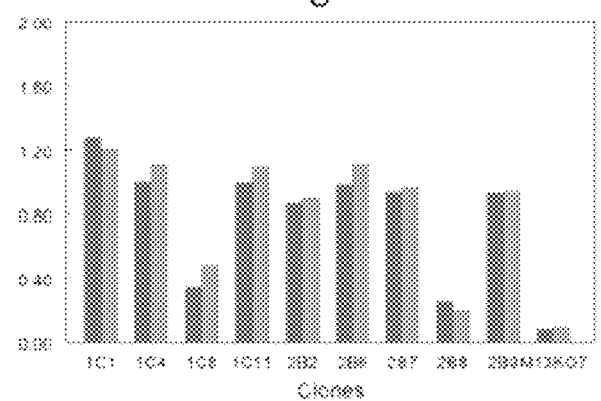
*FIG. 41*

| Protocol 1 | | | | |
|---|---|---|---|---|
| Rd | Coating | Selective Pressure | Input | Output | Yield |
| 1 | phenanthrene-BSA, 5µg/ml | Enrichment | $3\times10^{12}$ | $10^6$ | $3.3\times10^{-7}$ |
| 2 | | 1% DMSO solvent | $1.5\times10^{12}$ | $4.4\times10^4$ | $2.9\times10^{-8}$ |
| 3 | | Elute with 100µM phenanthrene | $2.4\times10^{12}$ | $1.4\times10^6$ | $5.8\times10^{-7}$ |

| Protocol 2 | | | | |
|---|---|---|---|---|
| Rd | Coating | Selective Pressure | Input | Output | Yield |
| 1 | 2-methy-phenanthrene-BSA, 5µg/ml | Enrichment | $3\times10^{12}$ | $10^6$ | $3.3\times10^{-7}$ |
| 2 | | 1% DMSO solvent | $1.3\times10^{12}$ | $3.6\times10^4$ | $2.8\times10^{-8}$ |
| 3 | | Elute with 100µM 2-methylphenanthrene | $1.4\times10^{12}$ | $4.2\times10^6$ | $3\times10^{-6}$ |

*FIG. 43*

(A) Monoclonal PCR amplification of scFv-insert of phage selection strategy #2
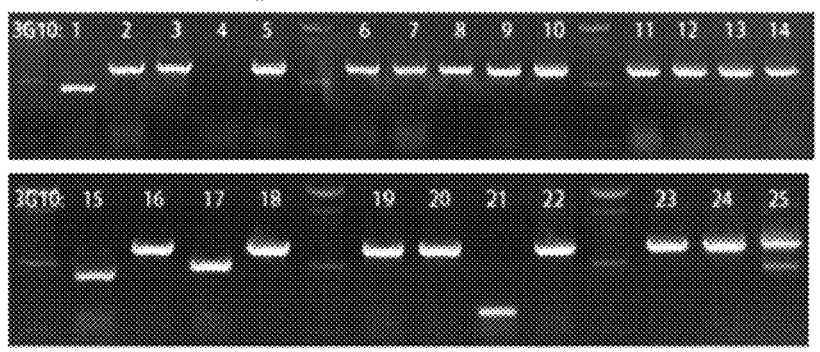
(B) BstNI fingerprint of representative clones from the 3rd output pools
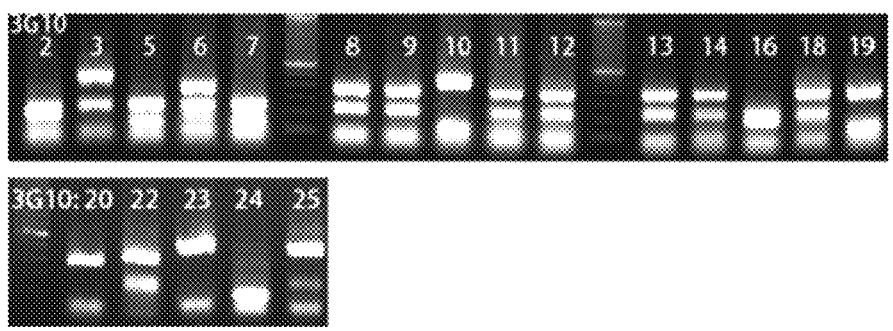
(C) Phage ELISA analysis of selected full-length clones.
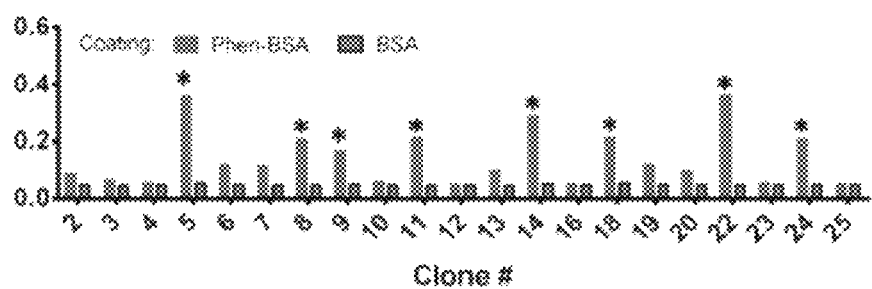
*FIG. 45*

Table 9 Summary of monoclonal yeast flow-cytometry analysis

| Library | #1 | #2 |
|---|---|---|
| Tested clones | 184 | 48 |
| Positives by Flow | 70 (38%) | 8 (17%) |
| Positives by cELISA | 65 (35%) | 6 (13%) |
| Diversity | 7 | 3 |

*FIG. 53*

| Kd, µM | A10 | D7 | G8 |
|---|---|---|---|
| Phen | - | 5.60 | 5.17 |
| 2mp | 8.28 | 7.23 | 2.03 |
| 3mp | 21.13 | 5.97 | 14.43 |
| 4mp | 23.51 | 4.66 | 0.94 |
| 9mp | - | 7.04 | 3.26 |

*FIG. 56*

| PAHs | A10 | D7 | G8 |
|---|---|---|---|
| Acenaphthene | ND | 15.65 | 24.8 |
| Acenaphthlene | ND | 31.03 | 70.8 |
| Anthracene | ND | 79.36 | ND |
| Benzo-[a]-anthracene | ND | ND | ND |
| Benzo-[a]-pyrene | ND | ? * | ND |
| Benzo-[b]-fluoranthene | ND | ND | ND |
| Benzo-[g.h.i]-perylene | ND | ND | ND |
| Benzo-[k]-fluoranthene | ND | ND | ND |
| Chrysene | ND | ND | ND |
| Dibenzo-anthracene | ND | ND | ND |
| Fluoranthene | ND | 1.63 | 2.40 |
| Fluorene | ND | 16.11 | 12.43 |
| Indeno-[1,2,3-cd]-pyrene | ND | 1.51 | ND |
| Naphthalene | ND | ND | ND |
| Phenanthrene | ND | 5.60 | 5.17 |
| Pyrene | ND | 1.54 | 2.02 |

*FIG. 57*

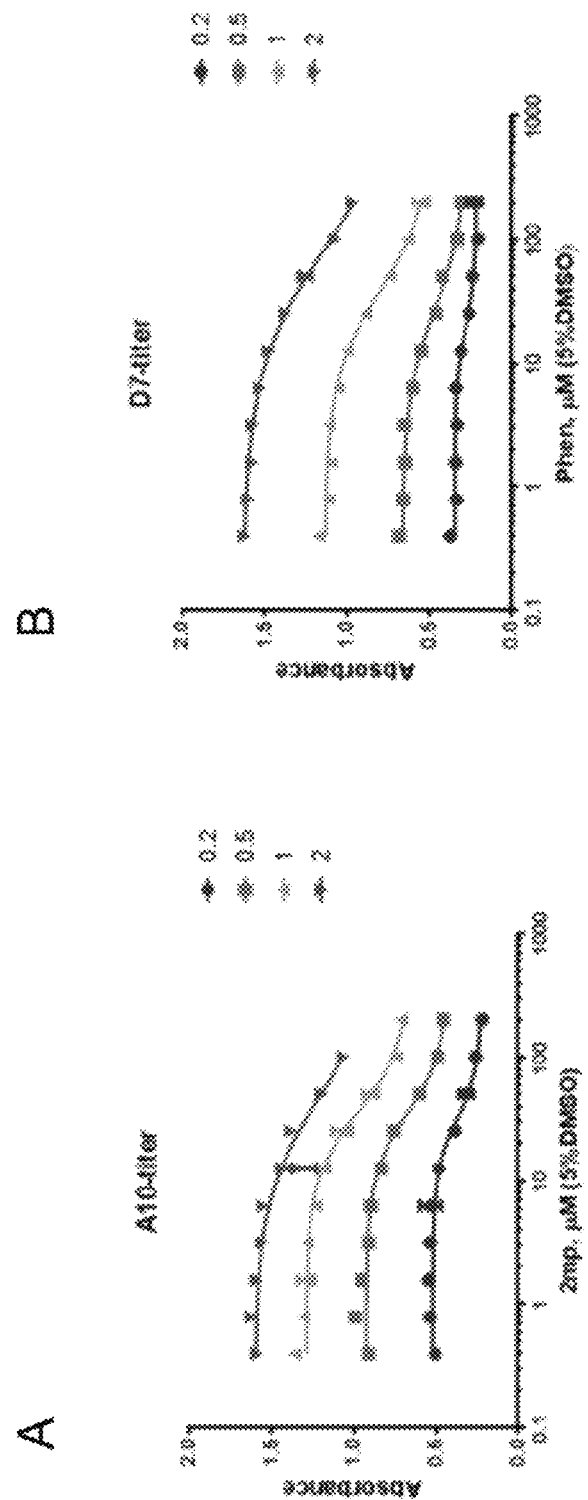
FIGS. 61A-B

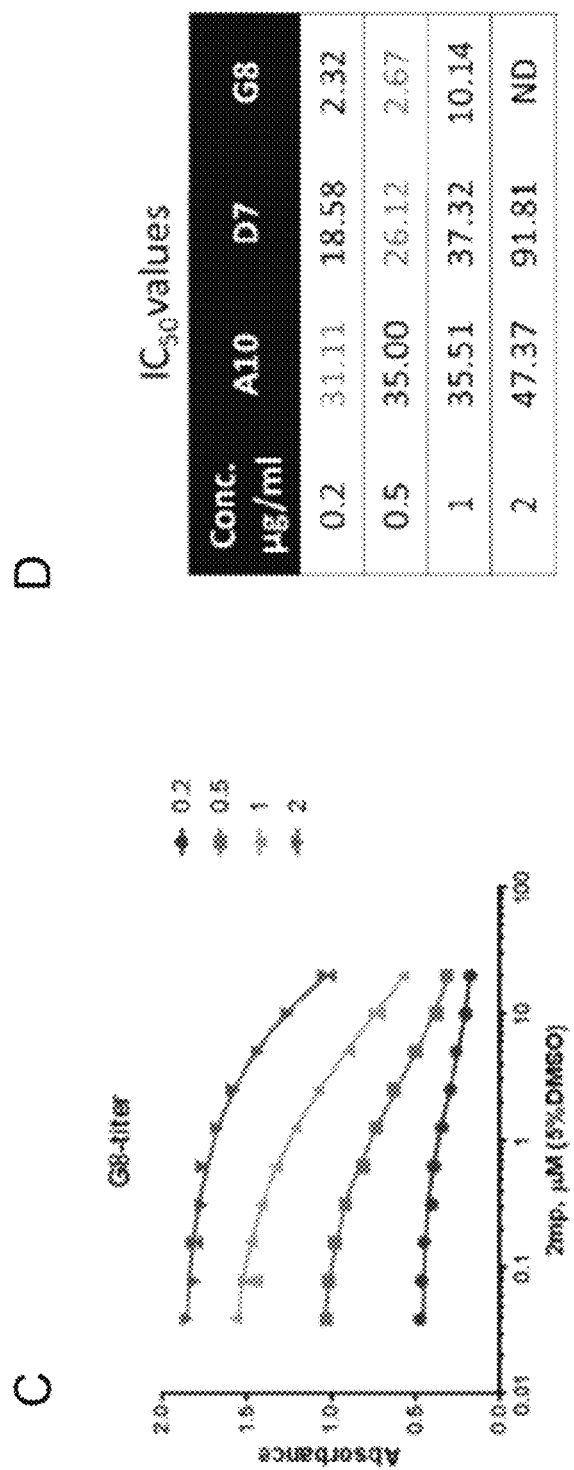
FIGS. 61C-D

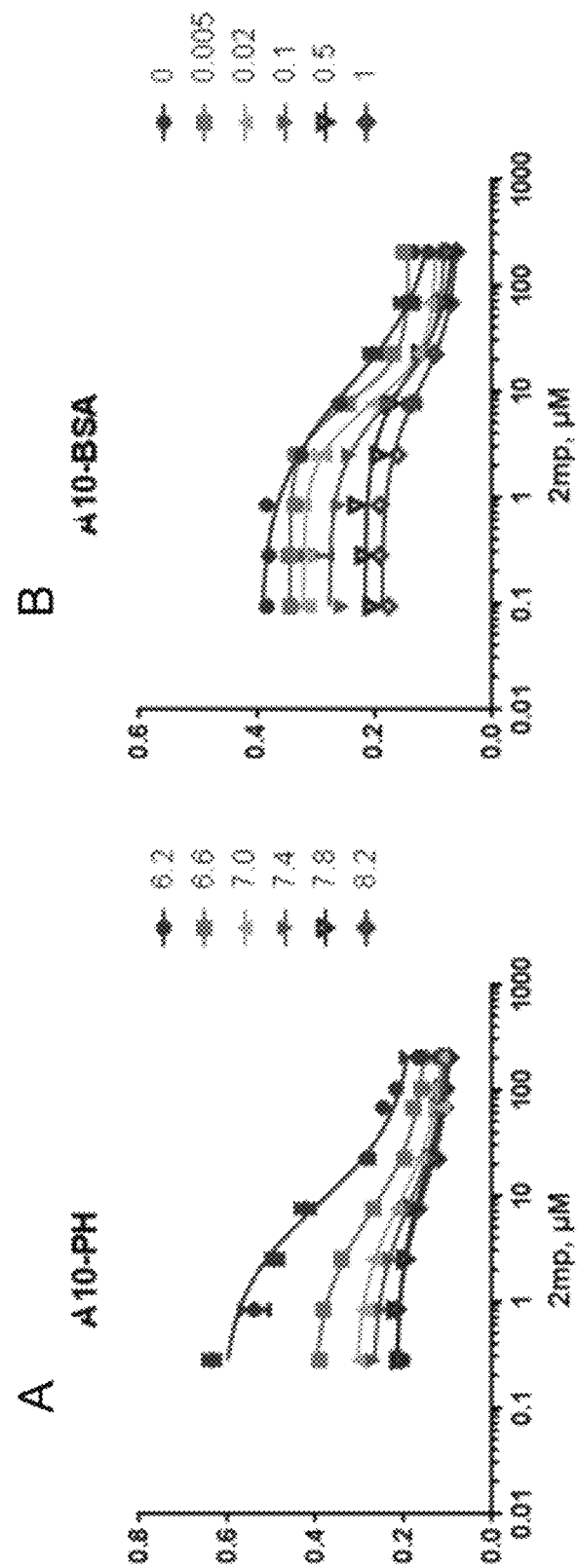
FIG. 62A-B

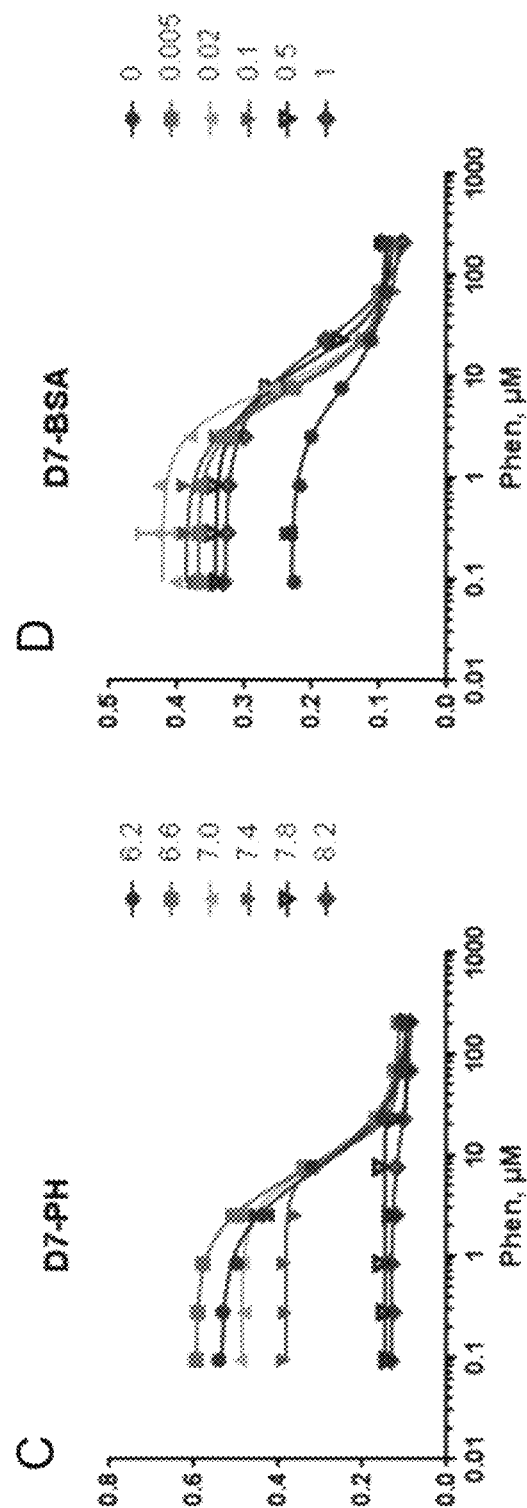
FIGS. 62C-D

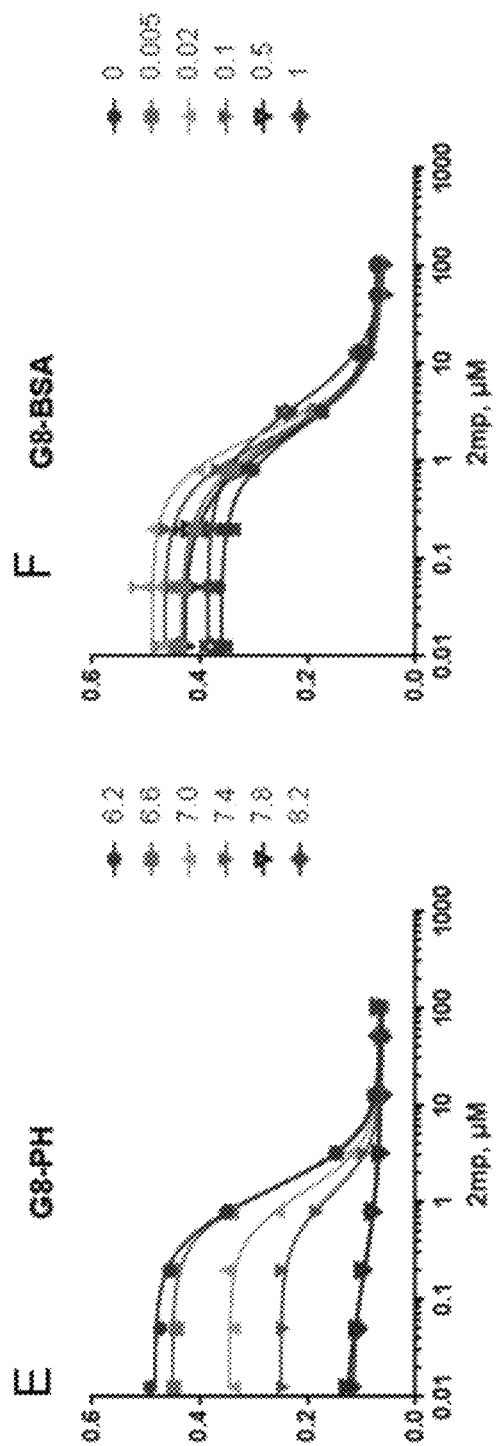
FIG. 62E-F

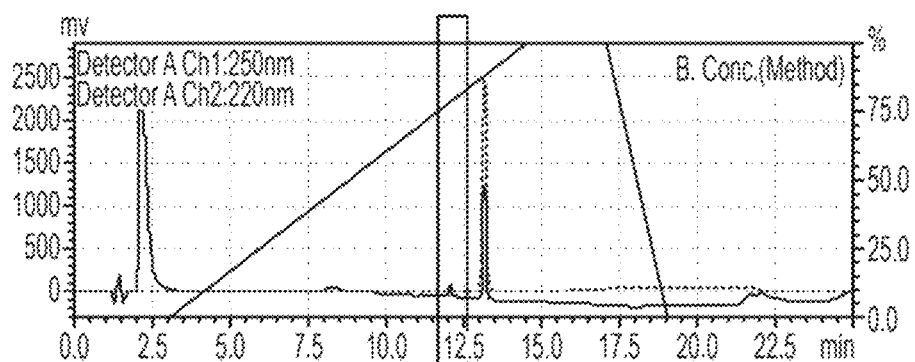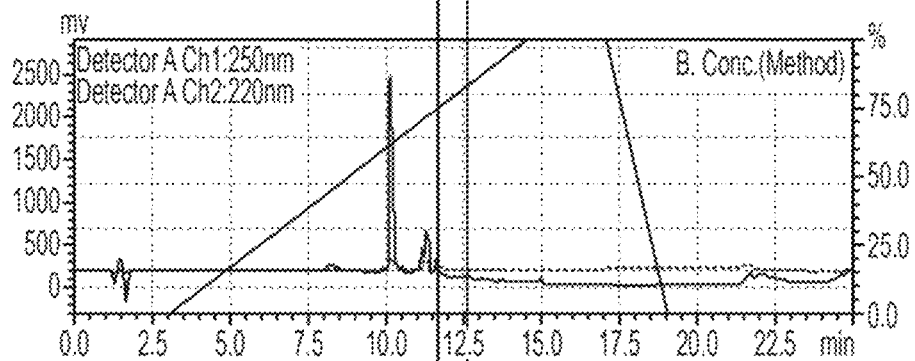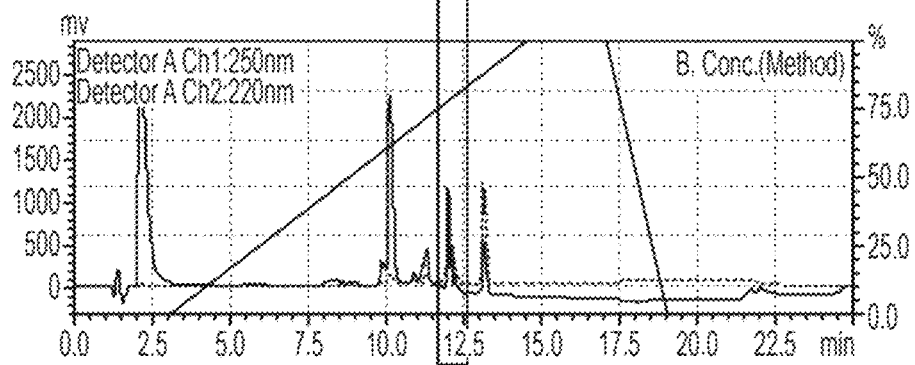
FIG. 64

| Injection # | Immunogen | Adjuvant | Intervals | Serum samples |
|---|---|---|---|---|
| 1 | PAH*-KLH | | - | - |
| 2 | PAH-KLH | Sigma adjuvant system (Sigma Aldrich, MO) ** | 14 | - |
| 3 | PAH-BSA | | 21 | 7 days after injection |
| 4 | PAH-KLH | | 19 | 7 days after injection |

*PAH conjugates are either 2-methylphenanthrene, or 2,7-dimethylphenanthrene.
**The adjuvant was mixed 1:1 with immunogen (50µg) for each injection.

FIG. 73

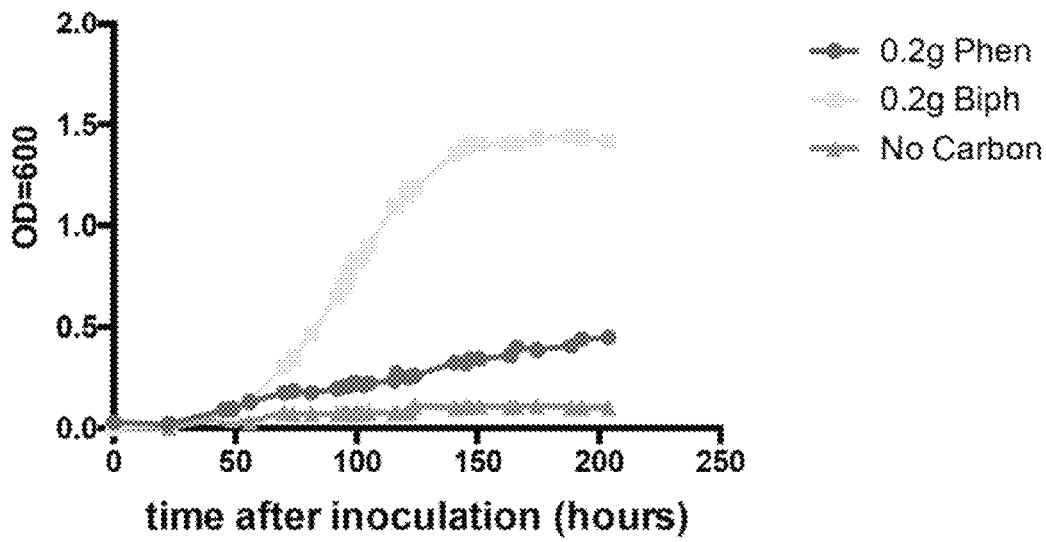
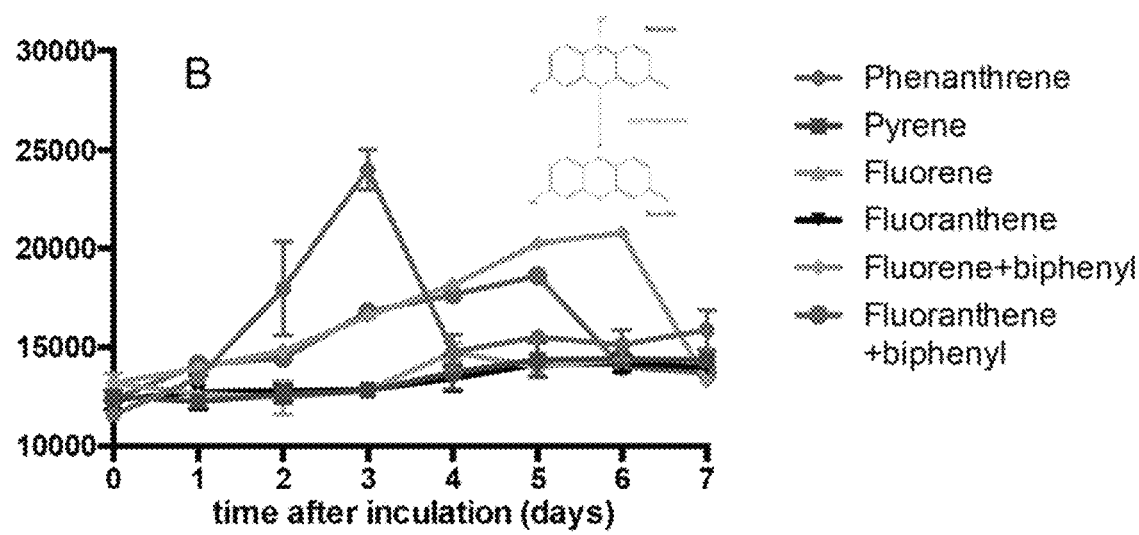
FIG. 79

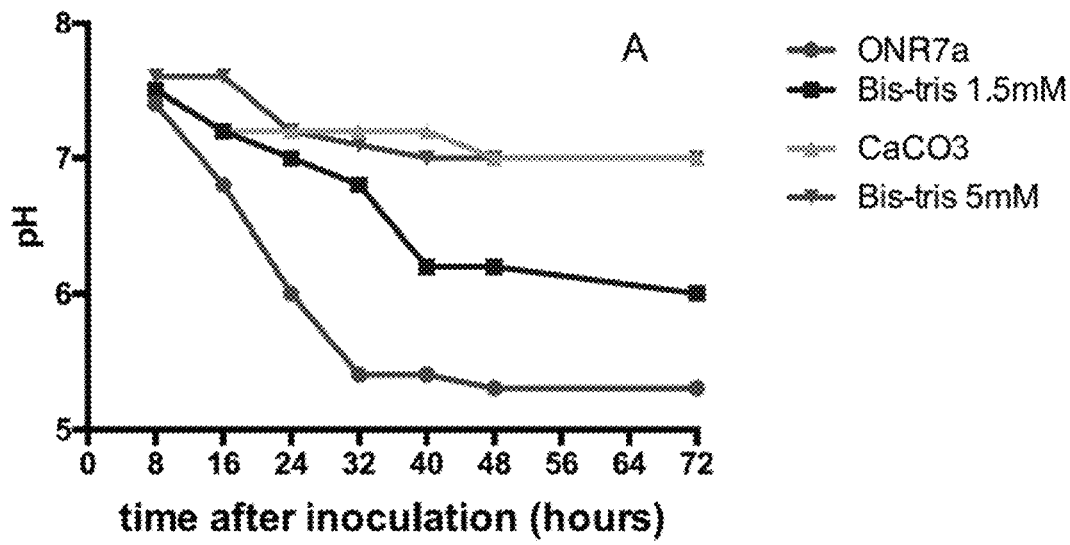
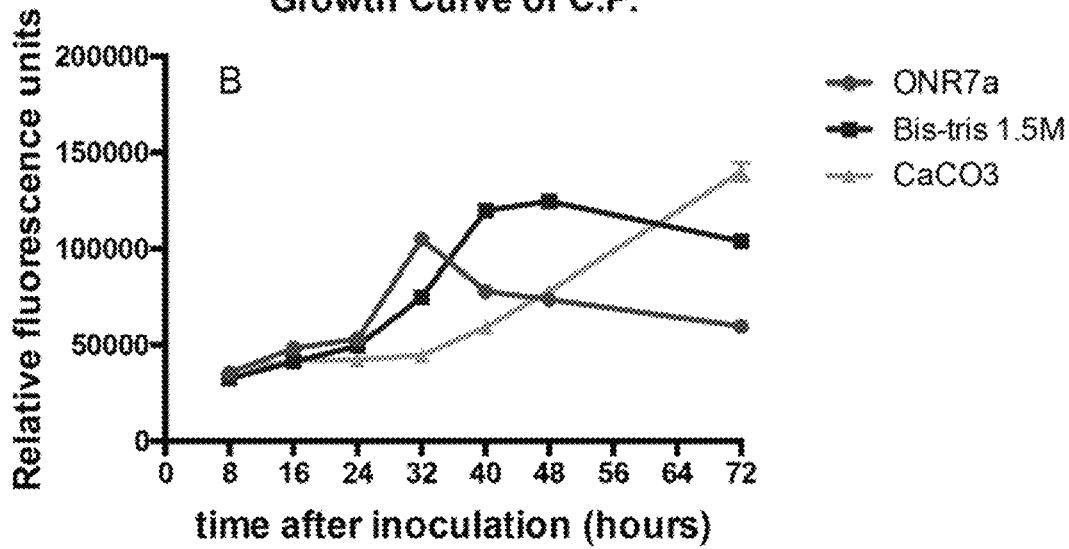
FIG. 80

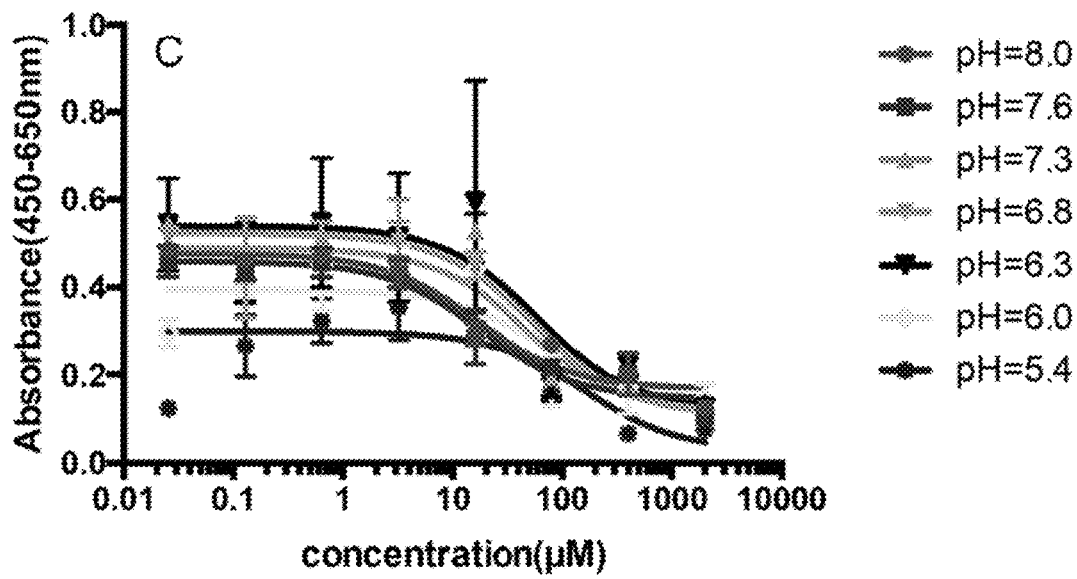
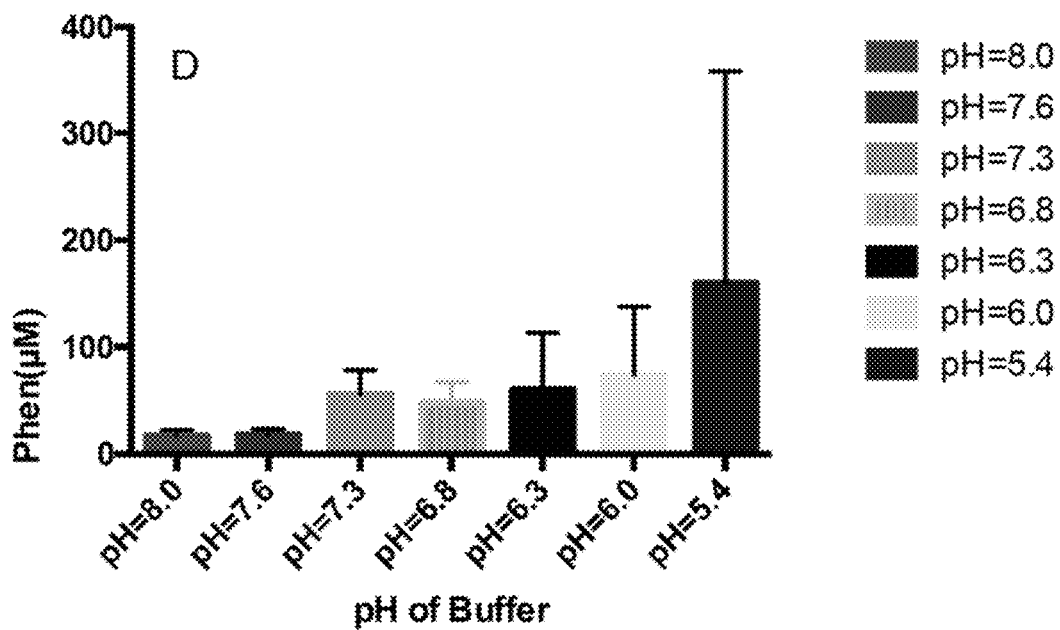
FIG. 80 - CONT.

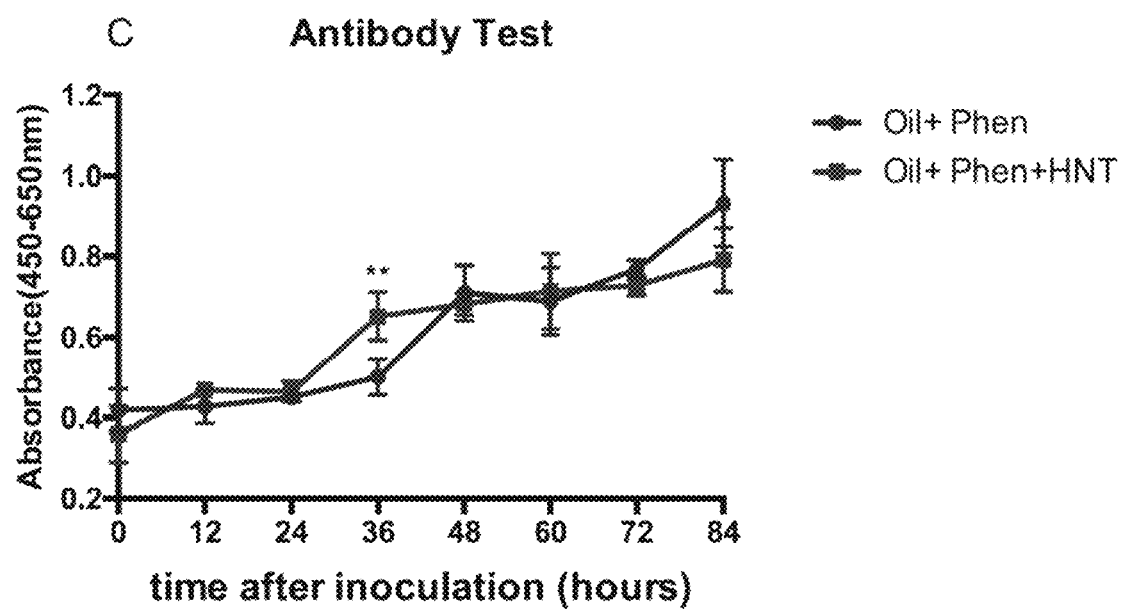
*FIG. 81 - CONT.*

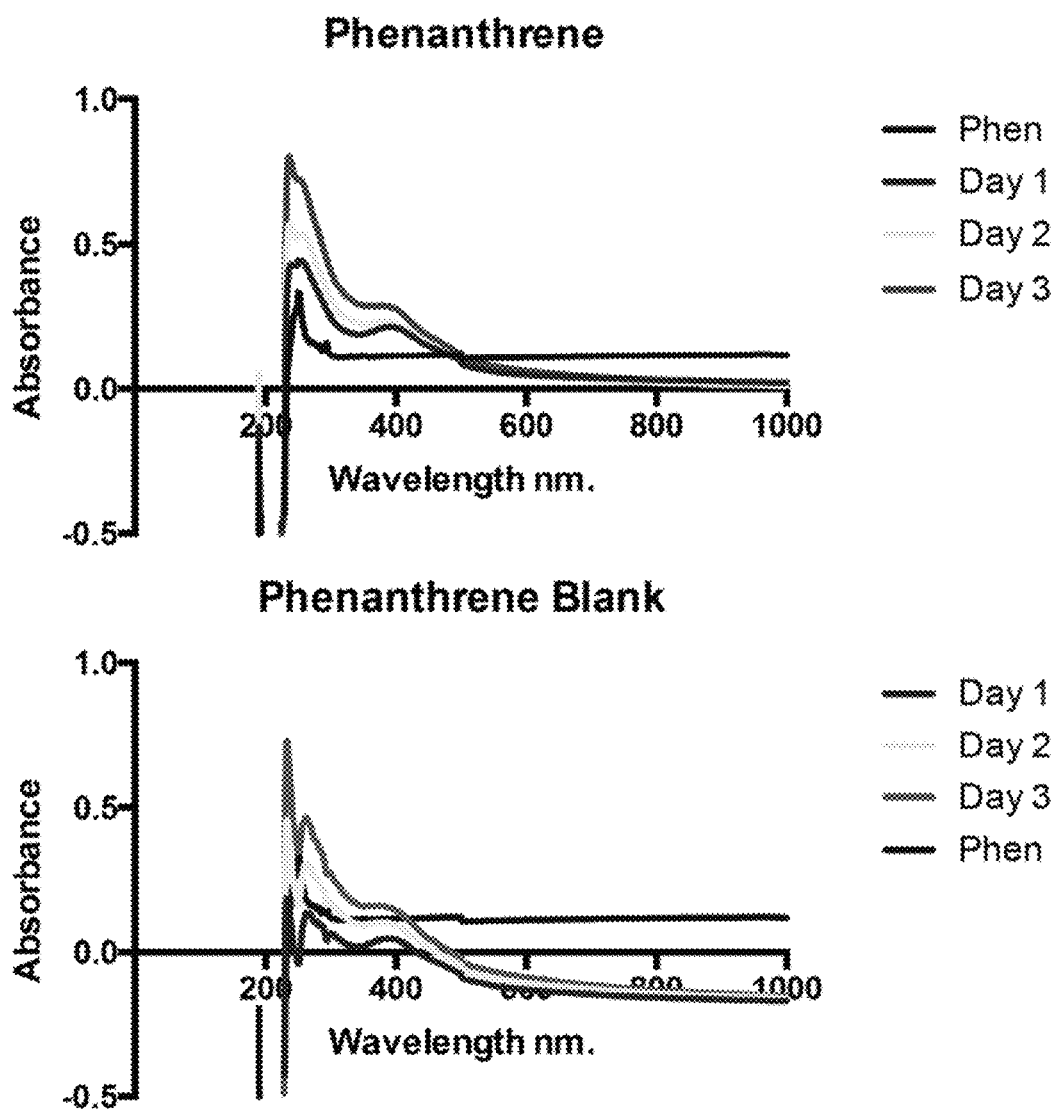
FIG. 84 - CONT.

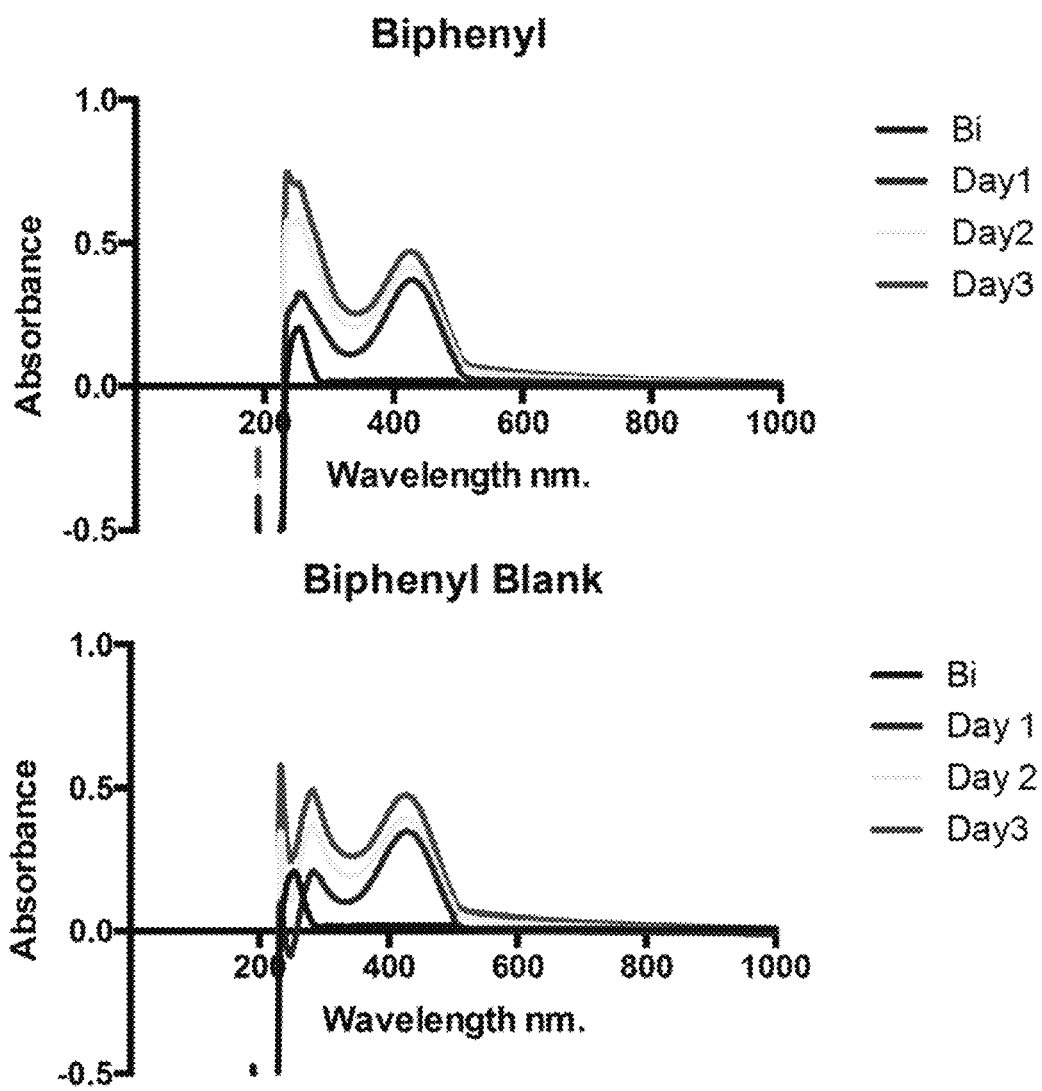
FIG. 85 - CONT.

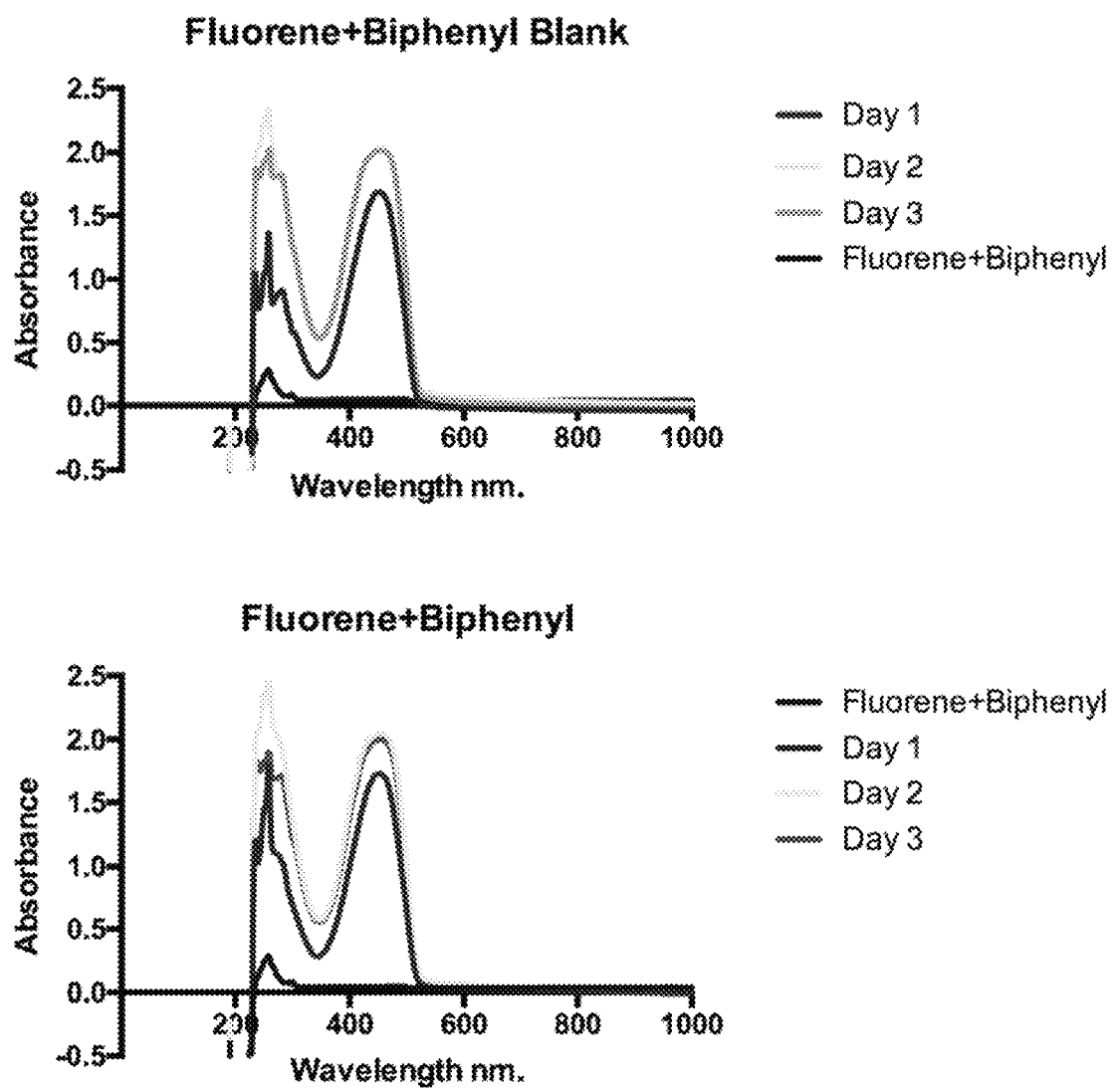
FIG. 85 - CONT.

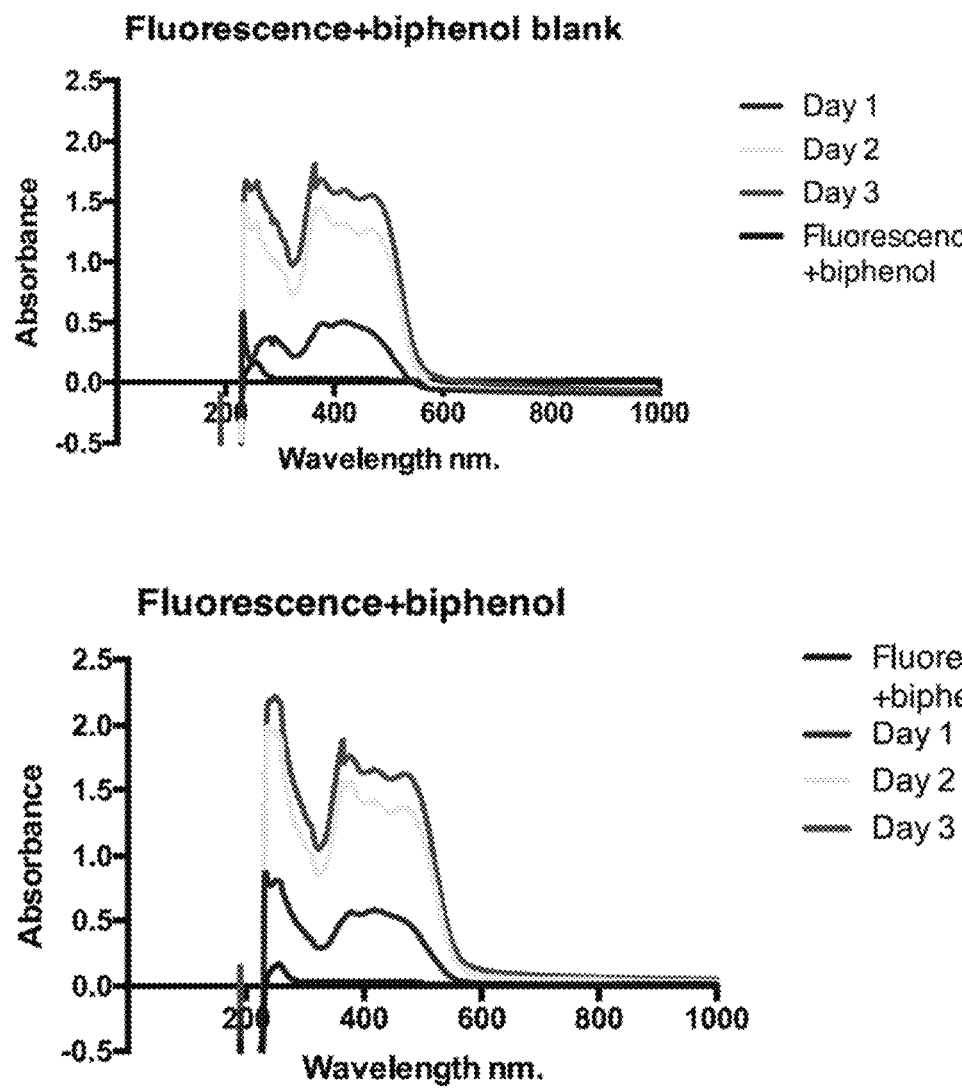
FIG. 85 - CONT.

… (1-MP), 2-methylphenanthrene (2-MP), 3-methylphenanthrene (3-MP), 4-methylphenanthrene (4-MP), 9-methylphenanthrene (9-MP), 3,6-dimethylphenanthrene (3,6-DMP).

PAH ANTIBODIES AND USES THEREOF

This application is a continuation-in-part application of PCT Application serial no. PCT/US2016/035275, filed Jun. 1, 2016, which claims priority to U.S. Provisional Patent Application Ser. No. 62/169,427, filed Jun. 1, 2015, the entire disclosure of each which are incorporated by reference in their entireties.

GOVERNMENT INTERESTS

This invention was made with government support under Grant Nos. 1U19ES020677 and 1U19ES020676 awarded by the National Institute of Environmental Health Sciences, and under Grant No. OISE-1253272 awarded by the National Science Foundation. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Jan. 25, 2018, is named 2937035-01-US2_SL.txt and is 125,651 bytes in size.

FIELD OF THE INVENTION

This invention is directed to recombinant antibodies capable of distinguishing between methylated and non-methylated derivatives of phenanthrene, a major polycyclic aromatic hydrocarbon present in crude oil.

BACKGROUND OF THE INVENTION

Polycyclic aromatic hydrocarbons (PAHs) are a class of toxic and persistent environmental contaminants. Many unalkylated PAHs enter the environment as a result of incomplete combustion and are thus referred to as "pyrogenic," while PAHs found in oils such as petroleum are referred to as "petrogenic." In crude oil, alkylated petrogenic PAHs often predominate and methylated forms of phenanthrene are a major component of many crude oil samples. The development of antibody tools to identify petrogenic PAHs derived from oil spills can improve the ability to monitor their migration, accumulation, and remediation in the environment.

SUMMARY OF THE INVENTION

The present invention provides a method of developing recombinant antibodies that are capable of distinguishing between methylated and non-methylated derivatives of phenanthrene, a major polycyclic aromatic hydrocarbon present in crude oil.

The present invention further provides seven recombinant antibodies, of which three have been characterized, that specifically recognize methlyated phenanthrenes, the major PAHs in petroleum. These antibody reagents can be used in biosensors and other analytical devices for rapid, on-site detection of PAHs that have entered the environment due to oil spills and other environmental contamination from petroleum products.

In accordance with this discovery, it is an object of the invention to provide a method of producing antibodies that monitor the migration, accumulation, and remediation of PAHs.

It is an additional object of this invention to provide particular recombinant antibodies that specifically recognize methlyated phenanthrenes, the major PAHs in petroleum.

An aspect of the invention is directed towards a recombinant antibody that specifically binds to a polycyclic aromatic hydrocarbon (PAH). One embodiment is directed towards a fragment of the recombinant antibody that specifically binds a PAH. In one embodiment, the recombinant antibody or fragment thereof that specifically binds to a PAH has an $IC_{50}$ less than or equal to 8.3 µM. In some embodiments, the recombinant antibody or fragment thereof that specifically binds to a polycyclic aromatic hydrocarbon (PAH) has an $IC_{50}$ less than or equal to 0.01 µM, 0.05 µM, 0.1 µM, 0.25 µM, 0.5 µM, 0.75 µM, 1 µM, 1.25 µM, 1.5 µM, 1.75 µM, 2 µM, 2.5 µM, 3.0 µM, 3.5 µM, 4.0 µM, 4.5 µM, 5.0 µM, 5.5 µM, 6.0 µM, 6.5 µM, 7.0 µM, 8.5 µM, 9.0 µM, 9.5 µM, 10.0 µM, 10.5 µM, 11.0 µM, 11.5 µM, 12.0 µM, 12.5 µM, 13.0 µM, or 13.5 µM. In some embodiments, the recombinant antibody or fragment thereof specifically binds to naphthalene, acenapthene, acenapthylene, phenanthrene, fluorine, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, dibenz[a,h]anthracene. In one embodiment, the PAH is methylated phanenthrene. In one embodiment, the PAH is petrogenic. In one embodiment, the recombinant antibody or fragment thereof specifically binds to the phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), 3,6-dimethylphenanthrene (3,6-DMP). In one embodiment, the recombinant antibody or fragment thereof that specifically binds to a PAH comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137. In one embodiment, the recombinant antibody or fragment thereof that specifically binds to a PAH comprises a variable domain having a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In one embodiment, the recombinant antibody or fragment thereof that specifically binds a PAH comprises the product expressed by clone D7, 2C1, H8, G8, 4E3, 3F4, 4C1, A10, 4H1, 3F9. In embodiments of the invention, the antibody or fragment that specifically binds to a polycyclic aromatic hydrocarbon (PAH) and is expressed by clone D7, 2C1, H8, G8, 4E3, 3F4, 4C1, A10, 4H1, or 3F9 is at least 90% of the amino acid sequence of any one of SEQ ID NOS: 37-46. In embodiments of the invention, the antibody or fragment expressed by clone D7, 2C1, H8, G8, 4E3, 3F4, 4C1, A10, 4H1, or 3F9 is 80%, 81%, 82%, 83%, 84%, 85%, 86%, 87%, 88%, 89%, 90%, 91%, 92%, 93%, 94%, 95%, 96%, 97%, 98%, 99%, or 100% identical of the amino acid sequence of any one of SEQ ID NOS: 37-46. In some embodiments, the antibody comprises any one of SEQ IDS NOS: 37-46. In some embodiments, the antibody or fragment thereof that specifically binds to a PAH is secreted by an engineered yeast cell. In some embodiments, the antibody or fragment thereof that specifically binds to a PAH comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137, and a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In some embodiments, the antibody or fragment thereof that specifically binds to a PAH comprises a variable domain having a variable light chain ($V_L$) amino acid comprising SEQ ID NO: 58, 67, 76, 83, 92, 101, 110, 119, 128, or 137, and a variable heavy chain (VH) amino acid sequence comprising SEQ ID NO: 57, 66, 75, 82, 91, 100, 109, 118, 127, or 136.

An aspect of the invention is directed towards a recombinant antibody that specifically binds to phenanthrene. One embodiment is directed towards a fragment of the recombinant antibody that specifically binds phenanthrene. In one embodiment, the antibody does not show substantial cross-reactivity against a PAH. In one embodiment, the recombinant antibody or fragment thereof does not show substantial cross reactivity against naphthalene, acenapthene, acenapthylene, phenanthrene, fluorine, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, dibenz[a,h]anthracene. In one embodiment, the recombinant antibody or fragment thereof specifically binds methylated phenanthrene. In some embodiments, the phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), 3,6-dimethylphenanthrene (3,6-DMP). In one embodiment, the recombinant antibody or fragment thereof that specifically binds to phenanthrene comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137. In one embodiment, the recombinant antibody or fragment thereof that specifically binds to phenanthrene comprises a variable domain having a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In one embodiment, the recombinant antibody or fragment thereof that specifically binds to phenanthrene has an $IC_{50}$ less than or equal to 8.3 µM. In some embodiments, the recombinant antibody or fragment thereof that specifically binds to a polycyclic aromatic hydrocarbon (PAH) has an $IC_{50}$ less than or equal to 0.01 µM, 0.05 µM, 0.1 µM, 0.25 µM, 0.5 µM, 0.75 µM, 1 µM, 1.25 µM, 1.5 µM, 1.75 µM, 2 µM, 2.5 µM, 3.0 µM, 3.5 µM, 4.0 µM, 4.5 µM, 5.0 µM, 5.5 µM, 6.0 µM, 6.5 µM, 7.0 µM, 8.5 µM, 9.0 µM, 9.5 µM, 10.0 µM, 10.5 µM, 11.0 µM, 11.5 µM, 12.0 µM, 12.5 µM, 13.0 µM, or 13.5 µM. In one embodiment, the recombinant antibody or fragment thereof specifically binds petrogenic phenanthrene. In one embodiment, the recombinant antibody or fragment thereof that specifically binds phenanthrene comprises the product expressed by clone D7, 2C1, H8, G8, 4E3, 3F4, 4C1, A10, 4H1, 3F9. In embodiments of the invention, the antibody or fragment that specifically binds phenanthrene and is expressed by clone D7, 2C1, H8, G8, 4E3, 3F4, 4C1, A10, 4H1, or 3F9 is at least 90% of the amino acid sequence of any one of SEQ ID NOS: 37-46. In embodiments of the invention, the antibody or fragment expressed by clone D7, 2C1, H8, G8, 4E3, 3F4, 4C1, A10, 4H1, or 3F9 is 80%, 81%, 82%, 83%, 84%, 85%, 86%, 87%, 88%, 89%, 90%, 91%, 92%, 93%, 94%, 95%, 96%, 97%, 98%, 99%, or 100% identical of the amino acid sequence of any one of SEQ ID NOS: 37-46. In some embodiments, the antibody comprises any one of SEQ IDS NOS: 37-46. In some embodiments, the antibody or fragment thereof that specifically binds to phenanthrene is secreted by an engineered yeast cell. In some embodiments, the antibody or fragment thereof that specifically binds to phenanthrene comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137, and a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In some embodiments, the antibody or fragment thereof that specifically binds to phenanthrene comprises a variable domain having a variable light chain ($V_L$) amino acid comprising SEQ ID NO: 58, 67, 76, 83, 92, 101, 110, 119, 128, or 137, and a variable heavy chain ($V_H$) amino acid sequence comprising SEQ ID NO: 57, 66, 75, 82, 91, 100, 109, 118, 127, or 136.

An aspect of the invention is directed towards a recombinant antibody that specifically binds methylated phenanthrene. One embodiment is directed towards a fragment of the recombinant antibody that specifically binds methylated phenanthrene. In one embodiment, the recombinant antibody or fragment thereof specifically binds methylated phenanthrene. In some embodiments, the phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), 3,6-dimethylphenanthrene (3,6-DMP). In one embodiment, the recombinant antibody or fragment thereof that specifically binds to methylated phenanthrene comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137. In one embodiment, the recombinant antibody or fragment thereof that specifically binds to methylated phenanthrene comprises a variable domain having a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In one embodiment, the recombinant antibody or fragment thereof that specifically binds to methylated phenanthrene has an $IC_{50}$ less than or equal to 8.3 µM. In some embodiments, the recombinant antibody or fragment thereof that specifically binds to a polycyclic aromatic hydrocarbon (PAH) has an $IC_{50}$ less than or equal to 0.01 µM, 0.05 µM, 0.1 µM, 0.25 µM, 0.5 µM, 0.75 µM, 1 µM, 1.25 µM, 1.5 µM, 1.75 µM, 2 µM, 2.5 µM, 3.0 µM, 3.5 µM, 4.0 µM, 4.5 µM, 5.0 µM, 5.5 µM, 6.0 µM, 6.5 µM, 7.0 µM, 8.5 µM, 9.0 µM, 9.5 µM, 10.0 µM, 10.5 µM, 11.0 µM, 11.5 µM, 12.0 µM, 12.5 µM, 13.0 µM, or 13.5 µM. In one embodiment, the recombinant antibody or fragment thereof specifically binds petrogenic methylated phenanthrene. In one embodiment, the recombinant antibody or fragment thereof that specifically binds methylated phenanthrene expressed by clone D7, 2C1, H8, G8, 4E3, 3F4, 4C1, A10, 4H1, 3F9. In embodiments of the invention, the antibody or fragment that specifically binds methylated phenanthrene and is expressed by clone D7, 2C1, H8, G8, 4E3, 3F4, 4C1, A10, 4H1, or 3F9 is at least 90% of the amino acid sequence of any one of SEQ ID NOS: 37-46. In embodiments of the invention, the antibody or fragment expressed by clone D7, 2C1, H8, G8, 4E3, 3F4, 4C1, A10, 4H1, or 3F9 is 80%, 81%, 82%, 83%, 84%, 85%, 86%, 87%, 88%, 89%, 90%, 91%, 92%, 93%, 94%, 95%, 96%, 97%, 98%, 99%, or 100% identical of the amino acid sequence of any one of SEQ ID NOS: 37-46. In some embodiments, the antibody comprises any one of SEQ IDS NOS: 37-46. In some embodiments, the antibody or fragment thereof that specifically binds methylated phenanthrene is secreted by an engineered yeast cell. In some embodiments, the antibody or fragment thereof that specifically binds to methylated phenanthrene comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137, and a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In some embodiments, the antibody or fragment thereof that specifically binds to methylated phenanthrene comprises a variable domain having a variable light chain ($V_L$) amino acid comprising SEQ ID NO: 58, 67, 76, 83, 92, 101, 110, 119, 128, or 137, and a variable heavy chain ($V_H$) amino acid sequence comprising SEQ ID NO: 57, 66, 75, 82, 91, 100, 109, 118, 127, or 136.

An aspect of the invention is directed towards a recombinant antibody or fragment thereof that specifically binds to a methylated phenanthrene. In one embodiment, the recombinant antibody or fragment thereof comprises a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136. In one embodiment, the antibody is an antibody fragment. In one embodiment, the methylated phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), 3,6-dimethylphenanthrene (3,6-DMP). Embodiments of the invention are directed towards a recombinant antibody that specifically binds to a methylated phenanthrene comprising a variable domain having a variable light chain (VL) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137, or having a variable heavy chain (VH) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136. In one embodiment, the recombinant antibody or fragment thereof that specifically binds methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136 has an $IC_{50}$ less than or equal to 8.3 μM. In one embodiment, the recombinant antibody or fragment thereof that specifically binds methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain (VH) amino acid sequence at least 90% identical to SEQ ID NO: 57, 66, 75, 82, 91, 100, 109, 118, 127, or 136, has an $IC_{50}$ less than or equal to 0.01 μM, 0.05 μM, 0.1 μM, 0.25 μM, 0.5 μM, 0.75 μM, 1 μM, 1.25 μM, 1.5 μM, 1.75 μM, 2 μM, 2.5 μM, 3.0 μM, 3.5 μM, 4.0 μM, 4.5 μM, 5.0 μM, 5.5 μM, 6.0 μM, 6.5 μM, 7.0 μM, 8.5 μM, 9.0 μM, 9.5 μM, 10.0 μM, 10.5 μM, 11.0 μM, 11.5 μM, 12.0 μM, 12.5 μM, 13.0 μM, or 13.5 μM. Embodiments of the invention are directed towards a recombinant antibody that specifically binds to a petrogenic methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136. In one embodiment, the antibody is an antibody fragment. In one embodiment, the recombinant antibody or fragment thereof that specifically binds methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136 is expressed by clone D7, 2C1, H8, G8, 4E3, 3F4, 4C1, A10, 4H1, 3F9. In embodiments of the invention, the antibody or fragment that specifically binds methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136 and is expressed by clone D7, 2C1, H8, G8, 4E3, 3F4, 4C1, A10, 4H1, or 3F9 is at least 90% of the amino acid sequence of any one of SEQ ID NOS: 37-46. In embodiments of the invention, the antibody or fragment expressed by clone D7, 2C1, H8, G8, 4E3, 3F4, 4C1, A10, 4H1, or 3F9 is 80%, 81%, 82%, 83%, 84%, 85%, 86%, 87%, 88%, 89%, 90%, 91%, 92%, 93%, 94%, 95%, 96%, 97%, 98%, 99%, or 100% identical of the amino acid sequence of any one of SEQ ID NOS: 37-46. In some embodiments, the antibody comprises any one of SEQ IDS NOS: 37-46. In some embodiments, the antibody or fragment thereof that specifically binds methylated phenanthrene comprising a variable domain having a variable light chain ($V_L$) amino acid sequence at least 90% identical to SEQ ID NO: 58, 67, 76, 83, 92, 101, 110, 119, 128, or 137, or having a variable heavy chain ($V_H$) amino acid sequence at least 90% identical to SEQ ID NO: 57, 66, 75, 82, 91, 100, 109, 118, 127, or 136 is secreted by an engineered yeast cell.

An aspect of the invention is directed to an engineered yeast cell that secretes the recombinant antibody or fragment thereof described herein.

An aspect of the invention is directed towards a method of detecting the presence of a methylated phenanthrene. In one embodiment, the method comprises (a) obtaining a sample; (b) contacting the sample with an antibody of the invention for at least a period of time sufficient for the antibody to bind its target; and (c) determining whether a methylated phenanthrene is present in the sample. In one embodiment, the sample comprises water, sand, soil, biological fluid, biological tissue or a combination thereof. In some embodiments, the phenanthrene is phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-dimethylphenanthrene (3,6-DMP).

An aspect of the invention is directed towards a method of detecting a petrogenic PAH in a sample. In one embodiment, the method comprises (a) obtaining a sample; (b) contacting the sample with an antibody of the invention for at least a period of time sufficient for the antibody to bind its target; and (c) determining whether a petrogenic PAH is present in the sample. In one embodiment, the sample comprises water, sand, soil, biological fluid, biological tissue or a combination thereof. In some embodiments, the PAH is selected from the group consisting of naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene.

An aspect of the invention is directed towards a method of environmental fingerprinting. In one embodiment, the method comprises (a) obtaining a sample; (b) contacting the sample with an antibody of the invention for at least a period of time sufficient for the antibody to bind its target; and (c) determining whether a petrogenic PAH is present in the sample. In one embodiment, the sample comprises water, sand, soil, biological fluid, biological tissue or a combination thereof. In some embodiments, the PAH is selected from the group consisting of naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene. In some embodiments, the phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-dimethylphenanthrene (3,6-DMP).

An aspect of the invention is directed towards a kit for the detection of petrogenic PAH in a sample. In some embodiments, the kit comprises a recombinant antibody of the invention.

An aspect of the invention is directed towards a kit for the detection of methylated phenanthrene in a sample. In some embodiments, the kit comprises a recombinant antibody of the invention.

An aspect of the invention is directed towards a method for measuring an amount of methylated polyaromatic hydrocarbon and an amount of unmethylated polyaromatic hydrocarbon in a sample. In one embodiment, the method comprises (a) obtaining a sample; (b) contacting the sample with at least a first antibody and a second antibody for a period of time sufficient for the first antibody and the second antibody to bind to their specific targets, wherein the first antibody specifically binds to methylated polyaromatic hydrocarbon and the second antibody specifically binds to unmethylated polyaromatic hydrocarbon; and (c) measuring the binding of the first antibody to a methylated polyaromatic hydrocarbon and the binding of the second antibody to an unmethylated polyaromatic hydrocarbon. In one embodiment, the method further comprises the step (d) determining the amount of methylated polyaromatic hydrocarbon relative to the amount of unmethylated polyaromatic hydrocarbon in the sample, wherein the amount of methylated polyaromatic hydrocarbon relative to the amount of unmethylated polyaromatic hydrocarbon indicates petrogenic contamination rather than pyrogenic contamination. In one embodiment, the amount of methylated PAH relative to unmethylated PAH of about 1:1 or greater indicates petrogenic contamination. In one embodiment, an amount of methylated PAH relative to unmethylated PAH of about 0.90:1, 0.91:1, 0.92:1, 0.93:1, 0.94:1, 0.95:1, 0.96:1, 0.97:1, 0.98:1, or 0.99:1 indicates the presence of petrogenic contamination. In one embodiment, the sample comprises water, sand, soil, biological fluid, biological tissue or a combination thereof. In one embodiment, the first antibody is clone A10. In one embodiment, the first antibody is SEQ ID NO: 37. In one embodiment, the first antibody is an antibody or fragment thereof that specifically binds to a methylated phenantherene. In one embodiment, the first antibody or fragment thereof is a recombinant antibody or fragment thereof that specifically binds to a methylated phenanthrene, wherein the antibody or fragment thereof comprises a variable domain having a variable light chain (VL) amino acid sequence at least 90% identical to SEQ ID NO: 58, 67, 76, 83, 92, 101, 110, 119, 128, or 137, or having a variable heavy chain (VH) amino acid sequence at least 90% identical to SEQ ID NO: 57, 66, 75, 82, 91, 100, 109, 118, 127, or 136. In one embodiment, the methylated PAH is methylated phenanthrene. In one embodiment, the methylated phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-di methylphenanthrene (3,6-DMP).

An aspect of the invention is directed towards a recombinant antibody or fragment thereof encoded by a nucleic acid. In some embodiment, the nucleic acid is at least 90% identical to a nucleic acid sequence comprising any one of SEQ ID NO: 47, 48, 49, 50, 51, 52, 53, 54, 55 or 56. In some embodiment, the nucleic acid sequence is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 47, 48, 49, 50, 51, 52, 53, 54, 55 or 56. In some embodiments, the recombinant antibody or fragment thereof is encoded by a nucleic acid comprising any one of SEQ ID NO: 47, 48, 49, 50, 51, 52, 53, 54, 55 or 56.

An aspect of the invention is directed towards a method for selecting hapten-specific recombinant antibody or fragment thereof. In one embodiment, the method comprises: (a) screening a phage display library comprising bacteriophages expressing an antibody or fragment thereof, wherein the screening comprises enriching from the phage display library at least one bacteriophage that expresses an antibody or fragment thereof that interacts with a hapten capable of being immobilized, and wherein said enriching comprises at least one cycle of panning; (b) screening a display library of yeast transformed with a nucleic acid encoding the antibody enriched from step (a), wherein the screening comprises at least one round of flow activated cell sorting (FACS) to competitively select for yeast cells that express hapten-specific recombinant antibodies or fragments thereof; and (c) isolating a hapten-specific recombinant antibody or fragment thereof from the identified transformed yeast. In one embodiment, the yeast cells are selected from the cells displaced to a lower position in the Q2 quadrant following competitive FACS. In one embodiment, step (a) in the method may further comprise at least one cycle that uses a solvent to exclude unstable antibodies and at least one cycle that uses soluble hapten. In one embodiment, step (b) in the method may further comprise addition of a soluble hapten to competitively select for yeast cells that express hapten-specific recombinant antibodies or fragments thereof. In one embodiment, step (b) is preceded by a pre-sorting step. In one embodiment, the hapten is immobilized prior to panning by binding to an immobilizing agent. In one embodiment, the immobilizing agent is bovine serum albumin. In one embodiment, step (a) may further comprise at least one cycle that enriches for antibodies that bind to the immobilizing agent-bound hapten. In one embodiment, step (c) may further comprise at least one round of sorting that specifically removes the antibodies that bind to the immobilizing agent from step (a). In one embodiment, step (a) comprises at least one cycle that uses a solvent to exclude unstable antibodies, at least one cycle that uses soluble hapten, at least one cycle that enriches for antibodies that bind to the immobilizing agent-bound hapten, or any combination thereof. In one embodiment, the hapten-specific recombinant antibodies or fragments thereof comprise an scFv. In one embodiment, the hapten is a polyaromatic hydrocarbon (PAH). In one embodiment, the PAH is selected from the group consisting of naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene. In one embodiment, an engineered yeast cell expresses a hapten specific antibody or fragment thereof produced by methods of the invention.

An aspect of the invention is directed towards a method for selecting hapten-specific recombinant antibody or fragment thereof from a phage-display library. In one embodiment, the method comprises: (a) enriching from the phage display library at least one bacteriophage expressing an antibody or fragment thereof that interacts with a hapten capable of being immobilized, wherein said enriching comprises at least one cycle of panning; (b) screening a display library of yeast transformed with a nucleic acid encoding the antibody enriched from the phage display library, wherein the screening comprises at least one round of flow activated cell sorting (FACS) to competitively select for yeast cells that express hapten-specific recombinant antibodies or fragments thereof; and (c) isolating a hapten-specific recombinant antibody or fragment thereof from the identified transformed yeast. In one embodiment, an engineered yeast cell expresses a hapten specific antibody or fragment thereof produced by methods of the invention.

An aspect of the invention is directed towards a recombinant antibody or fragment thereof that specifically binds to a methylated phenanthrene, wherein the antibody or fragment thereof comprises a variable domain having a variable light chain ($V_L$) amino acid sequence at least 90% identical to SEQ ID NO: 58, 67, 76, 83, 92, 101, 110, 119, 128, or 137, and a variable heavy chain ($V_H$) amino acid sequence at least 90% identical to SEQ ID NO: 57, 66, 75, 82, 91, 100, 109, 118, 127, or 136. In some embodiments, the antibody or fragment thereof comprises a variable domain having a variable light chain ($V_L$) amino acid sequence at least 90%, 91%, 92%, 93%, 94%, 95%, 96%, 97%, 98%, or 99% identical to SEQ ID NO: 58, 67, 76, 83, 92, 101, 110, 119, 128, or 137, and a variable heavy chain ($V_H$) amino acid sequence at least 90%, 91%, 92%, 93%, 94%, 95%, 96%, 97%, 98%, or 99% identical to SEQ ID NO: 57, 66, 75, 82, 91, 100, 109, 118, 127, or 136.

Other objects and advantages of this invention will become readily apparent from the ensuing description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 shows phage selection protocols. Two protocols were used to select phage particles into two different pools. Both protocol involved three steps: an initial enrichment using immobilized antigen, exclusion of antibodies sensitive to solvent (1% DMSO) and a final soluble hapten elution step. For Protocol 1, unsubstituted phenanthrene (Phen) conjugate was used as capture reagent and soluble Phen in elution step ("Pool 1", Top Table), while for Protocol 2, 2-methylated phenanthrene (2mp) was used in both conjugated and soluble formats ("Pool 2", Bottom Table). Yield was calculated as output divided by input phage numbers; enrichment was the yield of each round divided by the yield from first round.

indicate the yeast population differentiated by the competitor (Phen), as detected by flow-cytometry.

Figure 7:
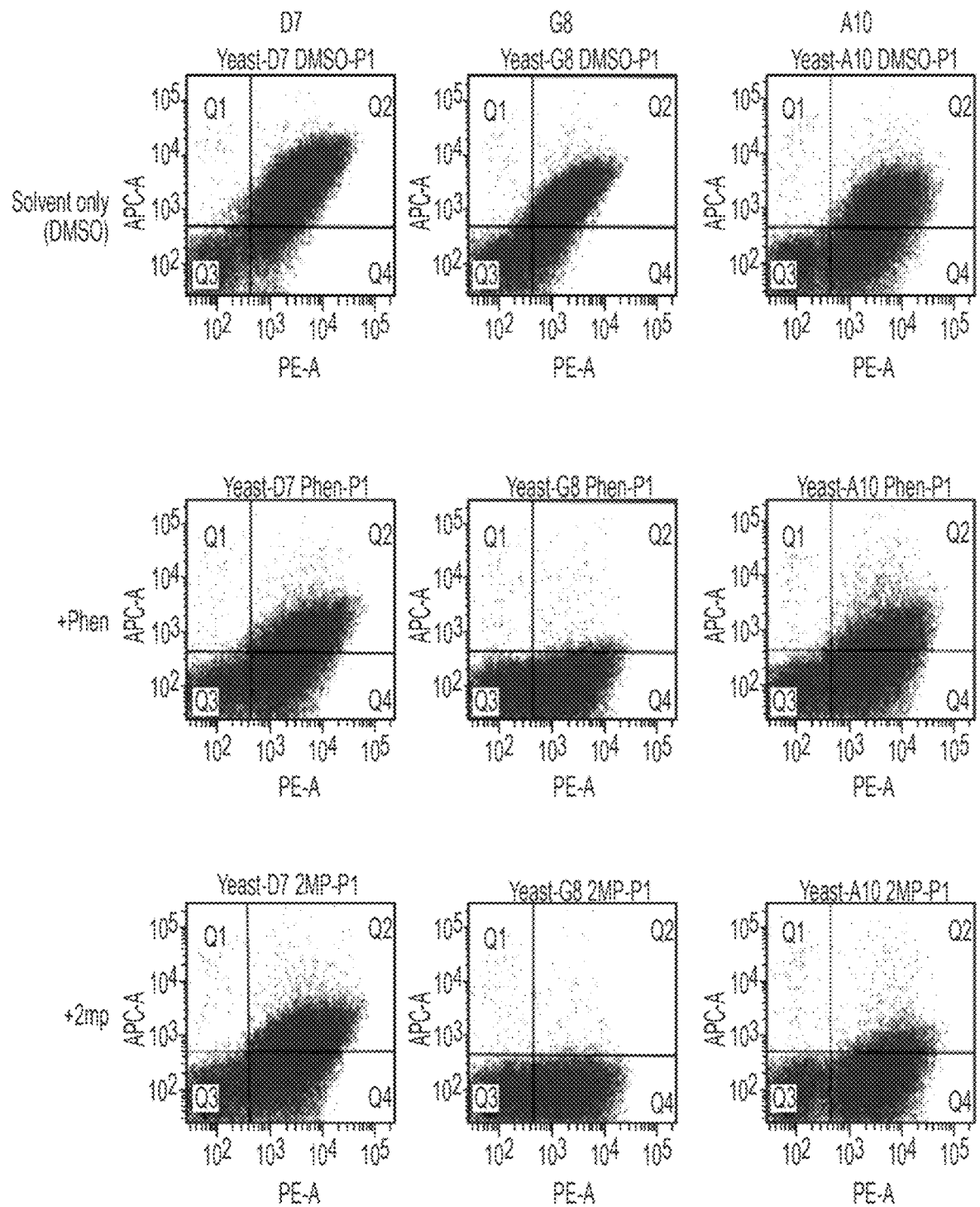

FIG. 7 shows that an analysis of monoclonal yeast by flow cytometry reveals clones with various binding capacities. Three representative clones are shown in three lanes. Top panels, yeast cells were incubated with Phen-BSA conjugate without soluble competitor ("DMSO"); Middle panels, yeast cells were incubated with Phen-BSA and soluble phenanthrene ("+Phen"); Bottom panels, yeast cells were incubated with Phen-BSA and soluble 2-methylphenanthrene ("+2mp").

FIG. 8 shows a summary of monoclonal yeast flow-cytometry analysis after selection by the methods described herein. These selection protocols yielded 17-35% true positives (activity in competitive ELISA).

Figure 9:
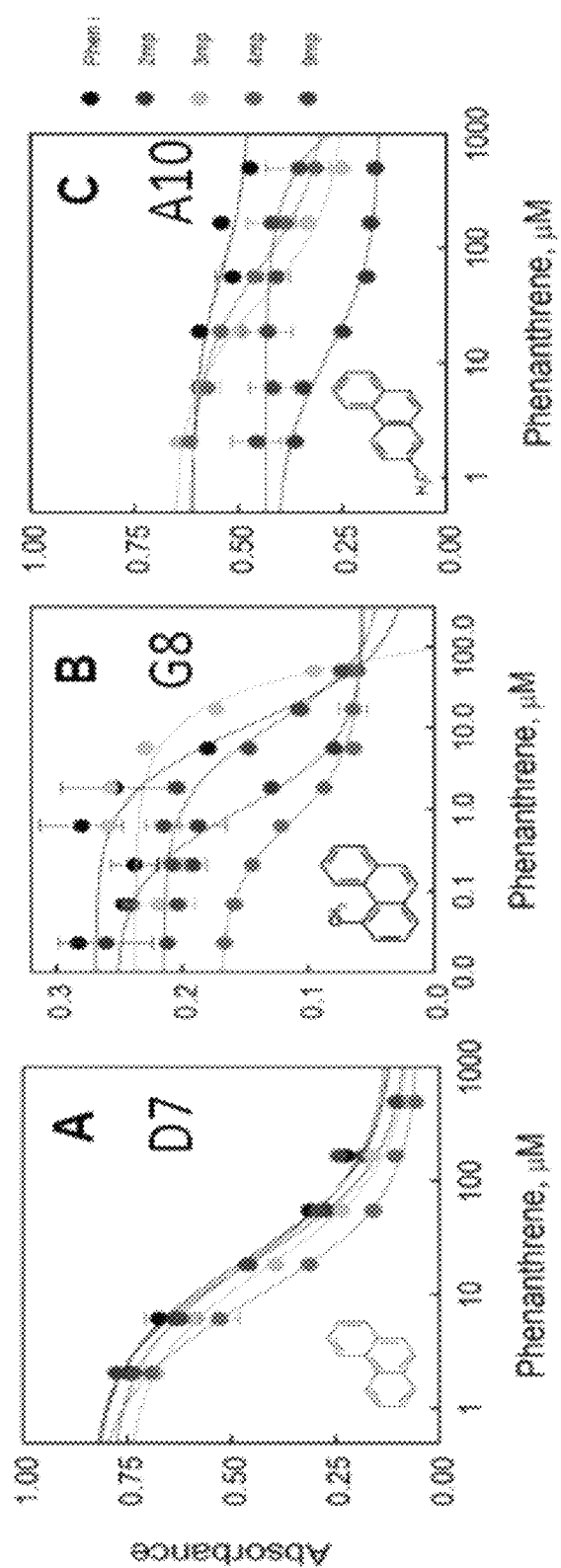

FIG. 9 shows competitive ELISA of selected clones to elucidate binding properties. See panels A-C. Purified scFv proteins from selected clones were incubated on a Phen-BSA coated plate in the presence of varying concentrations of competitors. The structures in each panel represent the ligand with the highest affinity for the respective scFv.

Figure 10:
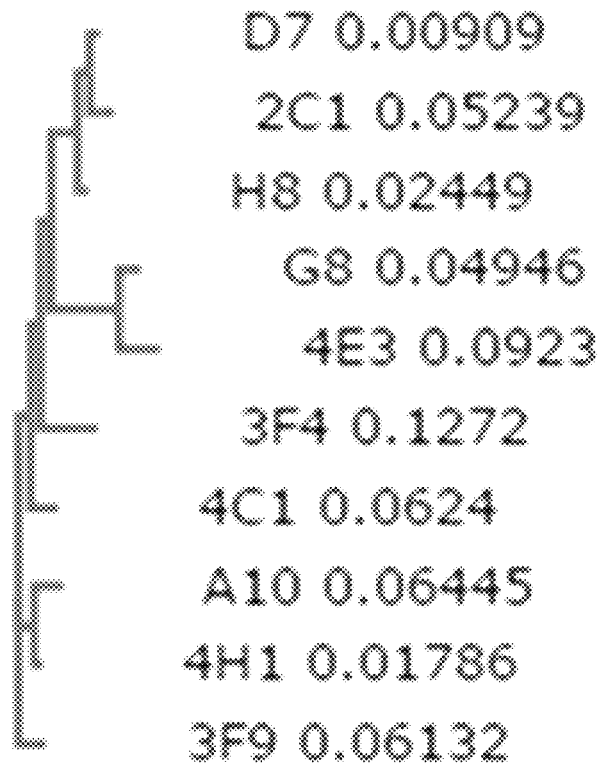

FIG. 10 shows the sequence alignment of the 65 clones that showed activity in competitive ELISA.

FIG. 11 shows the nucleic acid sequences for the forward and reverse primers for heavy chain (SEQ ID NOS: 11-19 in order of appearance).

FIG. 12 shows the nucleic acid sequences for the forward and reverse primers for light chain (SEQ ID NOS: 20-34 in order of appearance).

FIG. 13 shows the nucleic acid sequences for transfer primers (SEQ ID NOS: 35-36 in order of appearance).

Figure 14:
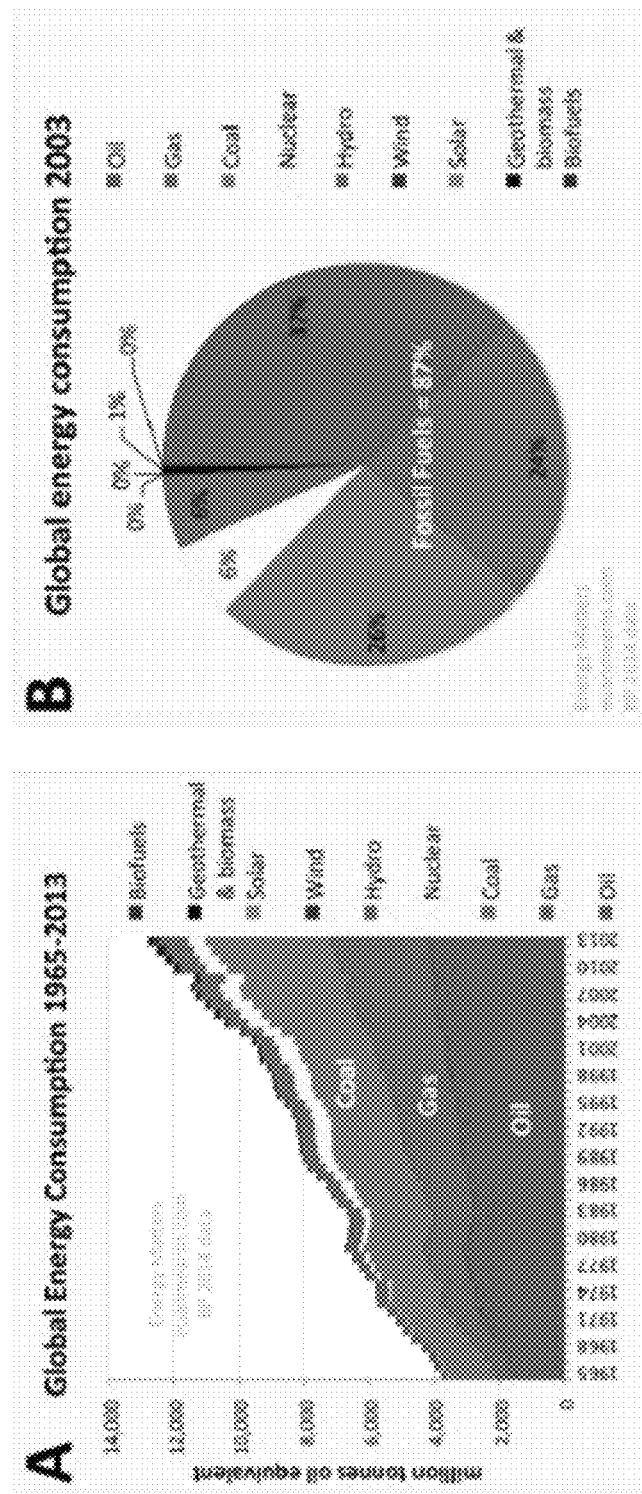

FIGS. 14A and B, and FIGS. 14 C and D are graphics showing the global energy trend—a BP statistical review. (A) The global energy consumption for the last 48 years. (B-D) The percentage of each energy type consumed in 2003, 2013 and 2014 respectively. (BP Statistical Review 2014 and 2015).

Figure 15:
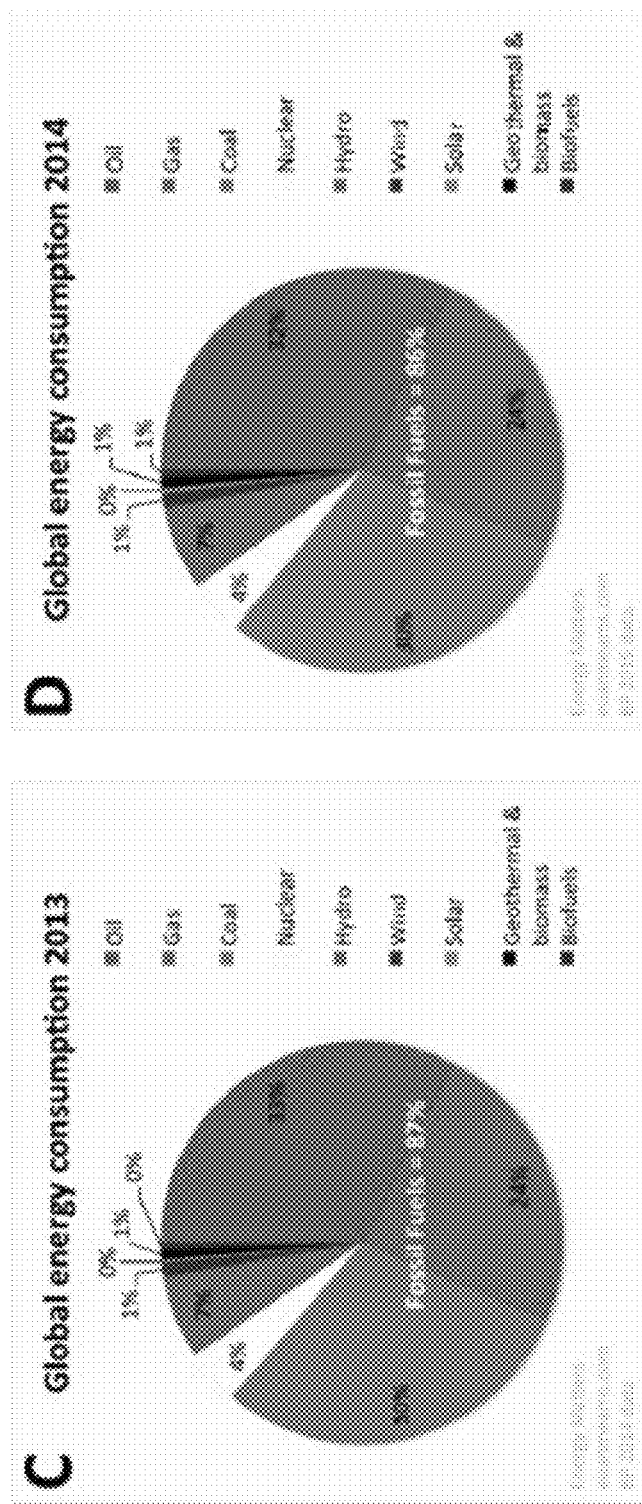

FIG. 15 shows the Top 10 oils spills in history.

Figure 16:
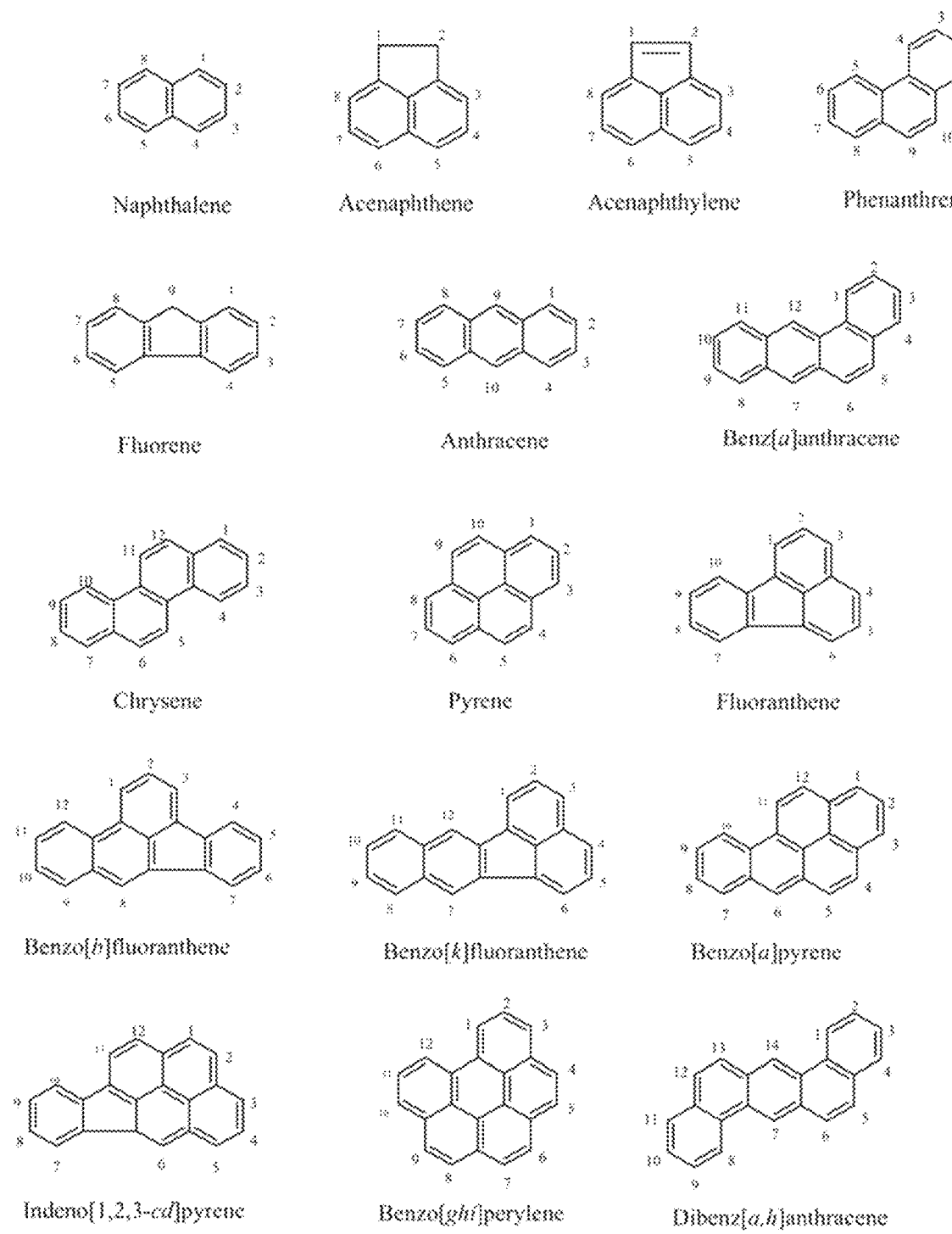

FIG. 16 shows the structures and nomenclatures of the 16 PAHs on the EPA priority pollutant list.

Figure 17:
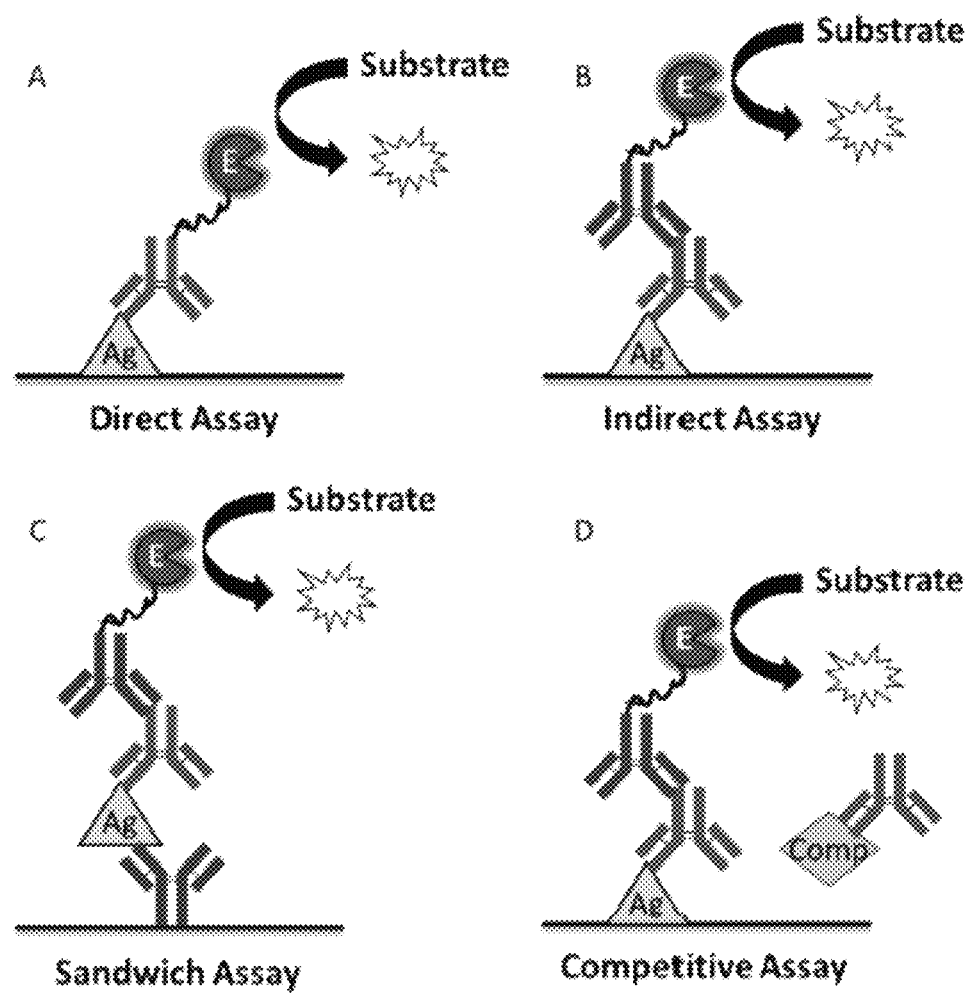

FIG. 17 shows ELISA formats. Orange triangles represent antigens that are immobilized directly on the plastic surface (panel A, B and D) or through interacting of a capture antibody (panel C in purple color). Blue Y-shaped fragments represent the antibodies of interest that bind to the antigen and/or competitor (green diamond in panel D). The enzymes shown in red circle are conjugated directly onto antibody of interest (blue antibody, panel A), or to secondary antibodies (brown antibody, panel B, C and D). The signals are detected by catalyzing substrate into colorimetric format (yellow explosion shape).

Figure 18:
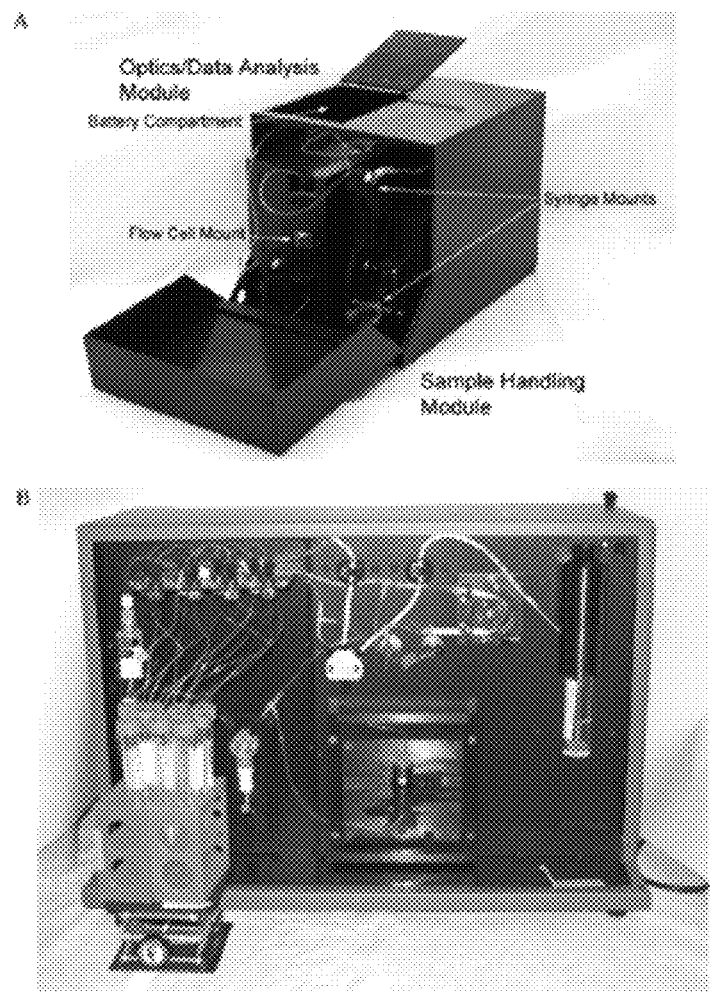

FIG. 18 shows KinExA-based immunosensors. (A) Field portable sensor. This battery-operated sensor permits sample analysis in remote areas without a power source. The sensor interfaces with a laptop computer or other control device through a wireless connection. (B) Inline sensor. This instrument has the ability to run and analyze up to 12 samples automatically. Adapted from Melton, S. J. et al. (2009).

FIG. 19 shows Recombinant antibody Formats. A whole antibody is shown on panel A. For phage display techniques, whole antibodies are too large to be displayed on the surface of the phage particle. Fab fragments, shown on panel B are smaller and can be easier to incorporate into the phage genome and display on the surface. They do not contain any of the Fc region which determines antibody isotype. The most common form of antibody fragment used for phage display is the scFv, shown on panel C. The scFv must be constructed using molecular techniques to join the antibody heavy and light chains with a flexible linker.

Figure 20:
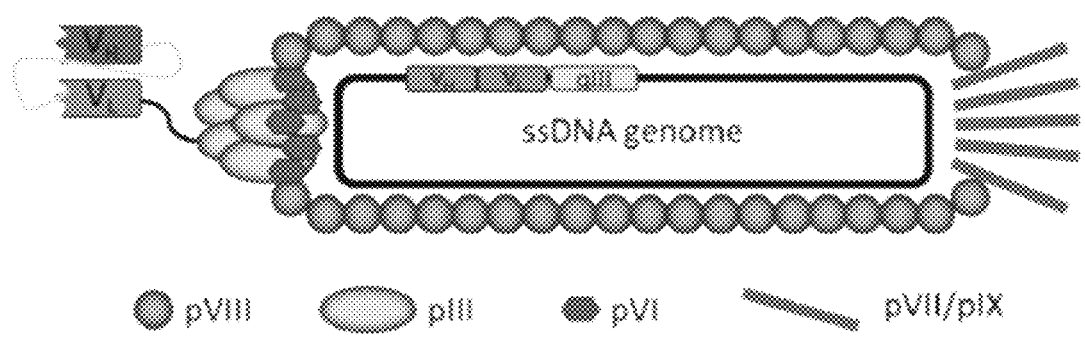

FIG. 20 is a schematic of an engineered filamentous phage structure. The genome of filamentous phage is a single-stranded DNA (ssDNA) shown as a black square and the antibody scFv sequence $V_H$(blue)-$V_L$(pink) is inserted next to a minor coat protein gene (gIII, yellow) in the genome. The expressed scFv protein is fused with pIII on one end of phage particle. Phage coat proteins are labeled in the figure legend.

FIG. 21 is a diagram showing a Two-step selection strategy. A few rounds of tightly-controlled panning are first performed to exclude majority undesirable population from the library. The final output pools were transferred into yeast display plasmid (step 6 and 7). Induced yeast cell.

Figure 22:
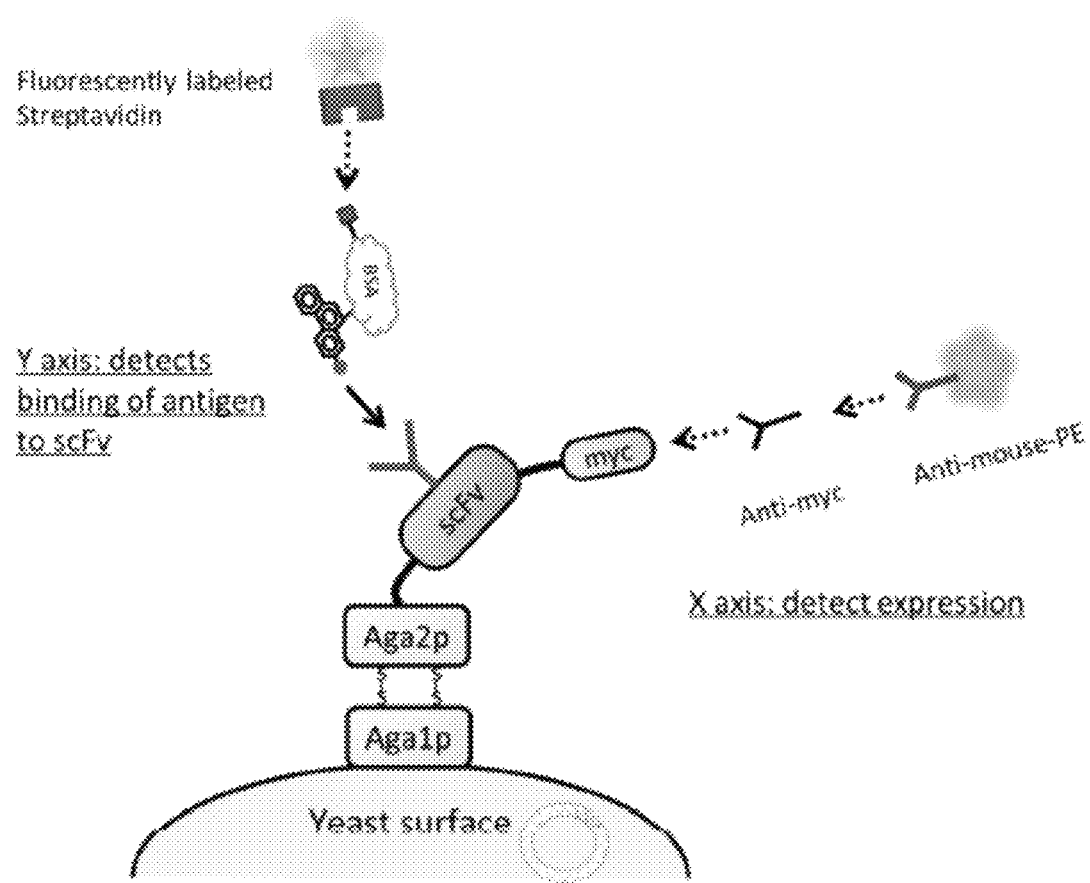

FIG. 22 is a schematic diagram of yeast display. The yeast display vector encodes for a fusion protein of the scFv with the yeast Aga2 mating protein which anchored the fusion protein on cell surface through two disulfide bonds with Aga1p mating protein. The fusion protein carries a epitope for monitoring surface expression by FACS using fluorescently labeled secondary reagents. An example of myc-tag detection is shown in this figure. And the scFv antibody is analyzed by antigens with a different epitope like biotin-streptavidin shown.

Figure 23:
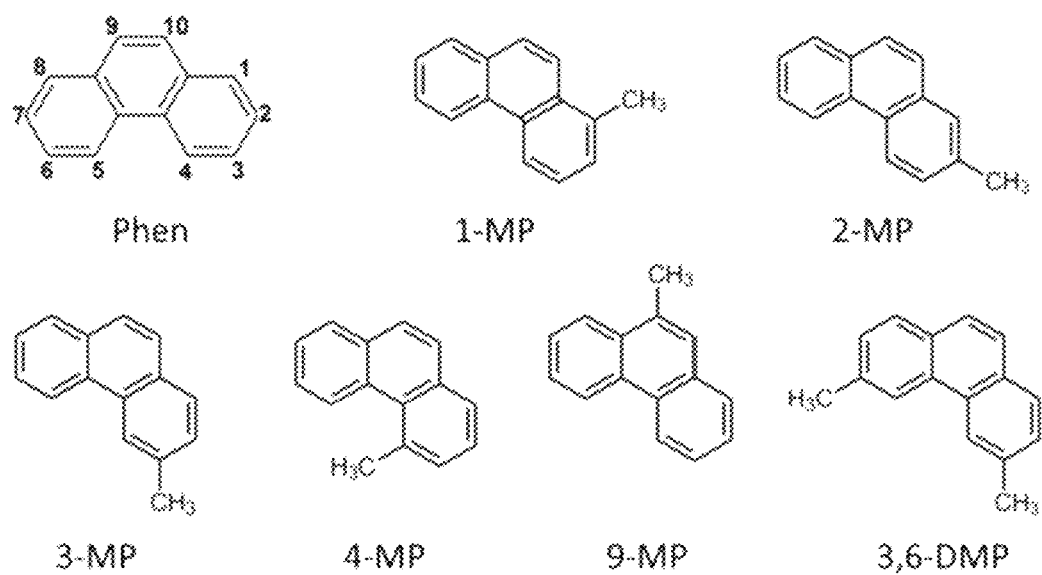

FIG. 23 shows the structure of phenanthrene (Phen) and methylated derivatives investigated. Abbreviations: Phenanthrene (Phen), 1-methylphenanthrene (1-MP), 2-methylphenanthrene (2-MP), 3-methylphenanthrene (3-MP), 4-methylphenanthrene (4-MP), 9-methylphenanthrene, 3,6-dimethylphenanthrene (3,6-DMP).

Figure 24:
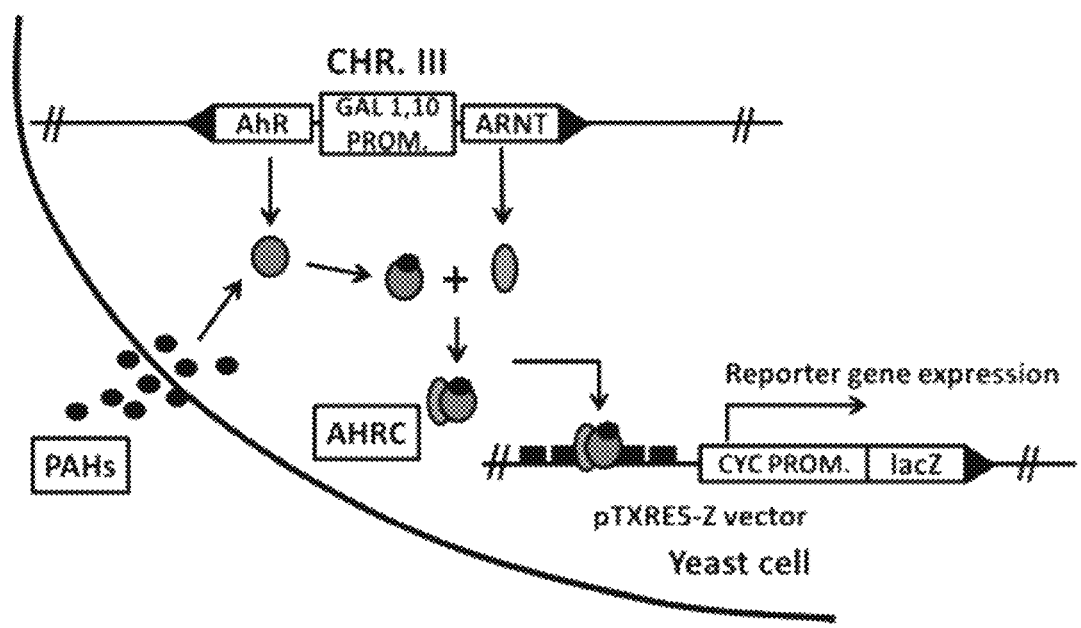

FIG. 24 is a schematic diagram of the yeast bioassay. Red circles represent aryl hydrocarbon receptor (AhR). Green ovals represent aryl hydrocarbon receptor nuclear translocator (ARNT). Black dots represent the polycyclic aromatic hydrocarbons (PAHs) used as agonists in the bioassay. AhR and ARNT genes are inserted in yeast chromosome III under the control of galactose promoter, and the reporter gene (LacZ) is regulated by five copies of the xenobiotic response elements (XRE) constructed in a plasmid, pTXRE5-Z.

Figure 25:
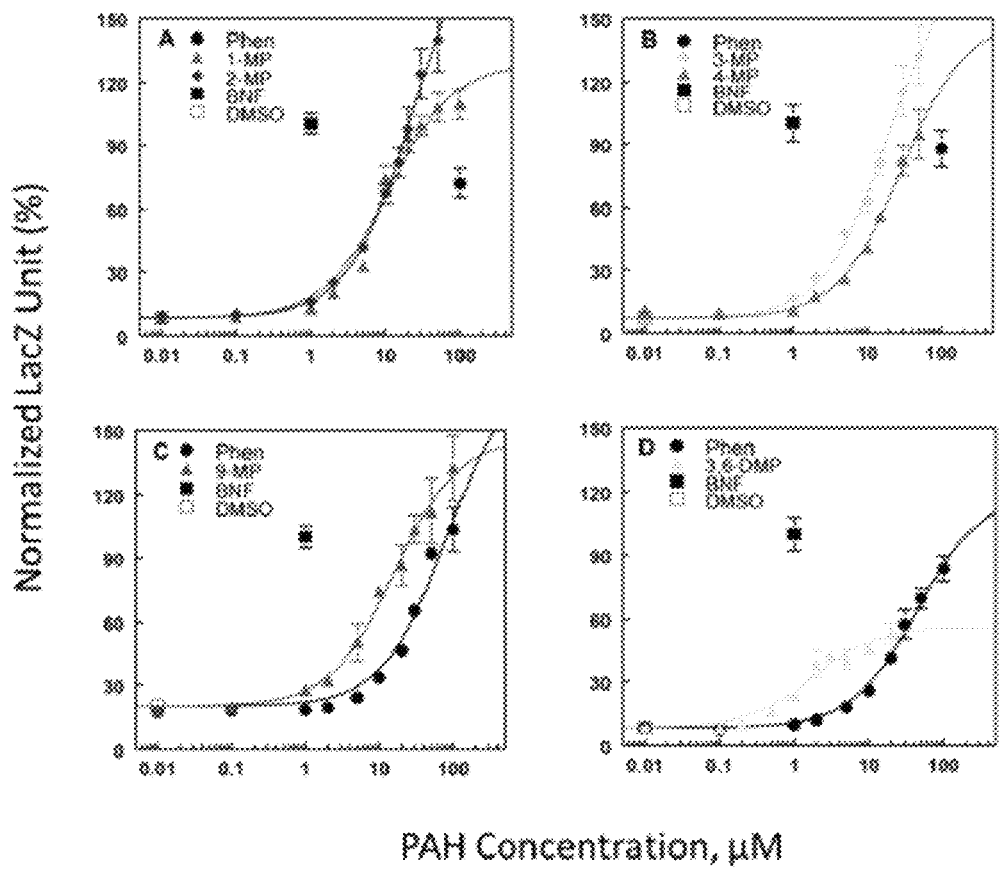

FIG. 25 shows graphs (panels A-D) of the ability of methylated phenanthrenes to the activate aryl hydrocarbon receptor. Data were expressed as the percentage of the maximum activity (1 μM beta-naphthoflavone (BNF) set as 100%). Data points represent the mean±SD (n=4); at least 3 independent experiments were performed for each tested compound. DMSO (1%) was included as a negative control; 100 μM phenanthrene treatment was included in each assay plate for calculation of relative $EC_{50}$.

FIG. 26 shows the curve fit coefficients for dose-response curves.

FIG. 27 shows the relative EC50 and EC25 with error calculated from 95% CI.

FIG. 28 shows the p values from ANOVA and post-test analysis.

FIG. 29 are bar graphs showing the relative $EC_{50}$ ($rEC_{50}$, Panel A) and $EC_{25}$ ($rEC_{25}$, Panel B) values for unsubstituted and substituted phenanthrenes. The $rEC_{50}$ and $rEC_{25}$ are defined as the concentrations of the methylated phenanthrene that induced 50% and 25%, respectively, of the activity observed after treatment with of 100 μM phenanthrene in the yeast bioassay. The data is expressed as mean±SEM. Significance, as determined by a post-test based on Student-Newman-Keuls analysis, is indicated as follows: *, p<0.001; , 0.001>p<0.01; *, 0.01<p<0.05.

Figure 30:
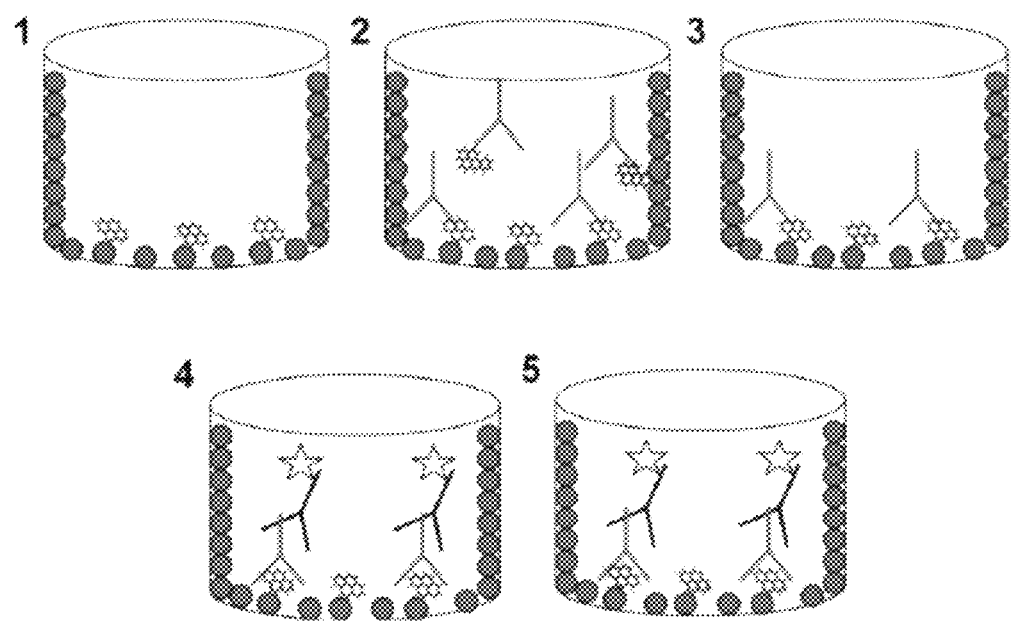

FIG. 30 is a schematic showing competitive ELISA Assay (see panels 1-5). BAP-13 Ab was pre-incubated with varying amounts of benzo[α]pyrene (BAP) before it was added to the plate, and the pyrene-BSA on the plate has to compete with the soluble benzo[α]pyrene for available BAP-13 binding sites. Because PAHs are hydrophobic, initial experiments were performed to determine how much organic solvent the assay can tolerate.

Figure 31:
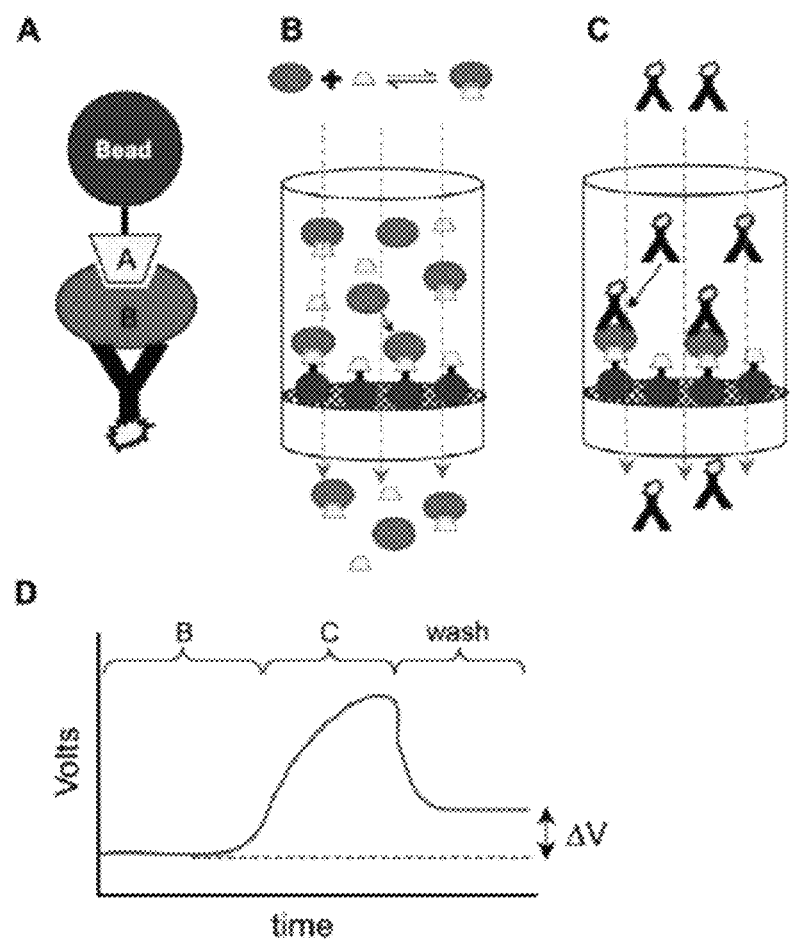

FIG. 31 shows an example of a Kinetic Exclusion Assay (EinExA), which was adapted from Darling, R. J. & Brault, P. A. (2004). (A) To create a probe to determine the equilibrium affinity between antibody B and its substrate A, molecule A is immobilized onto beads. The antibody was pre-incubated sufficiently with free A to reach equilibrium. (B) A mixture of A and B components is allowed to flow through the beads. Separation of free B from free A and AB components occurs as only free B binds to the immobilized A on the beads. (C) Next, a fluorescent detection probe is passed through the beads in excess to label any captured B, the beads are rinsed with buffer, and (D) fluorescence emission is measured in volts.

Figure 32:
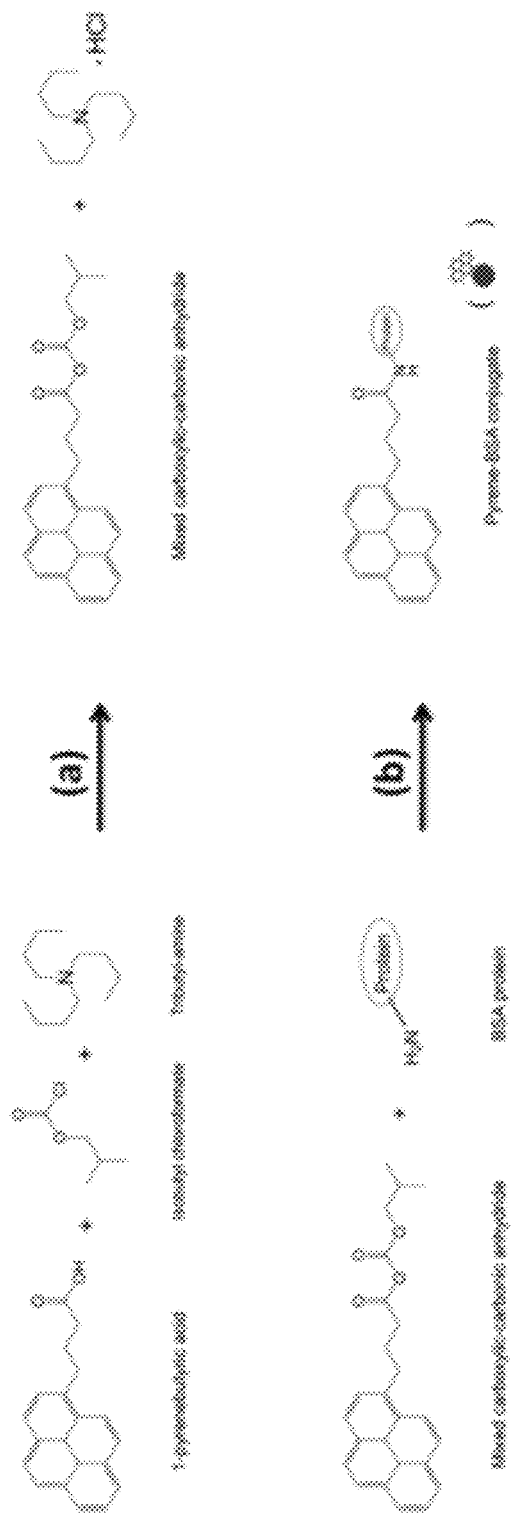

FIG. 32 shows chemical reactions for Hapten-protein conjugation via mixed anhydride method. An example of pyrene with a 4-carbon spacer conjugating to a protein molecule (BSA). Briefly, the 1-pyrenenbutyric acid was dissolved in the dry 1,4-dioxane. Then, the tributylamine and isobutyl chloroformate were added. After mixing, the solution was placed at 4° C. refrigerator for about 30 min to form the mixed carboxylic-carbonic anhydride ((a)). The second step involved adding the mixture dropwise to an aqueous solution of bovine serum albumin (BSA), and the amide bond was formed ((b)).

Figure 33:
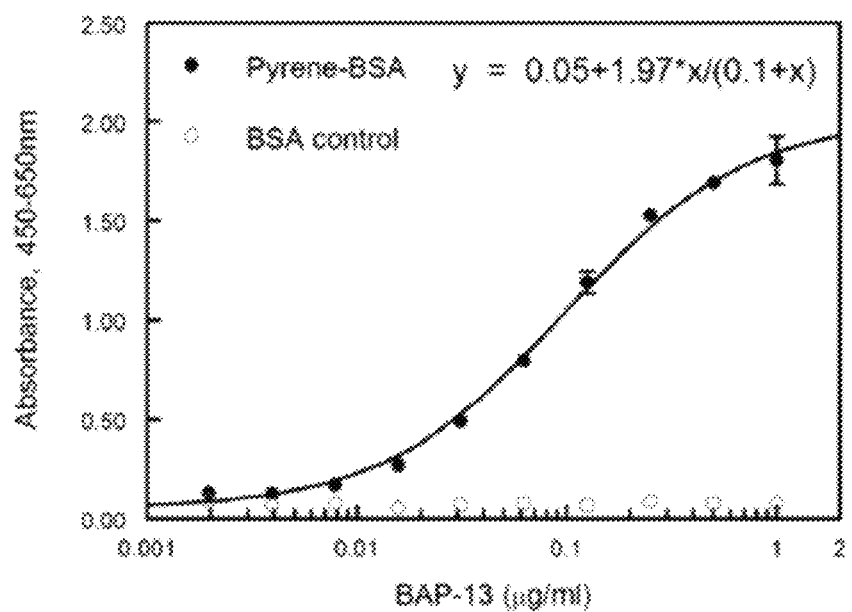

FIG. 33 is a graph showing the titration of BAP-13 antibody against pyrene-BSA via indirect ELISA. An aliquot of 5 µg/ml newly synthesized pyrene-BSA conjugates was immobilized onto ELISA plate surface, and probed by serially diluted BAP-13 antibody. The signal was generated by the colorimetric substrate which was proportional to the amount of BAP-13 captured by the conjugate.

FIG. 34 are graphs showing a binding test of BAP-13 antibody to benzo[α]pyrene. (A) Competitive ELISA (cELISA) method and (B) Kinetic exclusion assay (KinExA) method were used to test the binding property of BAP-13 monoclonal antibody to benzo[α]pyrene. Data from both methods were fitted into equation $y=a0-a1*x/(x+a2)$.

FIG. 35 shows curve fitting parameters.

FIG. 36 shows a mouse immunization procedure.

Figure 37:
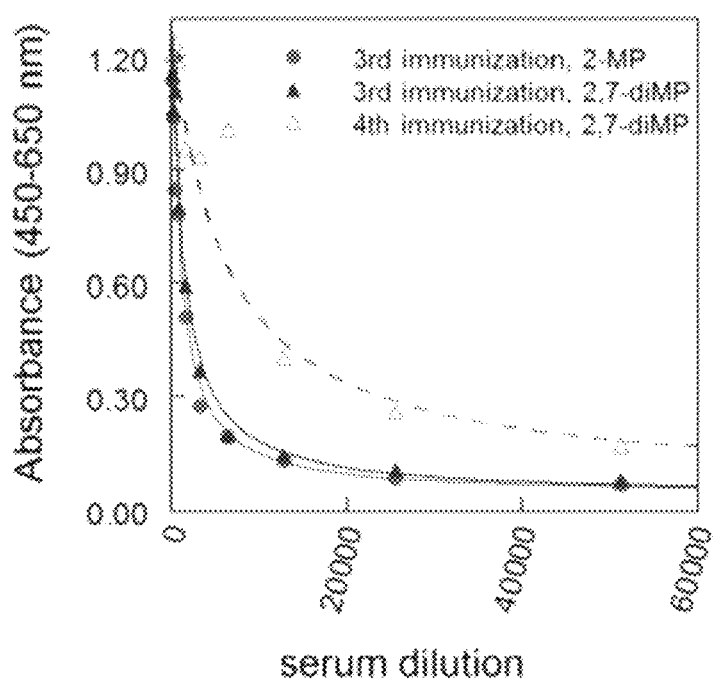

FIG. 37 is a graph showing the serum titer of mice immunized with 2-methylphenanthrene- and 2,7-dimethylphenanthrene-KLH conjugates.

Figure 38:
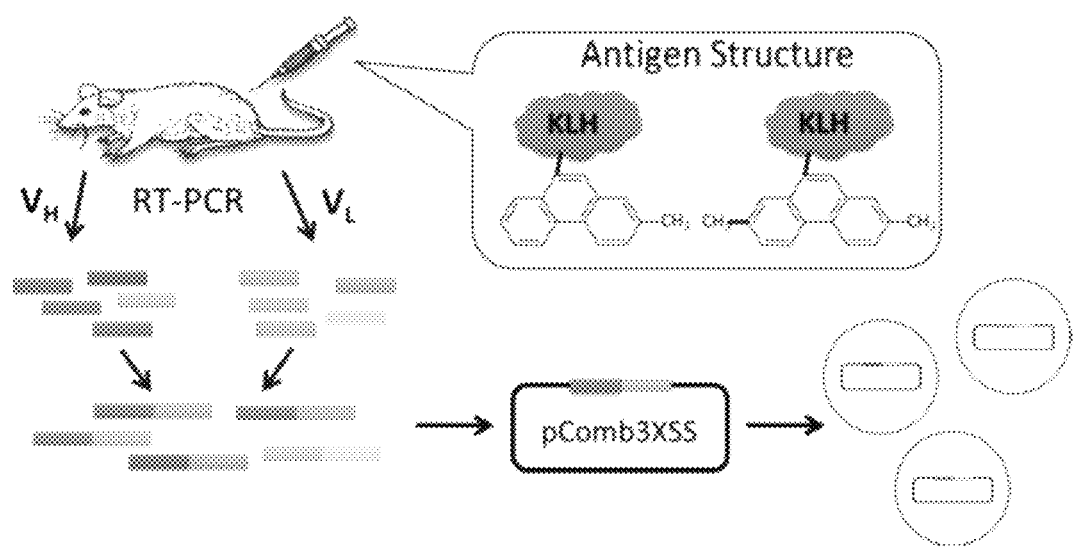

FIG. 38 is a schematic showing immune library construction. Spleen and WBC were collected from immunized animals and recombinant antibody technology was used to generate a library of single-chain variable fragments (scFv).

FIG. 39 shows photographs of gels depicting immune library quality. A, PCR amplification of the scFv insert of randomly selected clones. Of the clones analyzed, 14/16 clones were full-length. B, BstNI enzyme digestion of full-length clones to demonstrate library diversity.

FIG. 40 shows the steps taken in phage display selection-strategy #1.

FIG. 41 shows the quality test of single clones from phage display selection #1 output. A. BstNI enzyme digestion of full-length single clones to estimate output diversity. The majority of BstNI fingerprint showed the same pattern as 1C4, indicating a low diversity output. B. Monoclonal phage of full-length clones were used to test their ability to bind to Phen-BSA conjugate via indirect ELISA. M13KO7 was used as negative control. Bar graph represents duplicate samples for each clones.

Figure 42:
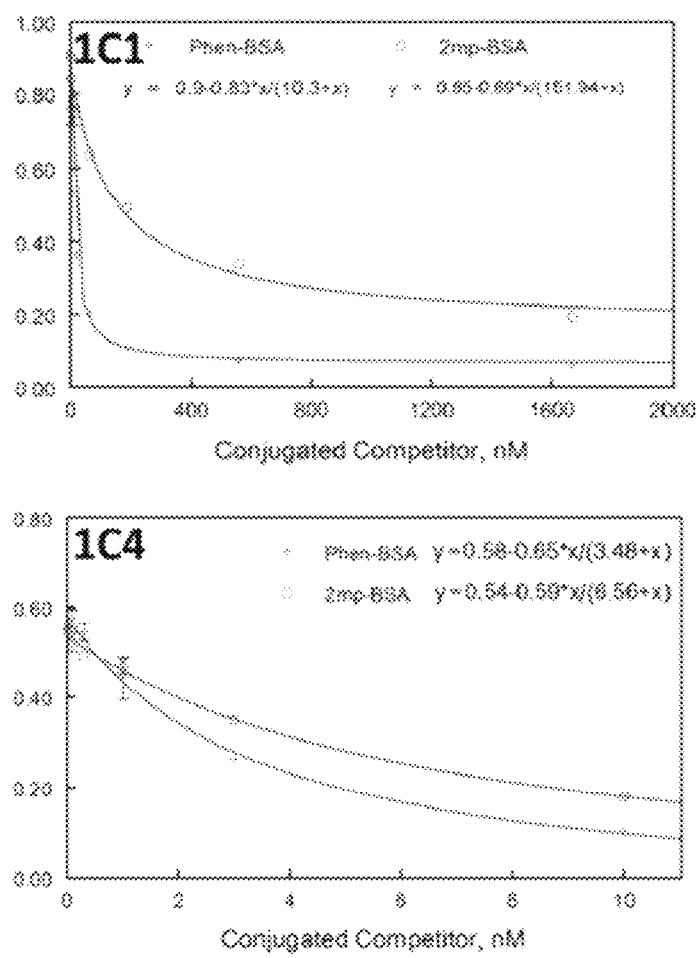

FIG. 42 are graphs of competitive ELISA of scFv clones binding to protein conjugates. Two clones discovered from phage library by selection strategy #1 were measured for their binding affinities to PAH-BSA conjugates. The inhibition of Phen-BSA (blue curve (*)) and 2-MePhen-BSA (red curve (open circles)) were shown for 1C1 (upper panel) and 1C4 (lower panel).

FIG. 43 shows the steps taken in Phage display selection-strategy #2.

Figure 44:
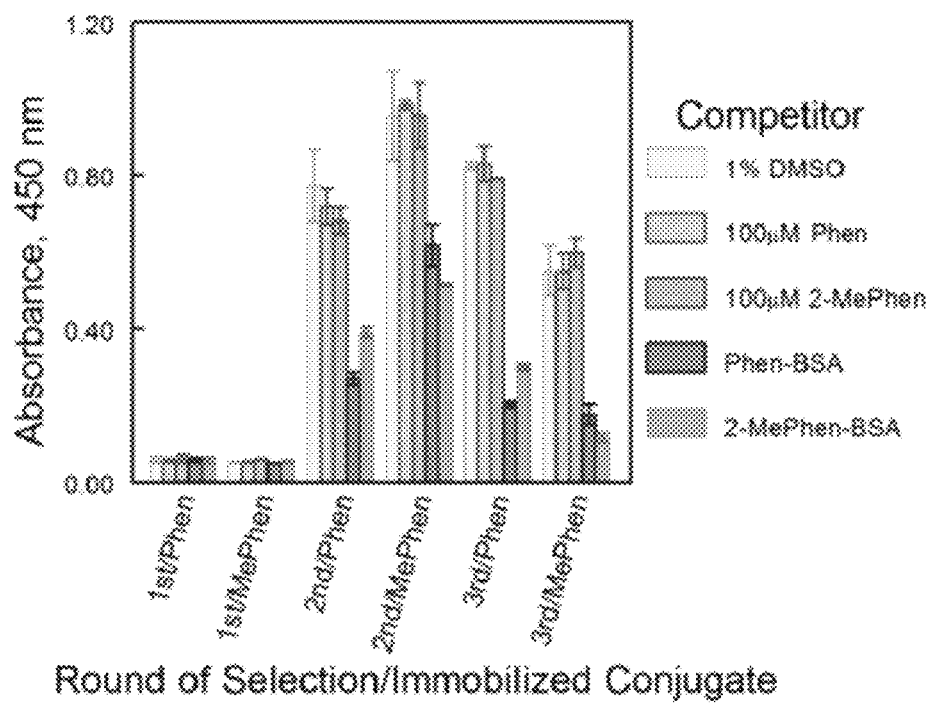

FIG. 44 is a bar graph of competitive phage ELISA. Phage pools recovered after each round of selection were tested for their ability to bind to immobilized phenanthrene-BSA (Phen) or 2-methylphenanthrene-BSA (MePhen), in the absence (1% DMSO) or presence of soluble competitors. Soluble protein conjugates were used as competitors at a concentration of 50 µg/mL (~0.75 µM). Phage binding to plates coated with BSA showed only background signal.

FIG. 45 shows the quality test of single clones from phage display selection #2 output. A PCR amplification of single clones from the final output pool of selection strategy #2. B. BstNI enzyme digestion of full-length single clones to estimate output diversity. The majority of BstNI fingerprint showed the same pattern as 1C4, indicating a low diversity output. C. Monoclonal phage of full-length clones were used to test their ability to bind to 2-MePhen-BSA or Phen-BSA conjugates via indirect ELISA. M13KO7 was used as negative control.

Figure 46:
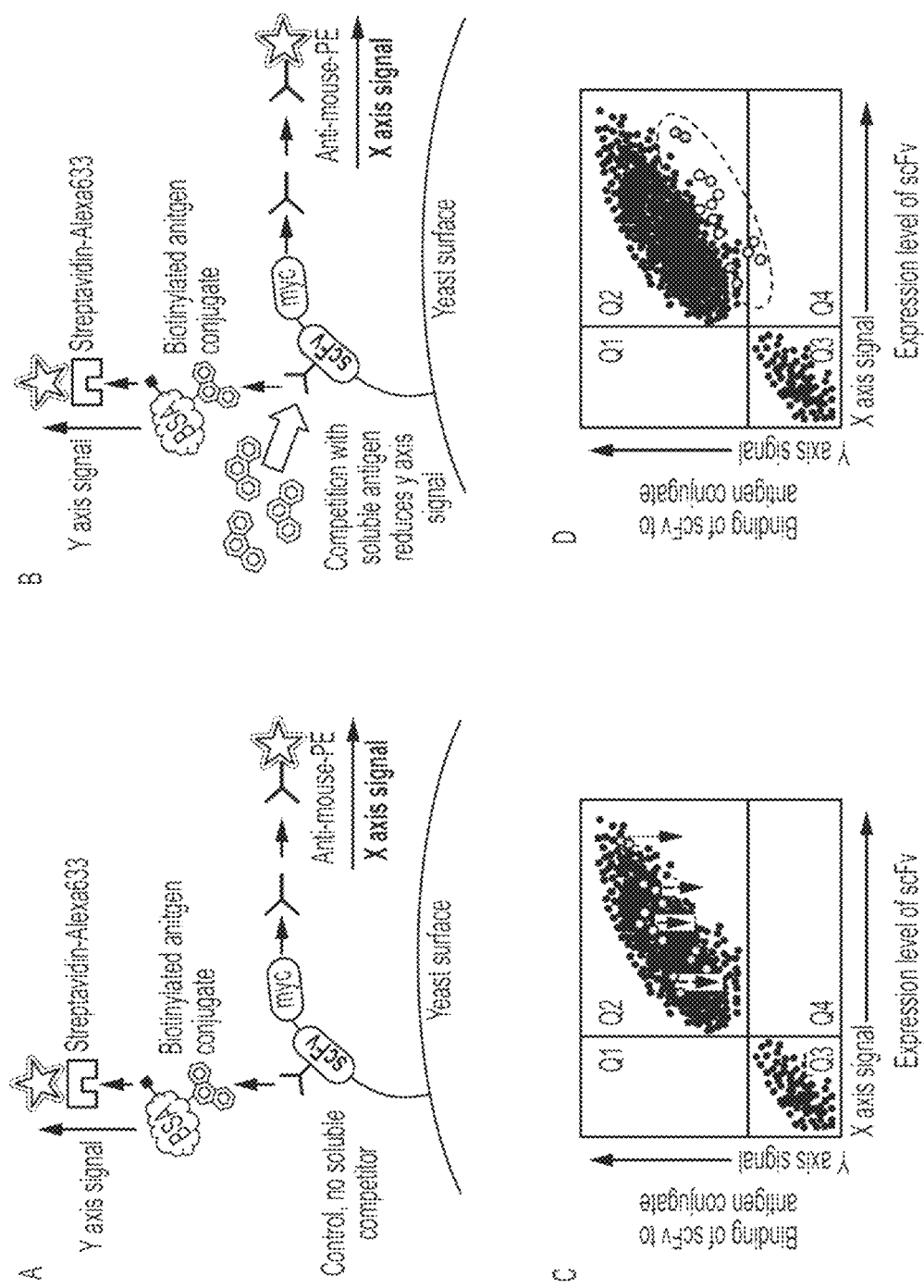

FIG. 46 is a schematic that shows a strategy for selection by competitive FACS (see panels A-D). The yeast cell population that both expresses scFv (as assessed by the signal on the X axis) and binds to the biotinylated phenanthrene-BSA conjugate (as assessed by the Y axis signal) is incubated in the presence of soluble hapten (phenanthrene or 2-methylphenanthrene). Those clones that bind to soluble antigen will show lower signals in the Y axis and will be enriched in the area of the Q2 quadrant circled in panel D.

Figure 47:
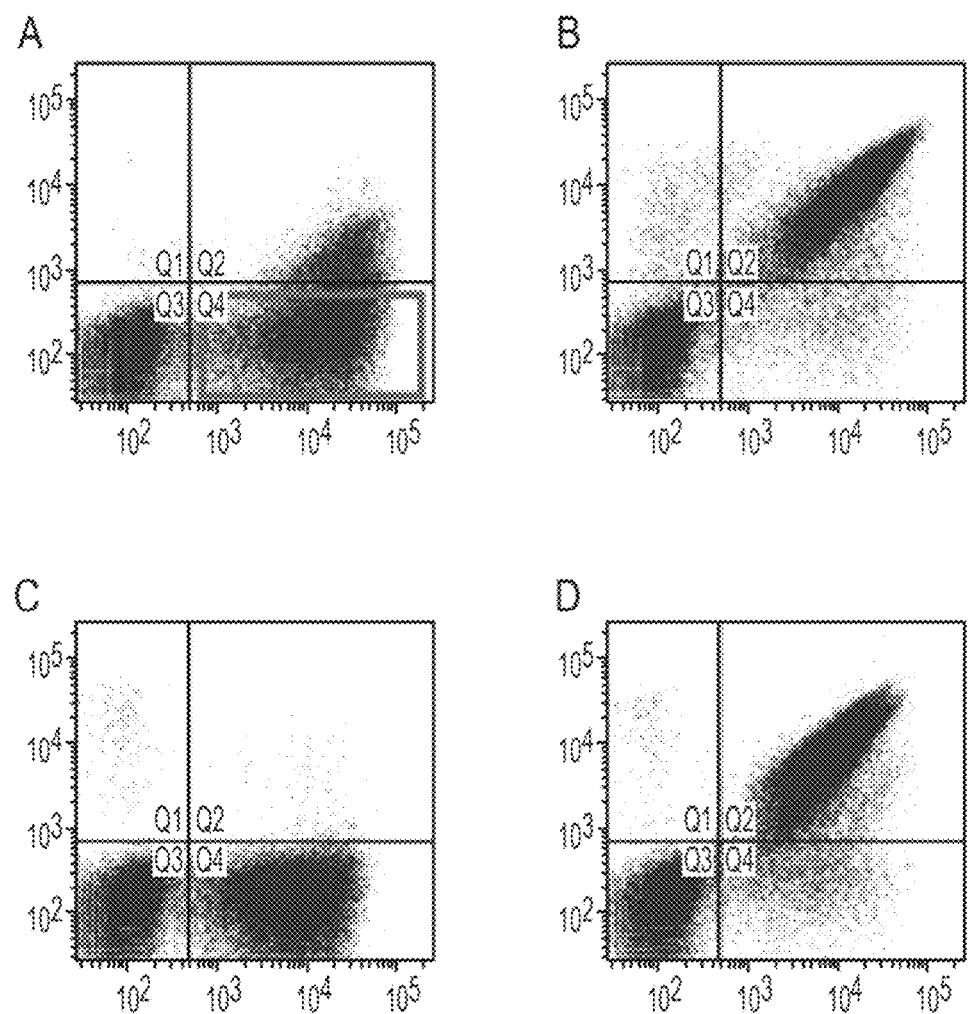

FIG. 47 shows graphs for the FACS of the yeast cells constructed using scFvs from the 3$^{rd}$ round of phage selection via Protocol 1. The yeast cells generated from Protocol 1 were tested to bind with BSA-Biotin (A) or Phen-BSA-Biotin (B). As flow data shown significant background signal when incubated with biotin-BSA (note high numbers of cells in Q2 quadrant), only those clones outlined in red in Panel A were carried forward for subsequent selections. After initial sorting, the yeast cells from the red box were tested again with BSA-Biotin (C) or Phen-BSA-Biotin (D), and the background signal was much cleaner than the original pool.

Figure 48:
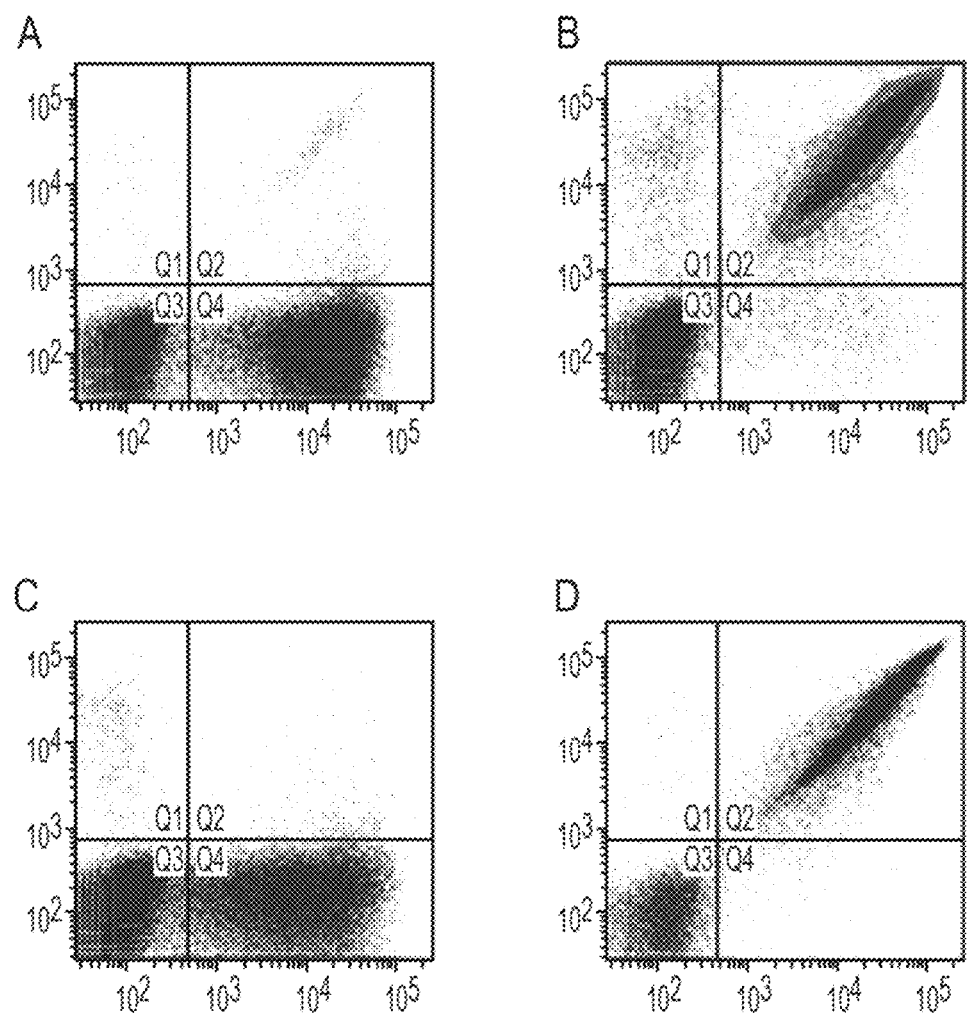

FIG. 48 shows graphs for the FACS of the yeast cells from Protocol 2. Similar to FIG. 47, the yeast cells generated from Protocol 2 were also tested to bind with BSA-Biotin (A) or 2-MePhen-BSA-Biotin (B). These cells showed very little background signal, and negative sorting was not required. However, signal of binding to 2-MePhen-BSA was relatively scattered, and high affinity binders from this pool were selected as outlined in red in Panel B. After initial sorting, the yeast cells were tested again with BSA-Biotin (C) or 2-MePhen-BSA-Biotin (D), and the shape of sorted yeast cells binding to 2-MePhen-BSA was much tighter in D.

Figure 49:
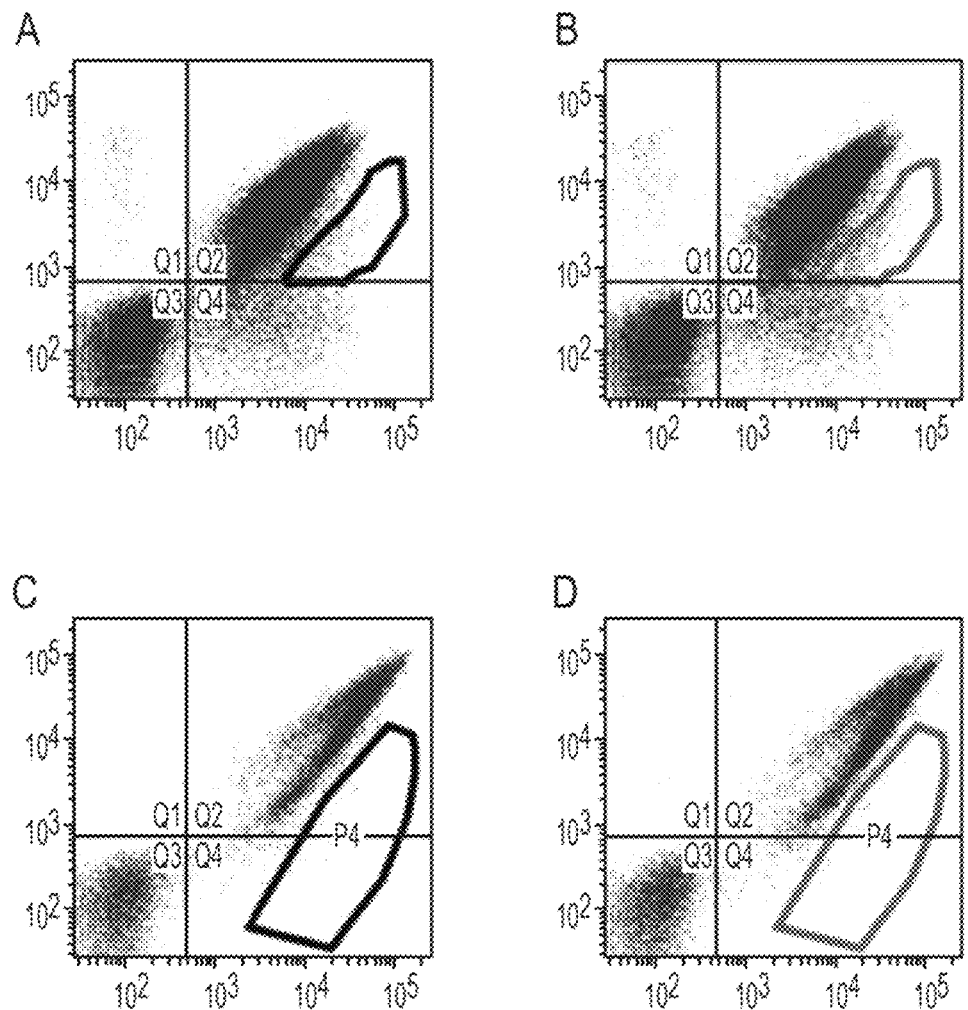

FIG. 49 shows graphs for competitive FACS of both pools. A and B, Yeast cells from the negative sort of Pool 1 incubated with Phen-BSA-Biotin in presence of 2% DMSO (A) or 200 µM soluble Phen in 2% DMSO (B). C and D, Yeast cells from the positive sort of Pool 2 were incubated with 2-MePhen-BSA in the presence of 2% DMSO (C) or soluble 2-MP in 2% DMSO (D). Cells in the red circle were collected for further analysis.

Figure 50:
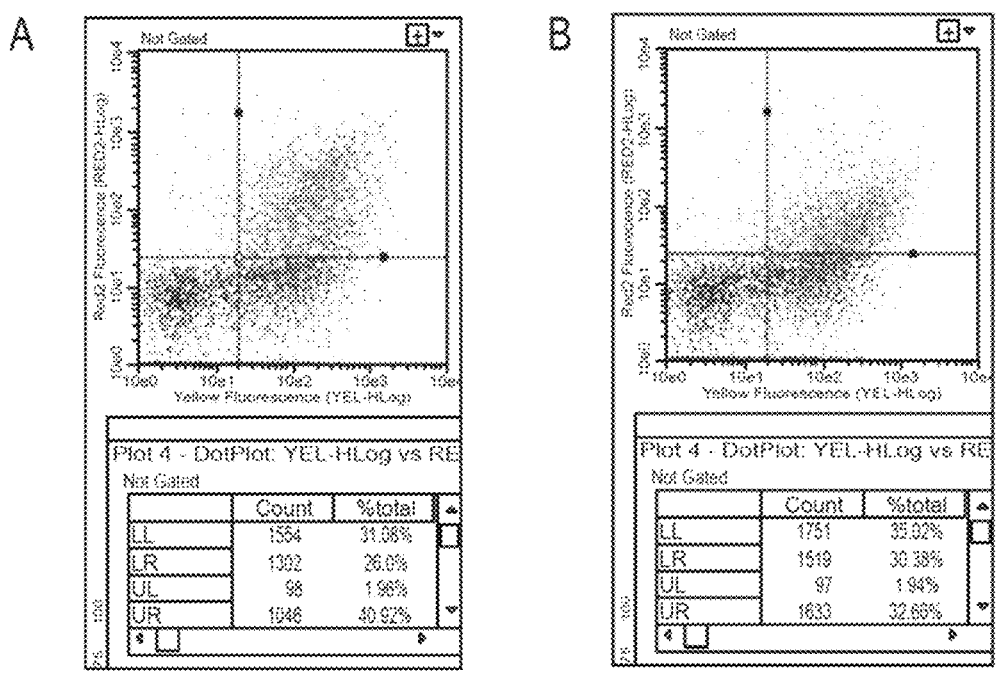

FIG. 50 shows graphs from competitive flow cytometry of Pool 1 yeast population after $2^{nd}$ sort. The yeast cells from $2^{nd}$ sort of Pool 1 were incubated with Phen-BSA-Biotin in the presence of 2% DMSO (A) or 200 µM soluble Phen (B).

Figure 51:
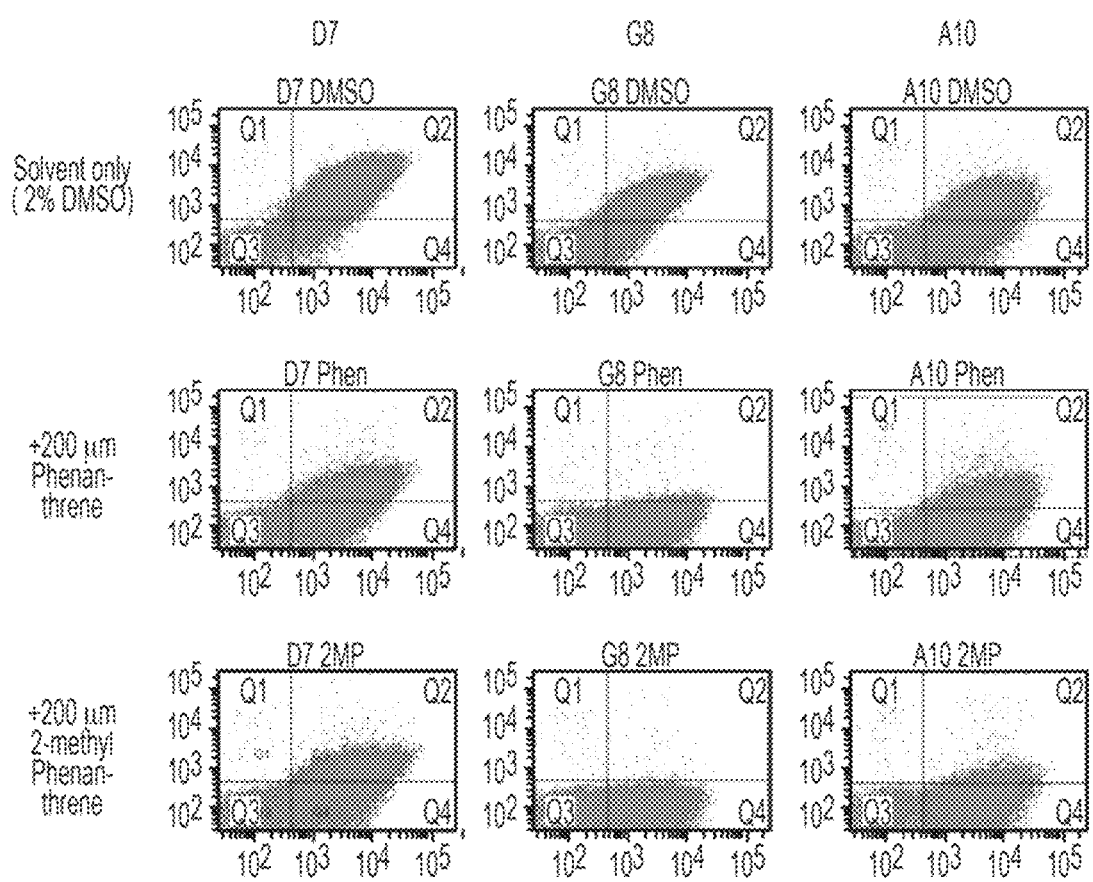

FIG. 51 shows graphs of the analysis of monoclonal yeast by flow cytometry that revealed clones with various binding capacities. Three representative clones are shown in three lanes. Top panels, yeast cells were incubated with the Phen-BSA-Biotin conjugate without soluble competitor; Middle panels, yeast cells were incubated with Phen-BSA-Biotin and soluble Phen; Bottom panels, yeast cells were incubated with Phen-BSA-Biotin and soluble 2-MP.

Figure 52:
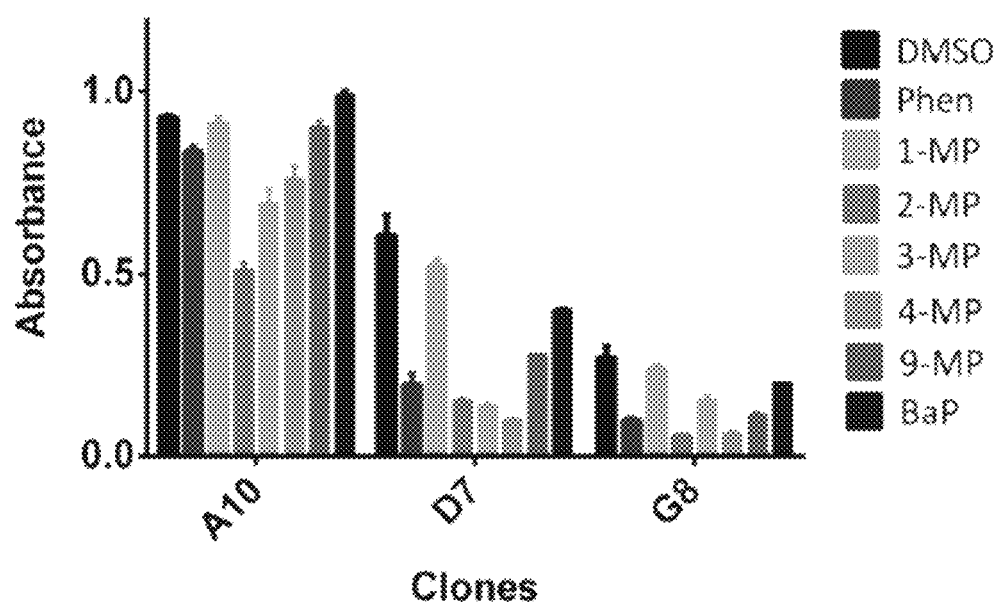

FIG. 52 is a bar graph showing a competitive ELISA of selected clones by various phenanthrenes and benzo-a-pyrene. Crude periplasmic extracts of each clones were used to initially test the specificity of scFv to different ligands. A single concentration (200 µM) of ligands were incubated with scFv in the antigen-coated wells, and the signals were compared to negative control (DMSO, black bar (1st bar for each clone group examined)).

FIG. 53 shows a summary of monoclonal yeast flow-cytometry analysis.

Figure 54:
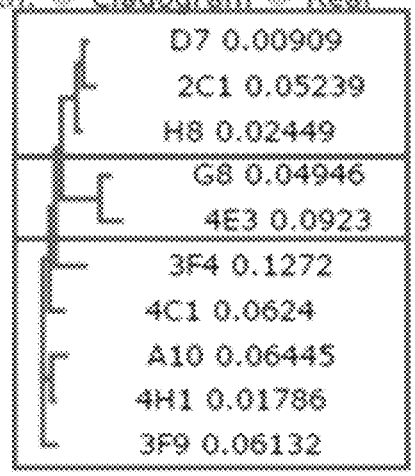

FIG. 54 is a phylogram showing the sequence alignment of the 65 clones that bound to soluble phenanthrene or 2-methylphenanthrene in competitive ELISA.

Figure 55:
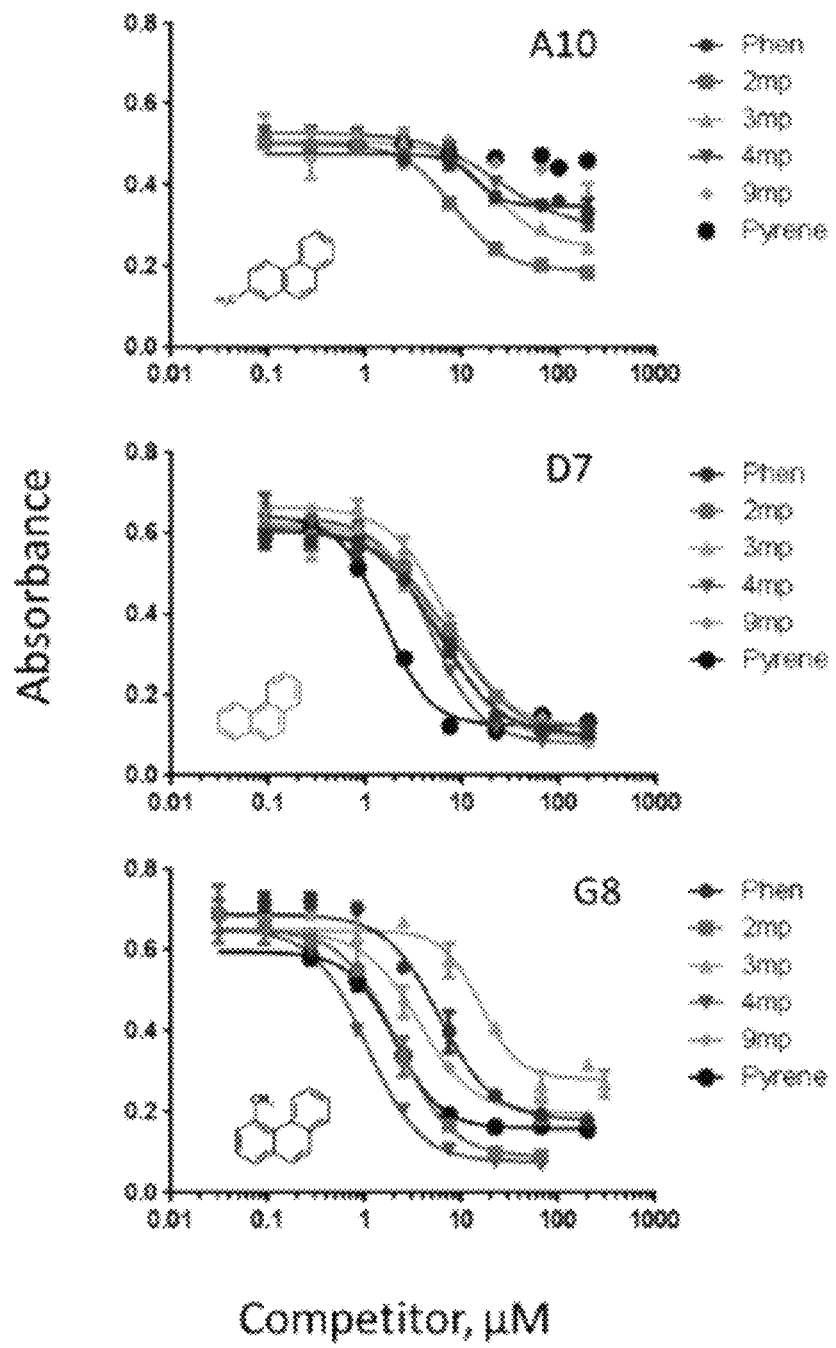

FIG. 55 are graphs of a competitive ELISA of selected clones to elucidate binding properties. Purified scFv proteins from selected clones were incubated on a phenanthrene-BSA coated plate in the presence of varying concentrations of competitors. The structure in each panel represents the ligand with the highest affinity for the respective scFv.

FIG. 56 shows the $IC_{50}$ values of three clones to various phenanthrenes.

FIG. 57 shows the $IC_{50}$ values of three clones to EPA's 16 PAHs.

Figure 58:
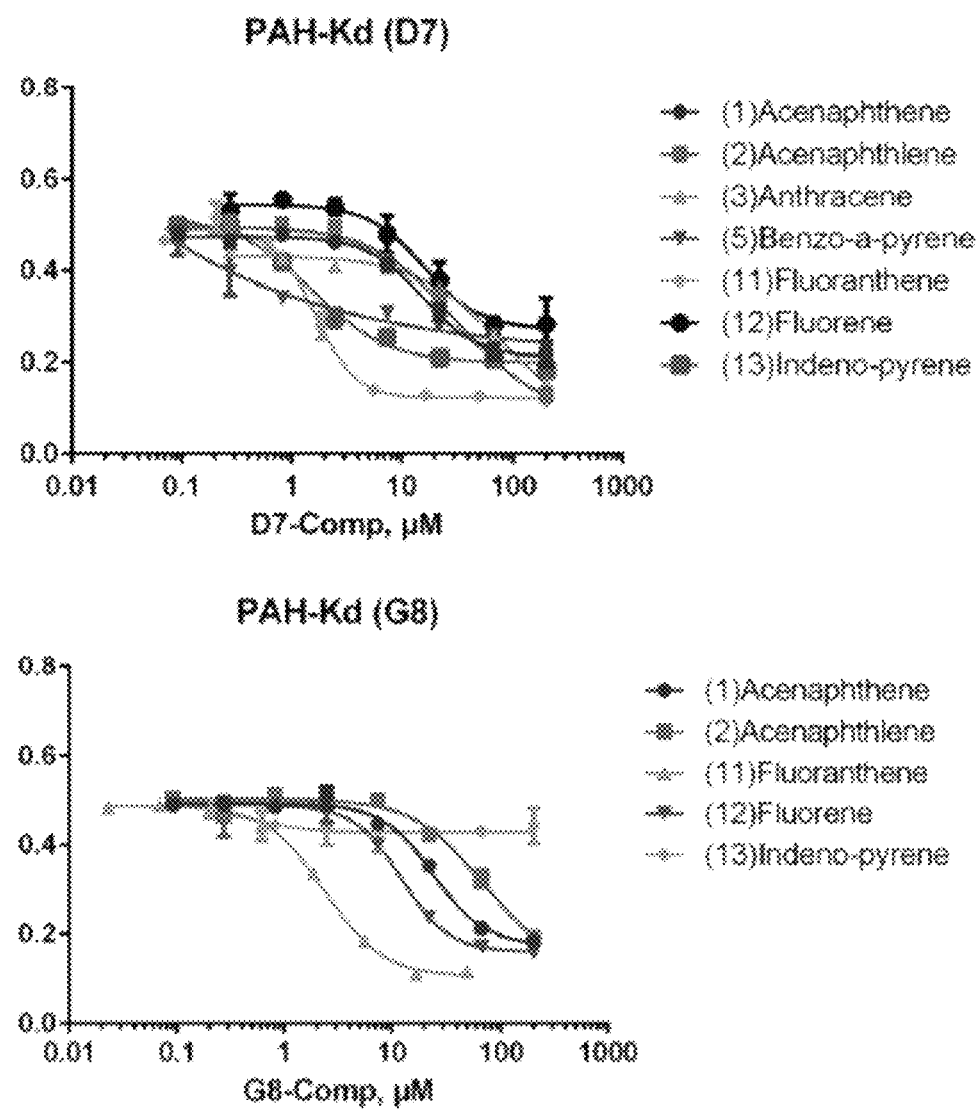

FIG. 58 are graphs of a competitive ELISA of two representative clones to measure their binding affinity with selected PAHs. PAHs that showed ability to inhibit scFv binding to immobilized antigen were tested by a comprehensive cELISA to calculate their $IC_{50}$ values. Data from most ligands were fitted in a dose-response curve, except for the inhibition of benzo-[a]-pyrene to D7.

Figure 59:
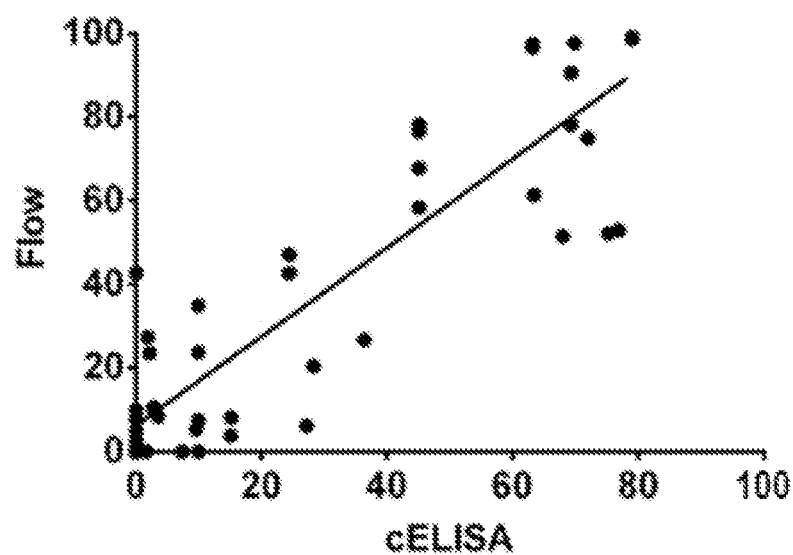

FIG. 59 is a graph showing the correlation of competitive flow method and cELISA analysis.

Figure 60:
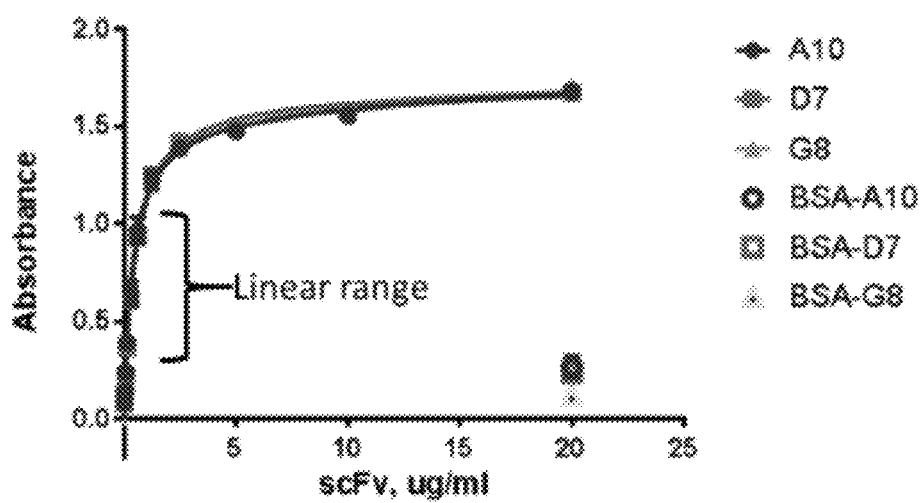

FIG. 60 is a curve showing the titration of three representative clones by indirect ELISA. Serially diluted scFv antibodies were applied onto ELISA plate coated with Phen-BSA conjugate (solid legends) or BSA negative control (open legends). And the scFv concentrations that give linear signal responses (enclosed in the figure) were chosen as the optimum response range for the subsequent binding assays.

FIGS. 61A-B and FIGS. 61C-D shows the optimization of scFv concentrations for competitive ELISA. Primary ligands for each clone (2-methylphenanthrene was used for (A) A10 and (C) G8, and phenanthrene was used for (B) D7) were used as competitors, and were serially diluted to incubate with scFv proteins at four concentrations (0.2, 0.5, 1, 2 µg/ml as shown in the figure legends). (D) The $IC_{50}$ values are shown in the table.

FIG. 62A-B, FIGS. 62C-D, and FIG. 62E-F are graphs of the optimization of pH and BSA concentration for competitive ELISAs. The cELISA assays for three representative clones and their primary ligands were performed at varying pHs (left panels) and BSA protein carrier concentrations (right panels). Optimum scFv concentrations obtained from FIG. 38 were used in these assays ([A10]=0.2 µg/ml, [D7] 1G81=0.5 µg/ml)

Figure 63:
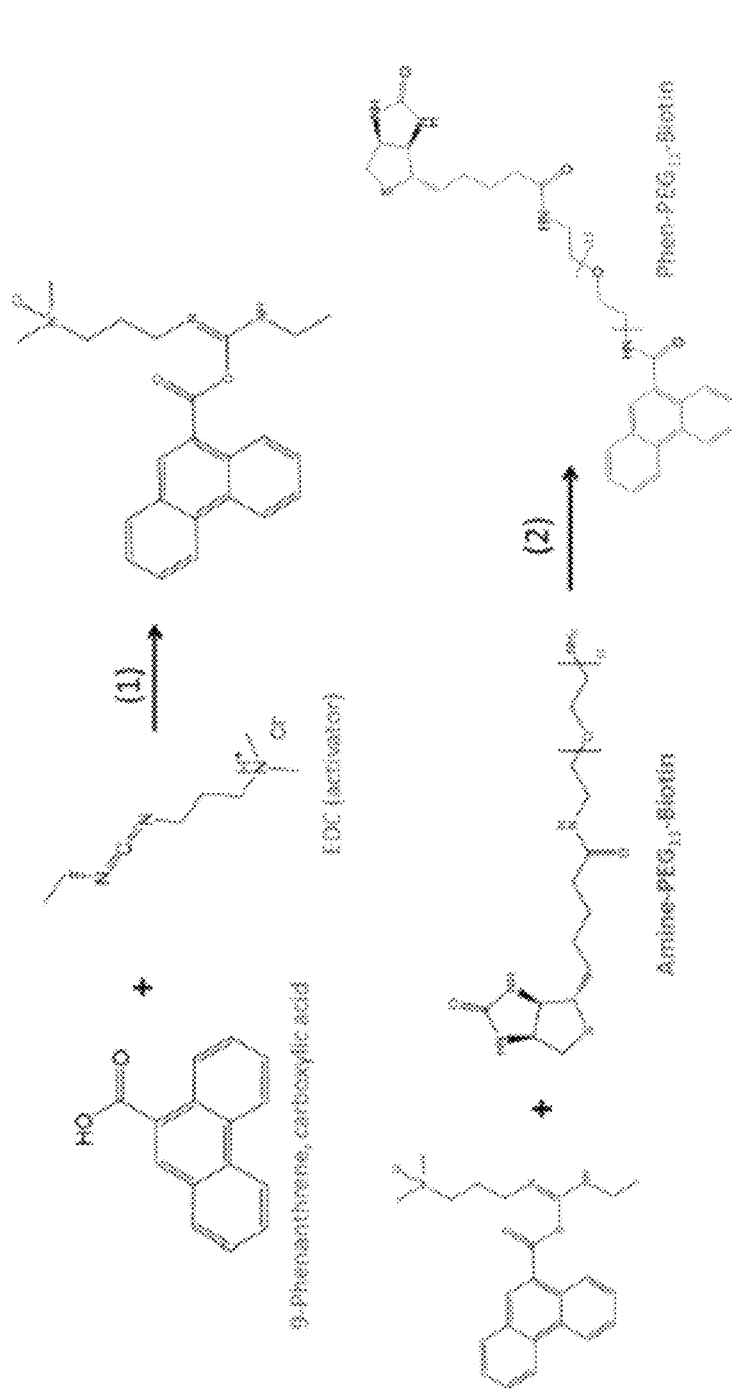

FIG. 63 is a schematic showing the synthesis of phenanthrene-biotin (Phen-Biotin) molecule.

FIG. 64 are graphs showing the HPLC analyses of the reactants and product. (A) An aliquot of 50 µl of 100 µM 9-phenanthrene-carboxylic acid (Phen-COOH) was loaded in HPLC analyzer, and the analyte was recorded at 220 nm and 250 nm. (B) 100 µl of Amine-PEG11-Biotin was analyzed at 5 mM. (C) 50 µl of the product was analyzed from the reaction of 100 µM Phen-COOH and 10 mM Amine-PEG11-Biotin. The peak in blue box represents the conjugate which are only present in the product mixture.

Figure 65:
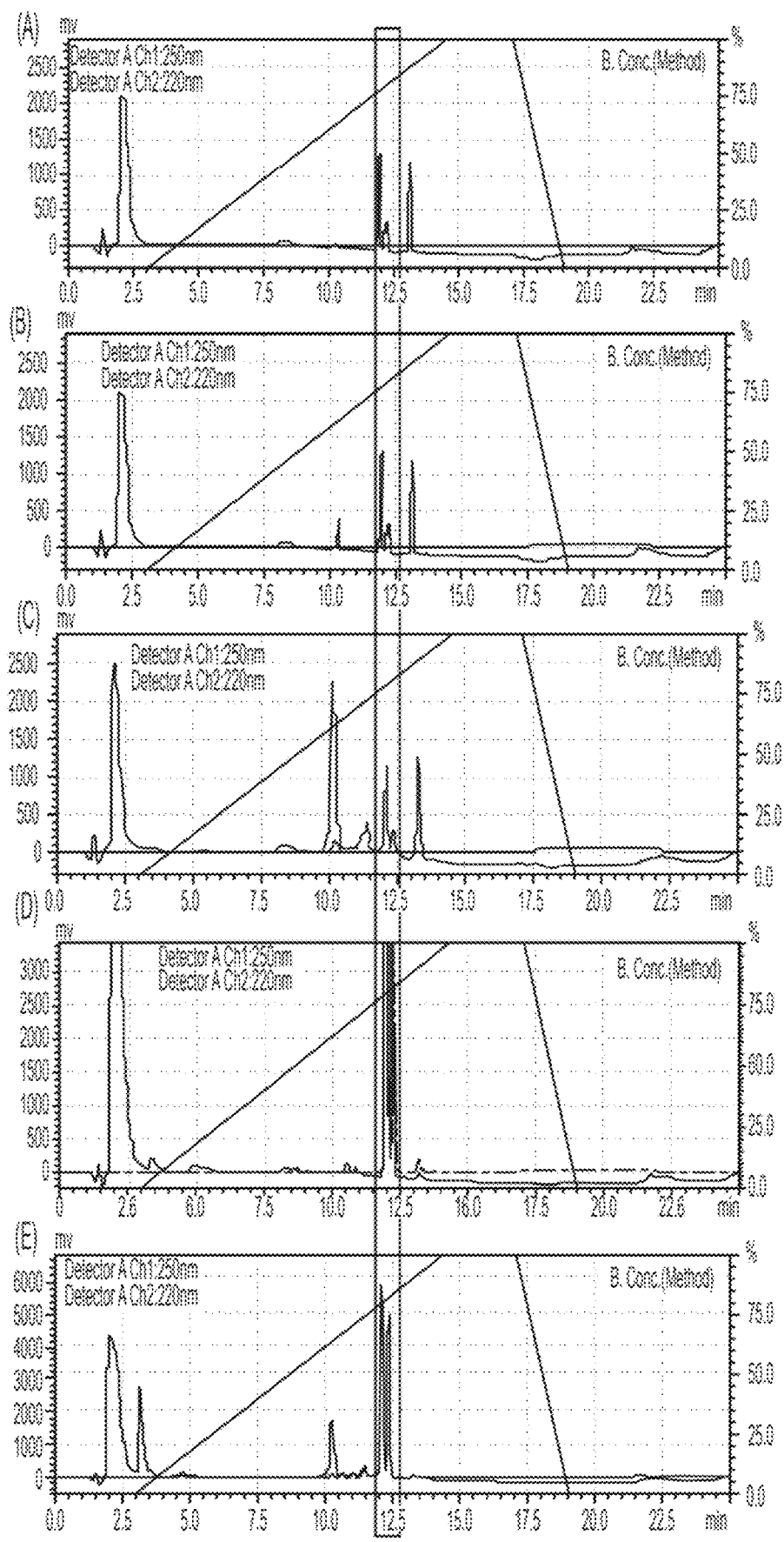

FIG. 65 are graphs showing the optimization of the ratio of reactants for high product yield. The concentrations of Phen-COOH:Amine-PEG11-Biotin:EDC are (A) 100 µM:100 µM:1 mM; (B) 100 µM:1 mM:1 mM; (C) 100 µM:10 mM:1 mM; (D) 1 mM:100 µM:10 mM; (E) 1 mM:5 mM:10 mM, respectively.

Figure 66:
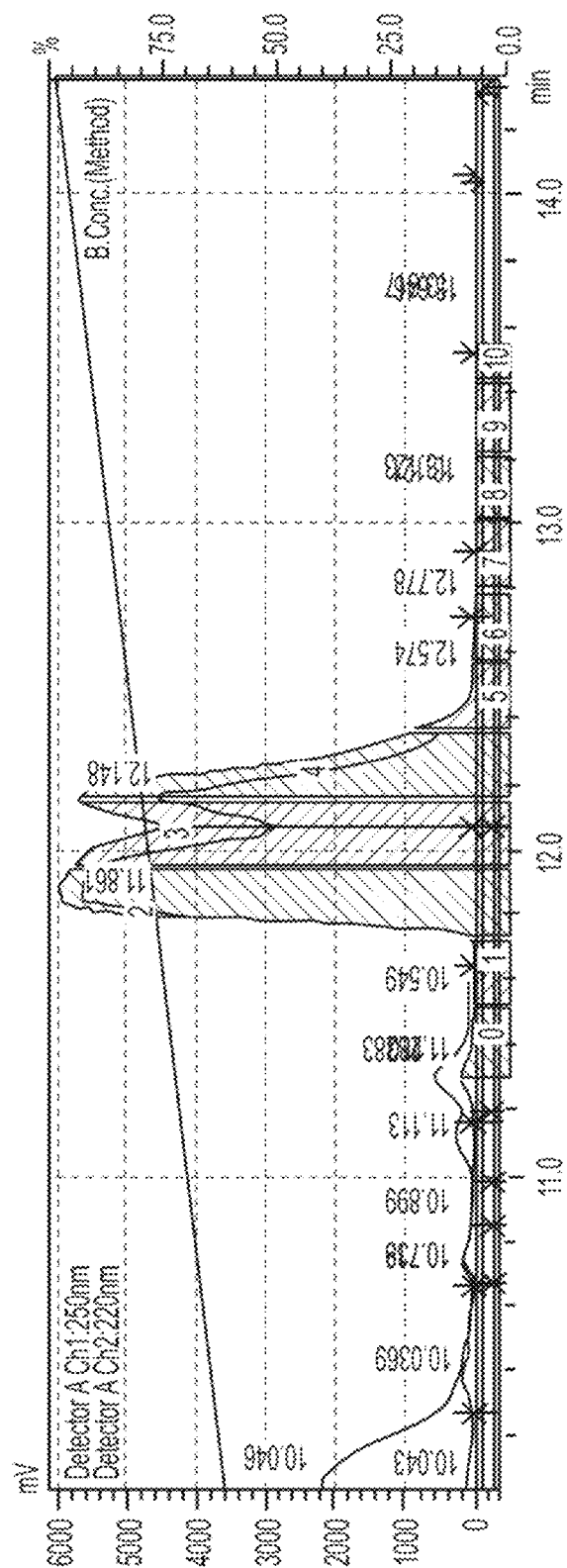

FIG. 66 is a graph showing the purification of Phen-Biotin conjugate by HPLC fractionation. A total of eleven fractions were collected (numbering from 0 to 10), and the major peak falls into three fractions (#2~#4).

Figure 67:
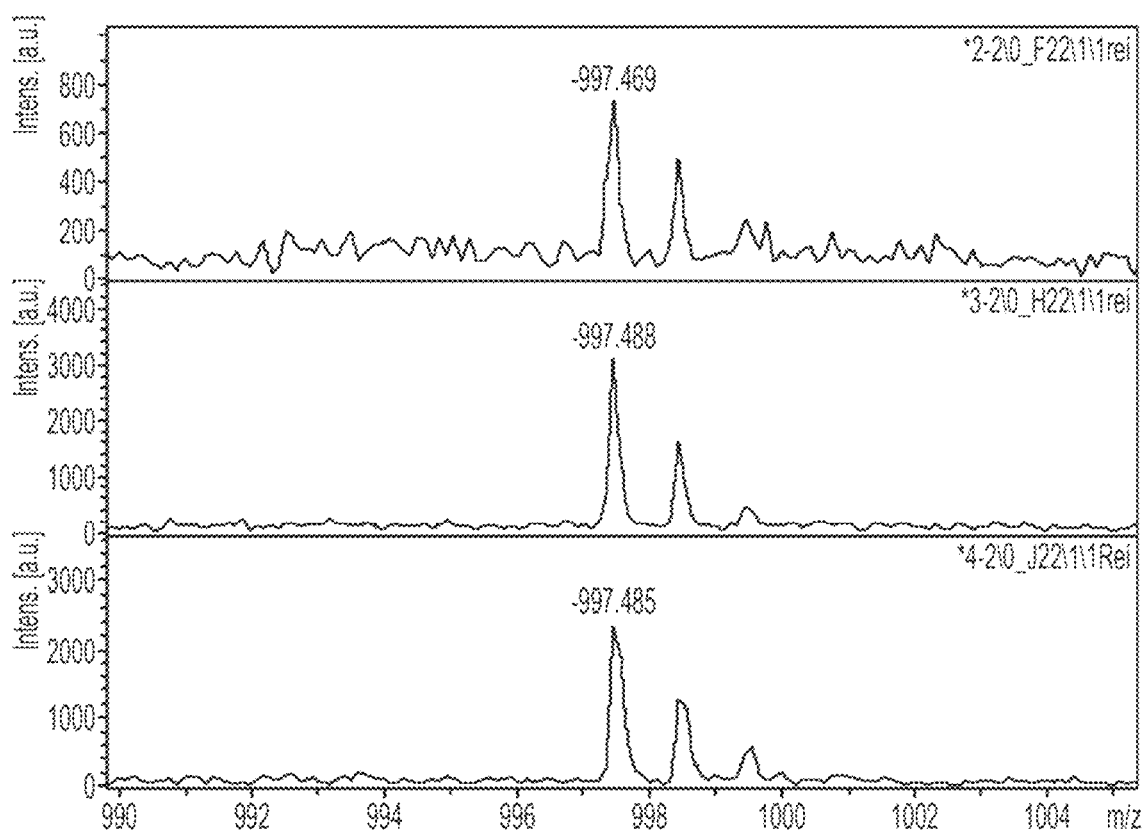

FIG. 67 shows graphs of MALDI-TOF mass-spectrometry analyses of purified Phen-Biotin. From top to bottom are three fractions (#2, #3, and #4) from HPLC purification in FIG. 66. The major peaks in each fraction were labeled with the molecular weight (997.5).

Figure 68:
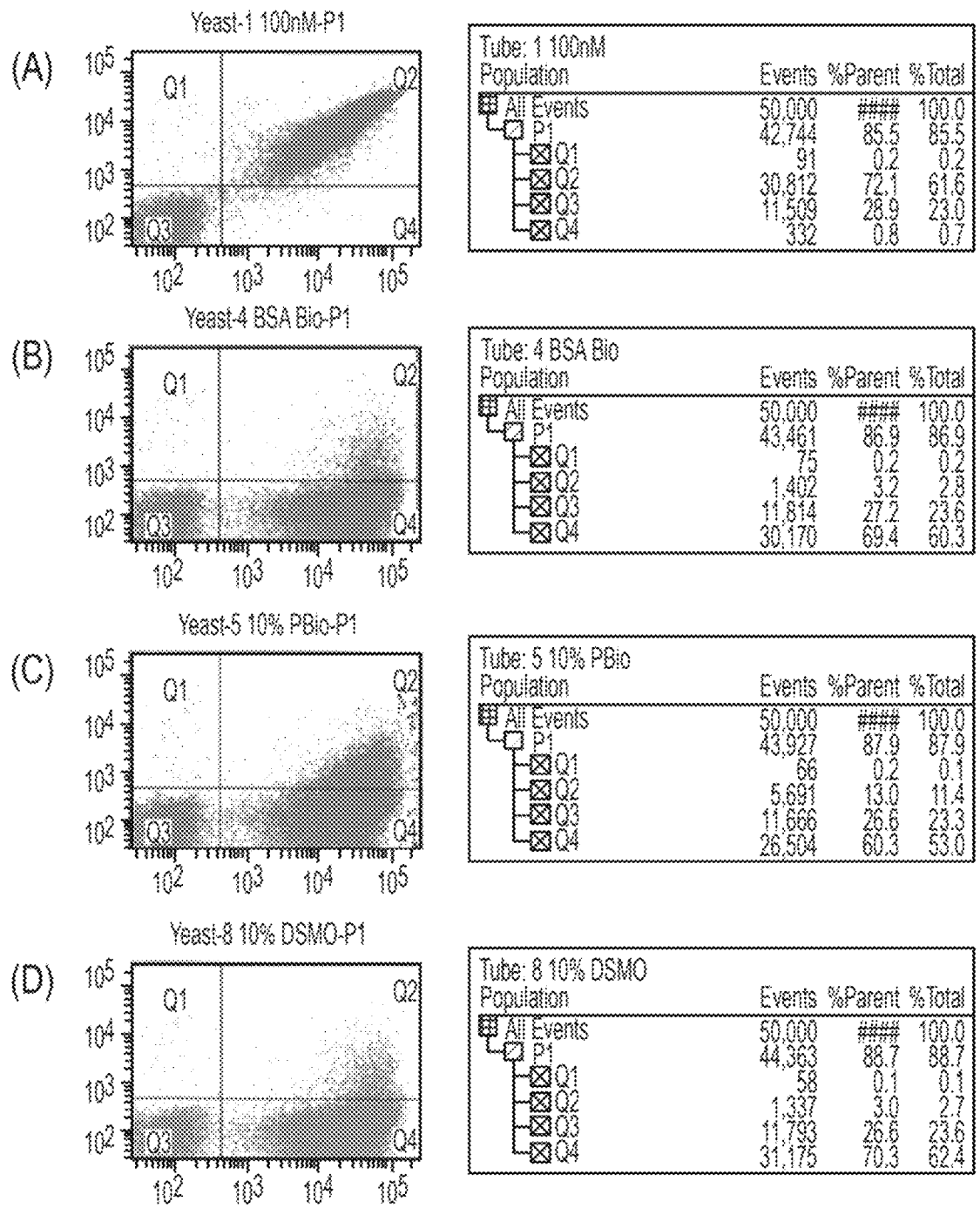

FIG. 68 shows flow cytometry of yeast display using the Phen-Biotin conjugates. Yeast cells were incubated with (A) 100 nM 2-MePhen-BSA-Biotin, (B) 100 nM BSA-Biotin negative control, (C) 10% Phen-Biotin conjugate or (D) 10% DMSO solvent control.

Figure 69:
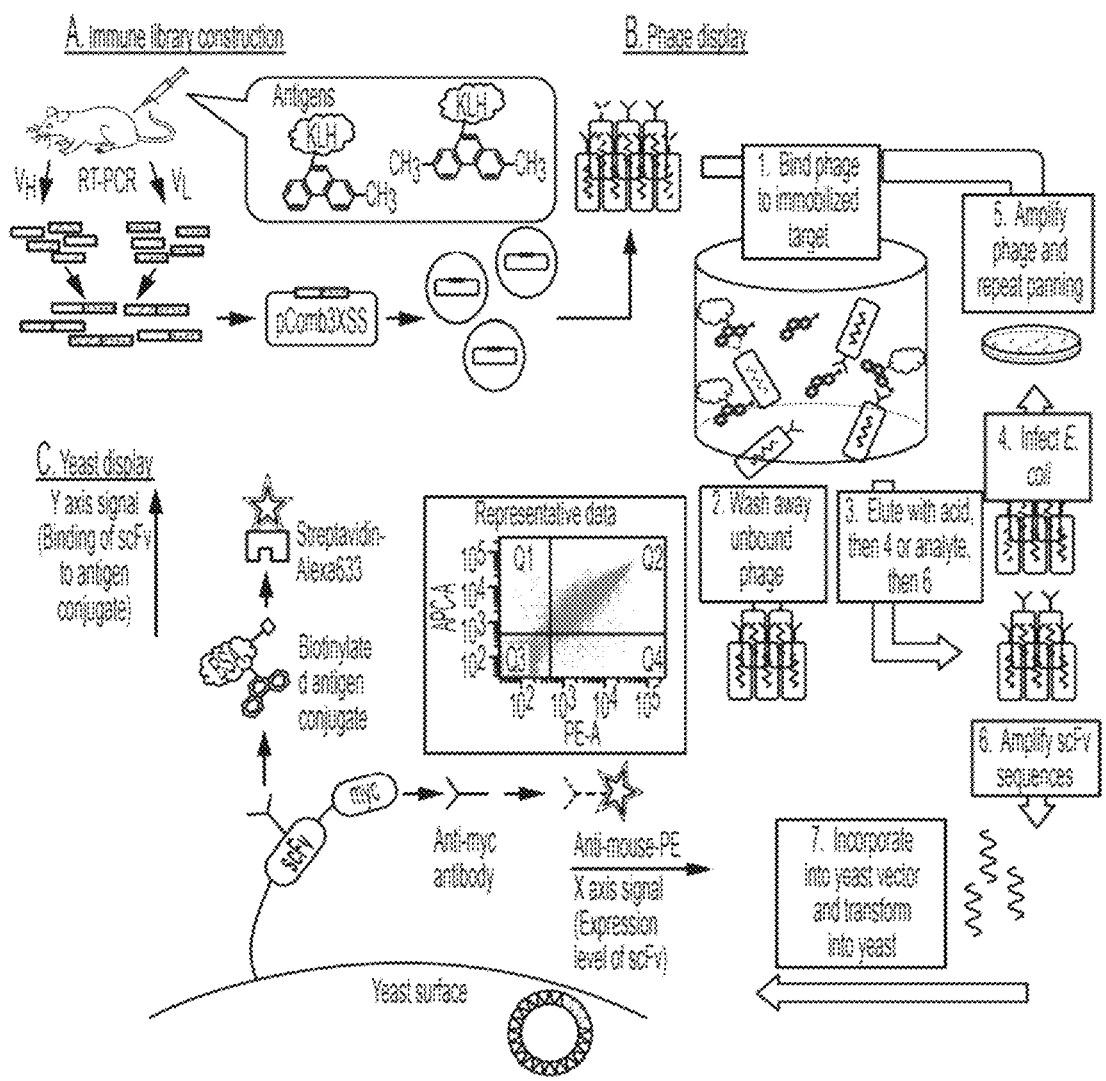

FIG. 69 is a schematic showing a strategy for developing recombinant antibodies against unsubstituted and methylated phenanthrenes. A, Immune library construction. Tissue from immunized animals was used to generate a library of single-chain variable fragments (scFv). B, Phage display selection. Phage panning (3 rounds) was performed and final output pools were transferred into yeast display plasmid (step 5 and 6). C, Yeast display analysis. The expression of scFv was measured by an anti-myc antibody-phycoerythrine-labeled anti-mouse antibody (x axis signal). The binding of the scFv to the biotinylated phenanthrene-protein conjugates was measured by streptavidin-Alexa633 fluorescence (y axis signal).

Figure 70:
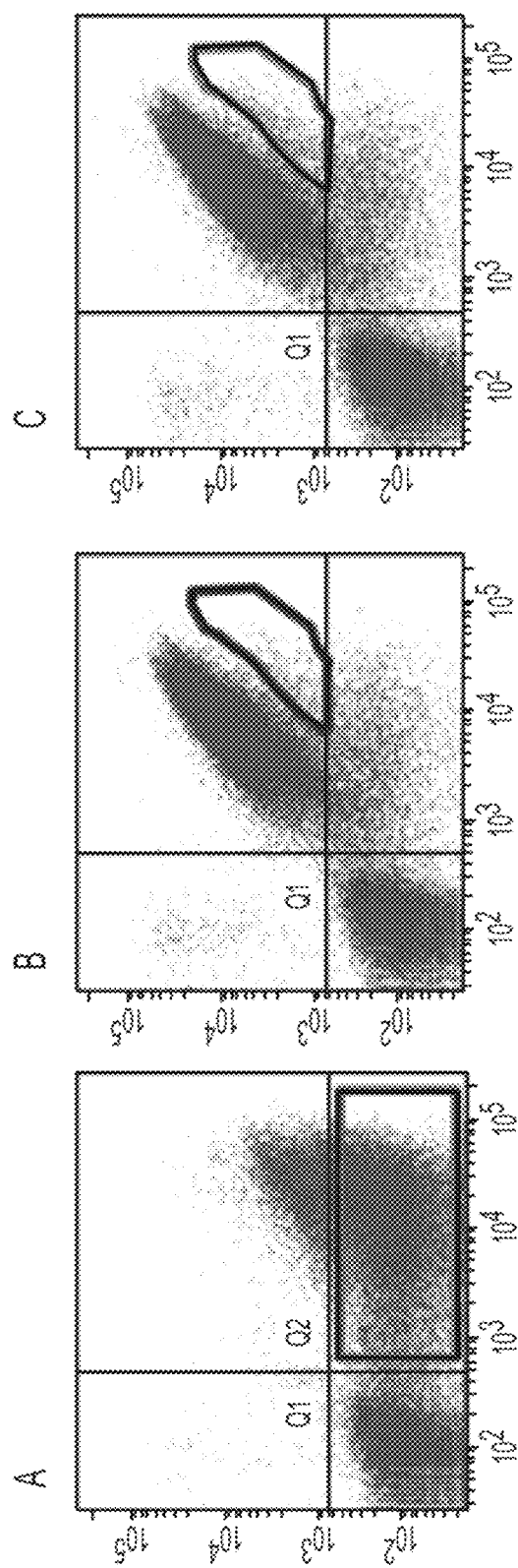

FIG. 70 are graphs showing FACS of the yeast cells derived from Protocol 1. A, Cells showed significant background signal when incubated with biotin-BSA (see Q2). Clones outlined in red were carried forward for subsequent selections. B, Yeast cells from A were incubated with biotin-BSA-phenanthrene. C, Yeast cells from A were incubated with biotin-BSA-phenanthrene+200 µM soluble phenanthrene. Cells in the red circle were collected for further analysis.

Figure 71:
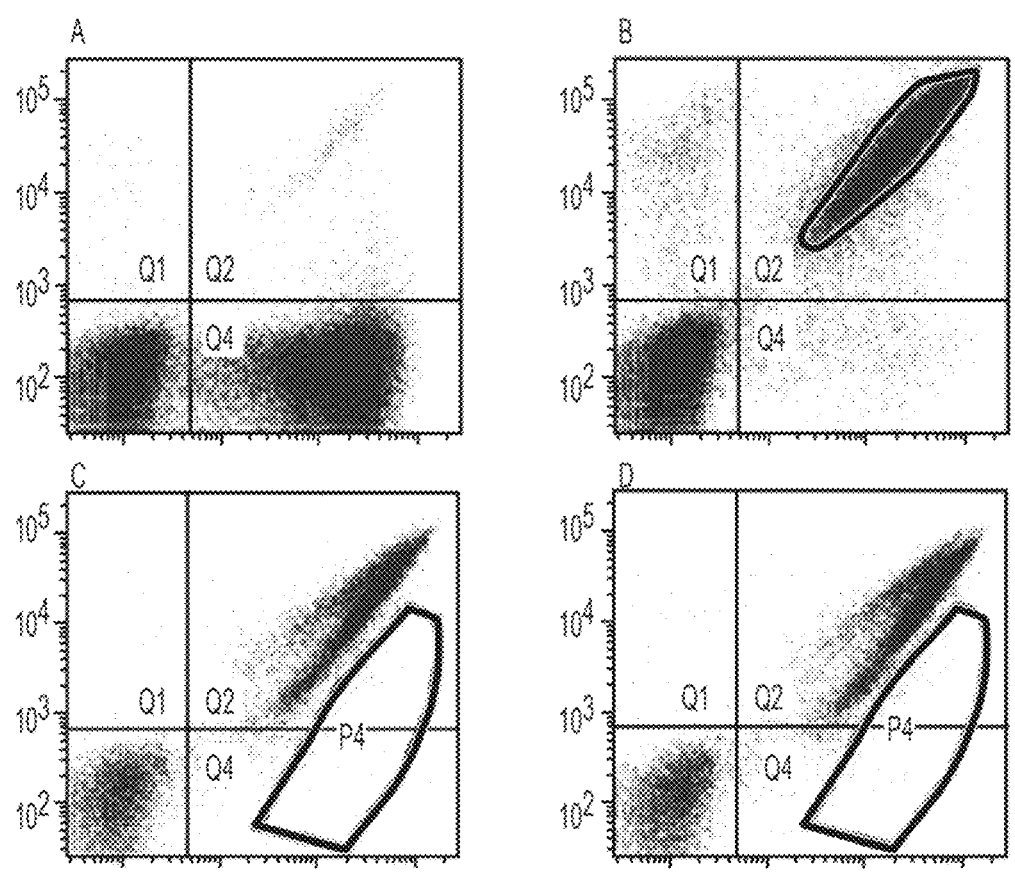

FIG. 71 are graphs showing FACS of yeast cells derived from Protocol 2. A, Cell with BSA-biotin (negative control). B, Cells incubated with biotin-BSA-2-methylphenanthrene. High affinity binders from this pool were selected as outlined in red. C and D, Yeast cells from the positive sort shown in B were incubated with biotin-BSA-2-methylphenanthrene in the absence (C) or presence (D) of soluble 2-methylphenanthrene.

Figure 72:
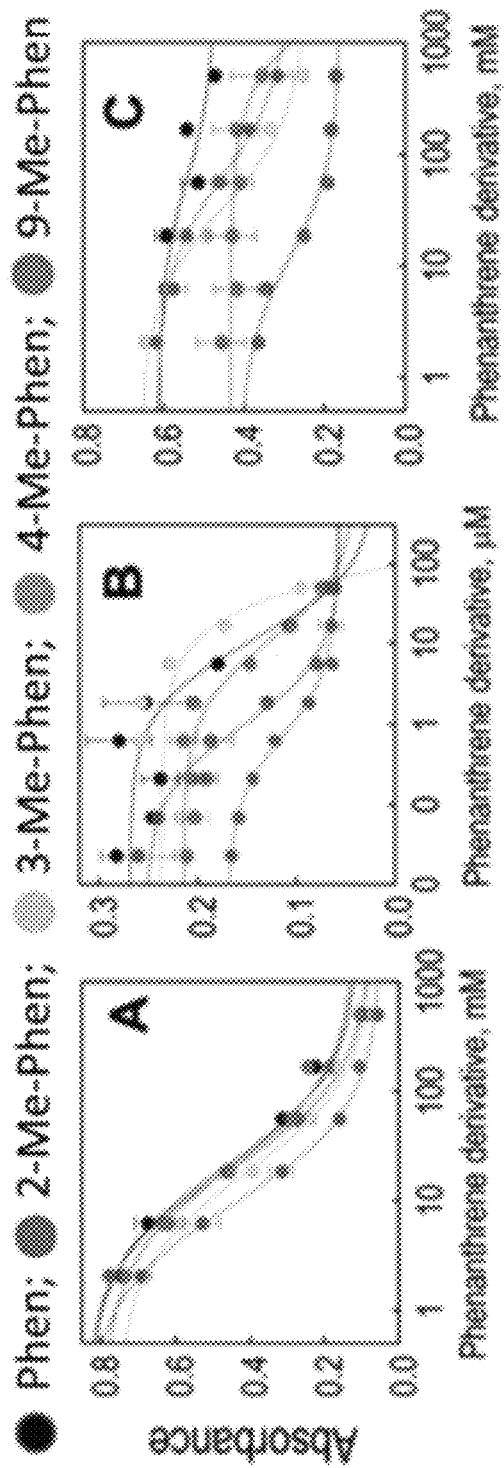

FIG. 72 are graphs showing results from a competitive ELISA. Purified scFvs from clones D7 (Panel A), G8 (Panel B) and A10 (Panel C) were incubated in microwell plate coated with phenanthrene-BSA in the presence of varying concentrations of competitors.

FIG. 73 shows mouse immunization procedures.

Figure 74:
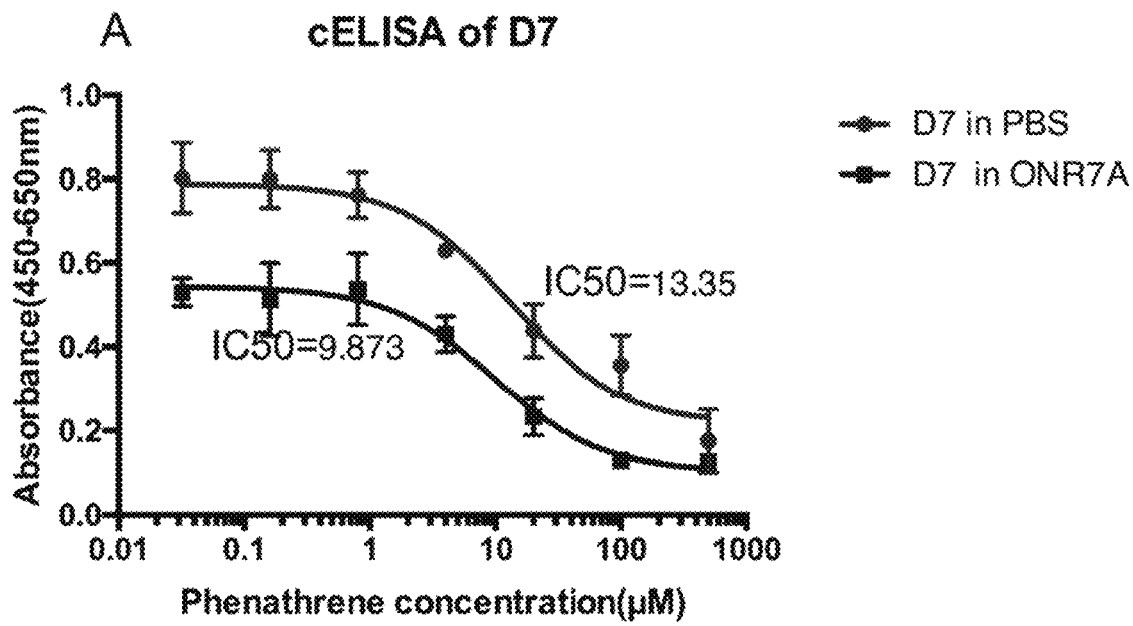

FIG. 74 is (A) a graph showing a comparison of competitive ELISA for phenanthrene, an abundant PAH in crude oil, in phosphate-buffered saline (ionic strength of serum) and ONR7a, an artificial environmental matrix that mimics seawater. The limit of detection of phenanthrene in this matrix is ~1 µM. Compared with two buffer PBS and ONR7A (article seawater), the IC50s of two curves were no different than 2 fold.

Figure 75:
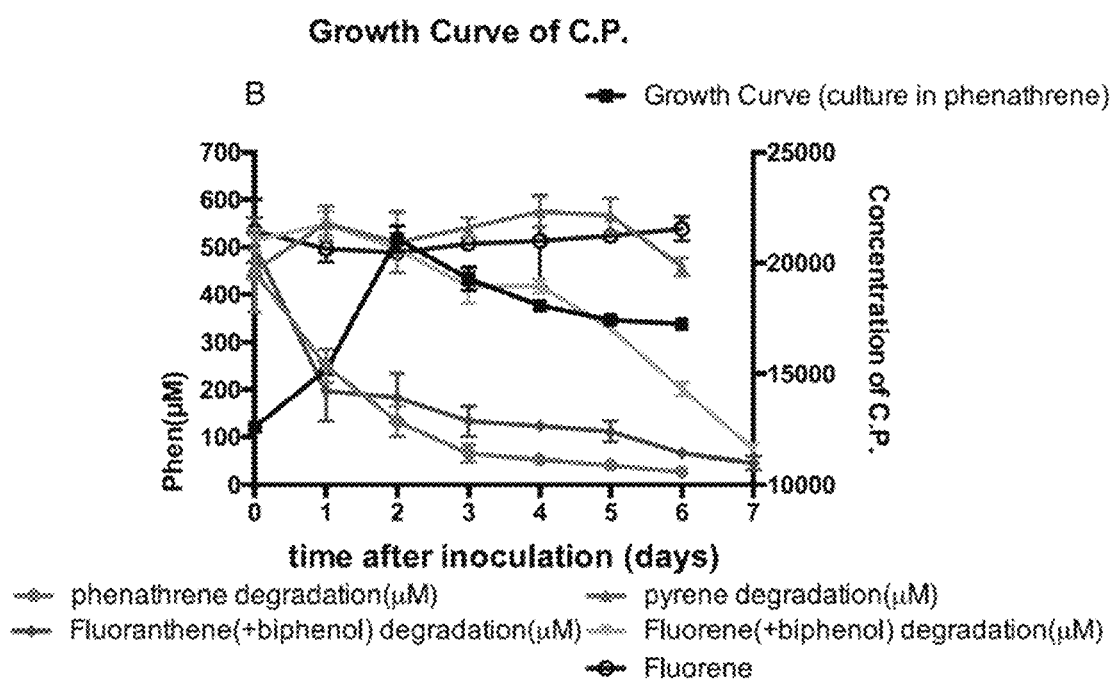

FIG. 75 is (B) a graph showing growth of C. pugetii in ONR7a (black squares and line) the presence of phenanthrene. Also shown is the degradation of individual PAHs (phenanthrene, brown; fluoranthene, red; fluorene, blue and green; and pyrene, magenta), as determined by the D7 antibody. Using this assay system, we were able to show that an additional component (biphenol) was important in stimulating the degradation of fluorene and fluoranthene. 4 kinds of PAHs were tested by antibody D7. Phenanthrene, fluorene and fluoranthene with biphenyl degradation can be detected. Solo pyrene and fluorene had no significant degradation.

Figure 76:
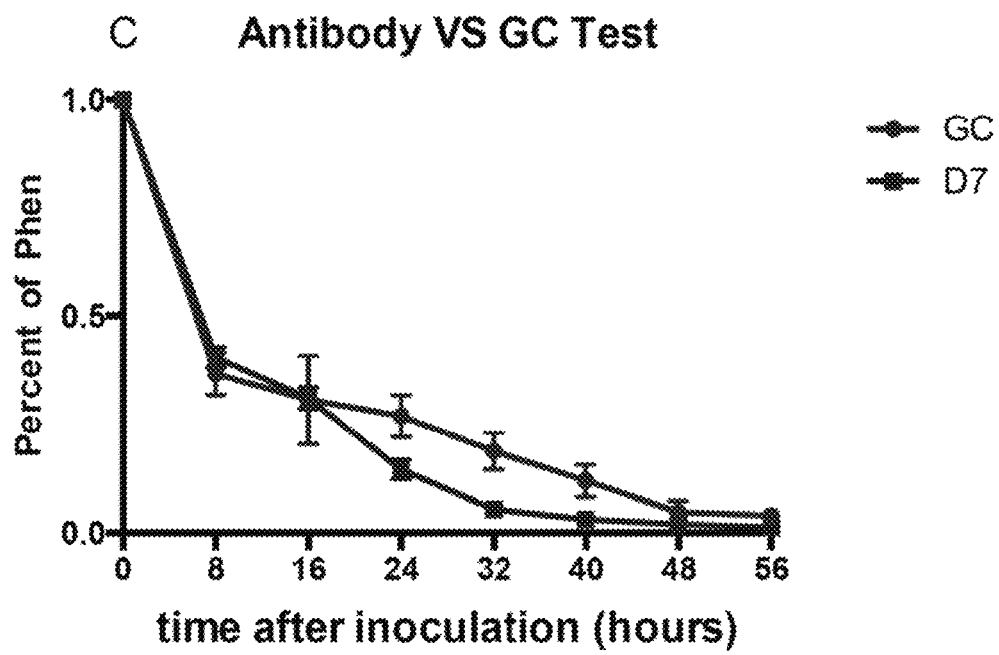

FIG. 76 is (C) a graph showing a comparison of competitive ELISA using the D7 antibody and GC in determining the time course of phenanthrene disappearance for 48 h after inoculation of a C. pugetii culture into synthetic seawater (ONR7a containing 500 µM phenanthrene and 1% DMSO). The phenanthrene degradation data was matched with gas chromatography.

Figure 77:
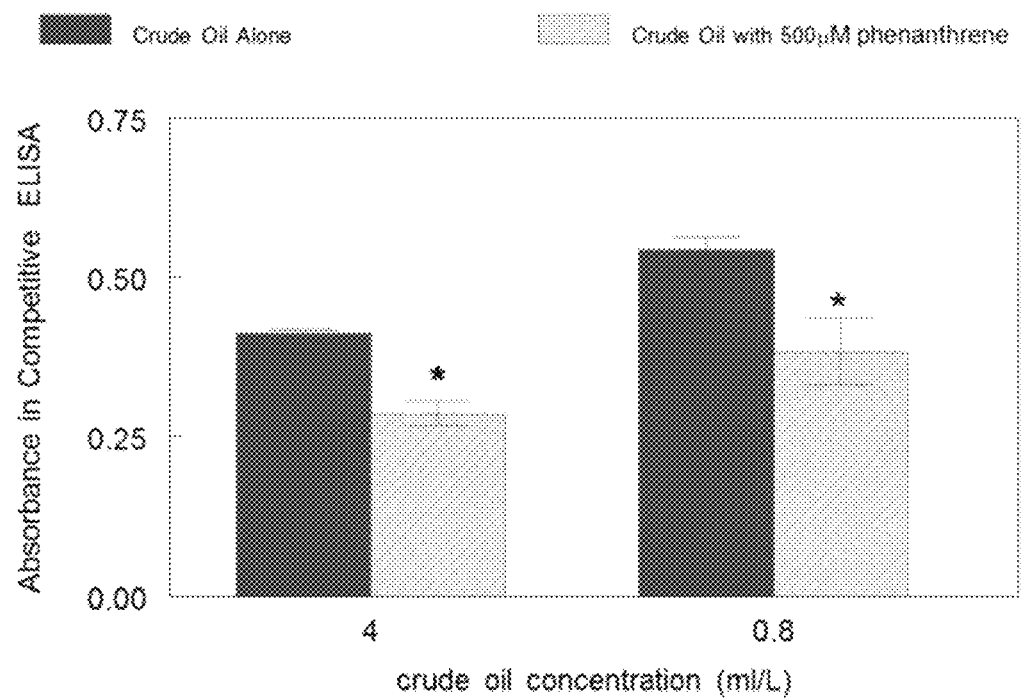

FIG. 77 is a bar graph showing that the D7 antibody can detect the model PAH, phenanthrene in a background of crude oil (4 and 0.8 mL/L). At both concentrations of crude oil, the presence of 500 µM phenanthrene decreased the absorbance in the immunoassay by 30% (*, $p<0.05$).

Figure 78:
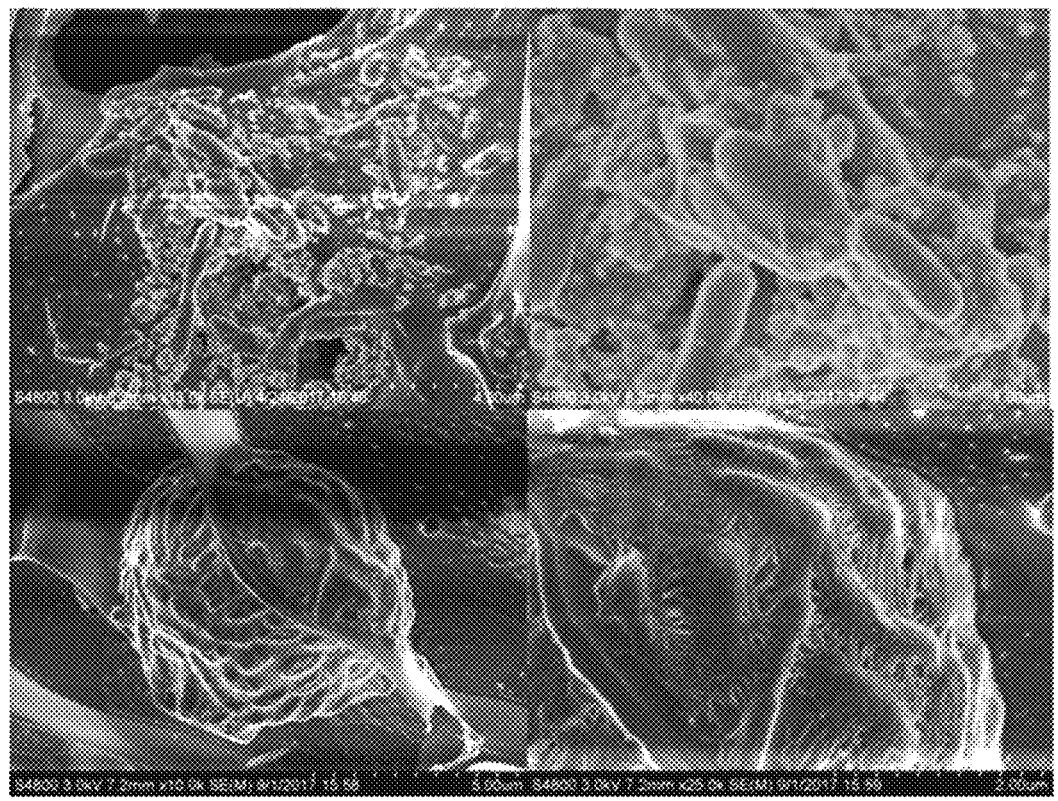

FIG. 78 are photographic images of the appearance of C. Pugetti in different carbon source under Cryo-electron Microsocopy (CEM). C. Pugetti is gram negative bacteria, which is one of the most common marine bacteria. C. Pugetti can degrade carbon source in crude oil, particularly, C. Pugetti has high ability to utilize PAHs (Phenanthrene, biphenyl and so on). A is the appearance of C. Pugetti cultured with phenanthrene crystal as solo carbon source. When cultured in crude oil, the bacteria can form biofilm significantly. The hydrophobicity of oil drop would also be increased by biofilm. The oil drop are attached by C. Pugetti on the surface (B).

FIG. 79 are graphs showing growth curves of C. Pugetti. The PAHs have 2-8 fused aromatic rings, meaning the solubility of PAHs is low. (A) The biphenyl crystal, which has 2 rings, can support C. Pugetti to grow up in the media in 7 days, the phenanthrene crystal (solubility lower than biphenyl by 1000 fold) is not a fast growth carbon source. (B) As the media was added 1% DMSO, 500 uM PAHs can be dissolved, and the bacteria can grow. As the low quantity carbon source cannot support high concentration bacteria, resazurin assay was used to test the growth. Phenanthrene is the targeted carbon source, which can highly support C. Pugetti growth. With biphenyl support, fluorene and fluoranthrene can also support the bacteria growth.

FIG. 80 are graphs showing that different pH environment can affect both C. Pugetti growth and antibody affinity. See panels A-D. C. Pugetti can change the pH environment in the artificial seawater (A). The acid environment can inhibit C. Pugetti growth, bis-tris was applied instead of TAPSO to stabilize pH environment (A)(B). In addition, the variable pH environment can effect the antibody affinity to soluble phenanthrene. pH=8.0 and pH=7.6 were most appropriate pH environment.

Figure 81:
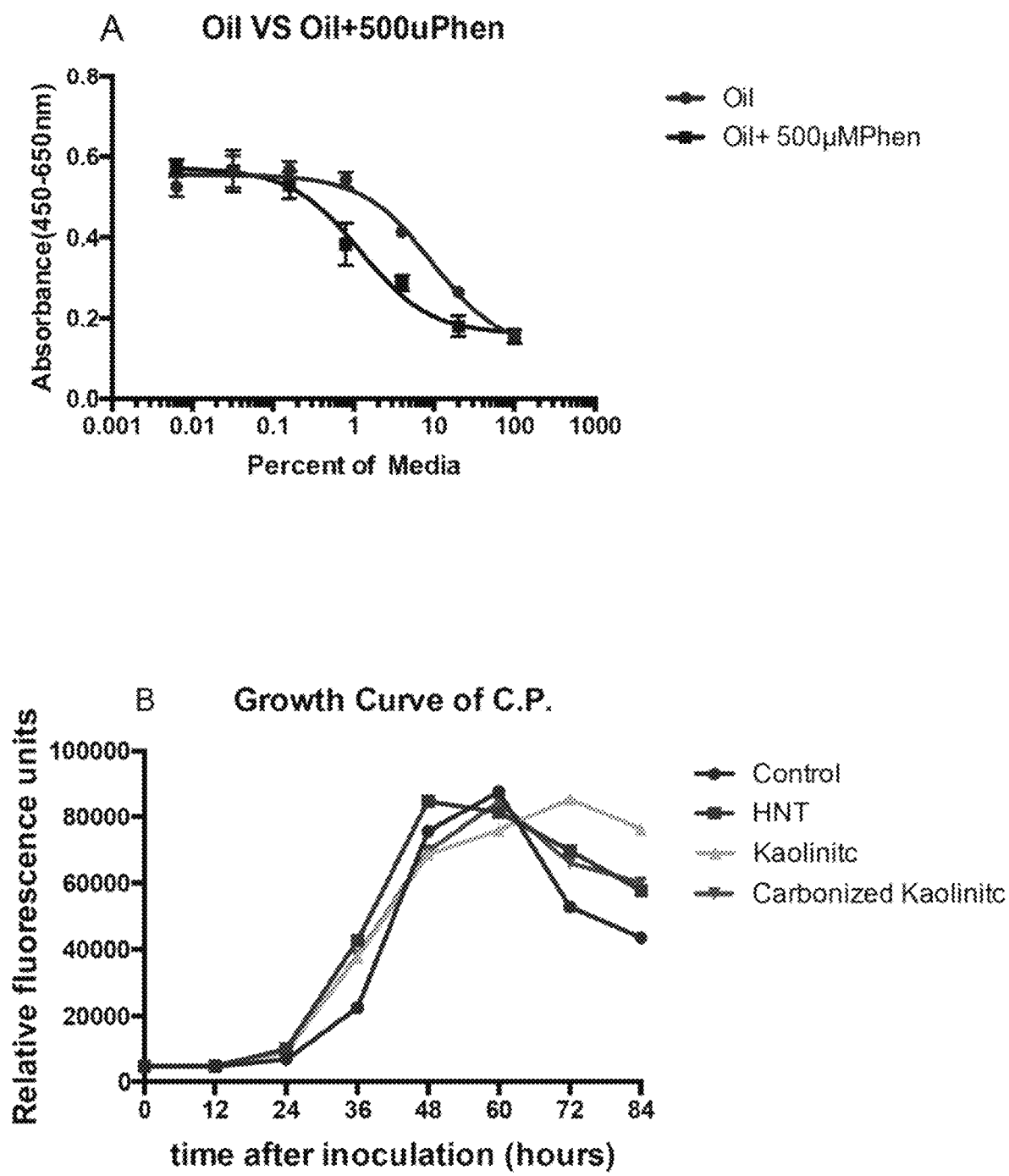

FIG. 81 are graphs showing that halloysite clay nanotubes can promote C. Pugetti growth and crude oil degradation. The competitive ELISA of crude oil and crude oil spiked with 500 uM phenanthrene showed the D7 antibody still has affinity for phenanthrene in crude oil contaminated seawater (A). As nanotubes were added (HNT, kaolinitc or carbonized kaolinitc), the growth of C. Pugetti was in advance nearly 12 hours (B). Phenanthrene degradation in the crude oil brought forward near 12 hours by adding HNT (C).

Figure 82:
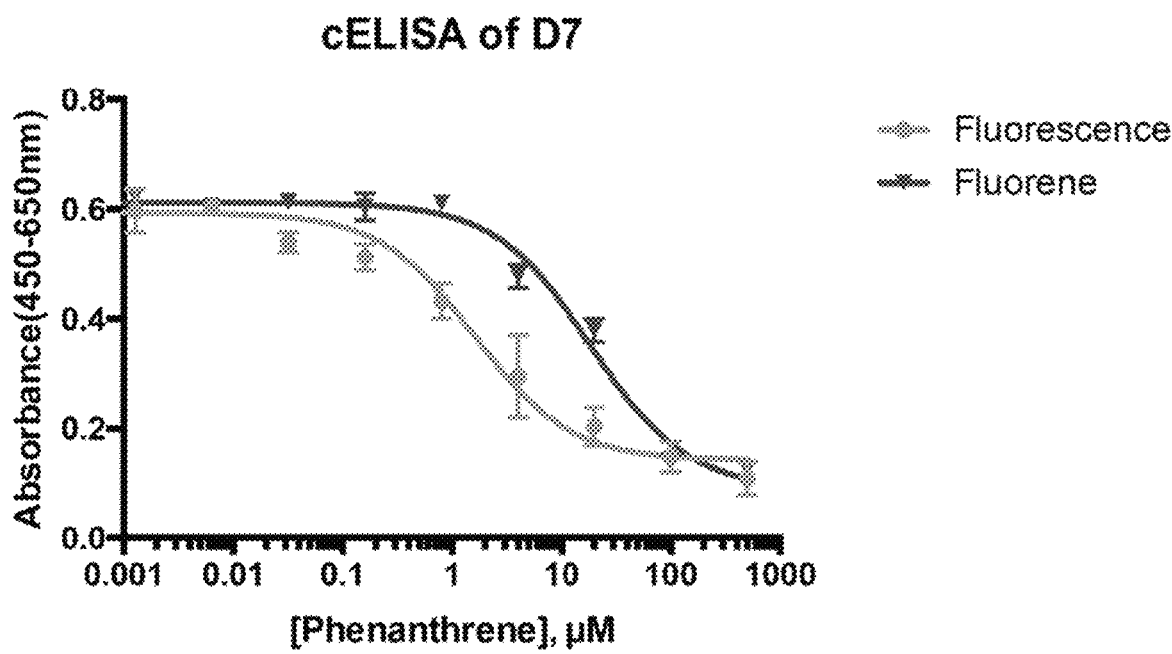

FIG. 82 is a graph showing the detection of other PAHs. The antibody can also detect fluorene and fluorescence. It has higher affinity for fluorescence (IC50=1.6 mM)

Figure 83:
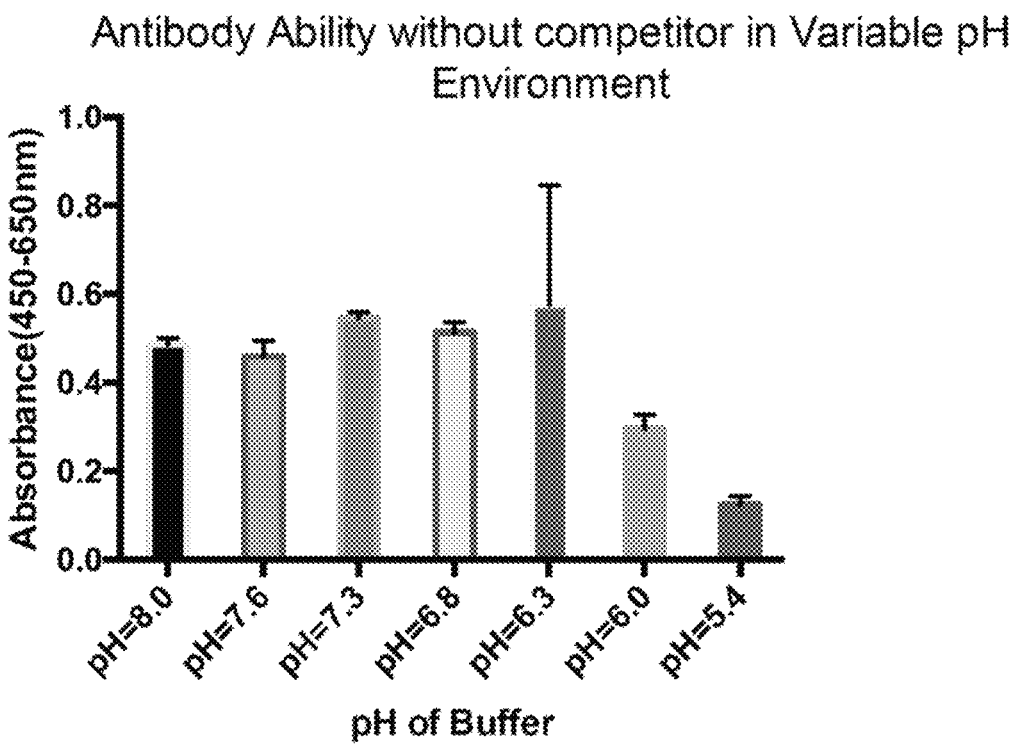

FIG. 83 is a bar graph showing the effect of pH change on the interaction with the tag on the antibody. The different pH buffers did not inhibit the antibody tag strongly, except at pH=6.0 and pH=5.4, which were at low pH.

Figure 84:
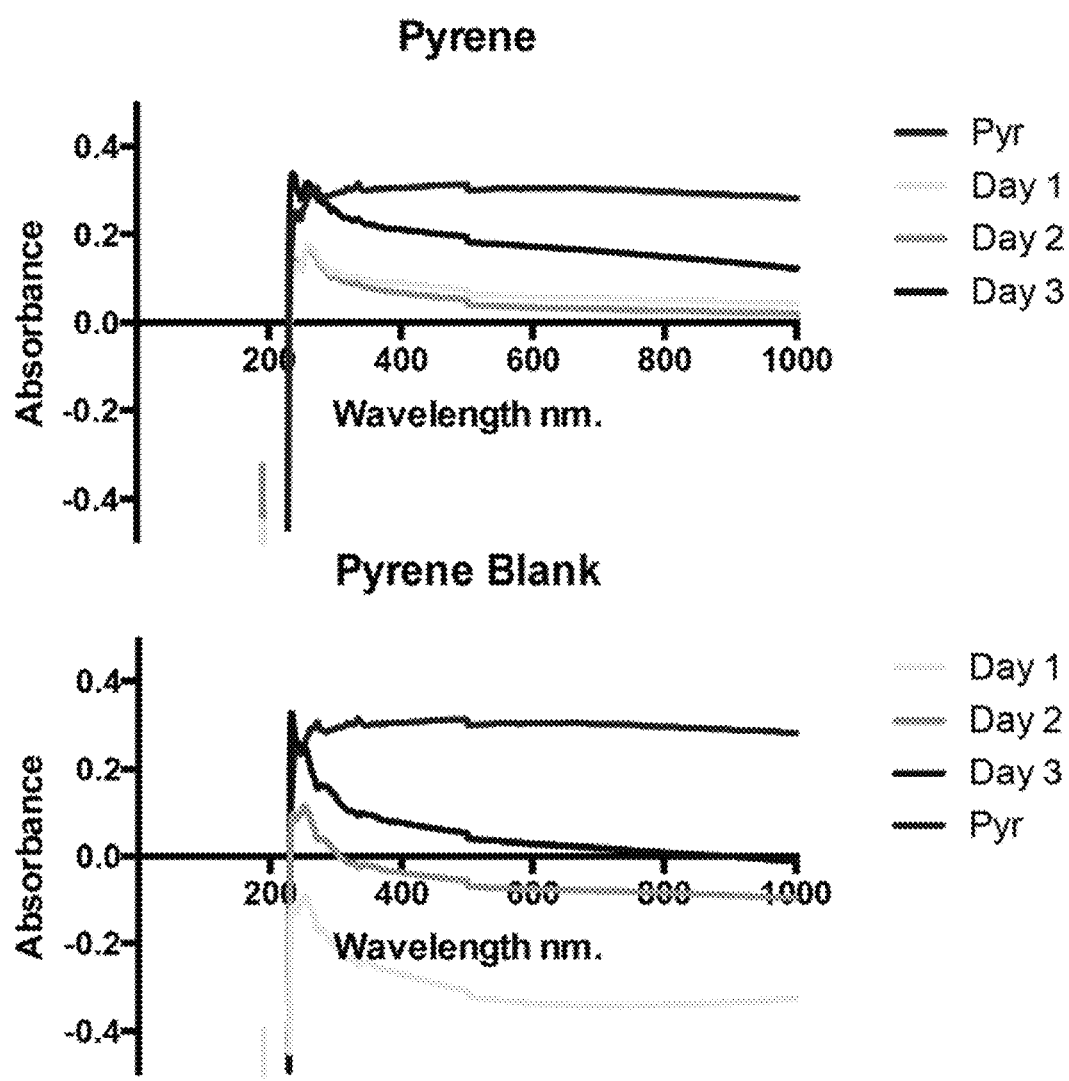

FIG. 84 are graphs of spectrum results of 3 Days Culture and Blanked by PAHs pyrene and phenanthrene. Different PAHs were applied as a solo carbon source, cultured in 3 days, then the 3 days culture media samples were scanned by spectrum separately, where the original media served as a control (Blank solution was ONR7A). Original media was then used as a blank scan. The spectrum results show the color change, indicating the PAHs had joined the reaction.

Figure 85:
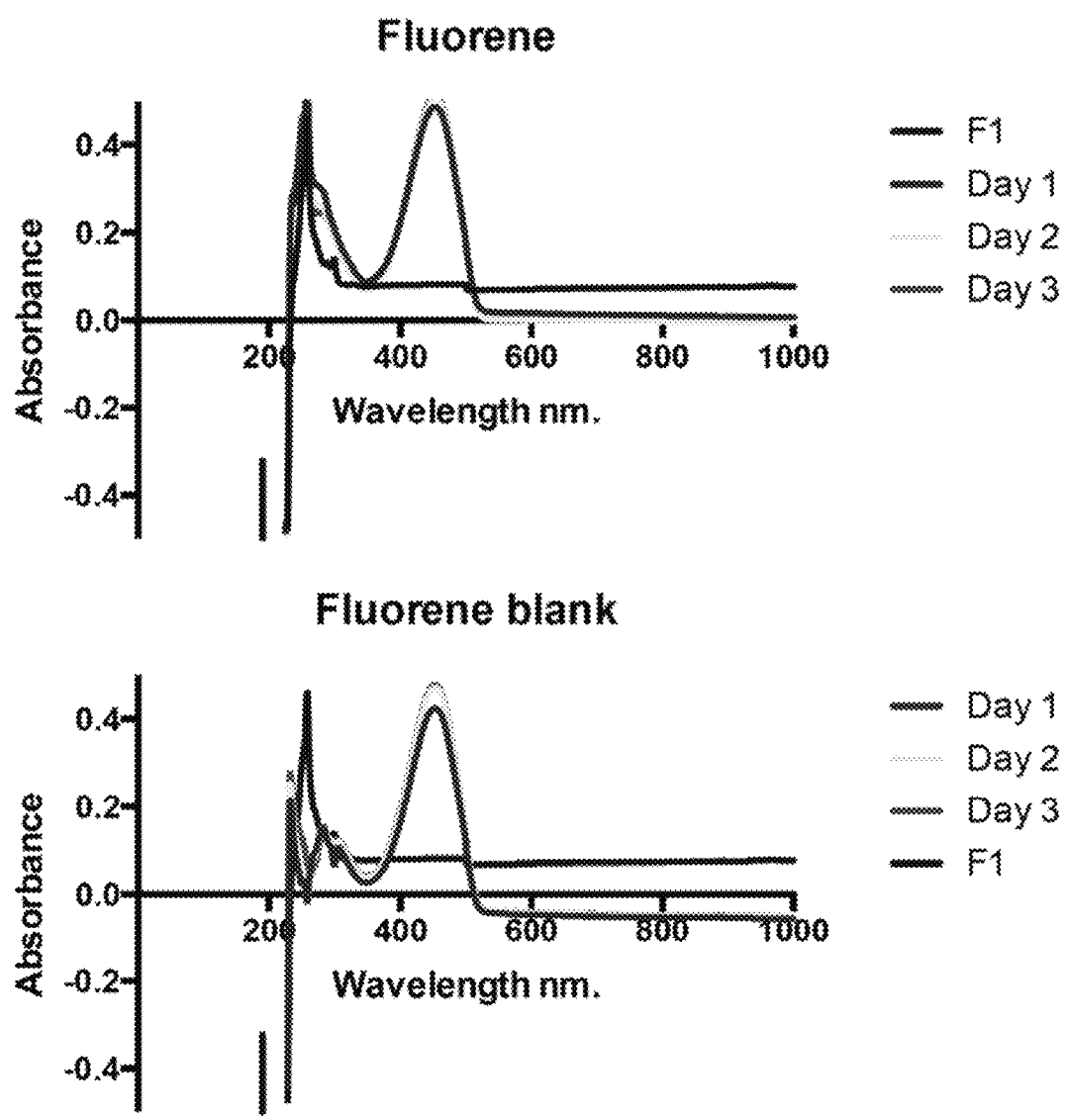

FIG. 85 are graphs of spectrum results of 3 Days Culture and Blanked by PAHs fluorine, biphenyl, fluorine+biphenyl, and fluorescence. Different PAHs were applied as a solo carbon source, cultured in 3 days, then the 3 days culture media samples were scanned by spectrum separately, where the original media served as a control (Blank solution was ONR7A). Original media was then used as a blank scan. The spectrum results show the color change, indicating the PAHs had joined the reaction.

DETAILED DESCRIPTION OF THE INVENTION

Abbreviations and Definitions

Detailed descriptions of one or more preferred embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Petroleum Pollution

Petroleum has long been a vital source of energy for the world, and will likely to remain so for decades to come. However, environmental contamination by petroleum is also a constant problem. Over the past decades, accidental oil spills have occurred around the world and have released large amounts of crude oil into the aquatic ecosystem. These oil spill events pose risks to marine life, endanger the ecosystem, and ultimately jeopardize human health through bioaccumulation in seafood.

The world is highly dependent on fossil fuel. Petroleum makes up more than 80% of the total energy consumption even with the rapid development of other forms of clean energy such as solar, wind, nuclear energies (FIG. 14). Worldwide, there has been an increasing need for energy in the last ten years, and this growth is unlikely to stop within few decades. Petroleum (or oil in FIG. 14) accounts for one-third of total energy demand; this energy source will be irreplaceable in the short term. Due to its fundamental role in global energy consumption, petroleum has a great impact on human life, including the world economy and social stability.

Petroleum is essential in almost every aspects of society, but can be problematic when it enters the environment without proper control. Crude oil in waters is of most concern because of its toxicity to marine life and its resistance to rapid biodegradation. Part of aquatic petroleum contamination is from natural seeps, which are a common, but relatively unstudied geologic feature. This type of contamination is not of much concern, because the petroleum is normally released at very slow rates under low pressure. The organisms around the seepage are adapted to the environment and some even metabolize it as an energy source. (Haritash and Kaushik, 2009; Heitkamp et al., 1988; Volkering et al., 1992) In contrast, anthropogenic oil spills occur during petroleum extraction, transportation and consumption. When these spills occur, the petroleum is released in high amounts, and because of industrial refinement, the composition of anthropogenic spills are often more toxic, and therefore more detrimental to the environment than natural seeps.

The petroleum in the waters endangers animals ranging from dolphins, turtles and seabirds to single-celled plankton, and affects marine lives by direct ingestion and inhalation or by external exposure through skin, eyes and feathers. Dolphins and whales can inhale oil through their blowholes when coming up to breathe on the surface; seabirds whose feathers are covered by oil on their feathers have difficulty flying and lose insulation ability. Vulnerable fish eggs and larvae are directly killed by petroleum exposure.

FIG. 15 lists the top ten largest oil spill accidents in history; each has released hundred millions of gallons of oils into waters. In 2010, the explosion of BP's Deepwater Horizon (DWH) oil rig released 170 million gallons of oil into Gulf of Mexico, ranking for the third largest oil spill accident in the world (FIG. 15). More than 8,000 birds, sea turtles, and marine mammals were found injured or dead in the six months after the spill. Dead and dying deep sea corals were discovered seven miles from the Deepwater Horizon well. The dolphins in Barataria Bay, a heavily-oiled area of the Louisiana coast, were shown to suffer from severe lung diseases (Schwacke et al., 2014) About 48 percent of tested dolphin in this population were seriously ill, and 17 percent were not expected survive. The number of sea turtles found stranded in the oil-contaminated area was five times above historical levels, and 75 percent were the highly endangered Kemp's Ridley turtles, which nest only in the Gulf of Mexico. (Inkley et al., 2013) The DWH spill also increased the risks to humans, especially for those in local communities and for workers involved in clean-up efforts. The volatile components of petroleum evaporate into the air, and were inhaled by the people nearby, while liquid products were absorbed through skin contact. Upon initial exposure to large quantity of petroleum, residents near the contaminated area were found to show a number of acute symptoms, including neurological problems (e.g. headaches, nausea), ocular disturbances (eyes), and respiratory distress. ((US). 2010) Chronic exposure to petroleum has been associated with higher incidence of multiple cancers including nasal, kidney, lung cancers and acute leukemia etc. (Lynge et al., 1997; Patel et al., 2004) In addition, a large quantity of dispersants was used to clean up the oil spills, and its effects on the ecosystem are largely unknown.

Petroleum Composition

Petroleum is formed by decomposition of ancient marine life under extreme heat and pressure in an anaerobic environment over hundreds of millions of years. The composition of crude oil varies widely from sources, but the major elements are carbon, hydrogen, sulfur, nitrogen, oxygen and trace amounts of metals. Hydrocarbons (solely made of carbon and hydrogen atoms) are the most abundant compounds found in the crude oils, and account for up to 85% of the overall mixture. Among various constituents, polycyclic aromatic hydrocarbons (PAHs), which consist of several fused benzene rings, are the most important pollutants. Benzene rings are very stable, and therefore persistent in the environment; they can also have toxic effects on organisms.

Because of the complexity of the PAH mixtures in the natural environment, the study of PAHs was hampered in the 1960s due to the lack of common standards for the research community. There was an urgent need to reduce a group of thousands of relevant compounds down to a representative handful. In 1976, the US Environmental Protection Agency (EPA) designated a list of 16 PAHs as priority pollutants (FIG. 16). This list was initially determined based on three criteria: the availability of analytical standards for these compounds in their pure forms; their occurrence in the environment; and demonstrated toxic effects in previous studies. (Keith, 2014) To strive for a clear resolution of standard compounds, the PAHs listed have been carefully separated and characterized, accompanied by the development of analytical sciences. (Wise et al., 2015) The idea of including a manageable number of compounds into a short list of standards has gained a tremendous success in the area of environmental determination of PAHs over past 40 years. As widely adopted, this standardized set of 16 analytes makes various pieces of experimental data comparable to one another, and surely promoted the advancement of PAH research.

After 40 years of study, an enormous knowledge of PAH environmental toxicity has been gained by using this 16 standard, selected PAHs. However, a large quantity of data also revealed other PAHs (such as alkylated PAHs, larger PAHs, and heterozygous PAHs) can be more relevant in certain applications than the EPA-selected 16 PAHs. The traditional list encompasses only unsubstituted PAHs, whereas methylated derivatives have not been specially distinguished and analyzed. However, methylated PAHs account for a relatively large proportion of total PAH contaminants and are abundant in cases such as oil spills. (Blumer, 1976) Depending on the contaminant composition, the risks of petroleum PAHs to wildlife can be underestimated by 40 to 70 times if only the 16 parent PAHs are taken into consideration (Barron and Holder, 2003). Recent studies have shown that methylated phenanthrenes comprised a major component of the bioavailable PAHs in the water that reached the shore after the DWH spill, while unmethylated phenanthrene was present at a relatively constant level regardless of the time of sampling (before or after the DWH event. (Allan et al., 2012).

The methyl/alkyl substitutions on the PAHs rings are thermodynamically unstable, and tend to be removed during the combustion process. Therefore, contaminants from pyrogenic source contain only the parent form of PAHs. The characteristic distribution of different type of PAHs is very helpful in tracing the origins of pollution. In fact, the ratio between a methylated versus an unmethylated PAH (phenanthrene, for instance) has been used to identify the sources of PAH contamination, i.e., whether it is of petrogenic or pyrogenic origin (Boonyatumanond et al., 2006; Saha et al., 2009).

Toxicity of Methylated PAHs

Polycyclic aromatic hydrocarbons (PAHs) in petroleum are of greatest concern due to their abundance, persistence, genotoxicity, carcinogenicity, and toxic effects on immune and reproductive systems and development. PAHs consist of multiple aromatic rings, with occasional substitution with alkyl groups around the benzene rings. Most previous studies have focused on unsubstituted PAHs, while methylated structures have not been specially distinguished and analyzed. However, the methylated derivatives account for a relatively large proportion of total PAH contaminants in cases such as oil spills. Among the PAHs present in the environmental samples, phenanthrenes are often one of the most abundant families. At present, the toxic effects of petrogenic PAHs have not been fully characterized, and the significance of the alkyl substitutions on the toxic effects in a unified system that analyzes specific steps in the processes that lead to toxicity is addressed herein.

The presence of PAH in the environment generates public health concerns, because of their abundance, persistence, genotoxicity, and carcinogenicity, their toxic effects on immune and reproductive systems and their ability to disrupt development (Cerniglia, 1992; Pfeifer et al., 2002). Most toxicological studies have been focused on the unsubstituted PAHs, especially the 16 PAHs on the EPA priority pollutant list. In recent years, more attention has been drawn to the PAH derivatives. Limited evidence has shown that methylation on the aromatic rings can significantly change the toxicological properties of PAHs. For instance, two methyl groups on the PAH, 7,12-dimethylbenzo[a]anthracene, creates a 20-fold higher carcinogenic effect than the parent compound; measured carcinogenicity was twice that of benzo[a]pyrene (a well-known PAH carcinogen) (Phillips et al., 1979). Structure-activity studies of PAH compounds have shown that the carcinogenic activity of methylated PAHs were comparable, if not higher than, that of non-methylated parental PAHs (Vendrame et al., 1999). Another study demonstrated that retene (7-isopropyl-1-methylphenanthrene) showed greater toxicity than unsubstituted phenanthrene in vivo; this compound delayed larvae development of marine fish and increased the mortality rate, as compared to the parent compound (Mu et al., 2014). These results highlight the importance of including methylated PAHs in future analyses of the toxicological properties of environmental samples.

Among the PAHs present in the environmental samples, methylated phenanthrenes are often one of the most abundant families (Chernova et al., 2001; Wang et al., 2011). The parental form of phenanthrene is considered as non-toxic, while a limited study of methylated phenanthrenes showed that they had weak mutagenicity or carcinogenicity in some model systems (LaVoie et al., 1982; LaVoie et al., 1981; Vondracek et al., 2007). Despite the abundance and toxic significance of methylation substitutions among PAHs, information regarding the toxicity of methylated phenanthrenes is inadequate, and far from systematic. Most data depends on a variety of experimental models or analysis of different steps that lead to toxic responses. When comparing effects of phenanthrene and its methyl-substituted derivatives, it is important to systematically study these compounds in a unified system that assesses specific steps in the processes that lead to toxic effects. However, the toxicity of methylated phenanthrenes is not well understood.

The toxicity of PAHs in mammals is mediated almost exclusively through the aryl hydrocarbon receptor (AhR) signaling pathway (Abel and Haarmann-Stemmann, 2010; Feng et al., 2013). The AhR is a ligand-activated transcription factor that directly binds and is activated by a wide variety of xenobiotics. AhR occurs in cells with its heterodimeric partner, the aryl hydrocarbon receptor nuclear translocator (ARNT), and together they form the aryl hydrocarbon receptor complex (AhRC). AhRC binds a DNA sequence called xenobiotic responsive element (XRE) and mediates downstream gene regulation. In the presence of PAHs, AhR can be activated by ligand binding, which subsequently induces drug-metabolizing enzymes for metabolism or clearance of the foreign compounds. PAHs often induce their own metabolism and clearance via changes in gene expression that are initiated by the ligand-AHRC complex. The metabolic induction initiated by the activated AhRC, however, sometimes creates PAH metabolites that form mutagenic adducts with DNA and proteins. The activation of the AhR is, therefore, an essential step for both PAH metabolism and toxicity. An example of this receptor-mediated relationship with toxicity is provided by the resistance of benzo(a)pyrene induced carcinogenesis in mice that are genetically engineered to lack AhR (Shimizu et al., 2000).

As discussed herein the examples, the inventors employed a yeast bioassay to measure the intensity of PAH-mediated AhR activation and signaling (Sun et al., 2014). The activation of AhR signaling pathway is a model to compare toxicities of various methylated phenanthrenes in a single system, since it is important to subsequent PAH toxicity in a wide variety of cell types and was therefore a reasonable 1st step as an indicator for potential toxicity. In one embodiment, the invention is directed to using the high ratio of methylated versus unmethylated phenanthrenes as an indicator of petrogenic contamination rather than pyrogenic origins.

Analytical Methods for PAH Detection

Extraction Techniques for PAHs in Field Samples.

PAHs in the field are present in a complex matrix, and a pre-cleaning step is often necessary to extract them into relatively pure forms before they can be accurately analyzed. There are a wide variety of solvent extraction techniques used, from traditional methods (Soxhlet extraction, ultra-sonication, mechanical shaking) to more advanced techniques (accelerated solvent extraction (ASE), supercritical fluid extraction (SFE), microwave-assisted extraction (MAE) etc). (Lau et al., 2010) These liquid-liquid techniques offer comparable extraction efficiencies, while advanced techniques are less time-consuming compared to traditional Soxhlet method. (Hollender et al., 2003; Wang et al., 2007).

The solid phase extraction method (SPE) provides a rapid, easy-to-perform alternative (Juhascik and Jenkins, 2009; Lau et al., 2010; Li and Lee, 2001) which can be used for on-site analysis. PAHs from samples are retained on the solid phase by specific sorbent, while other contaminants including salts are removed through several wash steps. Finally, adsorbed PAHs can be eluted in a small volume of solvent, which serves to both clean up and concentrate the analytes. The SPE kits have been developed commercially (Supra-Clean® SPE application pack offered by Perkin Elmer, PAH RaPID™ Assay offered by Osprey Scientific Inc), which makes on-site analysis much easier.

Current Technology for PAH Measurement.

Most analytical methods for detecting and measuring PAHs employ gas chromatography-mass spectrometry (GC-MS) or high-performance liquid chromatography (HPLC). Both methods separate the analytes based on their polarities, and directly identify each compound by the detector (a mass spectrometry for GC, and a UV or fluorescence detector for HPLC). Most research groups and federal agencies routinely use these methods as standard protocol for environmental sample analysis. However, both GC-MS and HPLC require high sample purity, as they are too sensitive to the compounds in the sample matrix with physical properties similar to PAHs. Besides, the instruments are expensive and laboratory-based, limiting their applications only to a small number of research units.

Efforts have been made to extend these applications in the field, after 20+ years of development reliable field-portable GC-MS instruments are finally becoming available. Since the emergence of first field portable GC-MS, the performance has been improved to reach laboratory-based analysis level. (Bednar et al., 2011) The major obstacle lies on the high-cost of the system, which can be over $100,000 to start up. And the battery can only hold at most 3 hours for most models, which limits its portability close to a power source. It still requires certain expertise, and therefore cannot be easily accessed by the general public.

Immunoassays as New Methods for Environmental Analysis.

Immunoassay is a classic antibody-based biochemical test first introduced in 1950s by the Nobel Prize winners Yalow & Berson (Yalow and Berson, 1959). They showed the high sensitivity of the immunological assay by detecting pico-gram level of human insulin in small volume of blood. Natural antibodies are produced by plasma cells as a defensive weapon against pathogens in the immune system. Because an antibody can specifically recognize its target, also known as an antigen, in a complex mixture with great sensitivity, it has been used in pharmaceutical, agricultural and research areas. (Darwish, 2006; Samarajeewa et al., 1991) With recombinant technologies, antibodies can now be engineered with additional functions or be directed towards new targets such low molecular-weight haptens. Its applications therefore have been extended to environmental studies as an alternative to analytical methods. (Diana and Thurman, 1997; Knopp, 2006; Lesnik, 2006; Sherry, 1997) Compared to conventional methods such as HPLC or GC, immunoassays provide outstanding advantages:

(1) Sensitive and Specific.

An antibody interacts with its ligand via a specific binding pocket that was customized for the ligand during the antibody development. Therefore, the antibody is able to identify selected target regardless of millions of other compounds in the matrix. Although the sensitivity of immunoassays varies depending on the affinity of the antibody used, the affinity of an antibody can easily reach micromolar to nanomolar level and can be further improved to picomolar after in vitro maturation process (Bostrom et al., 2009; Rajpal et al., 2005)

(2) Rapid and Easy to Use.

If the antibody is tolerant to certain matrix or solvent, the pretreatment step (sample cleanup, extraction or concentration) can be omitted. This saves the time and cost for processing the large volume of environmental samples, and also avoids the sample lost during the process. Some immunoassays, such as ELISA, can perform samples in parallel, and largely reduce the assay time for multiple samples.

(3) Cost-Effective.

Traditional methods require sophisticated analytical instrument and well-trained technicians to perform such assays, and the running reagents are expensive as well. On contrary, the cost of immunoassay is mainly due to the cost of developing antibody and early phase assays. Once suitable antibody has been generated, other cost for assay performance is negligible. On average, the cost of an immunoassay can be ten-fold lower than that of analytical method per assay. (Plaza et al., 2000; Szurdoki et al., 1996)

(4) Portability.

Since an immunoassay is simple and easy to set up, the assay can be performed directly on-site, whereas the analytical instrument limits the traditional methods to a laboratory setting. Traditionally, the number of samples to be detected was limited by the volume that can be transferred to an off-site laboratory; while for an on-site test there is no limitation for the sample volume. Hence, immunoassays can be used to pre-screen the environmental samples on-site and reduce the number of samples that are of interest for further study by analytical methods.

Immunoassays have been developed into various formats to meet specific application requirements. Two types of immunoassays are described and compared. Enzyme-linked immunosorbent assay (ELISA) is a type of immunoassay used for environmental analysis, and commercial ELISA kits are available for pesticides, carcinogenic organics, and toxins. Immunosensor that involves kinetic exclusion analysis (KinExA) is an advanced analytical technique, which directly measures the concentrations of unmodified analytes in solution. KinExA-based immunosensors can be set up to run a large number of samples automatically, and the filed-portable sensor model also allows analysis to be performed on-site.

The Enzyme-Linked Immunosorbent Assay (ELISA) is an immunoassay format used due to its simplicity and ease of performance. A typical ELISA involves an antibody reagent specifically recognizing the target antigen, and the affinity of binding between antibody and antigen is measured by the labeled enzyme such as horseradish peroxidase (HRP) or alkaline phosphatase (AP). ELISA can be performed in various formats, and common types include direct ELISA, indirect ELISA, sandwich ELISA, and competitive ELISA (FIG. 17). Direct ELISA involves attachment of the antigen to the polystyrene plate followed by incubation with an enzyme-labeled antibody. Indirect ELISA also involves the antigen-attachment step, but in this case, the primary antibody is not labeled. An enzyme-conjugated secondary antibody, directed at the first antibody, is then added. This format is used most often to screen specific antibodies from serum. Sandwich ELISA uses an unlabeled antibody, instead of the antigen, as capture reagent. Samples containing known or unknown antigen are then captured by the coated antibody. An enzyme-labeled antibody is then added for detection. The last type of competitive ELISA is modified from indirect ELISA, which involves the simultaneous addition of 'competing' ligand with primary antibody. The decrease in signal of samples where the second antibody is added gives a highly specific result. For environmental analysis, the pollutants are small molecular weight haptens, and cannot be labeled or attached onto plastic surface. Therefore, the competitive ELISA (cELISA) is most suitable format, as it can detect the ligand in the label-free form. An ELISA method can provide quantitative data when including ligand of interest at various concentrations as reference. The signal generated from the assay can be interpolated from the standard curve to determine the ligand concentration in a field sample. Alternatively, the test can also be configured to determine if a sample is positive or negative relative to a single standard (a "yes-no" or threshold result).

A relatively new technology, Kinetic Exclusion Assay (KinExA), has been developed to characterize the intermolecular interactions with more kinetic details as compared with an ELISA method (Blake et al., 1999; Darling and Brault, 2004). A typical KinExA instrument contains a flow cell compartment, and the micro-beads bearing the antigen are packed into the flow cell. The ligand-free antibodies in the solution are captured by the packed beads when passing through the flow cell, and the amount of captured antibodies can be quantified by the fluorescence-labeled secondary antibody and the fluorescence detector. The binding kinetics can be easily measured by KinExA. Given sufficient time, the free concentration of antibody can be probed when the antibody and ligand in the solution have reached equilibrium, and the dissociation constant (Kd) can be interpreted from the signal curve fitted at varying concentrations of the ligand. Alternatively, before the solution mixture reaches equilibrium condition, the free concentration of antibody can also be measured as a function of time to determine the association rate ($k_{on}$) or dissociation rate ($k_{off}$). The KinExA-based immunosensors have been developed in field-portable formats. The inline sensor (FIG. 18) mix assay components automatically and can be used to process a large sample set conveniently. The field-portable device (FIG. 18) powered by battery and easily controlled by a laptop. These sensors have been validated to monitor uranium concentration in the field, (Melton et al., 2009) and can be easily adapted for PAH detection if appropriate antibodies are available.

Both methods have been applied in the environmental studies. ELISA-based kits have been made commercially available in detecting total PAHs (e.g.PAH RaPID Assay®), and KinExA-based biosensor was also validated to achieve real-time quantification of PAHs (Spier et al., 2011). However, due to limited antibody availability, these kits cannot differentiate various PAHs or PAHs from different sources (e.g. petrogenic vs pyrogenic PAHs). Therefore, a new antibody that can differentiate PAHs (such as phenanthrene) or even distinguish methylated PAHs over unsubstituted PAHs can be readily incorporated into available platforms to identify the origins of contaminants.

Methylated phenanthrenes are abundant in the crude oil-contaminated waters. A better understanding of natural remediation processes and development of strategies to enhance contaminated site cleanup depends on accurate detection and measurement of contaminants prior to, during and following the remediation process. Immunosensors can be used to detect ligand at extremely low-levels; their sensitivity and potential for automation/high throughput provide new ways to solve problems in field and to improve the interface of environmental detection systems. However, the efficiency of the sensor systems depends highly on the quality of antibody employed.

At present, no immunoassay has been developed to detect contamination from crude oils. Compared to other analytical methods used, for example GC-MS and HPLC, antibody-based assays are much cheaper, faster, and more portable. An embodiment of the invention comprises a method of detecting the presence of a methylated phenanthrene in a sample by contacting the sample with an antibody as described herein for a period of time sufficient for the antibody to bind its target, and determining whether a methylated PAH is present in the sample. In one embodiment, the period of time is one (1) or more minutes. In one embodiment, the period of time is 5 or more minutes. In one embodiment, the period of time is fifteen (15) or more minutes. In one embodiment, the period of time is thirty (30) or more minutes. In one embodiment, the period of time is sixty (60) or more minutes. Non-limiting examples of PAHs include naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene. In one embodiment, the PAH is phenanthrene, Non-limiting examples of a methylated phenanthrene are 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-dimethylphenanthrene (3,6-DMP).

Non-limiting examples of the types of samples which can be analyzed by methods of the invention include environmental samples such as soil, sand, water, air, or any combination thereof; biological samples such as tissues or fluids (e.g. blood, serum); and consumer products such as food. In one embodiment, the sample is a water sample. In one embodiment, the sample is a food, such as seafood. For example, embodiments of the invention can be used to test seafood for the presence of PAHs, or measure the levels of PAHs, after an oil spill or similar contamination event. In another example, embodiments of the invention can be used to detect the presence of PAHs or measure the levels of PAHs in the blood of an individual tasked with cleaning up an oil spill or contamination event, which can serve as an indicator of the individual's level of PAH exposure.

An embodiment of the invention comprises a method of detecting the presence of a petrogenic PAH in a sample by contacting the sample with an antibody as described herein for a period of time sufficient for the antibody to bind its target, and determining whether a petrogenic PAH is present in the sample. Non-limiting examples of petrogenic PAHs are described herein, for example at FIG. 16.

An embodiment of the invention comprises a method of environmental fingerprinting a sample by contacting the sample with an antibody as described herein for a period of time sufficient for the antibody to bind its target, and determining whether a PAH is present in the sample. In one embodiment, the PAH is a petrogenic PAH. Non-limiting examples of petrogenic PAHs are described herein for example at FIG. 16.

Embodiments of the invention comprise kits comprising at least one antibody as described herein directed to at least one PAH, chemicals for the detection of antibody binding, and/or, optionally, instructions for using the kit. In one embodiment, the kit comprises at least one antibody that is directed to a petrogenic PAH. Non-limiting examples of petrogenic PAHs are described herein, for example at FIG. 16. In another embodiment, the kit comprises at least one antibody that is directed to a petrogenic PAH and at least one antibody that is directed to a pyrogenic PAH. In one embodiment the kit comprises at least one secondary antibody that is conjugated to an enzyme that catalyzes the deposition of a chromogen at the antigen-antibody binding site, a non-limiting example of which is HRP. Such enzymes and techniques for using them in the detection of antibody binding are well known in the art. Other embodiments of the kit are described herein.

An embodiment of the invention comprises a method for measuring an amount of methylated polyaromatic hydrocarbon and an amount of unmethylated polyaromatic hydrocarbon in a sample. Non-limiting examples of samples types are described herein. A non-limiting example of an antibody that is directed towards a methylated PAH comprises clone A10, or antibodies or fragments thereof as described herein. A non-limiting example of an antibody that is directed towards total PAHs (e.g., unmethylated PAH or methylated PAH comprises clone D7).

Such a method can be useful, for example, to detect and identify the source of PAH contamination. For example, one embodiment can be used to detect an oil spill in a body of water. In one embodiment, the method comprises contacting a sample with at least two antibodies for a period of time sufficient for the antibodies to bind their targets, wherein at least one antibody is directed to methylated PAH and at least one antibody is directed to unmethylated PAH or total PAH, and measuring the binding of the antibodies to their respective targets.

In one embodiment, the method can further comprise the step of determining the amount of methylated PAH relative to the amount of unmethylated PAH in the sample. In one embodiment, this measurement can be used to identify the source of contamination of a sample. For example, this measurement can be used to identify a source of contamination as petrogenic rather than pyrogenic. In another embodiment, this measurement can be used to determine if a consumer product, such as food, is safe to consume. In yet another embodiment, this measurement can be used to determine the severity of a contamination event. For example, a ratio of about 1:1, wherein the amount of methylated polyaromatic hydrocarbon relative to the amount of unmethylated polyaromatic hydrocarbon indicates petrogenic contamination rather than pyrogenic contamination.

In one embodiment, an amount of methylated PAH relative to unmethylated PAH of about 1:1 indicates the presence of petrogenic contamination. In one embodiment, an amount of methylated PAH relative to unmethylated PAH of about 0.90:1, 0.91:1, 0.92:1, 0.93:1, 0.94:1, 0.95:1, 0.96:1, 0.97:1, 0.98:1, or 0.99:1 indicates the presence of petrogenic contamination. In another embodiment, an amount of methylated PAH relative to unmethylated PAH of greater than 1:1 indicates the presence of petrogenic contamination. In another embodiment, an amount of methylated PAH relative to unmethylated PAH of greater than 1.5:1 indicates the presence of petrogenic contamination. In another embodiment, an amount of methylated PAH relative to unmethylated PAH of greater than 2:1 indicates the presence of petrogenic contamination. In one embodiment of the invention, decontamination procedures can be initiated if the the amount of methylated PAH relative to unmethylated PAH indicates petrogenic contamination. Non-limiting examples of decontamination procedures comprise phytoremediation, soil washing, bioremediation, thermal destruction of PAHs, chemical destruction of PAHs.

The recombinant PAH antibody or fragment thereof of the present invention can be immobilized onto a solid support in order to facilitate its binding to its target (e.g., a PAH) from a given sample. The immobilization of the recombinant PAH antibody or fragment thereof onto the solid support can be carried out prior to binding of the target to be detected or once the PAH target is bound to the antibody. If a solid support is used, it is convenient to block the excess binding sites on the carrier prior to the addition of the sample containing the target to be determined. The recombinant PAH antibody or fragment of the present invention can also be free in solution while the target (e.g., a PAH) is immobilized onto a solid support (e.g., a PAH is bound to a passive sampler (such as a hydrophobic membrane) when the sampler is contacted with a given sample (such as a contaminated water, dirt, or sand from an oil spill) and the passive sampler is then contacted with PAH antibody or fragment of the present invention).

The traditional approach to measuring the levels of organic contaminants in water is spot sampling (collecting water samples at a specific time point, followed by an extraction, clean-up, a concentration step and instrumental analysis). However an increasing number of studies have reported on the value and usefulness of passive samplers as an alternative for spot sampling of surface waters (Martin et al, 2003). Unlike spot sampling, passive sampling can enable determination of time-weighted average concentrations of the contaminants of interest, can permit sequestration of residues from episodic events, is not limited to constant water conditions, can allow the concentration of ultratraces and contaminant mixtures over extended periods of time (Martin et al, 2003), can be cheaper, and does not require on-site infrastructure for sampling. In one example, compositions and methods of the present invention can be adapted to the analysis of PAHs extracted from such passive samplers (Allan et al, 2012). In another example, antibodies and fragments thereof of the present invention can be a component of a passive sampler. In one embodiment, the passive sampler comprising the antibodies can be provided in a kit as described herein. In one embodiment, a passive sampler comprising antibodies and fragments thereof as described herein can be disposable. In one example, antibodies or fragments thereof as disclosed herein can be a component of a disposable passive sampler.

In one embodiment, a passive sampler as disclosed herein can be used to perform the methods of the present invention.

In one example, a passive sampler comprising PAH antibodies as disclosed herein can be used to determine the source of a PAH contamination event. In another embodiment, a passive sampler comprising PAH antibodies as disclosed herein can be used to measure the levels of at least one PAH. For example, a passive sampler containing antibodies as disclosed herein can be used to detect a petrogenic PAH contamination event, such as one resulting from an oil spill. In another example, a passive sampler containing antibodies as disclosed herein can be used to determine the levels of PAH in water, assisting in the determination of whether the water is safe to drink or for recreation events such as swimming.

The present invention provides kits comprising the recombinant antibody or fragments of the invention. In one embodiment, a kit can comprise one or more antibodies (as discussed herein) and a solid support. In some embodiments, the recombinant PAH antibody or fragment thereof can be readily visualized (e.g., because it is labeled with a detectable label, such as a fluorophore or chromophore). In other embodiments, the recombinant PAH antibody or fragment thereof is not readily visualized (e.g., because it is not labeled with a fluorophore or chromophore), thus the kit further comprises a visualization reagent, such as, e.g., a secondary antibody (which can be labeled with a detectable label), a fluorogenic or chromogenic enzyme substrate, a streptavidin conjugate, or any other suitable visualization reagent known to the skilled artisan.

In one embodiment, the kit further comprises a solid support. The solid support can be a solid phase that is a porous or non-porous water insoluble material. The solid support can have any one of a number of shapes, such as strip, rod, particles, including latex particles, magnetic particles, microparticles, beads, membranes, microtiter wells and plastic tubes. For example, any material is suitable as a solid support such that is able to bind sufficient amounts of the antibody to be bound on the surface of the solid support. The choice of solid phase material is determined based upon the assay format performance characteristics needed.

Materials suitable for a solid support include polymeric materials and glass such as, e.g., glass available as bioglass, ceramics, metals, and the like. Non-limiting examples of polymeric materials include cellulosic materials and materials derived from cellulose, such as fibre containing papers (e.g., filter paper, chromatographic paper, glass fiber paper, etc.); synthetic or modified naturally occurring polymers, such as nitrocellulose, cellulose acetate, poly (vinyl chloride), polyacrylamide, cross linked dextran, agarose, plastic, polyacrylate, polyethylene, polypropylene, poly(4-methylbutene), polystyrene, polymethacrylate, poly(ethylene terephthalate), nylon, polyvinyl butyrate), etc.) used by themselves or in conjunction with other materials. A solid support can be functionalized with other active groups such as amine(s), hydroxyl(s) or epoxide(s).

Recombinant Antibodies

Antibody development against haptens has been a tough problem for decades. Without being bound by theory, raising monoclonal antibodies with a high affinity to the antigen is greatly reduced for haptens with a molecular weight of 300 Da or less and monoclonal antibodies to such small-sized haptens, and can only be generated using the hapten conjugated to a carrier molecule, such as a large protein. Luckily, the technology of antibody production process has been revolutionized by the development of molecular biology methods for the expression of recombinant DNA. As discussed herein, the essential variable domains of antibodies were cloned and restructured into recombinant antibodies, and valuable tools like phage and yeast display technologies were used to produce and select these recombinant antibodies with specific binding properties.

A naturally occurring immunoglobulin is a Y-shaped molecule containing two heavy and two light polypeptide chains (FIG. 19). Each light chain (red) pairs with the upper part of a heavy chain (blue) and forms a branch of the "Y" shape, whereas the lower part of two heavy chains are linked together to form the stem of the "Y". The top ends of two branches consist of highly-mutable variable regions encoding antigen-binding sites that recognize unique antigens (e.g., the hypervariable regions). A single complementarity-determining region (CDR) is a segment of the variable region of an antibody that is complementary in structure to the epitope/target region to which the antibody binds and is more variable than the rest of the variable region. Accordingly, a CDR is sometimes referred to as hypervariable region. A variable region (e.g, from the heavy chain ($V_H$) and the light chain ($V_L$)) comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995)). In some embodiments, binding affinities and/or target specificities can be modified by altering the CDR regions, for example by site-directed mutagenesis. In some embodiments, a CDR region of the $V_H$ chain of a recombinant PAH antibody comprises at least 90%, 91%, 92%, 93%, 94%, 95%, 96%, 97%, 98%, or 99% of SEQ ID NO: 60, 61, 62, 69, 70, 71, 146, 77, 78, 85, 86, 87, 94, 95, 96, 103, 104, 105, 112, 113, 114, 121, 122, 123, 130, 131, 132, 139, 140, or 141. In some embodiments, a CDR region of the $V_H$ chain of a recombinant PAH antibody comprises SEQ ID NO: 60, 61, 62, 69, 70, 71, 146, 77, 78, 85, 86, 87, 94, 95, 96, 103, 104, 105, 112, 113, 114, 121, 122, 123, 130, 131, 132, 139, 140, or 141. In some embodiments, a CDR region of the $V_L$ chain of a recombinant PAH antibody comprises at least 90%, 91%, 92%, 93%, 94%, 95%, 96%, 97%, 98%, or 99% of SEQ ID NO: 63, 64, 65, 72, 73, 74, 79, 80, 81, 88, 89, 90, 97, 98, 99, 106, 107, 108, 115, 116, 117, 124, 125, 126, 133, 134, 135, 142, 143, or 144. In some embodiments, a CDR region of the $V_L$ chain of a recombinant PAH antibody comprises SEQ ID NO: 63, 64, 65, 72, 73, 74, 79, 80, 81, 88, 89, 90, 97, 98, 99, 106, 107, 108, 115, 116, 117, 124, 125, 126, 133, 134, 135, 142, 143, or 144.

When exposed to foreign antigen, immune system creates a large diversity antibody pool by somatic hypermutations on the variable domain genes and subsequently selects for antibodies with highest affinity. Antibodies against protein antigens have been made routinely by immunizing animals repeatedly and harvesting blood for polyclonal antibody or spleens to generate hybridoma cells (monoclonal antibody). However, these established procedures are not always applicable to low molecular weight haptens. First, antigens smaller than 10,000 Da are not immunogenic, and require conjugation to a large carrier protein such as bovine serum albumin (BSA) or keyhole limpet hemocyanin (KLH) to elicit immune responses. Because of the complication of involvement of carrier proteins which are much more immunogenic than haptens alone, antibodies specific for haptens alone rather than hapten-protein conjugates are very rare and can be difficult to discover in the total antibody population. The emergence of recombinant technology has made it possible to achieve exquisite antibody specificity when incorporated with advance screening methods such as phage and yeast display platforms. (Boder et al., 2000; Moghaddam et al., 2003) Since the majority binding information is stored in the variable regions, most of recombinant antibody fragments are reconstructed with a branch of Y-shape (FIG. 19, Fab) or only variable domains of heavy and light chains connected by a flexible linker (FIG. 19, scFv).

The six hypervariable regions (CDRs) confer antigen-binding/target-binding specificity to the antibody. However, even a single variable domain (or half of an Fv comprising only three hypervariable regions specific for an antigen) has the ability to recognize and bind its antigen/target, although at a lower affinity than the entire binding site. According to the invention, a recombinant antibody or fragment thereof contains a target binding site for a PAH. Non-limiting examples of antibody molecules include (a) a reconstituted (e.g., an intact form) antibody comprising an antigen-binding/target-binding variable region as well as a light chain constant domain (CL) and heavy chain constant domains, CH1, CH2 and CH3; (b) Fab fragments resulting from the papain digestion of an intact antibody comprising a single antigen-binding/target-binding site, and a CL and a CH1 region, the first constant domain (CH1) of the heavy chain; (c) F(ab')$_2$ fragments resulting from pepsin digestion of an intact antibody comprising two antigen-binding/target-binding sites; (d) Fab' fragments comprising the constant domain of the light chain (CL) and the first constant domain (CH1) of the heavy chain and which have only one antigen-binding/target-binding site; (e) an Fv fragment, which contains a complete antigen-recognition/target-recognition and antigen-binding/target-binding site that comprises a dimer of one heavy chain and one light chain variable domain in tight, non-covalent-association (e.g., in this configuration, the three hypervariable regions (CDRs) of each variable domain interact to define an antigen-binding site on the surface of the VH-VL dimer); and (f) a Single-chain FV (scFv) antibody fragment comprises the VL and VH domains of an antibody, wherein these domains are present in a single polypeptide chain (for example, the VL and VH regions are connected by a polypeptide linker which allows the scFv to form the structure for antigen-binding/target-binding). It is noted that Fab' fragments differ from Fab fragments by the addition of a few residues at the carboxy terminus of the heavy chain CH1 domain including one or more cysteines from the antibody hinge region.

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10-2.10.4.

Methods for making scFv molecules and designing suitable peptide linkers are disclosed in U.S. Pat. Nos. 4,704, 692, 4,946,778, R. Raag and M. Whitlow, "Single Chain Fvs." *FASEB* Vol 9:73-80 (1995) and R. E. Bird and B. W. Walker, "Single Chain Antibody Variable Regions," *TIBTECH*, Vol 9: 132-137 (1991). The most widely used flexible linker used to connect the heavy- and light-chain variable domains has the sequence (Gly-Gly-Gly-Gly-Ser)n (SEQ ID NO: 148). By adjusting the copy number "n", the length of this G-S linker can be optimized to achieve appropriate separation of the functional domains, or to maintain necessary inter-domain interactions. Besides the G-S linkers, many other flexible linkers have been designed for recombinant fusion proteins. These flexible linkers are normally rich in small or polar amino acids such as Gly and Ser, but can contain additional amino acids such as Thr and Ala to maintain flexibility, as well as polar amino acids such as Lys and Glu to improve solubility (Argos, *J Mol Biol.* 1990; 211:943-958; George and Heringa, *Protein Eng* 2002 15:871-879).

Several other types of flexible linkers, including KES-GSVSSEQLAQFRSLD (SEQ ID NO: 146) and EGK-SSGSGSESKST (SEQ ID NO: 147), have been applied for the construction of a bioactive scFv (Bird et al., *Science.* 1988; 242:423-426). The Gly and Ser residues in these linkers were designed to provide flexibility, whereas Glu and Lys were added to improve the solubility. These linkers were designed by computation methods and computational graphics. Specific amino acids, one near the carboxyl terminus of the antibody light-chain variable region ($V_L$) and one near the amino terminus of the heavy chain variable region ($V_H$) domain, were first selected. Additional non-limiting examples of protein linker regions can be found in Chen et al., (*Adv Drug Deliv Rev.* 2013; 65: 1357-1369), which is incorporated herein by reference in its entirety. In some embodiments, the GGGGS (SEQ ID NO:148) sequence is disrupted to insert an endonuclease restriction site into the linker region according to methods known in the art (see, for example, Zhu et al., *Anal Chem.* 2011; 83:3717-3724). Additionally, a large fluorescent protein can be coupled to the linker region (see, for example, Markin et al., *J Immunol Meth.* 2011; 364:40-49.).

In addition to the linkers described herein, a new linker sequence HHMHGKTQATSGTIQSMHGKTQATSGTIQ-SSR (SEQ ID NO: 149) has been designed that binds to gold nanoparticles. This sequence is derived from a published gold binding peptide (Kacar et al., *Biotechnol Bioeng* 2009; 103:696-705). However, no one has attempted to insert repeats of this sequence into the linker of an scFv. The insertion of this linker between the $V_H$ and $V_L$ domains of the scFv structure did not disrupt the binding activity or the thermal stability of the scFv but allowed the scFv to bind 4× more tightly to gold nanoparticles.

These antibody fragments can be further modified using conventional techniques known in the art, for example, by using amino acid deletion(s), insertion(s), substitution(s), addition(s), and/or recombination (and/or any other modification(s), e.g. post-translational and chemical modifications, such as glycosylation and phosphorylation, known in the art), alone or in combination. Methods for introducing such modifications in the DNA sequence underlying the amino acid sequence of an antibody (e.g., by site-directed mutagenesis) are well known to the skilled artisan; (e.g., Sambrook et al.; Molecular Cloning: A Laboratory Manual; Cold Spring Harbor Laboratory Press, 3rd edition 2001). For example, the variation can involve the addition or removal of one or more glycosylation sites in the Fc sequence (e.g., U.S. Pat. No. 6,254,868, the Examples section of which is incorporated herein by reference) or specific amino acid substitutions in the Fc sequence can be made (e.g., Hornick et al., 2000, *J Nucl Med* 41:355-62; Hinton et al., 2006, *J Immunol* 176:346-56; Petkova et al. 2006, *Int Immunol* 18:1759-69; U.S. Pat. No. 7,217,797; Hwang and Foote, *Methods* (2005) May; 36(1):3-10; Clark, 2000, *Immunol Today* 21:397-402; *J Immunol* 1976 117:1056-60; Ellison et al., 1982, *Nucl Acids Res* 13:4071-79; Stickler et al., 2011, *Genes and Immunity* 12:213-21). For example, post-translational modification of a recombinant protein (such as glycosylation of an antibody) can promote its stability (see Zheng et al., *MAbs*. 2011 November-December; 3(6): 568-576; and Jenkins et al., *Mol Biotechnol*. 2008 June; 39(2): 113-8).

The recombinant PAH antibodies or fragments thereof can be useful for PAH detection in an assay, for example, when out in the field. In one embodiment, the recombinant antibody or fragment thereof can be conjugated to a detectable label, such as an enzymatic, fluorescent or radioactive label. In some embodiments, the recombinant antibody or fragment thereof can be conjugated (e.g., physically linked) to BSA, biotin- or engineered to contain specific amino acid sequences (e.g. a myc epitope tag, a V-epitope tag, a His tag, and the like), or a combination thereof. The recombinant antibody or fragment conjugated to a detectable label encompasses direct labeling of the antibody or fragment by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody or fragment. In some embodiments, the detectable label can be coupled to an Fc portion of a reconstituted antibody, to a $V_H$ region, to a $V_L$ region, to a constant region of the light chain, to a constant region of the heavy chain, to the peptide linker, or a combination thereof. In some embodiments, the recombinant antibody or fragment can be indirectly labeled, wherein reactivity of the antibody is determined with a detectable substance that associates with and/or contacts the PAH antibodies or fragments.

Non-limiting examples of a detectable label include a fluorochrome/fluorophore, a chromophore, a hapten, a radioisotope/radioactive label, a luminescent label, an enzyme, and a chemiluminescence compound, such as acridine orange. Fluorochromes that can be used in the method of the present invention include, but are not limited to, IR dyes, Dyomics dyes, phycoerythrine, cascade blue, Oregon green 488, pacific blue, rhodamine green, 5(6)-carboxyfluorescein, cyanine dyes (e.g., Cy2, Cy3, Cy 3.5, Cy5, Cy5.5, Cy 7), (diethyl-amino)coumarin, fluorescein (i.e., FITC), tetramethylrhodamine, lissamine, oxazine, resorufin, Texas Red, AMCA, TRITC, and Alexa dyes. Haptens that can be used in the present invention include, but are not limited to, 5(6)-carboxyfluorescein, 2,4-dinitrophenyl, digoxigenin, rhodamine, bromodeoxy uridine, acetylaminoflurene, mercury trinitrophenol, estradiol, and biotin. Non-limiting examples of a radioactive label that can be used with the antibodies of the present invention include $^{31}P$, $^{33}P$, and $^{32}S$. Luminescent labels include, but are not limited to Qdot™ nanoparticles (supplied by the Quantum Dot Corporation, Palo Alto, Calif.). Non-limiting examples of enzymes that can be used in the present invention include soybean peroxidase, alkaline phosphatase, and horseradish peroxidase.

If the detectable tag is an enzyme, then the enzyme can generates a detectable signal, for example, upon addition of an activator, substrate, amplifying agent and the like. Enzymes which are suitable as detectable labels for the present invention and its corresponding substrates include:

| Enzyme | | Fluorogenic substrates |
|---|---|---|
| | Chromogenic substrates | |
| Alkaline Phosphatase | Substrates based on: p-nitrophenyl phosphate (p-NPP) 5-bromo-4-chloro-3-indolyl phosphate/nitroblue tetrazolium (BCIP/NBT) Fast-Red/naphthol-AS-TS phosphate | 4-methylumbelliferyl phosphate (4-MUP), 2-(5'-chloro-2'-phosphoryloxyphenyl)-6-chloro-4-(3H)-quinazolinone (CPPCQ), 3,6-fluorescein diphosphate (3,6-FDP), Fast Blue BB, Fast Red TR, or Fast Red Violet LB diazonium salts |
| Peroxidase | substrates based on: 2,2-azinobis(3-ethylbenzothiazoline-6-sulfonic acid) (ABTS) o-phenylenediamine (OPT) 3,3',5,5'-tetramethylbenzidine (TMB) o-dianisidine 5-aminosalicylic acid 3-dimethylaminobenzoic acid (DMAB) 3-methyl-2-benzothiazolinehydrazone (MBTH) 3-amino-9-ethylcarbazole (AEC) 3,3'-diaminobenzidine tetrahydrochloride (DAB) | 4-hydroxy-3-methoxyphenylacetic acid reduced phenoxazines reduced benzothiazines including Amplex ® Red reagent, Amplex UltraRed and reduced dihydroxanthenes |
| Glycosidase | o-nitrophenyl-β-D-galactoside (o-NPG) p-nitrophenyl-β-D-galactoside 4-methylumbelliphenyl-β-D-galactoside (MUG) [for β-D-galactosidase] | resorufin β-D-galactopyranoside fluorescein digalactoside (FDG) fluorescein diglucuronide 4-methylumbelliferyl•beta.-D-galactopyranoside, carboxyumbelliferyl β-D-galactopyranoside fluorinated coumarin β-D-galactopyranoside |
| | Luminescent Substrate | |
| Oxidoreductase (luciferase) | luciferin | |

With the full knowledge of antibody (scFv) sequences, the qualities of recombinant antibodies are much more reliable than polyclonal antibodies which can have lot-to-lot variability. (Baker, 2015) And it is easier to characterize the binding affinity and specificity of a highly purified scFv compared to polyclonal antibody in the serum mixture. Recombinant antibodies can also be manipulated at molecular level, such as mutagenesis to promote affinity maturation or shuffling between expression systems to use different expression machineries. More importantly, a recombinant antibody library can accommodate a fairly large diversity, up to $10^{11}$ distinct clones in a single library pool, and enriched the desirable binders in a few rounds of selections. (Sblattero and Bradbury, 2000) The large diversity of libraries greatly improves the chances of discovery of rare events like hapten-specific antibodies. When given suitable selection pressures, the antibodies present at low frequency in the original library can be highly enriched and become visible in the sub-populations. Multiple in vitro selection platforms have been developed to select for desirable antibodies from highly diverse libraries, and phage and yeast display are the most popular systems.

Phage Display.

Bacteriophage is a class of virus that infects and replicates in the bacteria. The structure of bacteriophage is composed simply of some coat proteins that encapsulate a DNA/RNA genome. Like other virus, bacteriophage use their host's metabolic machinery to complete their life cycles, including genome replication, essential protein synthesis, viral particle assembly, etc. Depends on the types of the phage, the host cells can be lysed immediately after phage replication (lytic cycle, such as T4 phage) or remain intact until host condition changes (lysogenic cycle, such as λ phage). M13 phage is an exception that engages in a viral lifestyle known as a chronic infection, which does not lyse the host during any stage of phage production.

M13 phage has been widely used as display vehicles for protein/polypeptide libraries (Georgieva and Konthur, 2011; Sidhu, 2001), and its non-lytic life cycle makes it easier to separate phage particles from the host cell/proteins mixtures as compared to lytic phage types. M13 is filamentous phage, and only infects host cells with F pilus on the surface. The genome of M13 is a circular single-stranded DNA (ssDNA) (FIG. 20), encapsulated by major coat protein pVIII and some minor coat proteins (PIII, PVI and PIX). During infection, the minor protein pIII attaches to the receptor at the tip of F pilus and mediates the release of phage genome into the bacteria cells. The ssDNA genome is then converted to the double-stranded (dsDNA) form and propagates with host multiplication. The infected genome uses bacteria machinery to produce coat proteins, assemble into phage particles and secret progeny without destroying the host cells.

M13 genome has been modified into phagemid plasmids for many recombinant DNA applications, and antibody phage display is one of the areas that has benefited from this technology. As shown in FIG. 20, recombinant antibody scFv sequences can be inserted into the phagemid in fusion to minor coat protein gene III (gIII). When assembled, the scFv-bearing phagemid will be encapsulated by the scFv-pIII fusion protein, and antibody phenotype and genotype is linked together in a phage particle. The upper part of FIG. 21 shows the process of phage display selection. Basically, phage particles are added into a microwell plate or immunotubes coated with antigen of interest. During incubation, the phage particles bearing desirable antibodies are bound to the immobilized antigen and remain in the plastic surface. After clearing away other non-desirable particles, the bound phage are eluted and infected into bacteria host cells for amplification. The enriched phage population can be used to go through the panning process again until the output is satisfactory.

Yeast Display and Fluorescence Activated Cell Sorting (FACS).

Yeast surface display is another powerful screening technology that has experiences fast development in the past decade. (Boder and Wittrup, 2000; Pepper et al., 2008) Compared to phage display system, yeast display uses the eukaryotic machinery to avoid biased expression of recombinant proteins in prokaryotic system. The α-agglutinin system developed by Wittrup et al is the anchor system adopted in most applications. (Boder et al., 2000; Boder and Wittrup, 1997) In an α-agglutinin system, the target recombinant protein (e.g. scFv) is expressed as a fusion protein with a mating factor protein Aga2p from a yeast display plasmid. Its partner protein Aga1p is stably expressed and anchored onto cell wall in a yeast strain that has been genetically modified for yeast display analysis. When expressed, the Aga2p-target fusion forms two disulfide linkages to Aga1P, and thus directs the target proteins to the cell wall. As a result, the displayed protein extends far away from the yeast cell surface, and ready to be analyzed.

A significant advantage of yeast display is the ability to incorporate flow-cytometry for analysis, which provides a great selection power. When a pool of yeast cells passes through the flow cell, they are separated as singlet and analyzed individually. Each cell was labeled with two parameters: the expression level of antibody scFv-Aga2p construct and the binding capacity of antibody to certain antigens. The expression level of scFv was monitored by a protein tag fused with scFv fragment and is shown on the x axis of the flow plot, while the binding capacity of expressed scFv to antigen was measured by the amount of antigen captured on the cell surface and is shown on they axis of flow plot (FIG. 22). The yeast cell population that both expressed scFv and bound to the biotinylated antigen will show a strong signal in the upper right (Q2) quadrant. As various clones have different levels of expression and binding strength, each clone can show a distinct pattern on the flow plot. With the power of fluorescence activated cell sorting (FACS), selection can be performed arbitrarily given any criteria/requirement.

A Two-Step Selection Strategy Combining Both Display Systems.

Phage particles have been used to select recombinant antibodies with high affinity and specificity for decades. This technique can easily screen an extremely large pool (up to $10^{11}$~$10^{12}$ clones) in a single step, and enrich the strongest binders within 2-3 rounds of selections. However, the output of selection always contains a relatively high level of nonspecific binders due to the intrinsic stickiness of phage particles. Since hapten antibodies are present at very low frequency in the library, the nonspecific background noise can overwhelm the real binding signal and makes it difficult to separate hapten-specific antibodies from antibodies that bind to hapten-protein conjugates. As for yeast display, the expression and binding characteristics of scFv can be accurately analyzed and selected by fluorescence-activated cell sorting (FACS). With the help of flow cytometry, each scFv-bearing yeast cell can be analyzed individually and the binding intensity can be measured quantitatively. However the number of yeast cells in each analysis is limited by the flow rate. Yeast display is a relatively new field and most applications are presently designed for protein antigens. In one embodiment, to adapt yeast display for hapten antibody screening, a competitive flow protocol was developed and combined with a pre-selection step by phage display to yield maximum hapten-specific antibodies from an immune library (FIG. 21).

A recombinant scFv antibody library (~6×10⁶ individual scFvs) was prepared from mice immunized with methylated phenanthrene-protein conjugates. Two selection systems, phage and yeast display, were used sequentially to select rare clones from this library that can bind to soluble phenanthrenes and/or methylated (alkylated) phenanthrenes. After three rounds of phage selection, selected scFv fragments were cloned into a yeast display vector to generate a yeast mini-library. Yeast display coupled with fluorescence-activated cell sorting (FACS) was used to analyze and select scFv pools that bound to soluble phenanthrene and/or methylated phenanthrenes. Finally, analysis of single cells isolated from these pooled samples allowed selection of three specific monoclonal scFvs, each with unique amino acid sequences and binding specificities as shown in the data from competitive ELISA as described herein.

In one embodiment, the present invention provides a method of developing recombinant antibodies that are capable of distinguishing between methylated and non-methylated derivatives of phenanthrene, a major polycyclic aromatic hydrocarbon present in crude oil. In another embodiment, the present invention provides particular recombinant antibodies that specifically recognize methylated phenanthrenes, the major PAHs in petroleum.

The generation of high-quality antibodies for low molecular weight haptens is not straightforward, as antigens smaller than 1000 Da are not immunogenic. In one embodiment, the present invention provides a method for selecting hapten-specific recombinant antibody or fragment thereof that specifically recognizes low molecular weight haptens. In one embodiment, the present invention provides a method for selecting hapten-specific recombinant antibodies or fragments thereof from a phage display library. In one embodiment, the hapten is a polyaromatic hydrocarbon (PAHs). Non-limiting examples of polyaromatic hydrocarbons include naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene.

In the first step of the method, a phage display library comprising bacteriophages expressing an antibody or fragment thereof is screened for those bacteriophages that interact with a hapten target. The phage display library screen step comprises one or more panning cycles designed to provide a specific selective pressure and enrich for the bacteriophage expressing the antibody or fragment thereof that binds the hapten.

In embodiments of the present invention, there can be one panning cycle. In other embodiments, there can be two or more panning cycles. In one embodiment, the panning cycle can enrich for a bacteriophage that binds to the hapten. In another embodiment, the panning cycle can use a solvent to exclude antibodies that are unstable in the solvent. Non-limiting examples of such solvents are DMSO, methanol, acetone, and other water miscible solvents. In still another non-limiting example, the panning cycle can use soluble hapten to enrich the pool of binders that bound to the hapten. Embodiments can comprise combination of panning cycles.

Immobilization of the hapten target prior to panning allows for enrichment of the bacteriophages expressing antibodies or fragments thereof that bind to the hapten target. In one embodiment, the hapten target is not immobilized when binding to the bacteriophage, but is capable of being immobilized following binding. In a non-limiting example, the phage display library is co-incubated with non-immobilized hapten, at least one phage binds the hapten, and the bacteriophage-hapten conjugate is subsequently immobilized to a support structure, such as a solid support, prior to panning cycles. In another embodiment, the hapten is immobilized prior to co-incubation with the bacteriophage. In this example, the bacteriophage binds the immobilized hapten, and the panning cycle is subsequently performed.

In other embodiments, immobilization of the hapten target is performed using an immobilization agent with the purpose of immobilizing the hapten-bound bacteriophage prior to panning. In certain embodiments, the immobilization agents are conjugated to the hapten. Non-limiting examples of such agents include bovine serum albumin (BSA); polypeptide protein tags such as Myc, chitin binding protein (CBP), maltose binding protein (MBP), and glutathione-S-transferase (GST); V-epitope tag; gold-binding peptide; and a combination thereof (see also, e.g., Jones et al., *Journal of Chromatography A* (1995), 707(1), 3-22), Wilcheck et al., *Immunology Letters* (2006), 103(1), 27-32; and Mondal et al., *Biomol Engin* 2006 June; 23(2-3):59-76. Epub 2006 March, each of which are hereby incorporated by reference in their entireties). In other embodiments, the immobilization agent is conjugated to the support structure, such as a solid support, and the unbound hapten or bacteriophage-bound hapten will interact with the conjugated immobilization agent. In a non-limiting example, the immobilization agent can coat the insides surfaces of a structure, such as a well, tube or column. In one example, a well in a multi-well dish can be coated with a composition that interacts with the hapten. Non-limiting examples of compositions which can coat a support structure and function as an immobilizing agent include poly-lysine, BSA, gelatin, and casein. In one embodiment, a panning cycle as described herein selects for antibodies that bind to immobilizing agent-bound hapten. In another embodiment, the panning cycle removes antibodies that bind to the immobilizing agent. In still another embodiment, the panning cycle removes antibodies that bind to the immobilizing agent-bound hapten.

The second step of the method comprises screening a display library of yeast cells transformed with a nucleic acid encoding at least one antibody enriched from the first step of the method by performing at least one round of flow activated cell sorting (FACS) to competitively select for yeast cells that express hapten-specific antibodies or fragments thereof. In one embodiment, the soluble hapten target is used to competitively select for those antibodies and fragments thereof that specifically bind the hapten. In another embodiment, the yeast cells are selected from lower signals in the Y axis, and can be enriched in the area of the Q2 quadrant of a FACs readout from a competitive FACS selection. In one embodiment, the yeast cells are selected from the cells displaced to a lower position in the Q2 quadrant following competitive FACS. In some embodiments, those yeast cells to be selected are displaced to lower positions in the Q2 quadrant in the presence of soluble antigen. In some embodiments, the FACS profile needs to be pre-sorted to remove interfering clones from Q2 quadrant of the profile. In some embodiments, the Q2 population of sorted yeast cells can be localized to the lower range on the y-axis and the higher range on the x-axis, for example, the circled population as shown in FIG. 49B.

In one embodiment, one round of FACS with competitive selection is performed. In another embodiment, two or more rounds of FACS are performed, with at least one round comprising competitive selection. In an embodiment, at least one round of negative cell sorting can be performed to remove cell populations that can cause interference during subsequent selection steps. For example, yeast cells that bind the immobilization agent can be removed from subsequent selection. In another embodiment, at least one round of positive cell sorting is performed to enrich cells that bind the hapten. In still another embodiment, at least one round of negative cell sorting is performed, at least one round of positive cell sorting is performed, and at least one round of competitive cell sorting is performed.

The third step of the method comprises isolating a hapten-specific recombinant antibody or fragment thereof from the identified transformed yeast. In an embodiment, the hapten-specific recombinant antibodies or fragments thereof comprise a single-chain variable fragment (scFv). Non-limiting examples of antibodies, recombinant antibodies, and fragments thereof that can be isolated are described herein. Non-limiting examples of antibodies, recombinant antibodies, and fragments thereof that can be selected are described herein.

Embodiments of the invention comprise antibodies, recombinant antibodies, and fragments thereof that are isolated by the methods as described herein. Non-limiting examples of antibodies, recombinant antibodies, and fragments thereof that can be isolated are described herein, for example those listed in FIG. 10.

For example, as shown in FIG. 7, antibody A had very little ability to differentiate among methylated versus unmethylated phananthrenes, while antibody B and antibody C showed binding to the 4-methyl and 2-methlyphenanthrenes, respectively. Further studies are underway to isolate additional antibodies from the library described herein and to further characterize the binding properties of the isolated scFvs.

Amino Acid Sequences of scFvs Identified from Screens

The amino acid sequence of Clone A10 (SEQ ID NO: 37) comprises the sequence below, wherein the $V_H$ region is bolded (SEQ ID NO: 57, wherein $V_H$ CDR regions 1, 2, and 3 are boxed therein as SEQ ID NOS: 60, 61, and 62 respectively), the $V_L$ region is italicized (SEQ ID NO: 58, wherein $V_L$ CDR regions 1, 2, and 3 are boxed therein as SEQ ID NOS: 63, 64, and 65 respectively), and the peptide linker sequence is underlined (SEQ ID NO: 59):

SAHAEAYLQQSGAELVKPGASVKLSCKASGYTFTSYWMHWVKQRPGQGLE

WIGEINPRNGRSNYNEKFKNKATVTVDKYSNTAYMQLSSLTSDDSAVYYC

TRDGGDYWGQGTTVTVSSGGGGSGGGGSGGGARGGGGS*DIVLTQSHKFM*

*STSVGDRVSITC*KASQDVGTAVA*WYQQKPGQSPKLLIY*WASTRHT*G*

*VPDRFTGSGSGTDFTLTISNVQSEDLADYFC*QQYSSYPLT*FGGGTK*

*LEMKRAS*

The amino acid sequence of Clone 3F4 (SEQ ID NO: 38) comprises the sequence below, wherein the $V_H$ region is bolded (SEQ ID NO: 66, wherein $V_H$ CDR regions 1, 2, and 3 are boxed therein as SEQ ID NOS: 69, 70, and 71 respectively), the $V_L$ region is italicized (SEQ ID NO: 67, wherein $V_L$ CDR regions 1, 2, and 3 are boxed therein as SEQ ID NOS: 72, 73, and 74 respectively), and the peptide linker sequence is underlined (SEQ ID NO: 68):

SAHAEAYLQQSAAELARPGASVKMSCKASGNTFTSYTMHWVKQRPGQGLE

WIGYINPSSGYTEYNQKFKDKTTLTADTSSSTAYMQLSSLTPEDSAVYYC

ARGPRYWGQGTLVTVSAGGGGSGGGGSGGGARGGGGS*DTTVTQSQKFMS*

*TSVGDRVSVTC*KASQNVGTNVAW*YQQKPGQSPKALIY*SASYRYS*GV*

*PDRFTGSGSGTDFTLTISNVQSEDLAEYFC*QQYNSYPYT*FGGGTKL*

*EIKRAS*

The amino acid sequence of Clone 3F9 (SEQ ID NO: 39) comprises the sequence below, wherein the $V_H$ region is bolded (SEQ ID NO: 75, wherein $V_H$ CDR regions 1, 2, and 3 are boxed therein as SEQ ID NOS: 145, 77, and 78 respectively), the $V_L$ region is italicized (SEQ ID NO: 76, wherein $V_L$ CDR regions 1, 2, and 3 are boxed therein as SEQ ID NOS: 79, 80, and 81 respectively), and the peptide linker sequence is underlined (SEQ ID NO: 240):

AHAQIQLQQPGAELVKPGASVKLSCKASGYTFTSYWMHWVKQRPGQLEW

IGEINPSNGRTNYNEKFKSKATLTVDKSSSTAYMQLSSLTSEDSAVYYCA

RDGGDYQGQGTTLTVSSGGGGSGGGGSGGGARGGGGS*DIVMSQSHKFMS*

*TSVGDRVSITC*KASQDVGTAVA*WYQQKPGQSPKLLIY*WASTRHT*GV*

*PDRFTGSGSGTDFTLTISNVQSGDLADYFC*QQYSSYPLT*FGGGTKL*

*EIKRAS*

The amino acid sequence of Clone 4C1 (SEQ ID NO: 40) comprises the sequence below, wherein the $V_H$ region is bolded (SEQ ID NO: 82, wherein $V_H$ CDR regions 1, 2, and 3 are boxed therein as SEQ ID NOS: 85, 86, and 87 respectively), the $V_L$ region is italicized (SEQ ID NO: 83, wherein $V_L$ CDR regions 1, 2, and 3 are boxed therein as SEQ ID NOS: 88, 89, and 90 respectively), and the peptide linker sequence is underlined (SEQ ID NO: 84):

SAHAEIQLQQSGAELVKPGASVKLSCKASGYTFTSYWMHWVKQRPAQGLE

WIGEINPRNGRSNYNEKFKNKATVTVDKYSNTAYMQLSSLTSDDSAVYYC

TRDGGDYWGQGTTLTVSSGGGGSGGGGSGGGARGGGGS*DIVLTQSQKFM*

*STSVGDRVSVTC*KASQNVGTNVA*WYQQKPGQSPKALIY*SASYRYS*G*

*VPDRFTGSGSGTDFTLTISNVQSEDLADYFC*QQYNSYPLT*FGGGTK*

*LEMKRAS*

The amino acid sequence of Clone 4H1 (SEQ ID NO: 41) comprises the sequence below, wherein the $V_H$ region is bolded (SEQ ID NO: 91, wherein $V_H$ CDR regions 1, 2, and 3 are boxed therein as SEQ ID NOS: 94, 95, and 96 respectively), the $V_L$ region is italicized (SEQ ID NO: 92, wherein $V_L$ CDR regions 1, 2, and 3 are boxed therein as SEQ ID NOS: 97, 98, and 99 respectively), and the peptide linker sequence is underlined (SEQ ID NO: 93):

SAHAEAYLQQSGAELVKPGASVKLSCKASGYTFTSYWMHWVKQRPGQGLE

WIGEINPRNGRSNYNEKFKNKATVTVDKYSNTAYMQLSSLTSDDSAVYYC

TRDGGDYWGQGTTVTVSSGGGGSGGGGSGGGARGGGGS*DIVLTQSHKFM*

*STSVGDRVSITC*KASQDVGTAVA*WYQQKPGQSPKLLIY*WASTRHT*GX*

*PDRFTGSGSGTDFTLTIXNVQSEXLXXYFC*XQYXXYPLT*FGGGTXW*

*K\*NAXXQVLNXX*

Without being bound by theory, it is noted that clones with a premature stop codon (i.e., as indicated with an asterisk in SEQ ID NO: 41) are not uncommon to discover in scFvs isolated from a library. Often, these truncated clones bind well to the antigen, even without all 6 CDRs.

The amino acid sequence of Clone D7 (SEQ ID NO: 42) comprises the sequence below, wherein the $V_H$ region is bolded (SEQ ID NO: 100, wherein $V_H$ CDR regions 1, 2, and 3 are boxed therein as SEQ ID NOS: 103, 104, and 105 respectively), the $V_L$ region is italicized (SEQ ID NO: 101, wherein $V_L$ CDR regions 1, 2, and 3 are boxed therein as SEQ ID NOS: 106, 107, and 108 respectively), and the peptide linker sequence is underlined (SEQ ID NO: 102):

SAHAEAYLQQSGAELVRPGTSVKVSCKAS GYAFTKYLIE WVKQRPGQGLEWIG VINPGSGSTSYNEKFRYK AILT

ADTSSSTAYMQLSSLTSDDSAVYFCAT IPASYRSDSLDQ WGQGTTVTVSS GGGGSGGGGSGGGARGGGGS DTT

*VTQSHKFMSTSVGDRVSITC KASQDVGTAVA WYQQKPGQSPKLLIY WASTRHT GVPDRFTGSGSGTDFTLTISNV*

*QSEDLADYFC QQYSSYPWT FGGGTKLEMKRAS*

The amino acid sequence of Clone H8 (SEQ ID NO: 43) comprises the sequence below, wherein the V$_H$ region is bolded (SEQ ID NO: 109, wherein V$_H$ CDR regions 1, 2, and 3 are boxed therein as SEQ ID NOS: 112, 113, and 114 respectively), the V$_L$ region is italicized (SEQ ID NO: 110, wherein V$_L$ CDR regions 1, 2, and 3 are boxed therein as SEQ ID NOS: 115, 116, and 117 respectively), and the peptide linker sequence is underlined (SEQ ID NO: 111):

SAHAEVQLQQSGTELVKPGASVKLSCKTS GYTFTKYLIE WVKQRPGQGLEWIG VINPGSGSTSYNEKFRYK AILT

ADTSSSTAYMQLSSLTSDDSAVYFCAT IPASYRSDSLDQ WGQGTTVTVSS GGGGSGGGGSGGGARGGGGS DTT

*VTQSHKFMSTSVGDRVSITC KASQDVGTAVA WYQQKPGQSPKLLIY WASTRHT GVPDRFTGSGSGTDFTLTISNV*

*QSEDLADYFC QQYSSYPWT FGGGTKLEMKRAS*

The amino acid sequence of Clone 2C1 (SEQ ID NO: 44) comprises the sequence below, wherein the V$_H$ region is bolded (SEQ ID NO: 118, wherein V$_H$ CDR regions 1, 2, and 3 are boxed therein as SEQ ID NOS: 121, 122, and 123 respectively), the V$_L$ region is italicized (SEQ ID NO: 119, wherein V$_L$ CDR regions 1, 2, and 3 are boxed therein as SEQ ID NOS: 124, 125, and 126 respectively), and the peptide linker sequence is underlined (SEQ ID NO: 120):

SAHAEAYLQQSGAELVRPGTSVKVSCKAS GYAFTKYLIE WVKQRPGQGLEWIG VINPGSGSTSYNEKFRY KAILT

ADTSSSTAYMQLSSLTSDDSAVYFCAT IPASYRSDSLDQ WGQGTTVTVSS GGGGSGGGGSGGGARGGGGS DTT

*VTQSHKFMSTSVGDRVSITC KASQDVGTAVA WYQQRPGQSPKLLIY WASTRHT GVPDRFTGSGSGTDFTLTISNV*

*QSEDLADYFC QQYKSYPLT FGGGTKLEIKRAS*

The amino acid sequence of Clone G8 (SEQ ID NO: 45) comprises the sequence below, wherein the V$_H$ region is bolded (SEQ ID NO: 127, wherein V$_H$ CDR regions 1, 2, and 3 are boxed therein as SEQ ID NOS: 130, 131, and 132 respectively), the V$_L$ region is italicized (SEQ ID NO: 128, wherein V$_L$ CDR regions 1, 2, and 3 are boxed therein as SEQ ID NOS: 133, 134, and 135 respectively), and the peptide linker sequence is underlined (SEQ ID NO: 129):

SAHAEAYLQQSGAELVRPGTSVKVSCKAS GYVFTNFLIE WVKQRPGQGLEWIG VINPGNGGAAYNEKFKG KAI

LTADKSSSTAYMQLSSLTSDDSAVYFCAR LPPSYDYDGDIDY WGQGTTVTVSS GGGGSGGGGSGGGARGGGG

*SDLVLTQSPASLAVALGQRATISC RASKSVTTSGYSLMH WYRQKPGQPPKLLIY PASNLES GVPARFSGSGSGTDFT*

*LNIHPVEEEDAATYYCQ HSRELPWTFG GGTKLEIKRAS*

The amino acid sequence of Clone 4E3 (SEQ ID NO: 46) comprises the sequence below, wherein the V$_H$ region is bolded (SEQ ID NO: 136, wherein V$_H$ CDR regions 1, 2, and 3 are boxed therein as SEQ ID NOS: 139, 140, and 141 respectively), the V$_L$ region is italicized (SEQ ID NO: 137, wherein V$_L$ CDR regions 1, 2, and 3 are boxed therein as SEQ ID NOS: 142, 143, and 144 respectively), and the peptide linker sequence is underlined (SEQ ID NO: 138):

SAHAQVQLQQSGAELVRPGTSVKVSCKASGYAFTNFLIEWVKQRPGQGLEWIGVINPGSGGTGYNEKFKGKA

TLTADKSSSTAYMQLNSLTSDDSAVYFCARLPPSYDYDGDIDYWGQGTTVTVSSGGGGSGGGGSGGGARGGG

GSDIVMSQSPASLAVSLGQRATISCRASKSVSSSGYSLIH*WYQQKPGQPPKLVIY*LASNLXS*GVPAXFSGSGSXTDFT*

*LNIHPVXXEDAATYYC*XHSXXLPWX*XXXXQAGNQXXXXXPXXXXDXXXXX\*XXXXT*

Nucleic Acid Sequences of scFvs Identified

The nucleic acid sequence of Clone A10 (SEQ ID NO: 47) comprises the sequence below, wherein the V$_H$ region is bolded (SEQ ID NO: 150, wherein V$_H$ CDR regions 1, 2, and 3 are boxed therein as SEQ ID NOS: 153, 154, and 155 respectively), the V$_L$ region is italicized (SEQ ID NO: 151, wherein V$_L$ CDR regions 1, 2, and 3 are boxed therein as SEQ ID NOS: 156, 157, and 158 respectively), and the peptide linker sequence is underlined (SEQ ID NO: 152):

AGCGCGCATGCCGAGGCTTATCTGCAGCAGTCTGGGGCTGAACTGGTGAAGCCTGGGGCTTCAGTGAAGCT

GTCCTGCAAGGCTTCTGGCTACACCTTCACCAGCTACTGGATGCACGAGTGGGTGAAGCAGAGGCCTGGAC

AAGGCCTTGAGTGGATTGGAGAGATTAATCCTAGAAACGGTCGTAGTAACTACAATGAGAAGTTCAAGAA

GAAGGCCACAGTGACTGTAGACAAATATTCCAACACAGCCTACATGCAACTCAGCAGCCTGACATCTGACG

ACTCTGCGGTCTATTACTGTACAAGAGATGGGGGTGACTACTGGGGCCAAGGCACCACTGTCACCGTCTCCT

CGGGTGGTGGTGGTTCTGGCGGCGGCGGCTCCGGCGGAGGTGCTCGAGGCGGTGGCGGATCGGACATTGT

GCTGACCCAGTCTCACAAATTCATGTCCACATCAGTAGGAGACAGGGTCAGCATCACCTGCAAGGCCAGTCAG

GATGTGGGTACTGCTGTAGCCTGGTATCAACAGAAACCAGGGCAATCTCCTAAACTACTGATTTACTGGGCAT

CCACCCGGCACACTGGAGTCCCTGATCGCTTCACAGGCAGTGGATCTGGGACAGATTTCACTCTCACCATTAGC

AATGTGCAGTCTGAAGACTTGGCAGATTATTTCTGTCAGCAATATAGCAGCTATCCTCTCACGTTCGGAGGGG

GGACCAAGCTGGAAATGAAACGCGCTAGC

The nucleic acid sequence of Clone 3F4 (SEQ ID NO: 48) comprises the sequence below, wherein the V$_H$ region is bolded (SEQ ID NO: 159, wherein V$_H$ CDR regions 1, 2, and 3 are boxed therein as SEQ ID NOS: 162, 163, and 164 respectively), the V$_L$ region is italicized (SEQ ID NO: 160, wherein V$_L$ CDR regions 1, 2, and 3 are boxed therein as SEQ ID NOS: 165, 166, and 167 respectively), and the peptide linker sequence is underlined (SEQ ID NO: 161):

AGCGCGCATGCCGAGGCTTATCTGCAGCAGTCTGCAGCTGAACTGGCAAGACCTGGGGCCTCAGTGAAGAT

GTCCTGCAAGGCTTCTGGCAACACCTTCACTAGCTACACGATGCACTGGGTAAAACAGAGGCCTGGACAGG

GTCTGGAATGGATTGGATACATTAATCCTAGCAGTGGATATACTGAATACAATCAGAAGTTCAAGGACAAG

ACCACATTGACTGCAGACACATCCTCCAGCACAGCCTACATGCAACTGAGCAGCCTGACACCTGAGGACTCT

GCGGTCTATTATTGTGCAAGAGGCCCCAGGTACTGGGGCCAAGGGACTCTGGTCACTGTCTCTGCGGGTGG

TGGTGGTTCTGGCGGCGGCGGCTCCGGCGGAGGTGCTCGAGGCGGTGGCGGATCGGACACAACTGTGACCC

AGTCTCAAAAATTCATGTCCACATCAGTAGGAGACAGGGTCAGCGTCACCTGCAAGGCCAGTCAGAATGTGG

GTACTAATGTTGCCTGGTATCAACAGAAACCAGGGCAATCTCCTAAAGCACTGATTTACTCGGCATCCTACCGG

TACAGTGGAGTCCCTGATCGCTTCACAGGCAGTGGATCTGGGACAGATTTCACTCTCACCATCAGCAATGTGC

ACTCTGAAGACTTGGCAGAGTATTTCTGTCAGCAATATAACAGCTATCCGTACACGTTCGGAGGGGGGACCAA

GCTGGAAATCAAACGCGCTAGC

The nucleic acid sequence of Clone 3F9 (SEQ ID NO: 49) comprises the sequence below, wherein the V$_H$ region is bolded (SEQ ID NO: 168, wherein V$_H$ CDR regions 1, 2, and 3 are boxed therein as SEQ ID NOS: 171, 172, and 173 respectively), the V$_L$ region is italicized (SEQ ID NO: 169, wherein V$_L$ CDR regions 1, 2, and 3 are boxed therein as SEQ ID NOS: 174, 175, and 176 respectively), and the peptide linker sequence is underlined (SEQ ID NO: 170):

AGCGCGCATGCCCAGATCCAACTGCAGCAGCCTGGGGCTGAACTGGTGAAGCCTGGGGCTTCAGTGAAGCT

GTCCTGCAAGGCTTCTGGCTACACCTTCACCAGCTACTGGATGCACTGGGTGAAGCAGAGGCCTGGACAAG

GCCTTGAGTGGATTGGAGAGATTAATCCTAGCAACGGTCGTACTAACTACAATGAGAAGTTCAAGAGCAAG

GCCACACTGACTGTAGACAAATCCTCCAGCACAGCCTACATGCAACTCAGCAGCCTGACATCTGAGGACTCT

GCGGTCTATTACTGTGCAAGAGATGGGGGTGACTACTGGGGCCAAGGCACCACTCTCACAGTCTCCTCGGG

TGGTGGTGGTTCTGGCGGCGGCGGCTCCGGCGGAGGTGCTCGAGGCGGTGGCGGATCGGACATTGTGATGT

CACAGTCTCACAAATTCATGTCCACATCAGTAGGAGACAGGGTCAGCATCACCTGCAAGGCCAGTCAGGATGT

GGGTACTGCTGTAGCCTGGTATCAACAGAAACCAGGGCAATCTCCTAAACTACTGATTTACTGGGCATCCACC

CGGCACACTGGAGTCCCTGATCGCTTCACAGGCAGTGGATCTGGGACAGATTTCACTCTCACCATTAGCAATGT

GCAGTCTGGAGACTTGGCAGATTATTTCTGTCAGCAATATAGCAGCTATCCTCTCACGTTCGGAGGGGGGACC

AAGCTGGAAATCAAACGCGCTAGC

The nucleic acid sequence of Clone 4C1 (SEQ ID NO: 50) comprises the sequence below, wherein the V$_H$ region is bolded (SEQ ID NO: 177, wherein V$_H$ CDR regions 1, 2, and 3 are boxed therein as SEQ ID NOS: 180, 181, and 182 respectively), the V$_L$ region is italicized (SEQ ID NO: 178, wherein V$_L$ CDR regions 1, 2, and 3 are boxed therein as SEQ ID NOS: 183, 184, and 185 respectively), and the peptide linker sequence is underlined (SEQ ID NO: 179):

AGCGCGCATGCCGAGATCCAACTGCAGCAGTCTGGGGCTGAACTGGTGAAGCCTGGGGCCTCAGTGAAGCT

GTCCTGCAAGGCTTCTGGCTACACCTTCACCAGCTACTGGATGCACTGGGTGAAGCAGAGGCCTGCACAAG

GCCTTGAGTGGATTGGAGAGATTAATCCTAGAAACGGTCGTAGTAACTACAATGAGAAGTTCAAGAATAA

GGCCACAGTGACTGTAGACAAATATTCCAACACAGCCTACATGCAACTCAGCCTGACATCTGACGACTC

TGCGGTCTATTACTGTACAAGAGATGGGGGTGACTACTGGGGCCAAGGCACCACTCTCACAGTCTCCTCGG

GTGGTGGTGGTTCTGGCGGCGGCGGCTCCGGCGGAGGTGCTCGAGGCGGTGGCGGATCGGACATTGTGCTG

ACCCAGTCTCAAAAATTCATGTCCACATCAGTAGGAGACAGGGTCAGCGTCACCTGCAAGGCCAGTCAGAATG

TGGGTACTAATGTAGCCTGGTATCAACAGAAACCAGGGCAATCTCCTAAAGCACTGATTTACTCGGCATCCTA

-continued

CCGGTACAGTGGAGTCCCTGATCGCTTCACAGGCAGTGGATCTGGGACAGATTTCACTCTCACCATTAGCAAT

GTGCAGTCTGAAGACTTGGCAGATTATTTCTGTCAGCAATATAACAGCTATCCTCTCACGTTCGGAGGGGGA

CCAAGCTGGAAATGAAACGCGCTAGC

The nucleic acid sequence of Clone 4H1 (SEQ ID NO: 51) comprises the sequence below, wherein the $V_H$ region is bolded (SEQ ID NO: 186, wherein $V_H$ CDR regions 1, 2, and 3 are boxed therein as SEQ ID NOS: 189, 190, and 191 respectively), the $V_L$ region is italicized (SEQ ID NO: 187, wherein $V_L$ CDR regions 1, 2, and 3 are boxed therein as SEQ ID NOS: 192, 193, and 194 respectively), and the peptide linker sequence is underlined (SEQ ID NO: 188):

AGCGCGCATGCCGAGGCTTATCTGCAGCAGTCTGGGGCTGAACTGGTGAAGCCTGGGGCTTCAGTGAAGCT

GTCCTGCAAGGCTTCTGGCTACACCTTCACCAGCTACTGGATGCACTGGGTGAAGCAGAGGCCTGGACAAG

GCCTTGAGTGGATTGGAGAGATTAATCCTAGAAACGGTCGTAGTAACTACAATGAGAAGTTCAAGAACAA

GGCCACAGTGACTGTAGACAAATATTCCAACACAGCCTACATGCAACTCAGCAGCCTGACATCTGACGACTC

TGCGGTCTATTACTGTACAAGAGATGGGGGTGACTACTGGGGCCAAGGGCACCACTGTCACCGTCTCCTCGG

GTGGTGGTGGTTCTGGCGGCGGCGGCTCCGGCGGAGGTGCTCGAGGCGGTGGCGGATCGGACATTGTGCTG

ACCCAGTCTCACAAATTCATGTCCACATCAGTAGGAGACAGGGTCAGCATCACCTGCAAGGCCAGTCAGGATG

TGGGTACTGCTGTAGCCTGGTATCAACAGAAACCAGGGCAATCTCCTAAACTACTGATTTACTGGGCATCCAC

CCGGCACACTGGANTCCCTGATCGCTTCACAGGCAGTGGATCTGGGACAGATTTCACTCTCACCATTANCAAT

GTGCAGTCTGAANACTTGNNANATTATTTCTGTCANCAATATANCANCTATCCTCTCACGTTCGGAGGGGGA

CCANCTGGAAATGAAACGCGCTNNCTCAGGTGCTGAACNNAANN

The nucleic acid sequence of Clone D7 (SEQ ID NO: 52) comprises the sequence below, wherein the $V_H$ region is bolded (SEQ ID NO: 195, wherein $V_H$ CDR regions 1, 2, and 3 are boxed therein as SEQ ID NOS: 198, 199, and 200 respectively), the $V_L$ region is italicized (SEQ ID NO: 196, wherein $V_L$ CDR regions 1, 2, and 3 are boxed therein as SEQ ID NOS: 201, 202, and 203 respectively), and the peptide linker sequence is underlined (SEQ ID NO: 197):

AGCGCGCATGCCGAGGCTTATCTGCAGCAGTCTGGAGCTGAGTTGGTAAGGCCTGGGACTTCAGTGAAGGT

GTCCTGCAAGGCCTCTGGATACGCCTTCACTAAATACTTGATTGAGTGGGTAAAGCAGAGGCCTGGACAGG

GCCTTGAGTGGATTGGAGTGATTAATCCTGGAAGTGGTAGTACTAGTTACAATGAGAAGTTCAGGTACAAG

GCAATATTGACTGCAGACACATCCTCCAGCACTGCCTACATGCAACTCAGCAGCCTGACATCTGATGACTCTG

CGGTTTATTTCTGTGCAACAATACCGGCCTCCTATCGGTCCGATTCCCTTGACTGCTGGGGCCAAGGCACCAC

GGTCACCGTCTCCTCGGGTGGTGGTGGTTCTGGCGGCGGCGGCTCCGGCGGAGGTGCTCGAGGCGGTGGCG

GATCGGACACAACTGTGACCCAGTCTCACAAATTCATGTCCACATCAGTAGGAGACAGGGTCAGCATCACCTG

CAAGGCCAGTCAGGATGTGGGTACTGCTGTAGCCTGGTATCAACAGAAACCAGGGCAATCTCCTAAACTACTG

ATTTACTGGGCATCCACCCGGCACACTGGAGTCCCTGATCGCTTCACAGGCAGTGGATCTGGGACAGATTTCA

CTCTCACCATTAGCAATGTGCAGTCTGAAGACTTGGCAGATTATTTCTGTCAGCAATATAGCAGCTATCCGTGG

ACGTTCGGTGGAGGCACCAAGCTGGAAATGAAACGCGCTAGC

The nucleic acid sequence of Clone H8 (SEQ ID NO: 53) comprises the sequence below, wherein the V$_H$ region is bolded (SEQ ID NO: 204, wherein V$_H$ CDR regions 1, 2, and 3 are boxed therein as SEQ ID NOS: 207, 208, and 209 respectively), the V$_L$ region is italicized (SEQ ID NO: 205, wherein V$_L$ CDR regions 1, 2, and 3 are boxed therein as SEQ ID NOS: 210, 211, and 212 respectively), and the peptide linker sequence is underlined (SEQ ID NO: 206):

AGCGCGCATGCCGAGGTGCAACTGCAGCAGTCTGGGACTGAACTGGTGAAGCCTGGGGCTTCAGTGAAGC

TGTCCTGCAAGACTTCTGGCTACACCTTCACTAAATACTTGATTGAGTGGGTAAAGCAGAGGCCTGGACAG

GGCCTTGAGTGGATTGGAGTGATTAATCCTGGAAGTGGTAGTACTAGTTACAATGAGAAGTTCAGGTACAA

GGCAATATTGACTGCAGACACATCCTCCAGCACTGCCTACATGCAACTCAGCAGCCTGACATCTGATGACTC

TGCGGTTTATTTCTGTGCAACAATACCGGCCTCCTATCGGTCCGATTCCCTTGACTGCTGGGGCCAAGGCACC

ACGGTCACCGTCTCCTCGGGTGGTGGTGGTTCTGGCGGCGGCGGCTCCGGCGGAGGTGCTCGAGGCGGTGG

*CGGATCGGACACAACTGTGACCCAGTCTCACAAATTCATGTCCACATCAGTAGGAGACAGGGTCAGCATCACC*

*TGC*AAGGCCAGTCAGGATGTGGGTACTGCTTGTAGCC*TGGTATCAACAGAAACCAGGGCAATCTCCTAAACTAC*

*TGATTTAC*TGGGCATCCACCCGGCACACT*GGAGTCCCTGATCGCTTCACAGGCAGTGGATCTGGGACAGATTT*

*CACTCTCACCATTAGCAATGTGCAGTCTGAAGACTTGGCAGATTATTTCTGT*CAGCAATATAGCAGCTATCCGT

GGACG*TTCGGTGGAGGCACCAAGCTGGAAATGAAACGCGCTAGC*

The nucleic acid sequence of Clone 2C1 (SEQ ID NO: 54) comprises the sequence below, wherein the V$_H$ region is bolded (SEQ ID NO: 213, wherein V$_H$ CDR regions 1, 2, and 3 are boxed therein as SEQ ID NOS: 216, 217, and 218 respectively), the V$_L$ region is italicized (SEQ ID NO: 214, wherein V$_L$ CDR regions 1, 2, and 3 are boxed therein as SEQ ID NOS: 219, 220, and 221 respectively), and the peptide linker sequence is underlined (SEQ ID NO: 215):

AGCGCGCATGCCGAGGCTTATCTGCAGCAGTCTGGAGCTGAGTTGGTAAGGCCTGGGACTTCAGTGAAGGT

GTCCTGCAAGGCCTCTGGATACGCCTTCACTAAATACTTGATTGAGTGGGTAAAGCAGAGGCCTGGACAGG

GCCTTGAGTGGATTGGAGTGATTAATCCTGGAAGTGGTAGTACTAGTTACAATGAGAAGTTCAGGTACAAG

GCAATATTGACTGCAGACACATCCTCCAGCACTGCCTACATGCAACTCAGCAGCCTGACATCTGATGACTCTG

CGGTTTATTTCTGTGCAACAATACCGGCCTCCTATCGGTCCGATTCCCTTGACTGCTGGGGCCAAGGCACCAC

GGTCACCGTCTCCTCGGGTGGTGGTGGTTCTGGCGGCGGCGGCTCCGGCGGAGGTGCTCGAGGCGGTGGCG

*GATCGGACACAACTGTGACCCAGTCTCACAAATTCATGTCCACATCAGTAGGAGACAGGGTCAGCATCACCTG*

*C*AAGGCCAGTCAGGATGTGGGTACTGCTGTAGCC*TGGTATCAACAGAGACCAGGGCAATCTCCTAAACTACTG*

*ATTTAC*TGGGCATCCACCCGGCACACT*GGAGTCCCTGATCGCTTCACAGGCAGTGGATCTGGGACAGATTTCA*

*CTCTCACCATCAGCAATGTGCAGTCTGAAGACTTGGCAGACTATTTCTGT*CAGCAATATAAAAGCTATCCTCTC

ACT*TTCGGAGGGGGGACCAAGCTGGAAATCAAACGCGCTAGC*

The nucleic acid sequence of Clone G8 (SEQ ID NO: 55) comprises the sequence below, wherein the V$_H$ region is bolded (SEQ ID NO: 222, wherein V$_H$ CDR regions 1, 2, and 3 are boxed therein as SEQ ID NOS: 225, 226, and 227 respectively), the V$_L$ region is italicized (SEQ ID NO: 223, wherein V$_L$ CDR regions 1, 2, and 3 are boxed therein as SEQ ID NOS: 228, 229, and 230 respectively), and the peptide linker sequence is underlined (SEQ ID NO: 224):

```
AGCGCGCATGCCGAGGCTTATCTGCAGCAGTCTGGAGCTGAGCTGGTAAGGCCTGGGACTTCAGTGAAGGT

GTCCTGCAAGGCTTCT|GGATACGTCTTCACCAATTTCTTGATAGAG|TGGGTAAAACAGAGGCCTGGACAGG

GCCTTGAGTGGATTGGG|GTGATTAATCCTGGAAATGGTGGTGCTGCCTATAATGAGAAGTTCAAGGGC|AA

GGCGATACTTACTGCAGACAAATCCTCCAGTACTGCCTATATGCAGCTTAGCAGTCTGACATCTGATGACTCT

GCGGTCTATTTCTGTGCAAGA|TTGCCCCCCTCGTATGATTACGACGGCGACATCGACTAC|TGGGGCCAAGGC

ACCACGGTCACCGTCTCCTCGGGTGGTGGTGGTTCTGGCGGCGGCGGCTCCGGCGGAGGTGCTCGAGGCGG

TGGCGGATCGGACCTTGTGCTCACTCAGTCTCCTGCTTCCTTAGCTGTGGCTCTGGGACAGAGGGCCACCATCT

CATGC|AGGGCCAGCAAAAGTGTCACTACATCTGGCTATAGTTTAATGCAC|TGGTACCGACAGAAACCAGGACA

GCCACCCAAACTCCTCATCTAT|CCTGCATCCAACCTAGAATCT|GGGGTCCCTGCCAGATTCAGTGGCAGTGGGT

CTGGGACAGACTTCACCCTCAACATCCATCCTGTGGAGGAGGAGGATGCTGCAACCTATTACTGT|CAGCACAG

TAGGGAGCTTCCGTGGACG|TTCGGTGGAGGCACCAAGCTGGAAATCAAACGCGCTAGC
```

The nucleic acid sequence of Clone 4E3 (SEQ ID NO: 56) comprises the sequence below, wherein the $V_H$ region is bolded (SEQ ID NO: 231, wherein $V_H$ CDR regions 1, 2, and 3 are boxed therein as SEQ ID NOS: 234, 235, and 236 respectively), the $V_L$ region is italicized (SEQ ID NO: 232, wherein $V_L$ CDR regions 1, 2, and 3 are boxed therein as SEQ ID NOS: 237, 238, and 239 respectively), and the peptide linker sequence is underlined (SEQ ID NO: 233):

```
AGCGCGCATGCCCAGGTCCAACTGCAGCAGTCTGGAGCTGAGCTGGTAAGGCCTGGGACTTCAGTGAAGGT

GTCCTGCAAGGCTTCT|GGATACGCCTTCACTAATTTCTTGATAGAG|TGGGTAAAACAGAGGCCTGGACAGG

GCCTTGAGTGGATTGGG|GTGATTAATCCTGGAAGTGGTGGTACTGGTTACAATGAGAAGTTCAAGGGC|AA

GGCAACACTGACTGCAGACAAATCCTCCAGCACTGCCTACATGCAGCTCAATAGTCTAACATCTGATGACTC

TGCGGTCTATTTCTGTGCAAGA|TTGCCCCCCTCATATGATTACGACGGCGACATCGACTAC|TGGGGCCAAGG

CACCACTGTCACCGTCTCCTCGGGTGGTGGTGGTTCTGGCGGCGGCGGCTCCGGCGGAGGTGCTCGAGGCG

GTGGCGGATCGGACATTGTGATGTCACAGTCTCCTGCTTCCTTAGCTGTATCTCTGGGGCAGAGGGCCACCAT

CTCATGC|AGGGCCAGCAAAAGTGTCAGTTCATCTGGCTATAGTTTAATACAC|TGGTACCAACAGAAACCAGGA

CAGCCACCCAAACTCGTCATCTAT|CTTGCATCTAACCTANATTC|TGGGGTCCCTGCCNNNTTCAGTGGCAGTGG

ATCTGGNACAGACTTCACCCTCAACATCCATCCTGTGNAGGANGAGGATGCTGCAACCTATTACTGTCANCAC

AGT|NNGGANCTTCCGTGGNNN|NNCGNGGNNNNCCAAGCTGGAAATCAANGCNCTANCTCNNNNCCTNAAC

ANNAANNTGATCNTCTNNNNAANANCTGAANNGNTGNCTNNACC
```

The present invention encompasses recombinant antibodies comprising scFv fragments, that bind to a target, such as a PAH. In one embodiment, an scFv fragment comprises a recombinant PAH antibody of the invention. In some embodiments, the PAH antibody or fragment thereof comprises at least 80% of the amino acid sequence of any one of SEQ ID NOS: 37-46. In some embodiments, the PAH antibody or fragment thereof comprises at least 85% of the amino acid sequence of any one of SEQ ID NOS: 37-46. In some embodiments, the PAH antibody or fragment thereof comprises at least 90% of the amino acid sequence of any one of SEQ ID NOS: 37-46. In some embodiments, the PAH antibody or fragment thereof comprises at least 91% of the amino acid sequence of any one of SEQ ID NOS: 37-46. In some embodiments, the PAH antibody or fragment thereof comprises at least 92% of the amino acid sequence of any one of SEQ ID NOS: 37-46. In some embodiments, the PAH antibody or fragment thereof comprises at least 93% of the amino acid sequence of any one of SEQ ID NOS: 37-46. In some embodiments, the PAH antibody or fragment thereof comprises at least 94% of the amino acid sequence of any one of SEQ ID NOS: 37-46. In some embodiments, the PAH antibody or fragment thereof comprises at least 95% of the amino acid sequence of any one of SEQ ID NOS: 37-46. In some embodiments, the PAH antibody or fragment thereof comprises at least 96% of the amino acid sequence of any one of SEQ ID NOS: 37-46. In some embodiments, the PAH antibody or fragment thereof comprises at least 97% of the amino acid sequence of any one of SEQ ID NOS: 37-46. In some embodiments, the PAH antibody or fragment thereof comprises at least 98% of the amino acid sequence of any one of SEQ ID NOS: 37-46. In some embodiments, the PAH antibody or fragment thereof comprises at least 99% of the amino acid sequence of any one of SEQ ID NOS: 37-46. In some embodiments, the PAH antibody or fragment thereof comprises any one of SEQ ID NOS: 37-46. In some embodiments, the amino acid sequence of a PAH antibody or fragment thereof is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 37, 38, 39, 40, 41, 42, 43, 44, 45 or 46.

In some embodiments, the PAH scFV fragments identified herein can be used to construct a Fab fragment. For example, a combination of a $V_H$ domain, a $V_L$ domain, a peptide linker and a constant region can be used to construct a Fab fragment. In one embodiment, the $V_H$ domain comprises at least 90%, 91%, 92%, 93%, 94%, 95%, 96%, 97%, 98%, or 99% of SEQ ID NO: 57, 66, 75, 82, 91, 100, 109, 118, 127, or 136. In another embodiment, the $V_H$ domain comprises SEQ ID NO: 57, 66, 75, 82, 91, 100, 109, 118, 127, or 136. In one embodiment, the $V_L$ domain comprises at least 90%, 91%, 92%, 93%, 94%, 95%, 96%, 97%, 98%, or 99% of SEQ ID NO: 58, 67, 76, 83, 92, 101, 110, 119, 128, or 137. In another embodiment, the $V_L$ domain comprises SEQ ID NO: 58, 67, 76, 83, 92, 101, 110, 119, 128, or 137. In some embodiments, the peptide linker sequence comprises at least 90%, 91%, 92%, 93%, 94%, 95%, 96%, 97%, 98%, or 99% of SEQ ID NO: 59, 68, 77, 84, 93, 102, 111, 120, 129, 138, 146, 147, 148, or 149. In some embodiments, the peptide linker sequence comprises SEQ ID NO: 59, 68, 77, 84, 93, 102, 111, 120, 129, 138, 146, 147, 148, or 149. In some embodiments, the constant domain comprises those sequences known in the art and readily apparent to the skilled artisan, for example the constant domain obtained from an immunoglobulin molecule.

In some embodiments, the PAH scFV fragments identified herein can be used to construct an intact, fully reconstituted antibody, for example as shown in FIG. 19A. For example, a combination of two $V_H$ domains, two $V_L$ domains, a peptide linker, and $V_H$ and $V_L$ constant regions can be used to construct a fully reconstituted antibody. In one embodiment, the $V_H$ domain comprises at least 90%, 91%, 92%, 93%, 94%, 95%, 96%, 97%, 98%, or 99% of SEQ ID NO: 57, 66, 75, 82, 91, 100, 109, 118, 127, or 136. In another embodiment, the $V_H$ domain comprises SEQ ID NO: 57, 66, 75, 82, 91, 100, 109, 118, 127, or 136. In one embodiment, the $V_L$ domain comprises at least 90%, 91%, 92%, 93%, 94%, 95%, 96%, 97%, 98%, or 99% of SEQ ID NO: 58, 67, 76, 83, 92, 101, 110, 119, 128, or 137. In another embodiment, the $V_L$ domain comprises SEQ ID NO: 58, 67, 76, 83, 92, 101, 110, 119, 128, or 137. In some embodiments, the peptide linker sequence comprises at least 90%, 91%, 92%, 93%, 94%, 95%, 96%, 97%, 98%, or 99% of SEQ ID NO: 59, 68, 77, 84, 93, 102, 111, 120, 129, 138, 146, 147, 148, or 149. In some embodiments, the peptide linker sequence comprises SEQ ID NO: 59, 68, 77, 84, 93, 102, 111, 120, 129, 138, 146, 147, 148, or 149. In some embodiments, the constant domain comprises those sequences known in the art and readily apparent to the skilled artisan, for example the constant domain obtained from an immunoglobulin molecule. In one embodiment, the reconstituted antibody is a monoclonal antibody. In some embodiments, the reconstituted antibody can be a chimeric antibody. In some embodiments, the reconstituted antibody can be humanized.

In some embodiments, the recombinant antibody or fragment thereof that specifically binds to a polycyclic aromatic hydrocarbon (PAH) has an $IC_{50}$ less than or equal to 0.01 µM, 0.05 µM, 0.1 µM, 0.25 µM, 0.5 µM, 0.75 µM, 1 µM, 1.25 µM, 1.5 µM, 1.75 µM, 2 µM, 2.5 µM, 3.0 µM, 3.5 µM, 4.0 µM, 4.5 µM, 5.0 µM, 5.5 µM, 6.0 µM, 6.5 µM, 7.0 µM, 8.5 µM, 9.0 µM, 9.5 µM, 10.0 µM, 10.5 µM, 11.0 µM, 11.5 µM, 12.0 µM, 12.5 µM, 13.0 µM, or 13.5 µM. In some embodiments, the recombinant antibody or fragment thereof that specifically binds to a polycyclic aromatic hydrocarbon (PAH) has an $IC_{50}$ less than or equal to 8.3 µM.

The invention provides for a recombinant antibody or fragment thereof that specifically binds to phenanthrene. In some embodiments, recombinant antibody or fragment thereof does not show substantial cross-reactivity against a PAH selected from the group consisting of naphthalene, acenapthene, acenapthylene, fluorene, anthracene, benz[a]anthracene, chrysene, benzo[b]fluoranthene, benzo[k]fluoranthene, benzo[a]pyrene, benzol[ghi]perylene, and dibenz[a,h]anthracene.

The present invention encompasses nucleic acids encoding scFv fragments that bind to a target, for example, a PAH. In some embodiments, the nucleic acid sequence encoding a PAH antibody or fragment thereof is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 47, 48, 49, 50, 51, 52, 53, 54, 55 or 56. In some embodiments, the nucleic acid sequence encoding a PAH antibody or fragment thereof comprises 80%, 81%, 82%, 83%, 84%, 85%, 86%, 87%, 88%, 89%, 90%, 91%, 92%, 93%, 94%, 95%, 96%, 97%, 98%, or 99% of SEQ ID NO: 150, 159, 168, 177, 186, 195, 204, 213, 222, or 231. In some embodiments, the nucleic acid sequence encoding a PAH antibody or fragment thereof comprises SEQ ID NO: 150, 159, 168, 177, 186, 195, 204, 213, 222, or 231. In some embodiments, the nucleic acid sequence encoding a PAH antibody or fragment thereof comprises 80%, 81%, 82%, 83%, 84%, 85%, 86%, 87%, 88%, 89%, 90%, 91%, 92%, 93%, 94%, 95%, 96%, 97%, 98%, or 99% of SEQ ID NO: 151, 160, 169, 178, 187, 196, 205, 214, 223, or 232. In some embodiments, the nucleic acid sequence encoding a PAH antibody or fragment thereof comprises SEQ ID NO: 151, 160, 169, 178, 187, 196, 205, 214, 223, or 232.

In some embodiments, the nucleic acids encoding PAH scFV fragments identified herein can be used to construct a nucleic acid encoding a Fab fragment. For example, a combination of nucleic acids encoding a $V_H$ domain, a $V_L$ domain, a peptide linker and a constant region can be used to construct a Fab fragment. In one embodiment, the nucleic acid encoding a $V_H$ domain comprises at least 90%, 91%, 92%, 93%, 94%, 95%, 96%, 97%, 98%, or 99% of SEQ ID NO: 150, 159, 168, 177, 186, 195, 204, 213, 222, or 231. In another embodiment, the nucleic acid encoding a $V_H$ domain comprises SEQ ID NO: 150, 159, 168, 177, 186, 195, 204, 213, 222, or 231. In one embodiment, the the nucleic acid encoding a $V_L$ domain comprises at least 90%, 91%, 92%, 93%, 94%, 95%, 96%, 97%, 98%, or 99% of SEQ ID NO: 151, 160, 169, 178, 187, 196, 205, 214, 223, or 232. In another embodiment, the nucleic acid encoding a $V_L$ domain comprises SEQ ID NO: 151, 160, 169, 178, 187, 196, 205, 214, 223, or 232. In some embodiments, the nucleic acid encoding a peptide linker sequence comprises at least 90%, 91%, 92%, 93%, 94%, 95%, 96%, 97%, 98%, or 99% of SEQ ID NO: 152, 161, 170, 179, 188, 197, 206, 215, 224, or 233. In some embodiments, the nucleic acid encoding a peptide linker sequence comprises SEQ ID NO: 152, 161, 170, 179, 188, 197, 206, 215, 224, or 233. In some embodiments, the nucleic acid sequence encoding a constant domain comprises those sequences readily available in the art and apparent to the skilled artisan, for example the constant domain obtained from an immunoglobulin molecule.

In some embodiments, the nucleic acids encoding PAH scFV fragments identified herein can be used to construct a nucleic acid encoding an intact, fully reconstituted antibody, for example as shown in FIG. 19A. For example, a combination of two $V_H$ domains, two $V_L$ domains, a peptide linker, and $V_H$ and $V_L$ constant regions can be used to construct a fully reconstituted antibody. In one embodiment, the nucleic acid encoding a $V_H$ domain comprises at least 90%, 91%, 92%, 93%, 94%, 95%, 96%, 97%, 98%, or 99% of SEQ ID NO: 150, 159, 168, 177, 186, 195, 204, 213, 222, or 231. In another embodiment, the nucleic acid encoding a $V_H$ domain comprises SEQ ID NO: 150, 159, 168, 177, 186, 195, 204, 213, 222, or 231. In one embodiment, the the nucleic acid encoding a $V_L$ domain comprises at least 90%, 91%, 92%, 93%, 94%, 95%, 96%, 97%, 98%, or 99% of SEQ ID NO: 151, 160, 169, 178, 187, 196, 205, 214, 223, or 232. In another embodiment, the nucleic acid encoding a $V_L$ domain comprises SEQ ID NO: 151, 160, 169, 178, 187, 196, 205, 214, 223, or 232. In some embodiments, the nucleic acid encoding a peptide linker sequence comprises at least 90%, 91%, 92%, 93%, 94%, 95%, 96%, 97%, 98%, or 99% of SEQ ID NO: 152, 161, 170, 179, 188, 197, 206, 215, 224, or 233. In some embodiments, the nucleic acid encoding a peptide linker sequence comprises SEQ ID NO: 152, 161, 170, 179, 188, 197, 206, 215, 224, or 233. In some embodiments, the nucleic acid sequence encoding the constant domain comprises those sequences known in the art and readily apparent to the skilled artisan, for example the constant domain obtained from an immunoglobulin molecule. In one embodiment, the reconstituted antibody is a monoclonal antibody. In some embodiments, the reconstituted antibody can be a chimeric antibody. In some embodiments, the reconstituted antibody can be humanized.

Unless otherwise defined, technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention.

As will be apparent to one of ordinary skill in the art from a reading of this disclosure, the embodiments of the present disclosure can be embodied in forms other than those specifically disclosed herein. The embodiments described herein are, therefore, to be considered as illustrative and not restrictive. Those skilled in the art will recognize, or be able to ascertain, using no more than routine experimentation, numerous equivalents to the specific embodiments described herein. The scope of the invention is as set forth in the appended claims and equivalents thereof, rather than being limited to the examples contained in the foregoing description.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Polycyclic aromatic hydrocarbons (PAHs) are a class of toxic and persistent environmental contaminants. A recombinant scFv antibody library (~6×106 individual scFvs) was prepared from mice immunized with methylated phenanthrene-protein conjugates. Two selection systems, phage and yeast display, were used sequentially to select rare clones from this library that can bind to soluble phenanthrenes and/or methylated (alkylated) phenanthrenes. After three rounds of phage selection, selected scFv fragments were cloned into a yeast display vector to generate a yeast mini-library. Yeast display coupled with fluorescence-activated cell sorting (FACS) was used to analyze and select scFv pools that bound to soluble phenanthrene and/or methylated phenanthrenes. Finally, analysis of single cells isolated from these pooled samples allowed us to select three specific monoclonal scFvs, each with unique amino acid sequences and binding specificities.

Materials

Chemicals (purities at 98% or higher) were purchased from the following sources: phenanthene (Phen, Sigma Aldrich), 2-methylphenanthrene (2-MP, Sigma Aldrich), 3-methylphenanthrene (3-MP, BOC Sciences), 4-methylphenanthrene (4-MP, Chem Service), 9-methylphenanthrene (9-MP, Crescent Chemical). Each compound was dissolved as 10 mM stock in DMSO. 9-Carboxyl-phenanthrene was purchased from Sigma Aldrich. 9-Carboxyl-7-methyl-phenanthrene, and 9-carboxyl-2,7-dimethyl-phenanthrene were synthesized in-house at the University of Texas Medical Branch in Galveston, Tex. Phage display plasmid pComb3XSS was obtained from The Scripps Research Institute. Both the yeast display plasmid pDNL6-GFP-myc (originally generated from pPNL6 plasmid and scFv expression plasmid POE-myc (generated from a pET based plasmid, pEP-D1.3 were modified in our laboratory to replace the V5 tag with a myc tag. Monoclonal anti-myc antibody 9E10 was purified in-house from the culture supernatant of 9E10 hybridoma cells (Developmental Studies Hybridoma Bank, University of Iowa).

Preparation of Protein Conjugates

9-Carboxyl-phenanthrene, 9-carboxyl-7-methyl-phenanthrene, and 9-carboxyl-2,7-dimethyl-phenanthrene) were conjugated onto protein carriers (BSA or KLH) using a mixed anhydride method. Briefly, 0.05 mmol of carboxylated hapten was dissolved in 2 ml anhydrous 1,4-dioxane. Equal molar amounts of tributylamine and isobutyl chloroformate were then added and the reaction was kept on ice for 30 minutes to form the mixed anhydride intermediate. Subsequently, the mixed anhydride was added dropwise into 2.5 ml protein carrier solution (40 mg of BSA or 20 mg of KLH) at pH 8.5 and the reaction was incubated at room temperature for about 4 hours. The reaction mixture was then centrifuged to remove the precipitates. The final product was first dialyzed against 0.01 M glycine at pH 9.0 to stop the reaction and then dialyzed in PBS buffer (10 mM $Na_2HPO_4$, 1.8 mM $KH_2PO_4$, 137 mM NaCl, 2.7 mM KCl, pH 7.4) for about another 2 days. The presence of phenanthrene derivatives on the conjugate was confirmed by indirect ELISA using monoclonal antibody BAP-13 (LifeSpan Biosciences, Seattle, Wash.), which recognizes PAHs with a broad cross-reactivity. PAH-BSA conjugates were further biotinylated with EZ-Link™ Sulfo-NHS-Biotin (Life Technology, Grand Island, N.Y.) for yeast display screening, and unreacted sulfo-NHS-biotin was removed using a PD-10 desalting column (GE Healthcare Life Sciences, Pittsburgh, Pa.). The concentrations of the conjugates were determined by a BCA protein assay kit (Pierce, Rockford, Ill.).

Immunization of Mice

PAH-KLH or PAH-BSA conjugates (50 μg) were mixed with the Sigma adjuvant system (Sigma Aldrich, MO) at 1:1 for each injection. Four female balb/c mice were divided into two groups, and each group was immunized intraperitoneally with the 2-methylphenanthrene or the 2,7-dimethylphenanthrene-conjugate. Four injections were given with alternating carrier proteins to avoid antibodies directed against protein carriers. Blood was taken seven days after the third and fourth injections to test the serum activity, and mice were sacrificed seven days after the final boost.

Immune scFv Library Construction

Seven days after fourth injection, mice were sacrificed, and total RNA was isolated from spleen tissues with Qiagen RNeasy mini kit (Qiagen, Valencia Calif.). RNA samples from the same group of mice were mixed together as the starting material for library construction. Isolated RNA (1~2 μg) was used in the first step of RT-PCR with oligo(dT)20 (SEQ ID NO: 241) or random hexamer primers, and the two amplified cDNA samples were pooled for maximum recovery of cDNA using SuperScript® III First-Strand Synthesis System for RT-PCR kit (Invitrogen, Carlsbad Calif.). This cDNA pool was subsequently used with a degenerate primer set (see FIG. 11 and FIG. 12) to amplify antibody variable regions of heavy and light chains. A second overlapping PCR was performed to link heavy and light chain together as full-length scFv fragments and to dd SfiI restriction sites on both ends. In some embodiments of the invention, PCR primer kits are provided, for example PCR primers having sequences shown in FIGS. 11-12 (such as SEQ ID NOS: 1-34).

The synthesized scFv fragments and pComb3XSS plasmid were digested with SfiI enzyme and ligated with T4 ligase. The newly synthesized plasmid with the scFv insert was then transformed into competent SS320 E. coli bacteria (Lucigen, Middleton, Wis.) by electroporation. Transformed T1 cells were incubated in SOC medium (2% peptone, 0.5% yeast extract, 10 mM NaCl, 2.5 mM KCl, 10 mM $MgCl_2$, 10 mM $MgSO_4$, and 20 mM glucose) overnight to generate the stock library, and aliquots of diluted culture were spread onto 2×YT-AG (2×YT supplement with 100 μg/ml ampicillin and 2% glucose) agar plates to estimate the library size. In addition, single colonies from the agar plate were used as templates to PCR-amplify the insert of pComb3 plasmid; these PCR products were digested with BstNI restriction enzyme to estimate the library diversity.

Phage Display Selection

Antibody phage library or output pools from previous rounds of selection were grown and infected with helper phage M13KO7 for phage production. Briefly, bacteria carrying scFv genes in pComb3XSS phagemid were cultured in 10 ml 2×YT-AG medium at 37C with shaking until they reached log-phage (OD600 at about 0.6), and infected with helper phage M13KO7 at a multiplicity of infection (MOI) of 20:1. The culture was then incubated at 37° C. without shaking for 30 minutes, and subsequently at the same temperature with shaking for another 30 minutes for optimum super-infection with helper phage. After centrifugation, the medium was removed and 10 ml new medium containing ampicillin and kanamycin but without glucose was added, and the culture was incubated at 30° C. with shaking overnight. The next day, the culture was centrifuged and the supernatant containing the phage particles was collected. Phages were concentrated by PEG precipitation. Briefly, ⅕ volume of PEG/NaCl solution (20% PEG-8000, 2.5 M NaCl) was added into culture supernatant and the mixture was incubated on ice for about 1 hour, centrifuged at 4500 rpm for about 30 minutes, and resuspended in 1 ml PBS buffer. The concentrated phage was used for subsequent rounds of selection.

Two selection protocols were performed towards two different targets (unsubstituted phenanthrene or 2-methylphenanthrene). A 96 well high binding plate (Corning, N.Y.) was coated with 50 μl 5 μg/ml antigen at 4° C. overnight. The next day, the plate was washed three times with PBST and blocked with 3% BSA at 25° C. for 1 hour. An aliquot of amplified phage (about $10^{12}$ cfu) prepared as described herein was also blocked with 3% BSA at 25° C. for 1 hour in PBS or PBS plus 1% DMSO. The blocked phages were then added into the antigen-coated plate, and incubated for about 1 hour. At this point, phages carrying desirable binders were bound to the plate, while the unbound phage was removed by washing (15× with PBST followed by 2× with PBS). Finally, the bound phage was eluted by one of two methods: 1) Acid elution with 200 μl glycine-HCl at pH 2.2 for about 8 minutes and immediate neutralization with 9 μl 2 M Tris at about pH 11 to yield a final pH of about 7.5. This method elutes the phage bound to the protein conjugates. At an earlier selection process, this method ensures that selection is comprehensive and does not exclude any rare binders. The second method involves competitive elution with 100 μM soluble analyte (phenanthrene or 2-methylphenanthrene) in 1% DMSO for about 30 minutes. This method was used in the final selection step to enrich a specific population which recognized soluble analytes rather than protein conjugates.

Half of the eluted phage were used to infect 10 ml log-phase T1 E. coli bacteria culture at 37° C. for about 30 minutes. An aliquot of infected culture was serially diluted and spread on 2×YT-AG plates to calculate the number of phage eluted (as "output" of this round of panning), and the rest of culture was incubated in fresh 2×YT-AG medium overnight at 37° C. The next day, phage particles was amplified from this culture and used as "input" for next round of panning.

Yeast Display and FACS Selection

After the final phage display selection step, the phagemids containing the scFv genes were isolated with miniprep kit (Qiagen, Valencia, Calif.), and scFv genes were amplified with a pair of transfer primers, shown in FIG. 13. Yeast display plasmid pDNL6-GFP-myc was digested with BssHII and NheI restriction enzymes and the linear plasmid was gel-purified without the GFP insert. Digested pDNL6 plasmid (500 ng) and purified scFv PCR product (1 μg) were transformed into EBY100 yeast competent cells with Yeast Transformation System 2 kit (Clontech, Mountain View, Calif.). The homologous region on the plasmid and PCR product flanking region led the formation of circular plasmid carrying scFv insert by the yeast homologous repair mechanism. In some embodiments of the invention, transfer primer kits are provided, for example transfer primers having sequences shown in FIG. 13 (such as SEQ ID NOS: 35-36).

For flow cytometry, the yeast library was incubated in growth medium SD-CAA at 30° C. overnight for activation. The next day, activated yeast cells were diluted in induction medium SG/R-CAA at OD600=0.5, and cultured again at 30° C. for about 16 hours. After induction, $10^7$ induced yeast cells (OD600=0.5) were washed twice with 0.5 ml wash buffer I (0.5% BSA supplemented with 2 mM EDTA), and once with 0.5 ml wash buffer II (0.5% BSA). Yeast cells were first incubated with 50 μl competitor (phenanthrene or 2-methylphenanthrene, 200 μM in PBS containing 1% DMSO) for about 30 minutes with rotation at 25° C. An additional aliquot (50 μl) of biotinylated protein-conjugate (BSA-biotin, phen-BSA-biotin, or 2mp-BSA-biotin at concentrations between about 60 and 200 nM) containing 2 µg/ml anti-myc antibody 9E10 was then added and the cells were incubated for another about 30 minutes. Yeast cells were washed three times with wash buffer II and stained with 4 µg/ml goat-antimouse-PE (Life Technologies, Grand Island, N.Y.) and 10 µg/ml streptavidin-Alexa633 (Life Technologies, Grand Island, N.Y.) in the dark room at 4° C. for about an hour. The stained yeast cells were washed three times with wash buffer II and resuspended in 1 ml PBS for flow-cytometry analysis. An identical procedure was used to stain pools after sorting by flow cytometry.

Monoclonal Analysis

The yeast cells collected from the final sorting were serially diluted and spread onto SD-CAA agar plate in 30° C. incubator to form single colonies. After 2~3 days, individual colonies from the plate were selected, inoculated into 0.5 ml SD-CAA medium in a 96 deep-well plates, and incubated at 30° C. overnight. On the second day, a 50 µl aliquot of the culture was transferred into 500 µl SG/R-CAA medium and induced overnight at 30° C. An aliquot (50 µl) of induced monoclonal yeast cell was subsequently transferred into a 96 well vacuum filter plate, and washed twice with 150 µl wash buffer 1 and once with 150 µl wash buffer II. The cells were stained in the same condition as described herein and suspended in 200 µl PBS for analysis.

Soluble scFv Expression and Purification

Flow-cytometry-positive scFvs were cloned into expression vector POE-myc. Briefly, pDNL6-scFv minipreps were prepared from a 3 ml overnight yeast culture of selected clones using Zymoprep™ Yeast Plasmid Miniprep II kit (Zymo Research, Irvine, Calif.), and the minipreps were used as template to PCR amplify the scFv insert from each clone. Both amplified scFv fragments and POE-myc plasmid were digested with BssHII and NheI restriction enzymes, and subsequently ligated with T4 ligase. An aliquot of the ligation mixture was used to transform BL21(DE3) bacteria and the transformed bacteria were used for soluble scFv production.

BL21(DE3) cells with unique scFv clones were grown in 1.4 L 2×YT plus ampicillin medium at 37° C. until log-phage (OD600=0.5), induced with 0.5 mM IPTG, and allowed to grow at 30° C. for about an additional 16 hours. After induction, the bacteria were harvested by centrifugation at 8000 g for about 15 minutes at 4° C., and the pellets were stored in −20° C. for at least 2 hours. The frozen pellets were briefly thawed and suspended in 40 ml of lysis buffer (1 mg/ml lysozyme in PBS plus EDTA-free protease inhibitor cocktail (Thermo Scientific, Waltham, Mass.) to prevent degradation). The lysis mixture was incubated on ice for about an hour, and then 10 mM $MgCl_2$ and 1 ug/ml DNase1 were added and the mixture was incubated at 25° C. for about 20 minutes. The final lysis mixture was centrifuged at 12000 g for about 20 minutes and the supernatant was collected as periplasmic extract.

Soluble scFv from periplasmic extract was purified using HisPur™ Cobalt Resin (Life Technology, Grand Island, N.Y.). The periplasmic extract (40 ml) was first incubated with 1 ml resin for an hour with rotation, and then the resin was gravity packed in a column. The resin column was washed with equilibration buffer (50 mM sodium phosphate, 300 mM sodium chloride, 10 mM imidazole, pH 7.4) until the A280 of flow through reached a baseline. The scFv was subsequently eluted with elution buffer (50 mM sodium phosphate, 300 mM sodium chloride, 150 mM imidazole, pH 7.4). Multiple fractions (1 mL each) of elutate were collected to insure protein had been eluted, and those fractions with protein were pooled and concentrated by using an Amicon ultra-15 device (EMD Millipore, Billerica, Mass.). The purified scFv was analyzed by SDS-PAGE gel and the protein concentration was determined using a BCA protein assay kit (Pierce, Rockford, Ill.).

Binding Characterization

Competitive ELISA was performed in 96 well high binding plates (Corning, Corning, N.Y.). Each well was coated with 2 µg/ml antigen at 4° C. overnight and blocked with 3% BSA. Antibody scFv was incubated in the antigen-coated well with or without soluble competitor, and the binding of scFv was accessed using anti-myc antibody (9E10) and goat-antimouse-HPR antibody (Sigma Aldrich, MO). The HRP signal was detected by adding Sureblue TMB microwell peroxidase substrate (KPL, Gaithersburg, Md.) and the reaction was stopped after 5 minutes using 1 M HCl. The incubation steps were performed at room temperature for an hour. The plate was washed three times with PBST (PBS buffer with 0.05% Tween 20) between steps.

In previous studies, the inventors tried to select antibodies against methylated phenanthrenes from a naïve library with a diversity of approximately $3 \times 10^{11}$. However, the selection was not successful because the scFvs selected from this library recognized hapten-protein conjugates, but not the soluble hapten. The inventors therefore constructed an immune phage display library for selection of antibodies that can recognize soluble phenanthrenes. Antibodies selected from such immune libraries have higher specificity and affinity than those selected from naïve libraries.

To construct the immune library, two phenanthrene derivatives, 9-carboxyl-7-methyl-phenanthrene and 9-carboxyl-2,7-dimethylphenanthrene, were conjugated with keyhole limpet hemocyanin or bovine serum albumin (BSA) and subsequently used as immunogens for balb/c mice. A total of four injections was given to each mouse, and blood serum samples were collected after the last two injections. The presence of antibodies to the phenanthrene-BSA conjugates was confirmed by an indirect ELISA. The mice were sacrificed seven days after the final injection and their spleen tissue was harvested as the starting material to synthesize cDNA.

Antibody variable domains from heavy chains (VH) and light chains (VL) were amplified using a pool of degenerate primers. The flanking regions of VH-reverse primers and VL-forward primers contain the same flexible linker sequence and were used as complementary regions in a second overlap extension PCR step to form a full-length scFv fragment. The final scFv product consists of a VH-linker-VL structure and has a total length about 800 bp. After gel purification and restriction endonuclease digestion, the 800 bp PCR fragment was inserted into the pComb3 plasmid. The differences between two 5'-overhang sequences in the SfiI digested fragments insured that the scFvs were inserted in the correct direction. Phagemids bearing scFv fragments were transformed into SS320 E. coli cell by electroporation to provide maximal transformation efficiency. An aliquot of the transformation culture was spread onto 2×YT-Amp plate for library size calculation, and single colonies from dilution plate were picked to estimate the library diversity. The size of this immune library was $6.2 \times 10^6$. Clone bearing full-length scFv (~800 bp) comprised 87.5% of the sequences, and 81.25% of clones had distinct sequences, as confirmed by BstNI fingerprint analysis.

Figure 1:
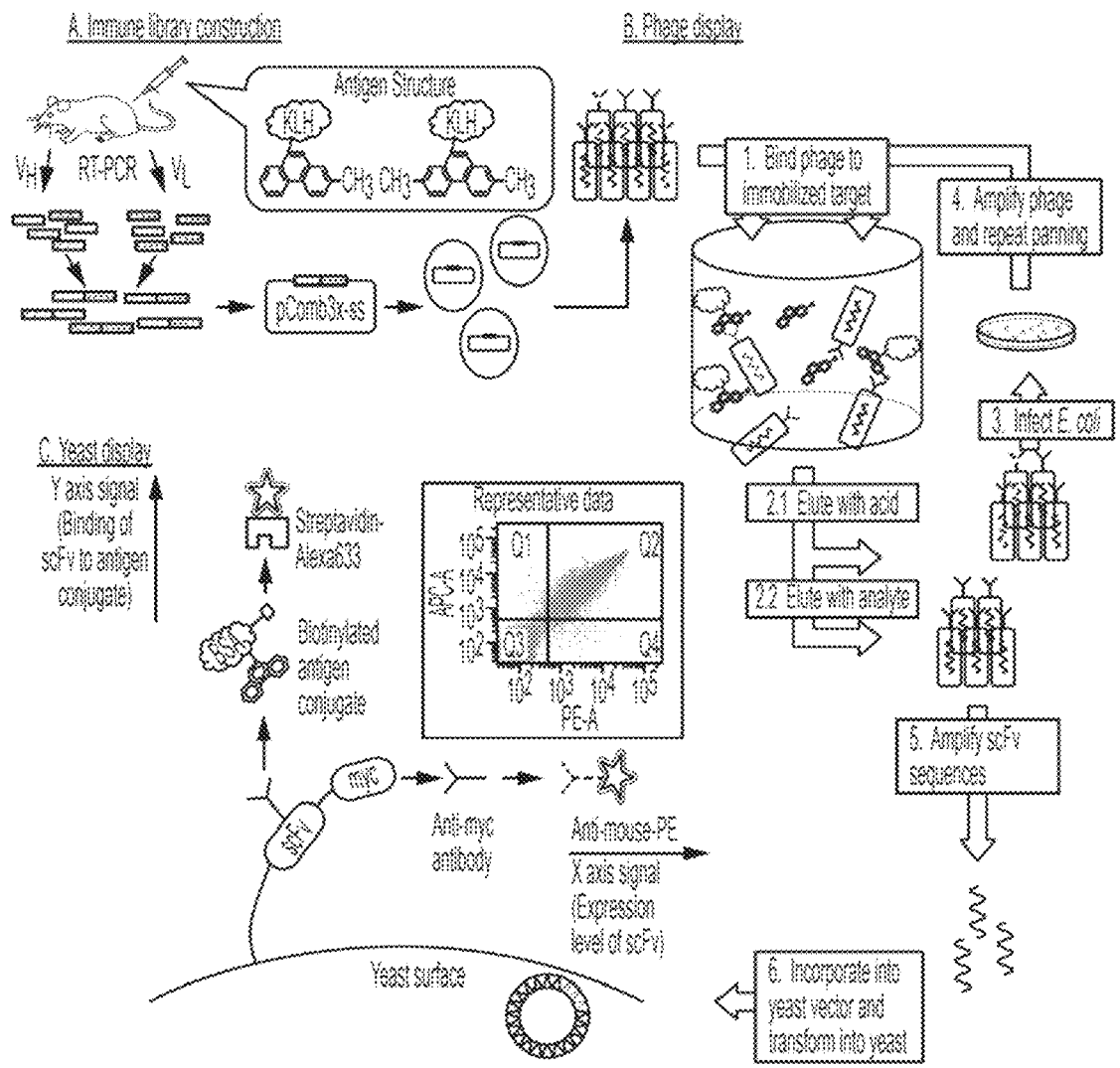
FIG. 1 shows the strategy for developing recombinant antibodies against methylated phenanthrenes. (A) Immune library construction. Spleen and WBC were collected from immunized animals and recombinant antibody technology was used to generate a library of single-chain variable fragments (scFv). The total library size was ~6.2×10$^6$, full-length insert were 87.5%, and diversity was 81.25%. (B) Phage display selection. Three rounds of tightly-controlled panning were performed as shown in the right side of the figure (steps 1 through 4). Two elution methods, acid (step 2.1) or soluble analyte (step 2.2), were used in different rounds of panning process. After acid elution, phage particles with scFv bound to immobilized antigens (both green and red phage) were collected, while with second elution method, the phage particles that recognized soluble analyte (only red phage) were enriched. The ultimate output pools were transferred into yeast display plasmid (steps 5 and 6). (C) Yeast display analysis. When induced, yeast cells display the antibody scFv fragment on their surface with a myc tag on its C-terminals. The expression level of scFv on cell surface is measured by an anti-myc antibody and phycoerythrine-labeled anti-mouse antibody (x-axis signal). The binding of the scFv to the biotinylated phenanthrene-protein conjugates was measured by streptavidin-Alexa633 fluorescence (y axis signal).

Because the library consists of ~5 million distinct scFv fragments, sophisticated selection protocols were required to identify the relatively rare antibodies that specifically recognized soluble hapten (phenanthrene and/or methylated phenanthrenes) in this large pool. The inventors therefore employed a combination of phage and yeast display selection systems as shown in FIG. 1. Phage display is useful for exploring a relatively large library and permits rapid removal of undesirable binders in a single panning; however, due to the nature of the phage particle, there is always a background level of non-specific binding during selections. Yeast display, on the other hand, can be coupled with Fluorescence-Activated Cell Sorting (FACS) and thus permits more specific controls over of selection parameters. This system favors the discovery of rare hapten-specific antibodies, since the detection of the competitive binding of hapten is difficult to detect in phage display selections. In this study, the inventors employed a combination strategy. Selection of phage displayed scFvs excluded undesirable binders from the immune library, and yeast display allowed the further analysis of the output pool and sort for binders that not only bound to the phenanthrene/methylphenanthrene-BSA-conjugates but also can be inhibited by soluble phenanthrene/methylphenanthrene.

Phage Selection

Initial studies showed that the number of panning steps must be limited in order to efficiently select for specific binders while maintaining the diversity of output pools. Multiple rounds of selection do not only select for the binders with highest affinity, but also allow clones with the highest growth rates to predominate during subsequent bacterial amplification. In addition, when selecting for hapten-specific antibodies, high affinity to hapten-protein conjugates does not necessarily mean high affinity to soluble hapten. In initial studies, a seven step selection process lead to the selection of a single clone that bound to the phenanthrene-BSA conjugate with high affinity ($K_d=10$ nM) but that did not recognize soluble phenanthrene or methylphenanthrene.

The inventors therefore adjusted the selection protocol as shown in FIG. 2. A total of three rounds of panning was performed against two different capture antigens, Phen-BSA (in Protocol 1) or 2MP-BSA (in Protocol 2). Each panning step was designed to provide a specific selective pressure. The first round enriched hapten-protein binders from the immune library; the second panning step introduced a solvent condition (1% DMSO) to exclude antibodies that were not stable in the solvent and hence are not be useful later when soluble haptens were applied. In the final round of panning, soluble hapten was added to enrich the pool of binders that bound to the soluble haptens. The input-to-output (yield) was used to determine the enrichment at each selection step. The last round of panning enriched the populations by 20-fold and 108-fold, respectively for Protocols 1 and 2. Although the number of phage that specifically bound to immobilized phenanthrene-BSA and/or 2-methylphenanthrene-BSA was further confirmed by phage ELISA, the inventors were not able to detect any inhibition by soluble phenanthrene or 2-methylphenanthrene in these pooled phage populations.

Yeast Display, FACS Selection and Competitive Flow Cytometry

The scFv fragments from the phage pools remaining after three rounds of selection from Protocol 1 and Protocol 2 were amplified, transferred into the yeast display plasmid, and transformed into two independent yeast pools. The yeast pools were induced to activate the expression of cell surface Aga2p-scFv-myc fusion proteins, as shown in FIG. 1. The scFv-bearing yeast cells were stained with two fluorescent dyes and analyzed with flow-cytometry independently, as shown by FIG. 1C. The expression level of scFv was monitored via the signal from the myc tag and is shown on the x-axis of the flow plot, while the binding capacity of expressed scFv to hapten-conjugates was detected by the signal from the biotinylated antigen and is shown on the y-axis of flow plot.

Figure 3:
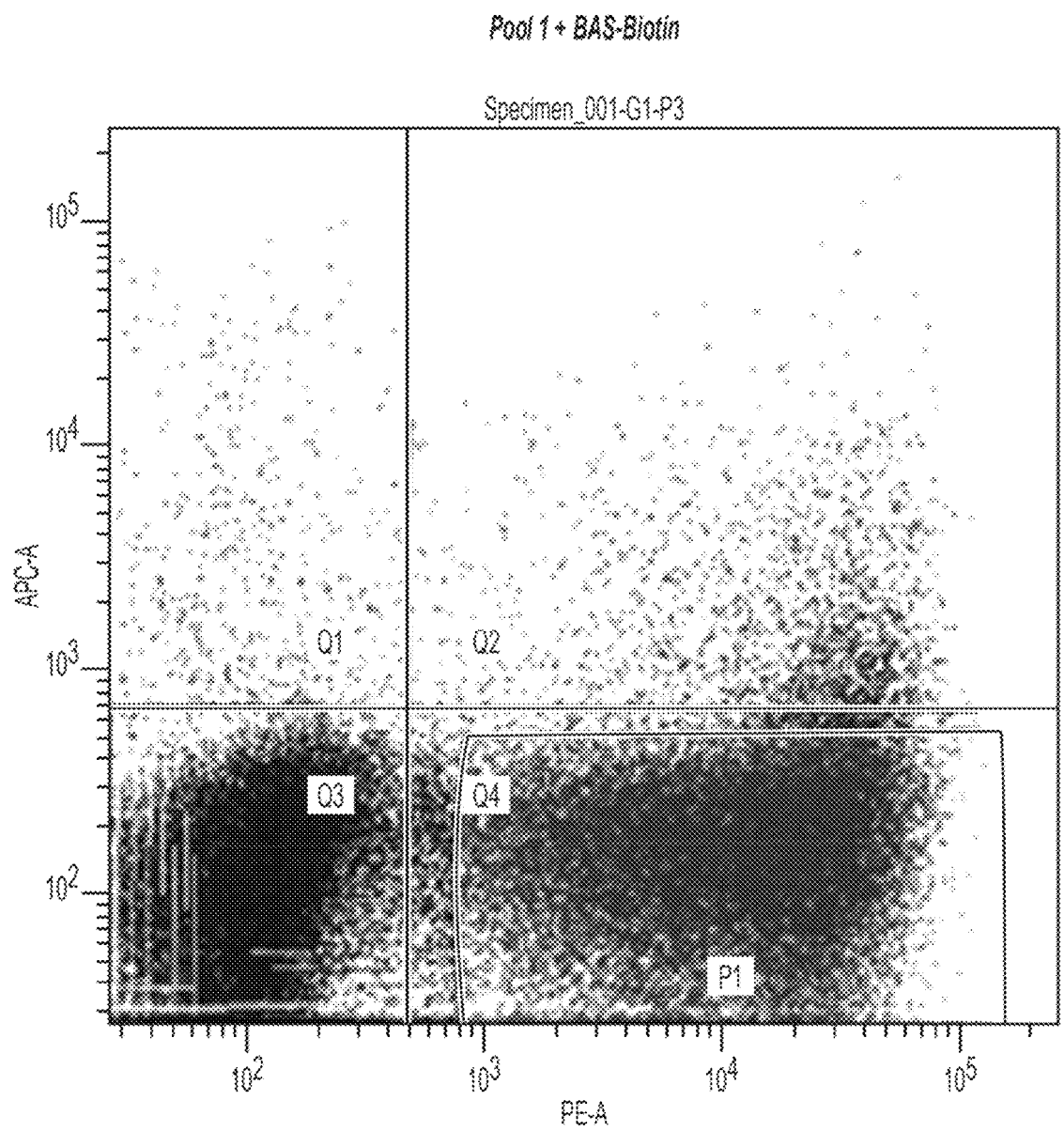
FIG. 3 shows the results of the first round of yeast sorting. This panel shows a yeast pool generated from Protocol 1 showing significant background signal when incubated with BSA-Biotin (see cells in Q2 quadrant). Only those clones outlined in red were carried forward for subsequent selection.
Figure 4:
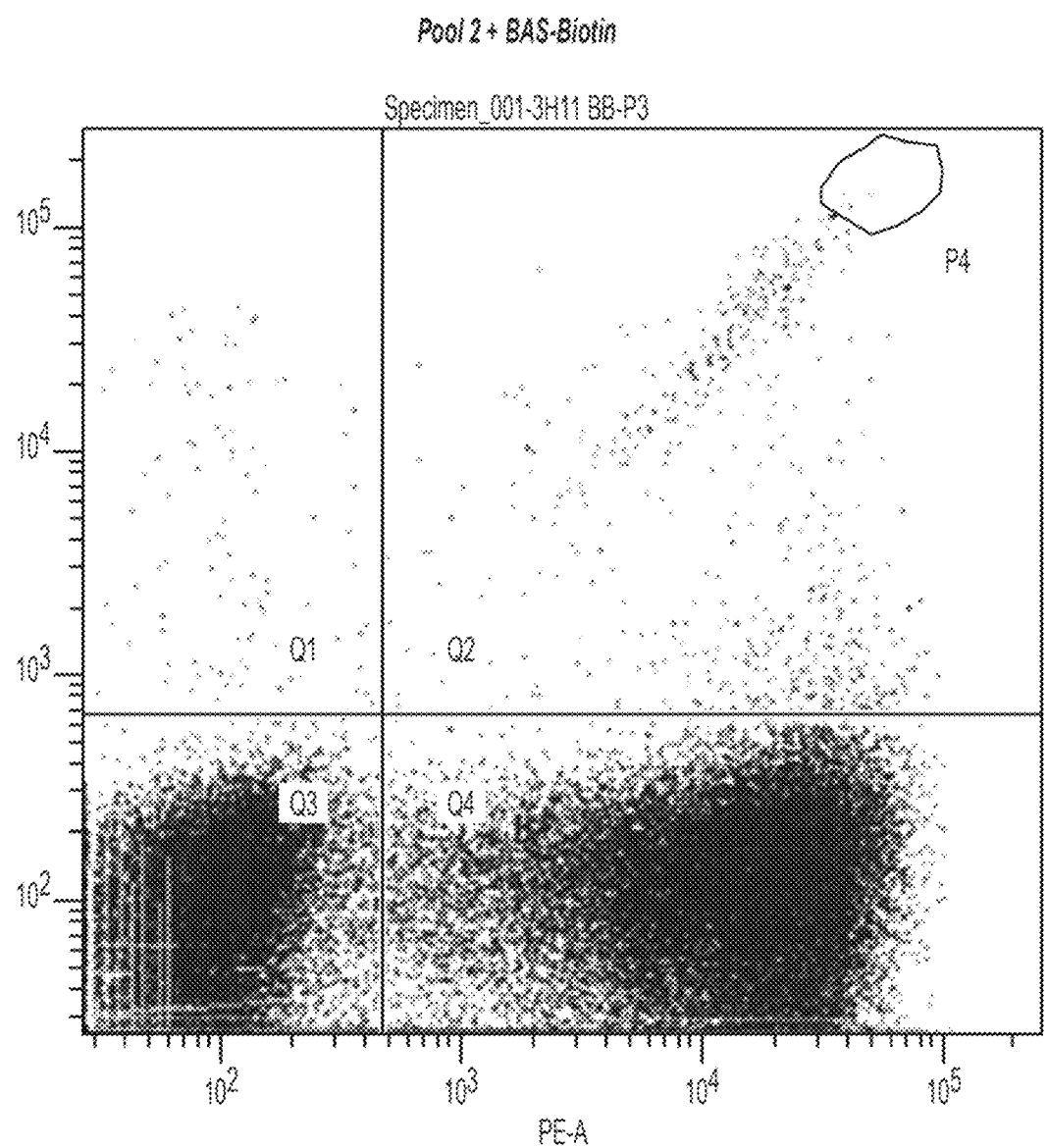
FIG. 4 shows additional results of the first round of yeast sorting. This panel shows a yeast pool generated from Protocol 2 showed very little background signal when incubated with BSA-biotin, so the presort step was omitted to avoid unnecessary loss of diversity. High affinity binders from this pool were selected as outlined in red.
Figure 5:
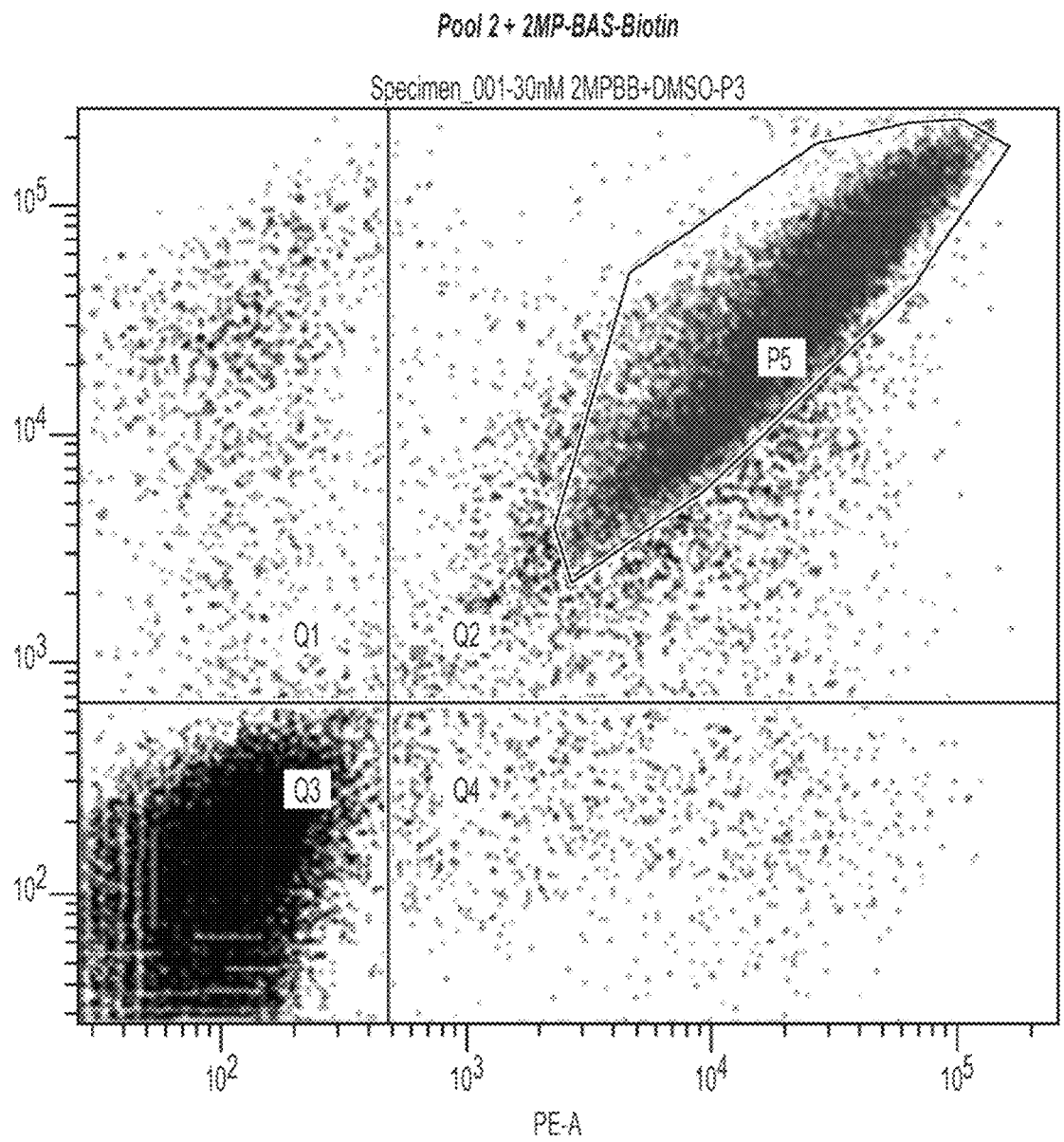
FIG. 5 shows additional results of the first round of yeast sorting. FACS of yeast cells from Protocol 2 selected in FIG. 4.

The strategy for the selection of hapten-specific antibodies involved two rounds of sorting. The first round of sorting removed cell populations that can cause interference during competitive binding with soluble hapten in the second selection. The yeast cells derived from Protocol 1 and 2 showed very different characteristics during the first FACS analysis. As shown in FIG. 3, non-specific binding of yeast cells from Protocol 1 in the presence of a mock antigen (biotin labeled BSA) was significant, and this population of non-specifically binding cells in Q2 quadrant will interfere with the competitive sorting planned in the second round of selection. Therefore, a negative selection of the Protocol 1 cells was performed by collecting only the cells in Q4 in order to exclude non-specific binders, as shown by FIG. 3. When the yeast cells derived from Protocol 2 were examined, the Q2 quadrant was relatively clean in the presence of BSA-Biotin, as shown in FIG. 4, but the binding to antigen (biotin labeled 2-methylphenanthrene-BSA) was not tight enough and the scattered population in Q2 and Q4 can overwhelm the small population that can be inhibited by soluble hapten in the next selection step. Therefore, Pool 2 was first sorted for tight binders to the biotin labeled 2-methylphenanthrene-BSA, as shown in the P5 gate in FIG. 5.

Figure 6:
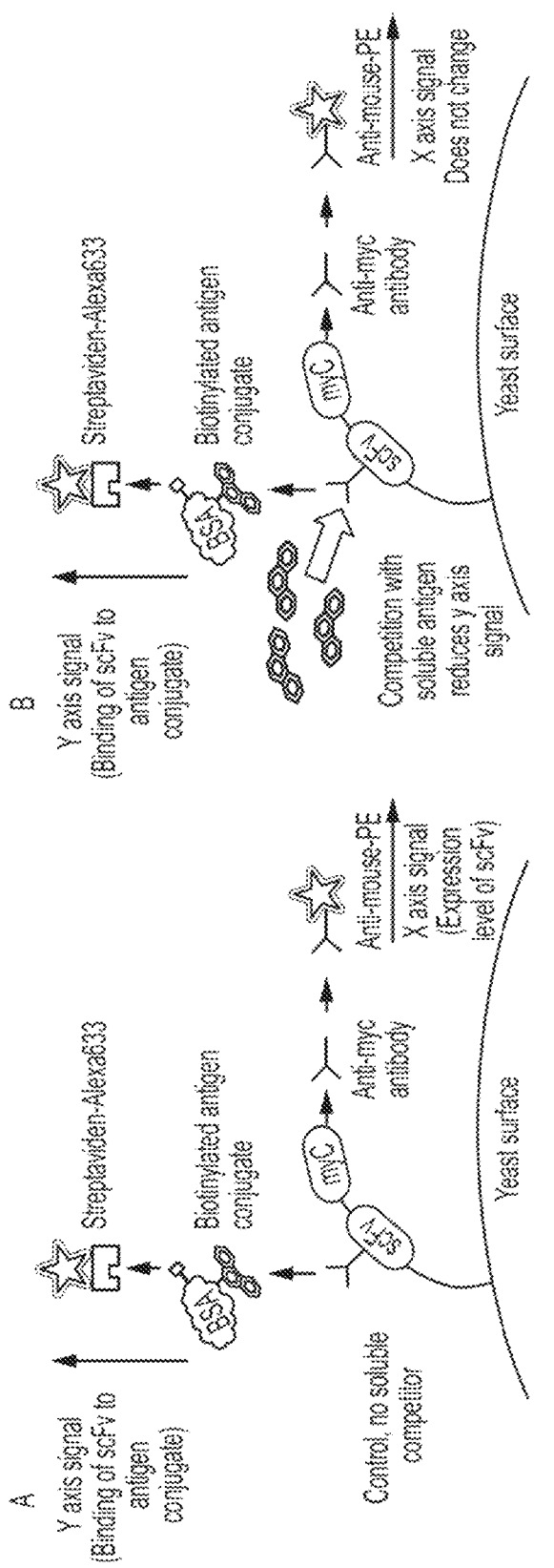
FIG. 6 shows yeast display competitive sorting for hapten-binding antibodies. Panels (A) and (B) show the diagram and corresponding flow-cytometry pattern of yeast cells stained with protein conjugate (Phen-BSA-Biotin used as an example) in the absence of soluble competitor. Panels (C) and (D) show the diagram and flow-cytometry pattern in the presence of soluble hapten (100 μM phenanthrene). The x-axis signal indicates the expression level of scFv fragment on yeast surface, which does not change in the presence of soluble competitors. However, the y-axis signal, which represents the binding of displayed scFv to hapten-protein-biotin conjugates, will be reduced if the yeast displayed scFv binds to soluble analyte. Circles in panel (C) and (D)

The second cell sort was designed to detect and enrich for antibodies that recognized soluble hapten, and a competitive screening assay was designed, as shown in FIG. 6. Yeast pools selected from the first FACS analysis were divided into two groups and incubated with 2% DMSO or soluble competitor (200 µM phenanthrene in 2% DMSO) in the presence of 30 nM biotin-labeled phenanthrene-BSA. Because the cell population was split after induction of cell surface scFvs, there was no change in the expression level of scFv fragments and the x-axis signal remained the same for the two groups. However, those cell surface antibodies that recognized soluble hapten are less able to interact with the biotinylated hapten-protein conjugate, and cells carrying antibodies with these binding characteristics show a decreased signal on the y-axis of the flow plot. Thus, by selecting the cell population that shifted down in the presence of soluble competitor, as shown in FIG. 6, red circle, the inventors were able to enrich for those rare surface-displayed antibodies that were specifically inhibited by the soluble haptens. The total cells selected in this gate is 0.6% of the total cells sorted in the absence of soluble hapten, shown by FIG. 6C, yellow circle, and ~1% of sorted cells in the presence of soluble hapten, shown by FIG. 6, red circle. Similar results were observed for the yeast cells derived from the Protocol 2 selection, using for 200 µM soluble 2-methylphenanthrene as the soluble competitor and 10 nM biotinylated 2-methylphenanthrene-BSA as the protein conjugate.

Competitive Flow Cytometry of Monoclonal Yeast Cells and Competitive ELISA of Periplasmic scFvs Single clones were induced individually and analyzed by competitive flow cytometry as described herein. The inventors examined 184 individual clones from cells selected in FIG. 6D and analyzed their binding to biotinylated phenanthrene-BSA in the presence of phenanthrene or 2-methylphenanthrene, as shown in FIG. 7. Seventy positive clones showed inhibition by one of the two competitors, (for an example, see clone A10 in FIG. 7), or by both (see clones D7 and G8 in FIG. 7). The positive scFv fragments were cloned into an expression vector to produce soluble scFv protein, and the crude periplasmic extracts were used to confirm binding of scFv to soluble hapten by competitive ELISA without the interference that can come from yeast cells. Of the 70 clones identified by competitive flow cytometry, 65 also shown activity in the competitive ELISA format. When theses 65 clones were sequenced, seven distinct scFv sequences were found. When similar selection protocols were applied to cells from Protocol 2, analysis of the 48 clones revealed 8 clones that were positive by competitive flow cytometry, six that were positive by competitive ELISA and 3 distinct scFvs with different binding properties. These data are summarized in FIG. 8.

Sequence Analysis

Sequence alignment shown in FIG. 9 indicated that positive clones appeared to fall into three family lines, related to the A10, D7, and G8 clones that showed distinct patterns during competitive flow cytometry (see FIG. 7). The binding characteristics of these three clones were explored as models to of the antibodies present in the immune library. Purified scFv were analyzed by competitive ELISA for their abilities to recognize as unsubstituted phenanthrene or methylated phenanthrenes, as shown in FIG. 9. Clone D7 bound to the phenanthrenes tested with no significant difference, while G8 and A10 were able to differentiate among various methylated phenanthrenes. G8 scFv bound to 4-methylphenanthrene most tightly, and A10 gravitated to 2-methylphenanthrene over other isomers.

In conclusion, the antibody immune library presented herein has several advantages over naive library, especially when high specificity is required for the antibodies of interest. Generating hapten antibodies is extremely difficult due to their small size, non-immunogenicity and the complications of the involvements of hapten-protein conjugates in the system. Here, using the combination of both phage and yeast display technologies, at least 10 distinct phenanthrenes-binding scFv antibodies with different binding activities were found. These antibodies can be adapted into field studies for detection of petrogenic/pyrogenic phenanthrenes in environmental samples suspected of contamination by crude oil.

Example 2—Methylated Phenanthrene Toxicology

The Example 2 herein demonstrates the different toxic effects between methylated phenanthrenes and unmethylated phenanthrene. A yeast bioassay system was used to analyze the potencies of phenanthrene and its derivatives in activating human aryl hydrocarbon receptor (AhR) signaling pathway. The methyl modifications around benzene rings were can influence AhR activation capacities.

Aryl hydrocarbon receptor, or AhR, is a ligand-activated transcription factor regulating organism's response to polycyclic aromatic hydrocarbons. As discussed herein, upon binding to the ligand, the cytosol AhR is activated and translocated into the nucleus, where AhR associates with its partner—ARNT and forms AHRC complex and regulates downstream gene expression. A variety of AhR target genes have been discovered (Boutros et al., 2011; Tijet et al., 2006; Watson et al., 2014), of these, cytochrome P450 1A1 (CYP1A1) enzyme is best-known for metabolizing most AhR ligands. CYP1A1 enzyme is responsible for both metabolically detoxifying and activating exogenous chemicals, and sometimes shows a paradoxical role in PAH-induced carcinogenicity (Shimada, 2006; Uno et al., 2001). On one hand, CYP1A1 protects organisms by detoxifying xenobiotic PAHs and converting them to hydroxyl containing metabolites. The reactive hydroxyl groups are rapidly conjugated to charged species by phase II enzymes, and the conjugates can be further excreted from cells through membrane transporters. On the other hand, the reactive intermediates formed during detoxification process, like epoxides, are often very reactive and generate oxidative damage via the formation of DNA and protein adducts, which are the leading cause of PAH carcinogenesis (Veglia et al., 2003). Outside this well-characterized role, AhR signaling has also been identified in many endogenous pathways, including regulation of female reproduction, development of liver and immune systems and cardiovascular physiology (Baba et al., 2005; Jin et al., 2014; Zhang, 2011).

Despite the complicated roles of AhR-CYP1A1 signaling on xenobiotic toxicity, it has been widely accepted that the toxic effects by PAH exposure are mediated exclusively via the activation of AhR signaling pathway (Bunger et al., 2003; Fernandez-Salguero et al., 1996; Mimura et al., 1997). Mouse models with modified AhR gene were developed and have provided direct evidence of the relationship of AhR pathway and toxicities of benzo[α]pyrene, a widely distributed PAH carcinogen (Kerley-Hamilton et al., 2012). The activation of AhR signaling pathway is the first step by which PAHs elicit their toxic effects in the organism, and can be investigated in order to understand the mechanisms of various PAH toxicity. To date, ligand-dependent AhR signaling intensities have been evaluated primarily for the parent form of PAHs, especially PAHs on the EPA priority list (Alnafisi et al., 2007), whereas methylated derivatives are overlooked. However, methylated PAHs are more abundant in petroleum than unmethylated PAHs, and limited evidences indicates that the methylation on the planar rings of PAHs can affect their toxicity (Hecht et al., 1974; Machala et al., 2008).

In this example, the inventors investigated a methylated PAH family, phenanthrene, which is very abundant in petroleum and is the major bioavailable pollutant in the Deepwater Horizon oil spill (Allan et al., 2012). In addition, phenanthrene has been shown to be toxic and bioaccumulated in various species (Amorim et al., 2011; Gust, 2006). The inventors tested the potencies of various methylated phenanthrenes in activating the AhR receptor in a modified yeast system, and included a whole profile of the monomethylated phenanthrenes (FIG. 23) to elucidate the effects of methylated positions on the AhR-activation process.

Material and Methods

Chemicals.

Available mono-methylation positions around the ring of phenanthrene backbone (purities at 98% or higher) were purchased from the following sources: phenanthene (Phen, Sigma Aldrich), 1-methylphenanthrene (1-MP, Crescent Chemical), 2-methylphenanthrene (2-MP, Sigma Aldrich), 3-methylphenanthrene (3-MP, BOC Sciences), 4-methylphenanthrene (4-MP, Chem Service), 9-methylphenanthrene (9-MP, Crescent Chemical), and 3,6-dimethylphenanthrene (3,6-DMP, AccuStandard). Their structures are shown in FIG. 23. Each compound was dissolved as 10 mM stock in DMSO and diluted to make working solutions ranging from $1\times10^{-2}$ to $1\times10^{-6}$ M.

Cell culture. An engineered *Saccharomyces cerevisiae* yeast strain, YCM3, was used for the present study. YCM3 was derived from the W303a yeast strain and is made available to investigators through the American Type Culture Collection (ATCC, strain MYA-3637). Human Ah receptor and ARNT genes were inserted onto chromosome III under the control of galactose promoter. YCM3 was transformed with a LacZ reporter plasmid that is expressed upon interaction with ligand activated AHRC (FIG. 24). This modification process was described in a previous study (Fox et al., 2008). The yeast cells were maintained in a glucose-containing medium (0.67% yeast nitrogen base without amino acids, 2% glucose, supplemented with 0.01% uracil, adenine, leucine, and histidine), and the bioassay was performed in a galactose-containing medium (2% galactose substituted for glucose in the medium described herein). Medium components were purchased from Sigma Aldrich Chemical Company.

Yeast bioassay. The YCM3 yeast cells were diluted into the galactose medium to a final A600 nm of 0.04, plated into 96-well plates at 200 µl/well, and treated with various concentrations of PAHs for 18 hr at 30° C. During this time, the human AhR and aryl hydrocarbon receptor nuclear translocator (ARNT) were expressed in the presence of galactose and activated by PAH ligands in the cell to form the aryl hydrocarbon receptor complex (AHRC). After 18 hrs of incubation, yeast cells were suspended by pipetting, a 25 µl aliquot from each well was transferred into another 96-well assay plate and mixed with 225 µl substrate solution (60 mM Na2HPO4, 40 mM NaH2PO4, 1 mM MgCl2, 10 mM KCl, 0.2% sarkosyl, 1 mM dithiothreitol, and 0.4 mg/ml ortho-nitrophenyl-β-galactoside; pH, 7.0). The assay plate was incubated for ~5 min at 37° C. and then 100 µl of a 1M Na2CO3 solution was added to stop the reaction and enhance the yellow color. Cell densities were determined from the first 96-well plate by measuring A600 nm and the color intensities of LacZ reactions determined by A405 nm from the corresponding wells of the second plate.

Statistics.

The LacZ units were calculated based on the formula:

$$LacZ\ unit = \frac{A_{450\ Sample} - A_{450\ empty}}{A_{600\ Sample} - A_{600\ empty}} \times \frac{1000\ units}{cell\ volume\ (ml) \times reaction\ time\ (min)} \quad (1)$$

$A_{450}$ sample is the measurement of a ligand-treated well at 405 nm absorbance and $A_{450}$ empty is the measurement of a well that contains only medium and no cells. $A_{600}$ sample is the measurement of yeast cell density of a ligand-treated well at 600 nm absorbance and $A_{600}$ empty is the measurement of a well that contains only medium and no cells. Cell volume is the amount of cell suspension added per well in ml (for example 0.025 ml) and reaction time is the time period of the colorimetric reaction (for example 5 min). The lacZ units were calculated as a percentage relative to the positive control (β-naphthaflavone signal set as 100%), and the dose response curves were fitted using SlideWrite program (version 7.01, Advanced Graphics Software, Inc.) using the 2 parameter curve:

$$y=m+a0*x/(a1+x) \quad (2)$$

where $m=LacZ_{DMSO}$ value from the assay plate, a0=maximum effect and a1=half maximum effective concentrations ($EC_{50}$).

Relative $EC_{50}$ and $EC_{25}$ ($rEC_{50}$ and $rEC_{25}$) values were further introduced to compare potencies of various methylated phenanthrenes. $rEC_{50}$ and $rEC_{25}$ were defined as the concentrations of the total PAH at which the AhR was activated to 50% or 25% of the activation observed in the 100 µM phenanthrene control, respectively. The 100 µM concentration was chosen because it was the maximum that can be achieved in the assay. The $rEC_{50}$ and $rEC_{25}$ and the errors associated with these values were calculated from the fitted curves. Specifically, the LacZ value corresponding to 50% or 25% of this value was calculated according to the following equations:

$$y(EC50)=[lacZ(100\ uM\ Phen)+LacZ(1\%\ DMSO)]/2 \quad (3)$$

$$y(EC25)=[lacZ(100\ uM\ Phen)+3*LacZ(1\%\ DMSO)]/4 \quad (4)$$

These calculated y values and the a0 and a1 values from the curve fits were then used to solve for x in equation (2) above. These x values represent the mean of rEC50 or rEC25 from the fitted curve. The error of rEC values were then derived from the fitted curves. Firstly, both an upper limit equation (with upper limit 95% CI parameters), and a lower limit equation (with the lower limit 95% CI of parameters) can be drawn using the 95% CI intervals for a0 and a1 determined from the curve fitting equation. The upper and lower 95% CI of $rEC_{50}$ and $rEC_{25}$ can then be determined from these curves. The SEM of the rEC can then be calculated using equation (5)

$$95\%\ CI=mean\pm(t\times SEM) \quad (5)$$

where t was obtained from a critical value table that depends on degree of freedom (dF=N−1) and significance value (α=0.05). The significance of the differences between $rEC_{50}$s and $EC_{25}$s of the different methylated phenanthrenes were determined using ANOVA followed by a post-test based on Student-Newman-Keuls analysis. Analyses were performed using GraphPad Instat 3.

Results

The inventors employed a yeast bioassay to measure the ability of various methylated phenanthrenes to induce human AhR activation. In this engineered yeast system, human Ah receptor and ARNT genes were inserted onto chromosome III under the control of galactose promoter, so that their expression can be switched on or off by medium constituents (galactose or glucose). S. cerevisiae expresses endogenous Hsp70 and Hsp90 proteins that are structurally and functionally similar to their counterparts in vertebrates (Wandinger et al., 2008) and these chaperones help regulate proper folding and expression of the human AhR and ARNT. The hydrophobic chemicals tested in this study are assumed to cross the cell membrane by passive diffusion, and previous studies have shown that the yeast cell wall does not impede the transport process when the test compounds are smaller than 760 daltons (Alnafisi et al., 2007). The compounds used in these assays fall below this molecular weight cut-off. Upon entering the cytoplasm, the test compounds bind to AhR and ARNT, whose synthesis is enhanced by the presence of galactose in the culture medium, and form the active complex AHRC.

During the induction process, YCM3 yeast cells were incubated with varying concentrations of phenanthrene and its methylated derivatives and their signaling activities were measured via a colorimetric substrate. 1% DMSO was used as the solvent control, since the PAHs were dissolved in this vehicle. The positive controls were β-naphthoflavone (BNF), which has been previously reported as a strong agonist of aryl hydrocarbon receptor (Alnafisi et al., 2007; De Nobel and Barnett, 1991). Because the inventors also wanted to compare unsubstituted phenanthrene to the methylated derivatives, a control of 100 µM phenanthrene was also included in each assay. In addition to activating the AhR, some of the tested compounds also inhibited cell accumulation. Differences in cell growth at the end of the 18 hr incubation period were normalized by measuring each culture's absorbance at 600 nm. Data points were excluded if the tested compound inhibited cell accumulation by more than 50% relative to the DMSO control.

Primary data from the yeast bioassay (absorbance at 405 nm) was converted to normalized LacZ units using the equation (1) described in the method section. Normalized LacZ units were then plotted versus the concentration of test compounds (methylated or unsubstituted phenanthrene) to generate the dose-response curves in FIG. 25. Half maximum effective concentrations ($EC_{50}$) were calculated from the curve as an indicator of AhR activation capacity. The constants determined for the curve fits are shown in FIG. 26.

The curve fits had an $r^2$ of greater than 0.99 for the 2-, 3-, 4- and 9-methylated derivatives; the $r^2$s for 1-MP 3,6-DMP curve were 0.97 and 0.96, respectively. These data demonstrate that the methyl group and its position on the phenanthrene backbone clearly affected the ability of each individual compound to activate the AhR and thus regulate the downstream reactions. The methylated derivatives also showed variations in their ability to saturate the bioassay. Assay of 1-MP reached its maximal response (109.04% of the positive control) at ~40 µM, while the assay continued to respond to 2-MP with an almost linear dose-response curve at concentrations up to 50 µM (FIG. 25A). The toxicity of 2-MP to the yeast cells at higher concentrations precluded data collection above this concentration. 3-MP and 4-MP were also toxic to the yeast cells at concentrations above 50 µM (FIG. 25B) and this concentration also failed to saturate the assay response. Unsubstituted phenanthrene and the 9-MP derivative were less toxic to the yeast cells and both of these compounds, at 100 µM led to some degree of saturation in the bioassay (FIG. 25C). The dose-response curve for the only commercially available dimethylphenanthrene 3,6-DMP (FIG. 25C) had a completely different shape than the rest of the curves and failed to achieve more than ~50% response in the assay. The inventors interpreted these data as a failure of soluble 3,6-DMP to reach the receptor and further activate the AhR process, since its estimated water solubility is ~16-fold lower than that of phenanthrene and ~3-fold lower than that of the monomethylated phenanthrenes (ref: US EPISuite (EPA, 2012)). As the inventors were unable to locate commercial sources for other dimethyl phenanthrenes, it is difficult to conclude whether this behavior is characteristic of dimethylated derivatives, or simply a solubility issue.

In order to more precisely compare the potencies of these compounds in AhR signaling, the inventors calculated relative $EC_{50}$ and $EC_{25}$ ($rEC_{50}$ and $rEC_{25}$) values, which were based on the concentrations that activated 50 percent and 25 percent of 100 µM phenanthrene effects, respectively. The $rEC_{50}$s and $rEC_{25}$s for each compound with SEM are provided in FIG. 27. One-way ANOVA and post-test analyses were then performed and the p values are provided in FIG. 28. These relative EC values provided better comparisons among the test compounds for three reasons: 1) determination of $rEC_{50}$ compensated for any variations among multiple assay plates; 2) the rEC values provided a way to compare each derivative directly to the planar phenanthrene; 3) the $rEC_{50}$ and $rEC_{25}$ avoided a determination of the maximum effect of each chemical because cytotoxicity of some compounds precluded data collection at higher concentrations. The $rEC_{50}$ values of various phenanthrene derivatives are shown in FIG. 29A. 1-MP and 2-MP were the most potent activators; with $rEC_{50}$s of 4.0 and 4.6 µM, respectively. The $rEC_{50}$ of 3-MP showed an intermediate value (5.8 µM), while the 9-MP and 4-MP were the least potent in the assay, with $rEC_{50}$s of 7.804 and 11.704, respectively. ANOVA of the entire data set yielded a p<0.0001, indicating that the differences observed among these compounds were highly significant. Post-test analysis showed that the $rEC_{50}$s of the methylated phenanthrenes tested were significantly different (p<0.001) from the unmethylated compound, and there were also significant differences in the $rEC_{50}$s of the 3 most potent monomethylated phenanthrenes (1-, 2- and 3-MP) and the least potent methylated phenanthrene (4-MP). The 3,6-dimethylated phenanthrene was also significantly more potent that 4-MP, but its $rEC_{50}$ value was not significantly different from the other monomethylated phenanthrenes.

Because toxicity and solubility issues prevented us from testing higher concentrations that can have maximized signaling for some of the compounds under study, the inventors also examined $rEC_{25}$ values as a method for comparing compounds of varying solubility and toxicity (Mallett et al., 1997). This analysis for 3,6-dimethylphenanthrene was of interest, since its solubility is less than that of other the compounds under study. When $rEC_{25}$ values were examined, as shown in FIG. 29B, the methylated phenanthrenes tested were again significantly more potent than unmethylated phenanthrene. The 3,6-dimethylated phenanthrene was now significantly more potent than the 3-, 4- and 9-MPs in the yeast bioassay. The order of potencies of the monomethylated derivatives remained the same as in the comparisons of the $rED_{50}$ values and significant differences were observed between 1-MP and 9-MP.

Discussion

This study was initiated because of an interest in comparing the toxicity of PAHs from petrogenic versus pyrogenic sources. The inventors chose to examine an early step of PAH interaction upon arrival in the cytoplasm, the binding and subsequent activation of the aryl hydrocarbon receptor signaling (AhR). This process is important to subsequent PAH toxicity in a wide variety of cell types and was therefore a reasonable indicator for a potency comparison of phenanthrenes with varying methyl substituents. The modified yeast model system was chosen to study the human aryl hydrocarbon receptor activation process for two reasons: 1) AhR is a widely studied receptor which binds to PAHs and induces subsequent changes in gene expression that in turn determine toxic effects; 2) The toxicological mechanism of PAHs can be complicated, and understanding the process one step at a time can be more useful than directly applying a more complicated system (mammalian cell culture or a whole animal) with many blinded steps.

The present data indicates that the presence of methyl groups on phenanthrene rings increased their potency in the AhR activation and signaling processes. This result can mean that the methylated derivatives thus have greater toxic potential than phenanthrene. In addition, the position of methyl modification can also play a role in toxicity. The methylphenanthrenes with methyl group in equatorial positions (1-MP, 2-MP and 3-MP) seem to have the highest potencies, while the derivatives with methyl group in the bay region (4-MP) or on the back (9-MP) are not as active in this assay. A similar AhR-activation pattern was observed in a rat liver system, where 1-MP, 2-MP and 3-MP were also stronger than 9-MP in AhR activation process; the methyl derivatives tested were stronger agonists than the parental phenanthrene (Vondracek et al., 2007). These findings also parallel research with polychlorinated biphenyls and dioxins, some of which are strong agonists of AhR. In the case of these compounds, chemical structural studies indicate chlorines at equatorial positions enhance binding affinity for the receptor and thus increase potency. Thus, our data are consistent with chemical structural data for PCBs and dioxins that explain interactions with AhR.

In summary, the methylated phenanthrenes are recognized to be abundant among the PAHs of petrogenic origin, and they activate AhR to induce transcriptional signaling more potently than does phenanthrene. Future studies are still required to reveal their toxicology in detail. Without being bound by theory, this study serves as a model to study the methylated PAHs systematically and provide insight into their mechanistic effects.

Example 3—Immunoassays in Environmental Studies

The Example 3 herein compares and validates immunoassays for environmental PAH assessment. The binding between a commercial monoclonal antibody (BAP-13) and its ligand (benzo[α]pyrene) was measured by both cELISA and KinExA. Performances of both methods were compared and validated for PAH detection.

Immunoassay refers to an antibody-based biochemical test that determines the concentration of a target molecule with high specificity. Compared to conventional analytical methods, immunoassay has several advantages such as strong selectivity, high sensitivity, rapid turnaround time, and excellent portability. Therefore, the immunoassays can be served to pre-screen the unknown field samples, and narrow down the quantity of positive samples to be transferred to laboratories for detailed analysis. A new immunoassay-based method was developed to monitor and analyze environmental PAHs level, especially to distinguish the amount of PAHs generated from petrogenic origins. The inventors thus compare and validate two immunoassays for use in PAH analysis.

Competitive ELISA. The competitive enzyme-linked immunosorbent assay (cELISA) is a common antibody-based technique to measure the concentration of the analyte in solution. The procedure is shown in FIG. 30, a microtiter plate is pre-coated with antigens through charge interactions and blocked by nonreactive proteins. (Step 1) For hapten analytes, the ligand is conjugated with a protein carrier to form a full antigen for coating. The antibody reagent is then added to the coated micro-wells in the presence of sample containing the ligand of interest, and interacts with both immobilized antigen and mobilized sample. (Step 2) After a period of incubation, the sample and/or antibody in the soluble phase is removed (Step 3) and the antibody binding to the immobilized antigens is labeled with secondary antibody (Step 4). Finally the binding signal is detected by a colorimetric substrate, and measured by a spectrometer. (Step 5) If there is no ligand in the sample, there will be no interference of antibody binding to the immobilized antigens, and thus will get a maximum signal. On the contrary, if ligand is present, the antibody will bind to its ligand in the solution and washed away when soluble phase is removed. Therefore, the amount of antibody immobilizing on the plate surface is reduced and signal is lower at the end.

Kinetic Exclusion Assay.

The kinetic exclusion assay (KinExA), developed by Sapidyne Instruments Inc, is a relatively new technology which can be used to characterize molecular interaction in more detail than a cELISA. These sensors operate on the principle of Kinetic Exclusion. In a 1:1 interaction, a mixture of three species (free A, free B, and AB complex) will exist in a ratio determined by the total concentration of A and B, the affinity of the AB interaction, and the time allowed for the reaction to proceed. As shown in FIG. 31, there are two forms of ligand A (indicated in yellow color) in a KinExA assay platform: the immobilized form attached to capture beads and the soluble form that is freely dissolved in the solution. The immobilized ligand-bead conjugates are packed into a micro-column as the solid phase to capture antibodies. The antibody B (red) is pre-incubated with the sample mixture containing the soluble form of ligand A, and the mixture is allowed to flow through the micro-column. Only the free form of antibody B that does not occupied by the ligand A can be captured by the immobilized phase, while the A-B complex and free ligand A run off the column. (FIG. 31B) The antibody retained on the micro-column can then be detected by the fluorescence-labeled secondary antibodies. (FIG. 31C) And the fluorescent intensity is recorded and the signal change between the equilibrium and initial stage (W) is proportional to the amount of free antibody B in the pre-mixed solution. (FIG. 31D).

Materials and Methods

Mixed Anhydride Conjugation.

Carboxylic PAH (1-pyrenenbutyric acid, purchased from Sigma Aldrich at 97% purity) was conjugated onto protein carriers (BSA or KLH) using a mixed anhydride method. Briefly, 0.05 mmol of carboxylated hapten was dissolved in 2 ml anhydrous 1,4-dioxane. Equal molar amounts of tributylamine (Sigma Aldrich, St. Louis, Mo.) and isobutyl chloroformate (Sigma Aldrich, St. Louis, Mo.) were then added and the reaction was kept on ice for 30 min to form the mixed anhydride intermediate. Subsequently, the mixed anhydride was added dropwise into 2.5 ml protein carrier solution (40 mg of BSA or 20 mg of KLH) at pH 8.5 and the reaction was incubated at room temperature for 4 hours. The reaction mixture was then centrifuged to remove the precipitates. The final product was first dialyzed against 0.01M glycine at PH 9 to stop the reaction and then dialyzed in PBS buffer (10 mM $NaHPO_4$, 1.8 mM $KH_2PO_4$, 137 mM NaCl, 2.7 mM KCl, PH 7.4) for another 2 days. The presence of phenanthrene derivatives on the conjugate was confirmed by indirect ELISA using monoclonal antibody BAP-13 (LifeSpan Biosciences, Seattle, Wash.) which recognizes PAHs with a broad cross-reactivity.

ELISA.

Competitive ELISA or indirect ELISA was performed in 96-well high binding plates (Corning, Corning, N.Y.). Each well was coated with 2-5 µg/ml pyrene-BSA at 4° C. overnight and blocked with 3% BSA. BAP-13 antibody (LifeSpan Biosciences, Seattle, Wash.) was incubated in the antigen-coated well with or without soluble benzo[α] pyrene, and the binding of antibody was accessed using goat-antimouse-HPR antibody (Sigma Aldrich, MO). The HRP signal was detected by adding Sureblue TMB microwell peroxidase substrate (KPL, Gaithersburg, Md.) and the reaction was stopped after 5 min using 1N HCl. The quantified signals were measured by reading $OD_{405}$-$OD_{600}$ values from microplate photometer. The incubation steps were performed at room temperature for an hour. The plate was washed three times with PBST (PBS buffer with 0.05% Tween 20) between steps.

KinExA.

Kinetic exclusion assay of antibody-antigen binding interactions were performed with KinExA 3000 immunoassay instrument (Sapidyne Instruments, Inc.). UltraLink biosupport beads (Thermo Fisher Scientific, Waltham, Mass.) were coated with antigen by suspending 50 mg of beads in 1.0 ml sodium carbonate buffer (PH=9.0) that contained 50 µg desirable antigen (pyrene-BSA). After 2 hours of rotation at 25° C., the beads were gently centrifuged, and the supernatant solution was decanted. Nonspecific protein binding sites that remained on the beads were quenched by the subsequent incubation of the beads with 1.0 ml of 1 mg/ml BSA for additional two hours or overnight at 25° C. The blocked beads were stored in 30 ml PBS buffer at 4° C. for up to a month before use. A beadpack approximately 4 mm high was created in the flow cell of the KinExA by drawing 450 µl of a suspension of the blocked beads (1.67 mg/ml) from beads reservoir and gently disrupted with a brief backflush of PBST (PBS buffer+0.05% Tween20), followed by a 20-s settling period to create a uniform and reproducible pack. In each sample tube, antibody was pre-incubated with different concentrations of the ligand (benzo[a]pyrene) for 30 min to achieve equilibrium, and 500 µl of the mixture was drawn past the beads, followed by 125 µl of the PBST buffer to wash out unbound primary antibody and excess soluble antigen. Another 500 µl of goat anti-mouse IgG conjugated to DyLight 649 (Jackson ImmunoResearch West Grove, Pa.) was drawn past the beads, and unbound labeled secondary antibody was subsequently removed by washing the beadpack with 2 ml PBST. BSA was present at 50 µg/ml in the reagent mixtures to reduce nonspecific binding of the antibodies in the instrument. Data acquisition and instrument control were accomplished using software provided by Sapidyne Instruments, Inc. The difference of voltages (delta, volt) between last 30s and first 30s of the assay was recorded as binding signal of each sample, and the data were fitted to calculate antibody affinities in SlideWrite software.

Results

Pyrene-BSA Conjugation.

As PAHs are small molecular-weight haptens, they cannot be directly immobilized onto plastic surface or activated beads. Full antigens (hapten-protein conjugates) have to be made as capture reagents in both cELISA and KinExA assays. The inventors chose BSA as the carrier protein to conjugate pyrene molecule onto protein surface due to its high water-solubility and stability. BSA (bovine serum albumin) is a plasma protein derived from cattle. It has a molecular weight of 66.5 kDa, includes 59 lysine of which more than 50 percent are readily accessible for linker conjugation, and is the most popular carrier proteins for heptan compounds. The conjugation hapten-BSA is through the peptide linkage between the amine group ($-NH_2$) of lysine on BSA and the carboxyl group ($-COOH$) of hapten compound. The commercial available carboxyl PAH (1-pyrenenbutyric acid) was conjugated onto BSA protein via a two-step mixed anhydride method (Gendloff et al., 1986; Jenner and Law, 1996; Matschulat et al., 2005). (FIG. 32) The 1-pyrenenbutyric acid was activated by equal molar of tributylamine and isobutyl chloroformate to form the mixed andride intermediate (Reaction a), and then the transferred onto the amine group of lysine when solution of BSA was added at PH 8.5 and 4° C. (Reaction b).

To validate the newly synthesized pyrene-BSA conjugate as a capture reagent for binding assays, the inventors tested whether an antibody that recognized PAHs can bind to the conjugate. A commercially available anti-PAH monoclonal antibody, BAP-13 was used to construct an indirect ELISA test. (FIG. 33) Basically, the ELISA plate was coated with the same concentration (5 µg/ml) of newly synthesized pyrene-BSA conjugates or BSA control from the mock reaction (same mixed anhydride reaction procedure without 1-pyrenencarboxylic acid). And serially diluted concentrations of antibody BAP-13 ranging from 6.67 to 0.0065 nM were applied onto both antigen-coated wells, and detected by the HRP-labeled secondary antibody. The BAP-13 binds to the pyrene-BSA conjugates in a dose-response manner, whereas it did not recognized the BSA control—no dose-dependent response and signal is below background ($A_{450-650}<0.1$).

Comparison of cELISA and KinExA: Using BAP-13 and Benzo[α]pyrene as an Example.

A commercially available monoclonal antibody, BAP-13 (LifeSpan Biosciences, Seattle, Wash.), was used to measure the concentration of its ligand—benzo[α]pyrene using both cELISA and KinExA methods to compare the sensitivities of two assays. BAP-13 monoclonal antibody was generated based on benzo[α]pyrene-BSA immunogen, and therefore was primarily targeting benzo[α]pyrene. This antibody has a broad cross-reactivity for a number of structurally related PAHs, which makes it good choice for analysis of total PAHs in an environmental sample. The ligands of BAP-13 include parent and some alkylated PAHs, with highest affinity to larger (four- to six-ring) compounds. (Scharnweber et al., 2001) The binding of BAP-13 and benzo[α]pyrene was measured by both cELISA (FIG. 34A) and KinExA (FIG. 34B). Synthesized conjugate, pyrene-BSA, was used to coat plastic plate or biosupport beads, and benzo[α]pyrene was applied as competitor to inhibit BAP-13 from binding to pyrene-BSA conjugate. As shown in FIG. 34, the signal of BAP-13 binds to pyrene-BSA was inhibited by the presence of benzo[α]pyrene in a dose-dependent manner. Data from both assays were fitted by SlideWrite Plus 7.01 software using a three-parameter equation:

$$y=a0-a1*x/(x+a2)$$

where a0 was the maximum signal response when no competitive ligand was in the solution, a1 was the maximum inhibition by the competitor, and a2 was the half maximum inhibitory concentration ($IC_{50}$) which indicated the ligand concentration when half of the inhibition was achieved. Both methods showed a good fitting with $R^2$s equal to 0.96 and 0.98 respectively, whereas the sensitivity of BAP-13 to benzo[α]pyrene was improved 242 fold in KinExA compared to cELISA (FIG. 35).

Discussion

In a KinExA test, the contact time between solution mixture and the immobilized beads is too short (<0.5s) to reach a new equilibrium state in the solution, and therefore the change of free B concentration can be omitted during the experiment. In the case of hapten ligands, it is common that the antibodies gravitate to the immobilized hapten-protein conjugates than to soluble hapten itself (due to the larger contact area, or multivalent effects etc). As there is no time for antibody to choose between soluble versus immobilized ligands in KinExA, the sensitivity is a lot better than a traditional cELISA experiment. (Su et al., 2007)

In conclusion, two antibody-based PAH detection methods were validated using as commercially available PAH-specific antibody (BAP-13) and its best ligand (benzo[α]pyrene). And the result implied both methods can be used to detect the ligand in solution, while the KinExA method has an exceptional sensitivity for haptens like PAH. Therefore, a new antibody with designated specificity for petrogenic PAHs can be readily adopted into simple cELISA or KinExA-based sensor system for better performance.

Example 4—Development of Antibody Specific for Methylated Phenanthrenes

The Example 4 herein describes the development of antibodies specific for methylated phenanthrenes. An immune phage-display library was synthesized. Phage display selections, followed by yeast display sorting, were performed to isolate desirable binders from the library. The selected clones were characterized with respect to affinity and specificity.

Antibody Production Systems.

Antibodies are important tools for research, diagnostic, therapeutic and environmental analyses, and the technologies for antibody development have been constantly improved over the past century. Polyclonal antibodies are the easiest type to make, yet not very reliable because they are a batch-dependent limited resource and can contain antibodies with unknown specificities. A big milestone in antibody technology was the generation of monoclonal antibodies (mAbs) employed hybridoma technology invented by Köhler and Milstein in 1975. The mAbs were constantly produced from cells fused of antibody producing spleen cells and an immortal myeloma cell lines. (Kohler and Milstein, 1975) However, the hybridoma technology are often limited to murine species because suitable immortal myeloma cell line are not available for other species. Besides, the limiting dilution procedure to identify positive clones can only screen a small number of single clones out of the whole hybridoma population, which makes it difficult to discover rare clones such as hapten-specific antibody.

Recombinant antibody technologies avoid using murine cell lines or immunization process, and achieve the generation of human antibodies (Lee et al., 2007). Recombinant antibodies also circumvent the diversity limitation of hybridoma technology by constructing large libraries that exceptionally resemble the immunoglobulin repertoires (Glanville et al., 2009). Furthermore, antibody display technologies allow improvement of antibodies in terms of affinity, stability, solubility, and sometimes even "bispecific". There are two types of recombinant antibody libraries based on the sources, a naïve library derived from non-immunized individuals or an immune library developed specific for certain antigens.

In initial studies, the inventors attempted to select antibodies against methylated phenanthrenes from a naïve library with a diversity of approximately $3 \times 10^{11}$ (Sblattero and Bradbury, 2000). This kind of libraries is created from non-immunized individuals, in this case that was the human peripheral blood lymphocytes, with a diversity as large as possible from which theoretically antibodies to any given antigen can be isolated. However, the theory can not apply well to the hapten antibodies. A combination of 4 rounds of phage display selection were used followed by 2 sorts of yeast display-FACS. (Ferrara et al., 2012) At the end of $2^{nd}$ yeast sorting, the monoclonal antibodies were confirmed to bind to protein-conjugates, but not soluble phenanthrenes.

The inventors thus prepared an immune phage display library for selection of antibodies that can recognize soluble phenanthrenes. An immune library is derived from immunized individuals, and is specific for the antigen used during immunizations. Animals injected with foreign antigens elicit adaptive immune responses, and start producing antibodies against given antigen. With repeated exposure to the same antigens, the antibody-producing B cells experience the affinity maturation process in vivo and generate antibodies of successively greater affinities. Therefore, antibodies selected from such immune libraries have higher specificity and affinity than those selected from naïve libraries (Peipp et al., 2001; Schwemmlein et al., 2006).

Antibody Selection Platforms.

Phage and yeast display systems are techniques that have pros and cons. A combination of multiple selection systems provides extraordinary advantages by complementing each other's shortcomings. Phage display is useful for exploring a relatively large library and permits rapid removal of undesirable scFvs from the library. Due to the nature of the phage particle, however, there is always a background level of non-specific binding; in addition, competitive binding to soluble hapten is difficult to detect in phage display selections (Fernando et al., 2008; Moghaddam et al., 2003). The yeast display system, on the other hand, is limited to smaller scFv libraries, but this display system can be coupled with Fluorescence-Activated Cell Sorting (FACS) to provide very strict controls over selection parameters (Gai and Wittrup, 2007; Weaver-Feldhaus et al., 2005). Initial selection of our library using phage display excluded undesirable scFvs and reduced the overall size of the library. Subsequent yeast display allowed us to further analyze the output pool and sort for clones that not only bound to the hapten-BSA-conjugates but also recognized soluble phenanthrene and/or methylated phenanthrene haptens. By combining two methods together, the inventors were able to identify rare clones with hapten-specific property from a large immune library of million-level diversity.

Materials and Methods

Materials.

Chemicals (phenanthrene and methylated phenanthrens) were purchased and prepared as described in Example 2. Carboxylic PAHs (9-Carboxyl-7-methyl-phenanthrene, and 9-carboxyl-2,7-dimethyl-phenanthrene) were synthesized in-house at the University of Texas Medical Branch in Galveston, Tex. Phage display plasmid pComb3XSS was obtained from The Scripps Research Institute. Both the yeast display plasmid pDNL6-GFP-myc (originally generated from pPNL6 plasmid (Feldhaus et al., 2003; Ferrara et al., 2012) and scFv expression plasmid POE-myc (generated from a pET based plasmid, pEP-D1.3 (Ayriss et al., 2007) were modified in our laboratory to replace the V5 tag with a myc tag. Monoclonal anti-myc antibody 9E10 was purified in-house from the culture supernatant of 9E10 hybridoma cells (Developmental Studies Hybridoma Bank, University of Iowa).

Preparation of Protein Conjugates.

9-Carboxyl-phenanthrene, 9-carboxyl-7-methyl-phenanthrene, and 9-carboxyl-2,7-dimethyl-phenanthrene) were conjugated onto protein carriers (BSA or KLH) using a mixed anhydride method same as described in Example 3. PAH-BSA conjugates were further biotinylated with EZ-Link™ Sulfo-NHS-Biotin (Life Technology, Grand Island, N.Y.) for yeast display screening, and unreacted sulfo-NHS-biotin was removed using a PD-10 desalting column (GE Healthcare Life Sciences, Pittsburgh, Pa.). The concentrations of the conjugates were determined by a BCA protein assay kit (Pierce, Rockford, Ill.).

Immunization of Mice.

PAH-KLH or PAH-BSA conjugates (50 μg) were mixed with the Sigma adjuvant system (Sigma Aldrich, MO) at 1:1 for each injection. Four female balb/c mice were divided into two groups, and each group was immunized intraperitoneally with the 2-methylphenanthrene or the 2,7-dimethylphenanthrene-conjugate. Four injections with alternating carrier proteins to avoid of antibodies directed against protein carriers. The blood was taken seven days after 3rd and 4th injection to test the serum activity, and mice were sacrificed 7 days after the final boost. The serum titers tested by indirect ELISA are shown FIG. 37.

Immune scFv Library Construction.

Seven days after fourth injection, mice were sacrificed, and total RNA was isolated from spleen tissues with Qiagen RNeasy mini kit (Qiagen, Valencia Calif.). RNA samples from the same group of mice were mixed together as the starting material for library construction. Isolated RNA (1~2 µg) was used in the first step of RT-PCR with oligo(dT)20 (SEQ ID NO: 241) or random hexamer primers, and the 2 amplified cDNA samples were pooled for maximum recovery of cDNA using SuperScript® III First-Strand Synthesis System for RT-PCR kit (Invitrogen, Carlsbad Calif.). This cDNA pool was subsequently used with a degenerate primer set (Schaefer et al., 2010) (see Appendix) to amplify antibody variable regions of heavy and light chains. A second overlapping PCR was performed to link heavy and light chain together as full-length scFv fragments and to add SfiI restriction sites on both ends (Schaefer et al., 2010).

The synthesized scFv fragments and pComb3XSS plasmid were digested with SfiI enzyme and ligated with T4 ligase. The newly synthesized plasmid with the scFv insert was then transformed into competent SS320 E. Coli bacteria (Lucigen, Middleton, Wis.) by electroporation. Transformed T1 cells were incubated in SOC medium (2% peptone, 0.5% yeast extract, 10 mM NaCl, 2.5 mM KCl, 10, mM MgCl2, 10 mM MgSO4, and 20 mM glucose) overnight to generate the stock library, and aliquots of diluted culture were spread onto 2×YT-AG (2×YT supplement with 100 µg/ml ampicillin and 2% glucose) agar plates to estimate the library size. In addition, single colonies from the agar plate were used as templates to PCR-amplify the insert of pComb3 plasmid; these PCR products were digested with BstNI restriction enzyme to estimate the library diversity.

Phage Display Selection.

Antibody phage library or output pools from previous rounds of selection were grown and infected with helper phage M13KO7 for phage production. Briefly, bacteria carrying scFv genes in pComb3XSS phagemid were cultured in 10 ml 2×YT-AG medium at 37° C. with shaking until they reached log-phage (OD600 at about 0.6), and infected with helper phage M13KO7 at a multiplicity of infection (MOI) of 20:1. The culture was then incubated at 37° C. without shaking for 30 min, and subsequently at the same temperature with shaking for another 30 min for optimum super-infection with helper phage. After centrifugation, the medium was removed and 10 ml new medium containing ampicillin and kanamycin but without glucose were added, and the culture was incubated at 30° C. with shaking overnight. The next day, the culture was centrifuged and the supernatant containing the phage particles was collected. Phage were concentrated by PEG precipitation. Briefly, ⅕ volume of PEG/NaCl solution (20% PEG-8000, 2.5M NaCl) was added into culture supernatant and the mixture was incubated on ice for 1 hr, centrifuged at 4500 rpm for 30 min, and resuspended in 1 ml PBS buffer. The concentrated phage were used for subsequent rounds of selection.

Selections were performed in immuno-tubes (Thermo Scientific, Waltham, Mass.) or micro-titer plates (Corning, N.Y.). Antigens were coated in tubes (4 ml) or plates (50 µl) at 4° C. overnight. The next day, plate was washed three times with PBST and blocked with 3% BSA at 25° C. for 1 hr. An aliquot of amplified phage (about $10^{12}$ cfu) prepared as described herein was also blocked with 3% BSA at 25° C. for 1 hr in PBS or PBS plus 1% DMSO. The blocked phage were then added into the antigen-coated tube/plate. At this point, phage carrying desirable binders were bound to the tube/plate, while the unbound phage were removed by washing. Finally, the bound phage were eluted by one of two methods: 1) Acid elution with 200 µl glycine-HCl at PH 2.2 for 8 min and immediate neutralization with 9 µl 2M Tris at pH 11 to yield a final pH of ~7.5. This method elutes the the phage bound to the protein conjugates. At earlier selection process, this method ensures that selection is comprehensive and does not exclude any rare binders; 2) Competitive elution with 100 µM soluble analyte (phenanthrene or 2-methylphenanthrene) in 1% DMSO for 30 min. This method was only used in the final selection step of Strategy #2 to enrich a specific population, which recognized soluble analytes rather than protein conjugates.

Half of the eluted phage were used to infect 10 ml log-phase T1 E. coli bacteria culture at 37° C. for 30 min. An aliquot of infected culture was serially diluted and spread on 2×YT-AG plates to calculate the number of phage eluted (as "output" of this round of panning), and the rest of culture was incubated in fresh 2×YT-AG medium overnight at 37° C. The next day, phage particles was amplified from this culture and used as "input" for next round of panning.

Yeast Display and Competitive FACS.

After the final phage display selection step, the phagemids containing the scFv genes were isolated with miniprep kit (Qiagen, Valencia, Calif.), and scFv genes were amplified with a pair of transfer primers (see Appendix). Yeast display plasmid pDNL6-GFP-myc was digested with BssHII and NheI restriction enzymes and the linear plasmid was gel-purified without the GFP insert. Digested pDNL6 plasmid (500 ng) and purified scFv PCR product (1 µg) were transformed into EBY100 yeast competent cells with Yeast Transformation System 2 kit (Clontech, Mountain View, Calif.). The homologous region on the plasmid and PCR product flanking region will lead the formation of circular plasmid carrying scFv insert by the yeast homologous repair mechanism (Hua et al., 1997; Oldenburg et al., 1997).

For flow cytometry, the yeast library was incubated in growth medium SD-CAA at 30° C. overnight for activation. The next day, activated yeast cells were diluted in induction medium SG/R-CAA at OD600=0.5, and cultured again at 30° C. for 16 hrs. After induction, $10^7$ induced yeast cells (OD600=0.5) were washed twice with 0.5 ml wash buffer I (0.5% BSA supplemented with 2 mM EDTA), and once with 0.5 ml wash buffer II (0.5% BSA). Yeast cells were first incubated with 50 µl competitor (phenanthrene or 2-methylphenanthrene, 200 µM in PBS containing 1% DMSO) for 30 min with rotation at 25° C. An additional aliquot (50 µl) of biotinylated protein-conjugate (BSA-biotin, phen-BSA-biotin, or 2mp-BSA-biotin at concentrations between 1 and 100 nM) containing 2 µg/ml anti-myc antibody 9E10 was then added and the cells were incubated for another 30 min. Yeast cells were washed 3 times with wash buffer II and stained with 4 µg/ml goat-antimouse-PE (Life Technologies, Grand Island, N.Y.) and 10 µg/ml streptavidin-Alexa633 (Life Technologies, Grand Island, N.Y.) in the dark room at 4° C. for an hour. The stained yeast cells were washed three times with wash buffer II and resuspended in 1 ml PBS for flow-cytometry analysis. The selected yeast population was sorted into 2 ml pre-warmed YPD medium, and incubated at 30° C. without shaking for 30 min before transferring into 30° C. shaker for two days. The sorted pool was analyzed again by flow cytometry using the same staining procedure. In each flow cytometry experiment, five controls were included for compensation test: 1) yeast cells without any primary and secondary antibodies; 2) yeast cells with goat-antimouse-PE only; 3) yeast cells with streptavidin-Alexa633 only; 4) yeast cells with 9E10 and goat-antimouse-PE; 5) yeast cells with biotinylated protein-conjugate and streptavidin-Alexa633.

Monoclonal Analysis.

The yeast cells collected from the final sorting were serially diluted and spread onto SD-CAA agar plate in 30° C. incubator to form single colonies. After 2~3 days, individual colonies from the plate were selected, inoculated into 0.5 ml SD-CAA medium in a 96 deep-well plates, and incubated at 30° C. overnight. On the second day, a 50 µl aliquot of the culture was transferred into 500 µl SG/R-CAA medium and induced overnight at 30° C. An aliquot (500 of induced monoclonal yeast cell was subsequently transferred into a 96 well vacuum filter plate, and washed twice with 150 µl wash buffer 1 and once with 150 µl wash buffer II. The cells were stained in the same condition as described herein and suspended in 200 µl PBS for analysis.

Soluble scFv Expression and Purification.

Selected scFvs were cloned into expression vector POE-myc to produce soluble scFv proteins. Briefly, plasmids containing scFv insert were used as template to PCR amplify the scFv insert from each clone. For phage clone, scFv was inserted in the pComb3 plasmid, and pComb3-scFv minipreps were prepared from 10 m overnight bacterial culture using QIAprep™ Spin Miniprep Kit (Qiagen, Valencia Calif.). For yeast clones, pDNL6-scFv minipreps were prepared from a 3 ml overnight yeast culture using Zymoprep™ Yeast Plasmid Miniprep II kit (Zymo Research, Irvine, Calif.). Both amplified scFv fragments and POE-myc plasmid were digested with BssHII and NheI restriction enzymes, and subsequently ligated with T4 ligase. An aliquot of the ligation mixture was used to transform BL21 (DE3) bacteria and the transformed bacteria were used for soluble scFv production.

BL21(DE3) cells with unique scFv clones were grown in 1.4 L 2×YT plus ampicillin medium at 37° C. until log-phage (OD600=0.5), induced with 0.5 mM IPTG, and allowed to grow at 30° C. for an additional 16 hrs. After induction, the bacteria were harvested by centrifugation at 8000 g for 15 min at 4° C., and the pellets were stored in −20° C. for at least 2 hrs. The frozen pellets were briefly thawed and suspended in 40 ml of lysis buffer (1 mg/ml lysozyme in PBS plus EDTA-free protease inhibitor cocktail (Thermo Scientific, Waltham, Mass.) to prevent degradation). The lysis mixture were incubated on ice for an hour, and then 10 mM $MgCl_2$ and 1 ug/ml DNaseI were added and the mixture was incubated at 25° C. for 20 min. The final lysis mixture was centrifuged at 12000 g for 20 min and the supernatant was collected as periplasmic extract.

Soluble scFv from periplasmic extract was purified using HisPur™ Cobalt Resin (Life Technology, Grand Island, N.Y.). The periplasmic extract (40 ml) was first incubated with 1 ml resin for an hour with rotation, and then the resin was gravity packed in a column. The resin column was washed with equilibration buffer (50 mM sodium phosphate, 300 mM sodium chloride, 10 mM imidazole, PH 7.4) until the A280 of flow through reached a baseline. The scFv was subsequently eluted with elution buffer (50 mM sodium phosphate, 300 mM sodium chloride, 150 mM imidazole, PH 7.4). A few 1 ml fractions of elution were collected to insure the protein had been eluted, and those fractions with protein were pooled and concentrated by using an Amicon ultra-15 device (EMD Millipore, Billerica, Mass.). The purified scFv was analyzed by SDS-PAGE gel and the protein concentration was determined using a BCA protein assay kit (Pierce, Rockford, Ill.).

Binding Characterization.

Competitive ELISA was performed similar as described in Example 3, except that an anti-myc antibody (9E10) was added before applying goat-antimouse-HPR secondary antibody to detect myc-tag on scFv construct.

Results

Immune Library Construction.

As data shown in Example 2, methyl groups on the equatorial positions—especially C1 and C2 methylations—are the most potent phenanthrene derivatives to activate AhR pathway (see FIG. 29), and are therefore of greatest concern among phenanthrene family. Consequently, the inventors chose two methylated phenanthrenes as haptens: one with C2 methylation (2-methyl-phenanthrene, or 2-MePhen) and one with methyl groups on both C2 and its symmetrical C7 positions (2,7-dimethyl-phenanthrene, or 2,7-diMePhen). To construct full immunogens, a carboxyl function group has to be added on both haptens for conjugation of haptens to protein carriers. Both C4 and C9 were the least potent methylation positions, and can be used to connect carrier proteins. Considering the steric effects, the inventors eventually chose to put carboxyl group on the C9 position. The designed haptens, 9-carboxyl-7-methyl-phenanthrene and 9-carboxyl-2,7-dimethylphenanthrene, were synthesized by Ansari laboratory (UTMB, TX) and conjugated with keyhole limpet hemocyanin (KLH) or bovine serum albumin (BSA) via mixed anhydride method.

The PAH-KLH or PAH-BSA conjugates were used as immunogens for BALB/c mice. Total of four injections with alternating carrier proteins to avoid of antibodies directed against protein carriers, and blood serum samples were collected seven days after last two injections (FIG. 36). Serially diluted serum samples were applied onto phenanthrene-BSA-coated plate, and the presence of antibodies to the conjugates was confirmed by an indirect ELISA (FIG. 37). After the third injection, mice injected with antigen have shown strong signals to protein conjugates, and the titer was further increased after the $4^{th}$ injection. Without being bound by theory, the hapten-specific antibodies cannot be differentiated out of the total serum sample, as the majority of antibodies can recognize, if not bind, the protein conjugates as a whole.

The process of library construction is shown on FIG. 38. Specifically, the mice were sacrificed 7 days after the final boost and their spleen tissues were harvested as the starting material for cDNA synthesis. Antibody variable domains from heavy chains (VH) and light chains (VL) were amplified using a pool of degenerate primers (Schaefer et al., 2010), which were adapted to our display system as shown in the Appendix. The flanking regions of VH-reverse primers and VL-forward primers contain the same flexible linker sequence, and were used as complementary regions in a second overlap extension PCR step to form a full-length scFv fragment. The final scFv product consisted of a VH-linker-VL structure, and had a total length ~800 bp. After gel purification and restriction endonuclease digestion, the 800 bp PCR fragment was inserted into the pComb3 plasmid. The differences between two 5'-overhang sequences in the SfiI digested fragments insured that the scFvs were inserted in the correct orientation. Phagemids bearing scFv fragments were transformed into SS320 *E. coli* cells by electroporation to provide maximal transformation efficiency. An aliquot of the transformation culture was spread onto 2×YT-Amp plates for library size calculation, and single colonies from the dilution plate were picked to estimate the library diversity. The size of this immune library was $6.2 \times 10^6$. Clone bearing full-length scFv (~800 bp) comprised 87.5% of the sequences (FIG. 39A), and 81.25% of clones had distinct sequences (FIG. 39B), as confirmed by BstNI fingerprint analysis. Because the library contained roughly 4.5 million distinct scFv fragments, sophisticated selection strategies were required to identify the rare antibodies that can recognize soluble hapten (phenanthrene and/or methylated phenanthrenes) in this large pool. The inventors therefore employed a combination of phage and yeast display selections to identify the rare clones that can bind to these soluble haptens, as shown in FIG. 22.

Phage Display—Strategy #1.

In the initial screening, the inventors employed a first loose then increasingly stringent panning conditions strategy to isolate scFv-phage particles specific for methylated phenanthrene. (Zhu et al., 2011) A 7-step selection process included gradually decreasing conjugate coating concentrations, incubation times and increasing the number of washes to enrich binders with highest affinities. The inventors also introduced solvent condition (10% MeOH) and competitors (Benzo[α]pyrene or parent phenanthrene) from third rounds to exclude clones that did not tolerate to the solvent or bound to the competitors. Since three out of four mice injections were done with KLH conjugates, the majority of selection procedures used BSA conjugates with one KLH alternative in the $5^{th}$ round to prevent antibodies specific for protein carrier or linker regions. During the last round of selection, input phage pool was pre-absorbed in BSA-coated tube before incubated with 2-MePhen-BSA-coated tube. The pre-absorption step can help reduce enormous non-specific binders from the input population, and push out the antigen-binding clones in the output pools. (FIG. 40)

After seven rounds of panning, individual clones were selected randomly and used as template for PCR amplification of scFv insert—roughly 40% clones showed full-length (~800 bp) inserts. And the full-length inserts were digested by BstNI restriction enzyme to get their own fingerprint. Most clones have shown a similar fingerprint as 1C4, whereas a few clones (e.g 1C1, 1C8, 2B8, 1B1) showed distinct digestion patterns (FIG. 41A). Sequencing analysis revealed that two clones with the same fingerprint—1C4 and 1C11—have the exact same sequence as well, indicating the uniformity of this phage output pool. The inventors further confirmed the binding of full-length scFv clones to the antigen conjugated by indirect phage ELISA. The 1C4-like clones showed strong binding signal in the assay, while only one clone (1C1) with other digestion patterns was positive (FIG. 41B). The inventors then transferred 1C1 and 1C4 into protein expression system, and purify soluble protein via the His-tag. Both clones bound to phenanthrene-BSA or 2-methylphenanthrene-BSA rather than pyrene-BSA. Besides, 1C4 bound to both Phen-BSA and 2-MePhen-BSA conjugates with high affinity (Kd<10 nM), and the affinity of 1C1 to Phen-BSA (Kd=10.3 nM) is much better than that of binding to 2-MePhen-BSA (KD=152 nM) (FIG. 42). But neither of them recognize soluble Phen or MePhen.

Multiple rounds of selection not only selected for the binders with highest affinity, but also allowed clones with the highest growth rates to predominant during subsequent bacterial amplification (t Hoen et al., 2012). In addition, when selecting for hapten-specific antibodies, high affinity to hapten-protein conjugates did not necessarily translate to high affinity to soluble hapten (Blake et al., 1996).

Phage Display—Strategy #2.

For the second strategy, the number of panning steps was limited in order to efficiently select specific binders while maintaining the diversity of output pools and the selection protocol was adjusted as shown in FIG. 43. Total of three rounds of panning were performed against two different capture antigens, phenanthrene-BSA (Protocol 1) or 2-methylphenanthrene-BSA (Protocol 2). Each panning step was designed to provide a specific selective pressure. The first round enriched for hapten-protein binders from the immune library; the second panning step introduced a solvent condition (1% DMSO) to exclude antibodies that were unstable in this solvent and hence is not be useful when soluble haptens were applied later in the selection process. In the final round of panning, soluble hapten was added to enrich the pool of binders that bound to the soluble haptens. The input-to-output ratio (yield) was used to determine enrichment at each selection step. The last round of panning enriched our populations by 20-fold and 108-fold, respectively, for Protocols 1 and 2.

The inventors tracked the binding of each phage output pool to immobilized Phen-BSA and/or 2-MePhen-BSA using competitive phage ELISA. As shown in FIG. 44, the enrichment after initial panning was not sufficient to show specific binding to the immobilized antigens in the assay. After second round, the binding signals became significant, and can also be inhibited by protein conjugates. Moreover, the phage pools from Protocol 1 (selected against Phen-BSA antigen) were more sensitive to Phen-BSA than 2-MePhen-BSA competitors; on the contrary, phage pools from Protocol 2 (selected against 2-MePhen-BSA) showed stronger inhibition by 2-MePhen-BSA. However, the inventors were not able to detect any inhibition by soluble phenanthrene or 2-methylphenanthrene in these pooled phage populations.

The diversity test of last round of selection was analyzed by the same procedure as used in Strategy #1. First, the insert of individual clones were amplified, and 84% were full-length as shown on the agarose gel (FIG. 45A). BstNI digestion of the full-length clones revealed an extremely diverse output—involving 52% distinct clones (FIG. 45B). Among the analyzed clones, one-third of the population positively bound to the antigen conjugates as confirmed by indirect phage ELISA (FIG. 45C). Since there were millions of clones selected by the end of each protocol, it is impractical to analyze each of them individually. The inventors proceeded to another platform—yeast display system for a more specific selection, as the inventors can have stronger control over the direction of selections when coupled with fluorescence-activated cell sorting (FACS).

Yeast Display Sorting.

The scFv fragments from the phage remaining after 3 rounds of selection from Protocol 1 and Protocol 2 were transformed into two independent yeast pools (Step 6 and 7 in FIG. 21). The transformed yeast cells were induced to activate the expression of cell surface Aga2p-scFv-myc fusion proteins and the scFv-bearing yeast cells were stained with two fluorescent dyes and analyzed with flow-cytometry (see schematic in FIG. 46A). The expression level of scFv was monitored by the signal from the myc tag and is shown on the x axis of the flow plot, while the binding capacity of expressed scFv to hapten-conjugates was detected by the signal from the biotinylated antigen and is shown on the y axis of flow plot. The overall strategy for competitive FACS is shown in FIG. 46. The yeast cell population that both expressed scFv (as assessed by the signal on the X axis) and bound to the biotinylated PAH-BSA conjugate (as assessed by the Y axis signal) is incubated in the presence of soluble hapten (phenanthrene or 2-methylphenanthrene). Those clones that bind to soluble antigen will show lower signals in the Y axis and can be enriched in the area of the Q2 quadrant circled in FIG. 46D.

1) Initial FACS Selection of Yeast Pools:

Before carrying out a competitive FACS, each yeast population derived from phage selection was first analyzed and cleaned up via a initial sorting to remove cell populations that can cause interference during subsequent selection steps. The inventors first explored the yeast population derived from phage selected via Protocol 1 (FIG. 43). Because the phage selection strategy had used unmethylated phenanthrene-BSA as the immobilized antigen, the yeast clones derived from these pooled phage were tested for their ability to bind to biotinylated Phen-BSA. After incubation of these cells with the biotinylated Phen-BSA, an anti-myc mouse monoclonal, and fluorescently labeled tags (see FIG. 46), the yeast pool directly after phage selection bound tightly to the Phen-BSA-Biotin conjugates with a tapered shape pointing towards the upper right corner, as shown in FIG. 47B (upper right point is the clone with highest expression level and binding affinity). However, when the same yeast population was stained with anti-myc antibody and BSA-Biotin without phenanthrene (a negative control in the FACS assay), a significant number of cells migrated in the Q2 quadrant (FIG. 47B). These non-specifically bound cells in Q2 quadrant can interfere with the competitive sorting planned for subsequent selections. A negative selection of these cells was therefore performed, by collecting only the cells in Q4, in order to exclude non-specific binders (boxed area in FIG. 47B). These negatively sorted cells, when re-examined for non-specific binding by staining with BSA-Biotin, now showed a much smaller population in the Q2 quadrant (FIG. 47C). The positive control (Phen-BSA-Biotin) still showed a similar shape as before the pre-sort (FIG. 47D), indicating there is no loss of specific binding clones during this pre-sort process.

When the yeast cells derived from Protocol 2 (FIG. 43) were examined, the first FACS analysis showed very different characteristics than the Protocol 1 cells, as shown in FIG. 48. For Protocol 2, the inventors used methylated phenanthrene conjugate (2-methylphenanthrene-BSA) as selection reagent, and therefore the inventors proceed to yeast sorting with biotinylated 2-methylphenanthrene-BSA (2-MePhen-BSA-Biotin). The Q2 quadrant of Pool 2 was relatively clean in the presence of BSA-Biotin (FIG. 48A), so a negative sort was not required. However, relatively few cells in this population bound to positive antigen 2-MePhen-BSA-Biotin and the scattered populations in Q2 and Q4 can overwhelm the small population that can be inhibited by soluble hapten in the subsequent competitive FACS selection. Therefore, these cells were first selected for those clones that bound tightly to 30 nM 2-MePhen-BSA-Biotin, as shown in P5 gate of FIG. 48B. After the 1st FACS, the Q2 quadrant of Pool 2 was still clean when incubating with BSA-Biotin negative control (FIG. 48C), while plot shape of sorted pool was much tighter with fewer scatter points (FIG. 48D) than before the initial sorting. And now, both pools were in clean and tight shapes, and ready for competitive FACS with soluble competitors.

2) Competitive FACS Selection of Yeast Pools:

A competitive cell sort was then performed, according to the strategy shown in FIG. 46. Yeast pools from the initial sorted cells were divided into two groups and incubated with 2% DMSO solvent control or soluble competitor also in 2% DMSO in the presence of biotinylated protein conjugates. Because the cell population was split after induction of cell surface scFvs, there was no change in the expression level of scFv fragments and the x axis signal can remain the same for the two groups. However, those cell-surface antibodies that recognized soluble hapten can be competitively inhibited from binding to the biotinylated hapten-protein conjugate, and cells carrying antibodies with these binding characterisitcs can show a decreased signal on the y axis of the flow plot. Thus, by selecting the cell population that shifted down in the presence of soluble competitor (FIG. 46D circle), the inventors were able to enrich for those rare surface-displayed antibodies that were specifically inhibited by the soluble haptens.

For Pool 1, the yeast cells after initial sort was incubated with 2% DMSO (FIG. 49A) or 200 µM soluble Phen (FIG. 49B) both in the presence of 30 nM biotin-labeled phenanthrene-BSA. And the yeast population under the major peak was gated for parallel comparison between solvent control and competitor. The total cells selected in this gate was ~0.6% of the total cells in the absence of soluble hapten (yellow circle, FIG. 49A) and ~1% of cells in the presence of soluble hapten (red circle, FIG. 49B). Thus, without being bound by theory, ~40% of the yeast clones in this very small population can contain antibodies that can recognize soluble hapten. And for Pool 2, a similar competitive FACS was performed. In this selection, 200 µM soluble 2-MePhen as the soluble competitor and 10 nM 2-MePhen-BSA-Biotin as the protein conjugate. In the absence of soluble hapten, the cells selected in P4 gate comprised ~0.7% of total cells (FIG. 49C), cells in this gate population increased to ~1% when soluble hapten was added (FIG. 49D). Similarly to Pool 1, these results indicate that roughly 30% yeast clones from this population can recognize the soluble hapten.

After competitive sorting, the enriched yeast cells were grown again and analyzed by competitive flow cytometry to confirm the enrichment of soluble PAH-specific population. Take Pool 1 as an example, the cells collected after competitive FACS were stained again with 30 nM Phen-BSA-Biotin in the presence of 2% DMSO (FIG. 50A) and 200 µM Phen (FIG. 50B). The inhibition of soluble Phen competitor can now be observed significantly compared to solvent control, as the whole population was shifted from Q2 quadrant to Q4 quadrant without moving leftward. Therefore, the inventors concluded that they have enriched the soluble PAH-specific clones by roughly 200-fold ($1^{st}$ sort is ~50% and $2^{nd}$ sort is 1%), and successfully made this rare population visible in polyclonal pool.

3) Flow Cytometry of Monoclonal Yeast Cells:

Yeast cells collected after $2^{nd}$ sort were spread onto agar plates at various dilution level to obtain isolated single colonies. A high-throughput monoclonal screening method was used to analyze ~100 clones at a time with Millipore Guava EasyCyte™ flow cytometer. A total of 184 individual clones sorted from Pool 1 were picked and analyzed for their binding to Phen-BSA-Biotin in the presence of soluble Phen or 2-MePhen. In summary, 70 out of 184 clones from Pool 1 showed changes of the monoclonal yeast cells' migration in flow cytometry in the presence of the soluble inhibitor, and the percentage (38%) of positive clones coincides with that of the estimated positive population in the competitive sorting pool (40%). Sequences analysis of positive clones revealed a high degree of repeatability of these 70 clones. (See Monoclonal Antibody Analysis for more detail) Therefore for Pool 2, only 48 clones were analyzed, and 8 were significantly inhibited by soluble competitor. FACS of three representative clones (D7, G8 and A10) are shown in FIG. 51. Clones D7 and G8 appeared unable to distinguish between the 2 soluble competitors, while the clone A10 appeared to show some tendency for the 2-MePhen over unsubstituted Phen.

Monoclonal Antibody Analysis:

Competitive ELISA of periplasmic scFvs and sequence analysis.

The 70 of the clones identified via FACS were subsequently cloned into an expression vector to produce soluble scFv protein, and the signal peptide at the N-terminal of scFv localized the recombinant protein into the periplasmic space. Periplasmic space is a narrow gap between bacterial inner cytoplasmic membrane and outer membrane. Periplasmic expression provides the oxidative environmental and enzymes catalyzing the formation of disulfide bonds, and protects the synthesized protein from proteolysis since less protease is present here than in cytoplasm. After induction, the bacteria cells were harvested by centrifuge and the periplasmic contents were released from cell pellets without breaking the inner cell membrane. The crude periplasmic extracts were separated from whole cell pellet and the presence of recombinant protein in the extracts were confirmed by SDS-PAGE and Western Blot analysis with a significant band around 30 KDa.

Initial analysis used crude periplasmic extracts to confirm binding of scFv to soluble hapten by competitive ELISA without the avidity or other interferences that can arise from the yeast display system. Of the 70 clones identified by competitive flow cytometry, 65 also shown activity in the competitive ELISA format. (Representative data shown in FIG. 52) When these 65 clones were sequenced, the majority of them (81.5%) are identical as Clone D7, and 6 other distinct scFv sequences were found. Similar selection protocols were applied to cells derived from Protocol 2 and analysis of 48 individual clones revealed 8 clones that were positive by competitive flow cytometry, 6 that were positive by competitive ELISA and 3 distinct scFvs with different binding properties (4C1, 4E3 and 4H1). These data are summarized in FIG. 53. Sequence alignment (FIG. 54) of the ten distinct clone sequences indicated that the positive clones appeared to fall into three family lines, related to the A10, D7, and G8 clones that showed distinct patterns during competitive flow cytometry (FIG. 51).

Competitive ELISA with Purified scFvs.

Since A10, D7 and G8 represent three distinct family based on the sequence alignment, the inventors next explored the binding characteristics of these three clones as models to of the antibodies present in the immune library. Purified scFv were prepared and analyzed by competitive ELISA for their abilities to recognize unsubstituted phenanthrene or methylated phenanthrenes, as shown in FIG. 55. A fixed concentration of scFv proteins were incubated with Phen-BSA conjugate coated in the microtiter plate, in the presence of varying concentrations of ligands in 5% DMSO. The data for each ligands were fitted in a four-parameter dose-response curve: y=a0+a1/(1+(x/a2)^a3), where a2 represented the $IC_{50}$ value of scFv to the corresponding ligand. The $IC_{50}$ values were summarized in FIG. 56. Clone D7 bound to the phenanthrenes tested with no significant difference ($IC_{50}$s around 4~8 µM), while G8 and A10 were able to differentiate among various methylated phenanthrenes. Specifically, A10 did not recognized parent phenanthrene or 9-MP, but bound to 2-MP with the affinity of 8.28 µM. And G8 was more sensitive to the phenanthrenes tested compared to the other two clones, and its best ligand is 4-MP at sub-micromolar affinity and the worst ligand is 3-MP with $IC_{50}$ of 14.43 µM.

Cross-reactivity of three representative clones against EPA 16 PAHs.

A real-world field sample is a complex mixture and contains a variety of PAH compounds. An understanding of the abilities of antibody to recognize various PAHs can greatly facilitate the development and application of these antibodies into field studies. In the final assessment, the inventors determined the cross-reactivity of these three scFv clones among 16 structurally related EPA priority PAH species via competitive ELISAs. First, the inventors inhibited the binding of scFv to the immobilized Phen-BSA by high concentrations (50 µM) of PAHs to determine if the scFv can recognize the ligand. If the signal of ligand-inhibited sample showed less than 20% decrease than that of control sample (5% DMSO), the ligand was considered as non-reactive for the antibody. (As shown ND in FIG. 57) None of the 16 PAHs showed significant inhibition to A10 scFv antibody, indicating that A10 probably is the most specific clone for phenanthrene family. For these ligands that showed higher than 20% inhibition at 50 µM, the inventors next performed a competitive ELISA with serially diluted concentrations of ligands ranging from 200 µM to 0.091 µM (FIG. 58). D7 and G8 showed slightly different tendency for the ligands. D7 bound to three PAHs—fluoranthene, indeno-[1,2,3-cd]-pyrene and pyrene—at highest affinity (1.5 µM), which was about 4-fold more sensitive than binding to phenanthrenes. G8 also bound tightly to fluoranthene and pyrene with $IC_{50}$s of 2.4004 and 2.0204 respectively, but did not recognize indeno-[1,2,3-cd]-pyrene. However, the best ligand of G8 was still 4-MP ($IC_{50}$ of 4-MP was 0.94 µM). And G8 was hence most specific for methylated phenanthrenes.

Discussion

The selection process seems to be complicated, but you get what you select for. Without being bound by theory, the output of selection is not random, and the selection pressure was the driven force for the enrichment of specific populations. For the first method of phage display selection, the inventors performed a strategy including seven-round selection (FIG. 40). The final output contains only 2 distinct scFv clones, and both bound to Phen-BSA conjugate at nanomolar affinity but did not recognize soluble hapten in cELISA assay (FIG. 41 and FIG. 42). Without being bound by theory, the amplification process between each round of selection can boost the fast-growing clones to outgrow in the population regardless the binding specificity. And since the inventors have performed so many rounds of selection, the predominant conjugate-binding population with fastest growth rate (e.g. clone 1C1 and 1C4) finally overwhelmed the infrequent hapten-binding clones. In fact, the doubling time of clone 1C4 was about 20 minutes, much shorter than average doubling time of the total population which was 25-30 minutes. While for the Strategy #2, the inventors kept the number of panning within three rounds, and the outcome remained high diversity since the difference of growth rate was not the major selection pressure any more.

For the second strategy, the same library was diverged into two directions by using two antigen conjugates: Phen-BSA (Protocol 1) or 2-MePhen-BSA (Protocol 2). After three rounds of phage selection, the specificity to soluble haptens was still hard to tell as the high level of background signal obscured any inhibition of soluble competitors. However even with high noise, the inventors can still tell the difference between two pools: Pool 1 showed higher inhibition by Phen-BSA conjugates, while Pool 2 was more sensitive to 2-MePhen-BSA conjugates (FIG. 44). By the end of yeast sorting, the difference of two pools was even more obvious. For Pool 1, 70 clones were identified as inhibited by soluble haptens, 65 were confirmed positive by cELISA, and 53 out of 65 clones (81.5%) were of the same sequence as D7. After characterization of binding properties, D7 were shown to be the only clone that bound to both unmethylated and methylated pheanthrenes at the same affinity. The high ratio of D7 in Pool 1 has proved that the selection pressure of Protocol 1 by Phen-BSA conjugate directed the enrichment of unmethylated phenanthrene-specific antibodies. And since the whole library was immunized with methylated phenanthrene-KLH conjugates, the phenanthrene-specific antibodies can recognize methylated phenanthrenes as well. In addition, none of the clones identified from Pool 2 was similar to D7, and they showed specificity to one or more methylated phenanthrenes rather than unmethylated phenanthrene.

Without being bound by theory, the outputs of given screen procedure are highly dependent on the selection pressures and the assay conditions can be designed in order to achieve the desirable outcomes. On the other hand, the same library can also be used to isolate clones with various specificities if guided with different experiment design.

Thus, the inventors have developed an immune antibody library specific for phenanthrene and/or methylated phenanthrenes, and employed a combination of phage and yeast display technologies to screen the library for specific binders. So far, the inventors have discovered ten distinct clones with various binding capacity from the library based on two selection protocols, and the ten clones falls into three sequence family. Binding analysis of three clones, each representing a sequence family line, revealed that one clone (A10) bound to methylated phenanthrenes with low affinity (high $IC_{50}$ values) but high specificity (no cross-reactivity to other PAHs), one clone (G8) bound to PAHs with highest affinity and bound to methylated phenanthrene (especially 4-MP) with some cross-reactivity to other PAHs, and last clone (D7) did not differentiate methylations on phenanthrene and can be used to measure the total amount of phenanthrenes as reference.

Combination of Phage and Yeast Display Technologies.

When analyzing the levels of PAHs in the environment it is important to distinguish its origins, since PAHs can also occur in the environment from pyrogenic sources. For analytical methods applied for PAH detection, for example GC-MS and HPLC, the bulky equipment limits their application directly on site. Antibody-based immunoassays on the other hand are fast, simple, inexpensive, portable, and have high sensitivity and specificity comparable to analytical methods. However, there are no suitable antibodies for petroleum-specific PAHs because of the difficulty to generate antibodies that distinguish a methyl group change on a small hapten. Recombinant antibody libraries are valuable sources to isolate antibodies with rare specificities, and a powerful and comprehensive screening method is required to identify a few clones at low frequency. The inventors have described a combination of two selection platforms—phage and yeast displays—to complement each other for the best outcomes.

Phage display platform has been widely used for three decades, and has successfully selected antibodies that were difficult or impossible to get by traditional hybridoma method. Phage display can screen billions of clones within a few of hours and rapidly amplify the selected sub-population in bacterial cultures. Besides, the diversity of desirable antibodies is correlated with the size of the library, and since phage display can accommodate considerably large size libraries, it is most suitable to be used as an initial enrichment platform.

Yeast display is an alternative selection approach using a eukaryotic expression apparatus. It is compatible with flow cytometry to visualize each clone individually and quantitatively select a specific population via FACS. In a phage display selection, the outcome is "blind": the inventors can only tell the selection efficiency by the input and output phage numbers, but have no assessment on the behavior of individual clones within a pool of phage. In contrast, yeast display coupled with flow cytometry can measure multiple parameters (the expression level of the scFv and the binding capacity of scFv to biotinylated antigens) simultaneously and reveal individual clones in a two-dimensional plot. And FACS can specify any area in the plot to be sorted. Here the inventors developed a competitive flow strategy, which is useful for hapten antibody selections. The inventors sorted two pools in different ways (FIG. 47A and FIG. 48B) but the underlying principles were the same: to get rid of yeast cells underneath the major peak where the competitive changes occur.

Compared to standard yeast display protocols, the inventors did not focus on the population on the upper right corner which can have the highest binding affinity to the protein antigens. Because of their strong binding to the protein conjugates, this population was even less likely to be inhibited by the soluble competitor compared to other moderate binding clones. On the contrary, the inventors were looking into the population that accumulated underneath the major peak when soluble hapten competitors were applied. This population is fairly small: 0.4% from Pool 1 and 0.3% from Pool 2. But when the inventors amplified this 0.4% or 0.3% population, the inventors were able to see a significant competition by soluble haptens (FIG. 50).

Besides, competitive flow method can also be used to infer the binding capacity during monoclonal analysis. Binding analysis using purified protein or at least crude periplasmic extracts required a series of downstream processes including cloning individual scFv sequences into expression system, bacterial culture induction, periplasmic extraction and purification etc. The heavy workload limits the number of single clones that can be tested after final sorts. Yeast cells coupled with flow cytometry can be adopted into high-through put format as described in Example 4, and hundreds of single clones were analyzed without making purified protein in a short time (FIG. 51). To compare the sensitivities of competitive flow (cFlow) and competitive ELISA (cELISA) methods, the inventors used the ten clones identified in this study as model and found that the inhibition of ligand to antibody in cFlow correlated that in cELISA (FIG. 59). The correlation strength (r2) of two methods is 0.78. Therefore, cFlow can be used as initial monoclonal screening method to exclude the majority of undesirable clones, and to reduce the number of potential clones need to be transferred into expression system for detailed analysis.

Condition Optimization of Binding Assays.

As IC50 values were used as indicators for antibody-hapten binding affinity, assay conditions can be optimized for the most sensitive range. A typical dose-response curve of antibody binding to the immobilized antigen takes the form of sigmoid shape, and the most sensitive concentrations of antibody to be inhibited by competitors are the linear range indicated in FIG. 60. High concentrations of antibody require large amount of competitors to overcome the plateau phase before getting inhibited signals. The inventors first optimized the concentrations of scFv antibodies in their linear range between 0.2 to 2 µg/ml (FIG. 61). Soluble phenanthrene was used as model for D7, and 2-methylphenanthren was used for A10 and G8. The concentrations of each clone were determined by two factors: the maximum signal can be higher than 0.5, while the IC50 values was minimum. The optimum concentration for A10 was set to be 0.2 µg/ml, and 0.5 µg/ml for D7 and G8. Next, the inhibition of three clones was measured by their ligands at varying PH conditions and BSA carrier protein concentrations. As shown in FIG. 62, the clones tested prefer lower PH of 6.2 or 6.6, and D7 completely lose its binding property at PH higher than 7.8. As for carrier protein concentration, six gradients from 0 to 1% of BSA were added during incubation step, and 0.02% BSA seems to best facilitate the binding assay for the three clones.

Chemical Engineering of Phen-Biotin Molecule.

During yeast display selection, the inventors have synthesized a biotinylated hapten molecule (phenanthrene-biotin, or Phen-Biotin) as an alternative labeling reagent for yeast display selection. The use of Phen-Biotin instead of Phen-BSA-Biotin was to eliminate the interference of BSA protein carrier and selected for hapten-specific clones rather than conjugate-specific antibodies. EZ-Link™ Amine-PEG11-Biotin (Thermo Scientific, Waltham, Mass.) was used to conjugate with 9-phenanthrene-carboxylic acid (Phen-COOH). The amine group can be reacted with carboxyl groups on the C-9 position of phenanthrene using 1-ethyl-3-(3-dimethylaminopropyl) carbodiimide (EDC), a carbodiimide crosslinker (FIG. 63). EDC reacts with the carboxyl group and forms an amine-reactive O-acylisourea intermediate (reaction (1)), and the intermediate quickly reacts with the amine group to form a peptide bond and release of an isourea by-product (reaction (2)). The 11 repetitive PEG spacer arm creates a 53.2 Å-long linkage between biotin and phenanthrene, and allows interactions of both molecules to their binding partners simultaneously without interference from each other.

The reaction was carried out in MES buffer at PH 5.5 as the EDC-mediated activation process was most efficient around PH 5~6. The initial reaction followed the protocol provided with EZ-Link™ Amine-PEG11-Biotin product, and used a ratio of Phen-COOH:Amine-PEG11-Biotin:EDC=1:100:10. As shown in FIG. 64, each reactant showed its own retention pattern in HPLC analysis, and there was a new peak highlighted by the blue box shown in the product but not present in any of the reactant. This peak around 12 min-retention time can be the Phen-Biotin conjugate, and the reaction condition was optimized to raise the peak for high reaction yield. Specifically, various concentrations of reactants were applied, while the EDC activator was always 10-fold higher than Phen-COOH to ensure fully activation of the carboxyl group. When a low dose of Phen-COOH (100 μM) was incubated with increasing concentrations of Amine-PEG11-Biotin (100 μM, 1 mM and 10 mM), no significant increase was observed (FIG. 65 A-C). However, when a high dose of Phen-COOH (1 mM) was used, the product peak was dramatically increased with low level (100 μM) or high level (5 mM) of Amine-PEG11-Biotin. (FIG. 65 D-E) Finally, the optimum reaction was chosen to be 1 mM Phen-COOH plus 5 mM Amine-PEG11-Biotin and 10 mM EDC, and the reaction product was fractionated to isolate purified Phen-Biotin conjugate. The inventors collected eleven fractions from 11.3 min until 13.5 min, and the product peaks were shown on Fraction #2~#4(FIG. 66). The presence of Phen-Biotin conjugate in Fraction #2~#4 was further confirmed by MALDI-TOF mass spectrometry: the theoretical MW of Phen-Biotin was 975, and the two peaks were sodium ionized (975+23=998) and potassium ionized (975+39=1014) conjugates respectively.

The purified Phen-Biotin conjugate can be used as labeling reagent to detect antibody binding to phenanthrene hapten in yeast display. As shown in FIG. 68, the yeast cells derived from Protocol 1 phage selection were incubated with protein conjugates and hapten-biotin conjugate. The yeast cells binding to Phen-Biotin (FIG. 68C) were shifted upwards in Q2 Quadrant (13.0%) as compared to BSA-biotin negative control (3.2%) and DMSO solvent control (3%). The binding pattern of Phen-Biotin was not as tight as that of Phen-BSA-biotin protein conjugate, probably because of the multivalent avidity effect of protein conjugates amplified the binding signal compared to monovalent Phen-biotin molecule. By using this hapten-biotin conjugate, the inventors can direct select binders that recognize soluble haptens without competitive sorting. However since this yeast population contained non-specific binders that bound to BSA-biotin and DMSO controls in the absence of antigens, a initial clean-up step as described in Example 4 can be performed to preclude any interference in the Q2 quadrant.

Summary.

In this study, the inventors have discovered ten distinct scFv antibodies that bind to phenanthrene and/or methylated phenanthrenes at micromolar affinity. The affinity of antibodies can be further improved by generating a derived library through mutagenesis and screening the library for better binders (Bostrom et al., 2009; Chames et al., 1998; Rajpal et al., 2005). Even with these existing antibodies, a combination of two or more different clones can differentiate the sources of PAHs (petrogenic or pyrogenic). Furthermore, the immune library was of millions of diversity, and can not be analyzed from a single screening process. Additional clones can be identified if other selection strategies were employed such as using of hapten-biotin molecules described herein. The inhibition of soluble competitors. However even with high noise, the inventors can still tell the difference between two pools: Pool 1 showed higher inhibition by Phen-BSA conjugates, while Pool 2 was more sensitive to 2-MePhen-BSA conjugates (FIG. 44). By the end of yeast sorting, the difference of two pools was even more obvious. For Pool 1, 70 clones were identified as inhibited by soluble haptens, 65 were confirmed positive by cELISA, and 53 out of 65 clones (81.5%) were of the same sequence as D7. After characterization of binding properties, D7 were shown to be the only clone that bound to both unmethylated and methylated pheanthrenes at the same affinity. The high ratio of D7 in Pool 1 has proved that the selection pressure of Protocol 1 by Phen-BSA conjugate directed the enrichment of unmethylated phenanthrene-specific antibodies. And since the whole library was immunized with methylated phenanthrene-KLH conjugates, the phenanthrene-specific antibodies can recognize methylated phenanthrenes as well. In addition, none of the clones identified from Pool 2 was similar to D7, and they showed specificity to one or more methylated phenanthrenes rather than unmethylated phenanthrene.

In our experience, the outputs of given screen procedure are highly dependent on the selection pressures and the assay conditions can be carefully designed in order to achieve the desirable outcomes. On the other hand, the same library can also be used to isolate clones with various specificities if guided with different experiment design.

Example 5—Combining Yeast Display and Competitive FACS to Select Rare Hapten Specific Clones from Recombinant Antibody Libraries The development of antibodies to low molecular weight haptens remains challenging due to both the low immunogenicity of many haptens and the cross-reactivity of the protein carriers used to generate the immune response. Recombinant antibodies and display technologies have greatly advanced antibody development; however, new techniques are still required to select rare hapten-specific antibodies from large recombinant libraries. In this example, the inventors used a combination of phage and yeast display to screen an immune antibody library (size, $4.4 \times 10^6$) against hapten markers for petroleum contamination (phenanthrene and methylated phenanthrenes). Selection via phage display was used first to enrich the library between 20 and 100-fold for clones that bound to phenanthrene-protein conjugates. The enriched libraries were subsequently transferred to a yeast display system and a newly developed competitive FACS procedure was employed to select rare hapten-specific clones. Competitive FACS increased the frequency of hapten-specific scFvs in our yeast-displayed scFvs from 0.025-0.005% in the original library to between 13-35% in selected pools. The presence of hapten-specific scFvs was confirmed by competitive ELISA using periplasmic protein. Three distinct antibody clones that recognize phenanthrene and/or methylated phenanthrenes were selected and their distinctive binding properties were characterized. These are first antibodies that can distinguish between methylated (petrogenic) versus unmethylated (pyrogenic) phenanthrenes; such antibodies will be useful in detecting the sources of environmental contamination. This selection method can be adopted in the selection of other hapten-specific recombinant antibodies.

Antibodies to low molecular weight haptens are invaluable tools for many analytical applications. In drug analysis, competitive immunoassays are still the mainstay in the screening and semi-quantitative analysis of hundreds of different xenobiotics and drugs of abuse[P1]. In addition, fully automated, high-throughput antibody-based systems are available in laboratories to help physicians to make timely decisions about drug dosage and safe therapeutic levels[P1,P2]. The demand for diagnostic immunoassays to monitor the safe and effective use of prescribed drugs will continue to increase as health care evolves to more personalized interventions and to products tailored to the individual patient[P3]. In addition to their utility in clinical diagnostics, hapten-specific antibodies also play an important role in environmental monitoring, where immunoassays are most often used on-site to provide near real-time information on the extent of environmental contamination or on the progress of site remediation. Thus, antibodies directed toward low molecular weight contaminants, including pesticides[P4], PCBs[P5], biotoxins[P6], PAHs[P7-P9] and metals[P10-P12] have proven useful to assess the safety of food, water and the ecosystem.

The generation of high-quality antibodies for low molecular weight haptens has never been straightforward. Antigens smaller than 1000 Da are not immunogenic, but can induce a T cell-dependent immune response when conjugated to protein. Because these carrier proteins are often more immunogenic than haptens alone, the antibodies thus generated often have an extended binding sites that includes, in addition to the hapten, portions of the protein used in conjugation. Thus most anti-hapten antibodies bind much more tightly to the hapten-protein conjugates than to the soluble hapten, because of the greater number of interactions at the binding site (for specific examples, see[P13,P14]). Antibodies with primary specificity for soluble haptens are often very rare in the antibody repertoire of immunized animals or from monoclonal antibodies prepared from immune tissue.

Recombinant antibodies such as single-chain fragment variable antibodies (scFvs) have greatly advanced antibody development.[P15] Recombinant antibodies can be manipulated at molecular level to modify their binding properties[P16,P17] and they can be shuffled between different expression systems during the selection and production processes[P18]. In addition, given the concerns about the reproducibility of many published studies that utilize antibody-based reagents[P19], new requirements for rigor in biomedical research can ultimately demand that antibodies be sequenced and expressed as recombinant proteins[P20]. Antibody libraries of high diversity can be created using recombinant technology[P21], and the large numbers ($10^6$-$10^{11}$) of distinct antibody clones from which to select theoretically improves the chances of discovering rare clones, including hapten-specific antibodies. When suitable selection procedures can be employed, even antibodies present at very low frequency in the original library can be highly enriched and become visible in the sub-populations.

In this example, a new selection procedure is described for the identification and subsequent isolation of rare, hapten-specific recombinant antibodies from a relatively large immune library (~$4.4 \times 10^6$). The inventors developed a new, competitive fluorescence activated cell sorting (FACS) protocol that, when combined with pre-selection via phage and yeast display, yields high percentages (20-40%) of hapten-specific scFvs in the final pool of selected cells, even though no binding to soluble hapten can be detected using standard selection strategies. In the example, the inventors used competitive FACS to isolate antibody populations that can distinguish between methylated and unmethylated phenanthrene, because antibodies for alkylated polycyclic aromatic hydrocarbons can serve as markers for environmental petroleum contamination.[P22, P23] However, this method can be widely applicable to the isolation of a wide variety of scFvs directed toward soluble antigens.

Experimental

Materials.

Chemicals (purities at 98% or higher) were purchased from the following sources: phenanthene (Phen, Sigma Aldrich), 2-methylphenanthrene (2-MP, Sigma Aldrich), 3-methylphenanthrene (3-MP, BOC Sciences), 4-methylphenanthrene (4-MP, Chem Service), 9-methylphenanthrene (9-MP, Crescent Chemical). Each compound was dissolved as 10 mM stock in DMSO. 9-Carboxyl-phenanthrene was purchased from Sigma Aldrich. 9-Carboxyl-7-methyl-phenanthrene, and 9-carboxyl-2,7-dimethyl-phenanthrene were synthesized in-house at the University of Texas Medical Branch in Galveston, Tex. Phage display plasmid pComb3XSS was obtained from The Scripps Research Institute. Both the yeast display plasmid pDNL6-GFP-myc (originally generated from pPNL6 plasmid[P18,P24] and scFv expression plasmid POE-myc (generated from a pET based plasmid, pEP-D1.3[P25] were modified in our laboratory to replace the V5 tag with a myc tag. Monoclonal anti-myc antibody 9E10 was purified in-house from the culture supernatant of 9E10 hybridoma cells (Developmental Studies Hybridoma Bank, University of Iowa).

Protein Conjugates, Mouse Immunization and Immune Library Preparation.

9-Carboxyl-phenanthrene, 9-carboxyl-7-methyl-phenanthrene, and 9-carboxyl-2,7-dimethyl-phenanthrene) were conjugated with protein carriers (BSA or KLH) using a mixed anhydride method[P26]. Details of conjugate synthesis, purification and characterization are provided herein. Immunization of mice with these conjugates and the subsequent construction of an scFv immune library are also discussed herein.

Phage Selection.

Antibody phage library or output pools from previous rounds of selection were grown and infected with helper phage M13KO7 for phage production as described herein.

Two selection protocols were performed towards two different targets (unsubstituted phenanthrene or 2-methylphenanthrene). A 96-well high binding plate (Corning, N.Y.) was coated with 50 µl of antigen (5 µg/mL) at 4° C. overnight. The next day, plate was washed three times with PBS containing 0.05% Tween 20 (PBST) and blocked with 3% BSA at 25° C. for 1 hr. An aliquot of amplified phage (about $10^{12}$ cfu,) was also blocked with 3% BSA at 25° C. for 1 hr in PBS or PBS plus 1% DMSO. The blocked phage were then added into the antigen-coated plate, and incubated for 1 hr. Unbound phage were removed by washing (15× with PBST followed by 2× with PBS) and the bound phage were eluted by one of two methods: 1) Acid elution with 200 µl glycine-HCl at PH 2.2 for 8 min and immediate neutralization with 2M Tris to yield a final pH of ~7.5. Early in the selection process, this method ensures that selection is comprehensive and does not exclude any rare binders; 2) Competitive elution with 100 µM soluble analyte (phenanthrene or 2-methylphenanthrene) in 1% DMSO for 30 min. This method was used in the final selection step to enrich a specific population which recognized soluble analytes rather than protein conjugates.

Half of the eluted phage were used to infect 10 ml log-phase T1 E. coli bacteria culture at 37° C. for 30 min. An aliquot of infected culture was serially diluted and spread on 2×YT-AG plates to calculate the number of phage eluted (as "output" of this round of panning), and the rest of culture was incubated in fresh 2×YT-AG medium overnight at 37° C. The next day, phage particles were amplified from this culture and used as "input" for next round of panning.

Phage ELISA.

Phage ELISA was performed in 96-well high binding plates (Corning, Corning, N.Y.). Each well was coated with 2 µg/ml antigen at 4° C. overnight and blocked with 3% BSA. Phage pools recovered from each selection were incubated in the antigen-coated well with solvent control (1% DMSO), 100 µM soluble hapten (Phen or 2-MePhen) or 50 µg/mL soluble protein conjugate (phen-BSA or 2-MePhen-BSA). The binding of phage particle to the immobilized antigens on the plate was measured using anti-M13-HRP antibody (GE Healthcare, Little Chalfont, United Kingdom). The HRP signal was detected by adding Sureblue TMB microwell peroxidase substrate (KPL, Gaithersburg, Md.) and the reaction was stopped after 5 min using 1N HCl. The incubation steps were performed at room temperature for an hour. The plate was washed three times with PBST between steps.

Yeast Display and Competitive FACS.

After the final phage selection, the phagemids containing the scFv genes were isolated with a miniprep kit (Qiagen, Valencia, Calif.), and scFv genes were amplified with a pair of transfer primers (FIG. 11, FIG. 12). Yeast display plasmid pDNL6-GFP-myc was digested with BssHII and NheI restriction enzymes and the linear plasmid was gel-purified without the GFP insert. Digested pDNL6 plasmid (500 ng) and purified scFv PCR product (1 µg) were transformed into $EBY_{100}$ yeast competent cells with Yeast Transformation System 2 kit (Clontech, Mountain View, Calif.). The homologous region on the plasmid and PCR product flanking region will lead the formation of circular plasmid carrying scFv insert by the yeast homologous repair mechanism[P27,P28].

For flow cytometry using a Beckham FACS Aria, the yeast library was incubated in growth medium SD-CAA at 30° C. overnight for activation. The next day, activated yeast cells were diluted in induction medium SG/R-CAA at $OD_{600}$=0.5, and cultured again at 30° C. for 16 hrs. After induction, $10^7$ induced yeast cells ($OD_{600}$=0.5) were washed twice with 0.5 ml wash buffer I (0.5% BSA supplemented with 2 mM EDTA), and once with 0.5 ml wash buffer II (0.5% BSA). Yeast cells were first incubated with 50 µl competitor (200 µM phenanthrene or 2-methylphenanthrene in PBS containing 1% DMSO) for 30 min with rotation at 25° C. An additional aliquot (50 µl) of biotinylated protein-conjugate (BSA-biotin, phen-BSA-biotin, or 2mp-BSA-biotin at concentrations between 60 and 200 nM) containing 2 µg/ml anti-myc antibody 9E10 was then added and the cells were incubated for another 30 min. Yeast cells were washed 3 times with wash buffer II and stained with 4 µg/ml goat-antimouse-PE (Life Technologies, Grand Island, N.Y.) and 10 µg/ml streptavidin-Alexa633 (Life Technologies, Grand Island, N.Y.) in the dark room at 4° C. for an hour. The stained yeast cells were washed three times with wash buffer II and resuspended in 1 ml PBS for flow-cytometry analysis. An identical procedure was used to stain pools after sorting by flow cytometry. In each flow cytometry experiment, five controls were included for compensation tests: 1) yeast cells without any primary and secondary antibodies; 2) yeast cells with goat-antimouse-PE only; 3) yeast cells with streptavidin-Alexa633 only; 4) yeast cells with 9E10 and goat-antimouse-PE; 5) yeast cells with biotinylated protein-conjugate and streptavidin-Alexa633.

Monoclonal Analysis.

The yeast cells collected from the final FACS sort were serially diluted and spread onto SD-CAA agar plate in 30° C. incubator to form single colonies. After 2~3 days, individual colonies from the plate were selected, inoculated into 0.5 ml SD-CAA medium in a 96 deep-well plates, and incubated at 30° C. overnight. On the second day, a 50 µl aliquot of the culture was transferred into 500 µl SG/R-CAA medium and induced overnight at 30° C. An aliquot (50 µl) of the induced monoclonal yeast cells was subsequently transferred into a 96-well vacuum filter plate, and washed twice with 150 µl wash buffer I and once with 150 µl wash buffer II. The cells were stained as described herein and suspended in 200 µl PBS for FACS analysis using a Guava easyCyte Flow cytometer.

Soluble scFv Expression and Purification.

Flow-cytometry-positive scFvs were cloned into expression vector POE-myc. Details of cloning, bacterial transformation, and induction are available in Supporting information. Soluble scFv from periplasmic extract was purified using HisPur™ Cobalt Resin (Life Technology, Grand Island, N.Y.). The periplasmic extract (40 ml) was first incubated with 1 ml resin for an hour with rotation, and then the resin was gravity packed in a column. The resin column was washed with equilibration buffer (50 mM sodium phosphate, 300 mM sodium chloride, 10 mM imidazole, PH 7.4) until the $A_{280}$ of flow through reached a baseline. The scFv was subsequently eluted with 50 mM sodium phosphate, 300 mM sodium chloride, 150 mM imidazole, pH 7.4. A few fractions (1 mL each) of eluate were collected to insure the protein had been eluted, then those fractions with protein were pooled and concentrated using an Amicon ultra-15 device (EMD Millipore, Billerica, Mass.). The purified scFv was analyzed by SDS-PAGE and the protein concentration was determined using the BCA protein assay (Pierce, Rockford, Ill.).

Binding Characterization of Soluble scFvs.

Competitive ELISA was performed in 96-well high binding plates (Corning, Corning, N.Y.). Each well was coated with 2 µg/ml antigen at 4° C. overnight and blocked with 3% BSA. Antibody scFv was incubated in the antigen-coated well with or without soluble competitor, and the binding of scFv was accessed using anti-myc antibody (9E10) and goat-antimouse-HPR antibody (Sigma Aldrich, MO). The HRP signal was detected as described herein for Phage ELISA. The incubation steps were performed at room temperature for an hour. The plate was washed three times with PBST between steps.

Results and Discussion

In initial studies, the inventors attempted to select antibodies against methylated phenanthrenes from a naïve library with a diversity of approximately $3 \times 10^{11}$ [P21]. However, the scFvs selected from this library recognized phenanthrene-protein conjugates, but not soluble phenanthrene. The inventors therefore prepared an immune phage display library for selection of antibodies that can recognize soluble phenanthrenes. Antibodies selected from immune libraries have higher specificity and affinity than those selected from naïve libraries[P29,P30]. After immunization, serum antibodies to phenanthrene-BSA conjugates were confirmed by indirect ELISA. (FIG. 37). Mice were sacrificed 7 days after the final injection and splenic tissue was used as the starting material for cDNA synthesis. Antibody variable domains from heavy chains (VH) and light chains (VL) were amplified using a pool of degenerate primers[P31]. These primers were adapted to the display system as shown in FIG. 73, FIGS. 11-12. The flanking regions of VH-reverse primers and VL-forward primers contain the same flexible linker sequence, and were used as complementary regions in a second overlap extension PCR step to form a full-length scFv fragment. The final scFv product had a VH-linker-VL structure, and a total length of ~800 bp. After gel purification and restriction endonuclease digestion, the 800 bp PCR fragment was inserted into the pComb3 plasmid. The differences between two 5'-overhang sequences in the SfiI digested fragments insured that the scFvs were inserted in the correct orientation. Phagemids bearing scFv fragments were transformed into SS320 *E. coli* cells by electroporation to provide maximal transformation efficiency. The size of this immune library was $6.2 \times 10^6$. Clones bearing full-length scFv (~800 bp) comprised 87.5% of the sequences, and 81.25% of clones had distinct sequences, as confirmed by BstNI fingerprint analysis (FIGS. 11-12). The final library size was calculated to be $4.41 \times 10^6$.

Because the library contained ~4.4 million distinct scFv fragments, sophisticated selection strategies were required to identify the rare antibodies that can recognize soluble hapten (phenanthrene and/or methylated phenanthrenes) in this large pool. The inventors therefore employed a combination of phage and yeast display selections to identify the rare clones that can bind to these soluble haptens, as shown in FIG. 69. Phage display is useful for exploring a relatively large library and permits rapid removal of undesirable scFvs from the library. However, the output of selection always contains a relatively high level of nonspecific binders due to the intrinsic 'stickiness' of phage particles. Preliminary experiments had indicated that anti-hapten antibodies were are present at very low frequency in the library; thus any nonspecific background noise can overwhelm the true binding signals and make it very difficult to detect anti-hapten antibodies using competitive phage ELISA[P32,P33]. The yeast display system is limited to smaller scFv libraries, but this display system can be coupled with Fluorescence-Activated Cell Sorting (FACS) to provide very strict controls over selection parameters[P34,P35]. Initial selection of our library using phage display excluded undesirable scFvs and reduced the overall size of the library. Subsequent yeast display allowed us to further analyze the output pool and sort for clones that not only bound to the hapten-BSA-conjugates but also recognized soluble phenanthrene and/or methylated phenanthrene haptens.

Phage Selection.

Initial studies showed that the number of panning steps had to be limited in order to efficiently select specific binders while maintaining the diversity of output pools. Multiple rounds of selection not only selected for the binders with highest affinity, but also allows clones with the highest growth rates to predominant during subsequent bacterial amplification[P36]. In addition, when selecting for hapten-specific antibodies, high affinity to hapten-protein conjugates did not necessarily translate to high affinity to soluble hapten[P13]. In initial studies, a 7-step selection process led to the selection of a single scFv that bound to the phenanthrene-BSA conjugate with high affinity ($K_d$=10 nM) but did not recognize soluble phenanthrene or methylphenanthrene. The selection protocol was thus adjusted as shown in FIG. 43. Total of three rounds of panning were performed against two different capture antigens, phenanthrene-BSA (Protocol 1) or 2-methylphenanthrene-BSA (Protocol 2). Each panning step was designed to provide a specific selective pressure. The first round enriched for phage that bound to the hapten-protein conjugate; the second panning step introduced a solvent condition (1% DMSO) to exclude antibodies that were unstable in this solvent and hence can not be useful when soluble haptens were applied later in the selection process. In the final round of panning, soluble hapten was added to enrich the pool of binders that bound to soluble hapten. The input-to-output ratio (yield) was used to determine enrichment at each selection step. The last round of panning enriched our populations by 20-fold and 108-fold, respectively, for Protocols 1 and 2. Phage from round 3 bound immobilized phenanthrene-BSA and/or 2-methylphenanthrene-BSA using by competitive phage ELISA, as shown in FIG. 44; however, the inventors were not able to detect any inhibition by soluble phenanthrene or 2-methylphenanthrene in these pooled phage populations.

Yeast Display, Preliminary FACS Selection and Competitive FACS.

The scFv fragments from the phage remaining after 3 rounds of selection (FIG. 43) were amplified, transferred into the yeast display plasmid and transformed into two independent yeast pools. The transformed yeast cells were induced to activate the expression of cell surface Aga2p-scFv-myc fusion proteins and the scFv-bearing yeast cells were stained with two fluorescent dyes and analyzed with flow-cytometry (see schematic in FIG. 46A). The expression level of scFv was monitored by the signal from the myc tag and is shown on the x axis of the flow plot, while the binding capacity of expressed scFv to hapten-conjugates was detected by the signal from the biotinylated antigen and is shown on the y axis of flow plot. The strategy for competitive FACS is shown in FIG. 46. The yeast cell population that both expressed scFv (as assessed by the signal on the X axis) and bound to the biotinylated phenanthrene-BSA conjugate (as assessed by the Y axis signal) is incubated in the presence of soluble hapten (phenanthrene or 2-methylphenanthrene). Clones that bind to soluble antigen will show lower signals in the Y axis and can be enriched in the area of the Q2 quadrant circled in FIG. 46D.

The inventors first explored the yeast population derived from phage selected via Protocol 1. Selection of hapten-specific antibodies from this pool involved two rounds of sorting. The first round removed cell populations that can cause interference during subsequent selection steps. As shown in FIG. 70A, when yeast cells derived from the Protocol 1 selection were stained with anti-myc antibody and BSA-labeled with biotin but not phenanthrene (a negative control in the FACS assay), a significant number of cells migrated in the Q2 quadrant. These biotin-binding cells in Q2 quadrant can interfere with the competitive sorting planned for subsequent selections. Biotin-binding clones were removed by collecting only the cells in Q4, in order to exclude non-specific binders (see boxed area in FIG. 70A). These negatively sorted cells, when re-examined for their binding to BSA-biotin, now showed a much smaller population of cells in the Q2 quadrant. A competitive cell sort was then performed, according to the strategy shown in FIG. 46. Yeast pools from the negatively sorted cells were divided into two groups and incubated with 2% DMSO (FIG. 70B) or soluble competitor (200 µM phenanthrene in 2% DMSO) in the presence of 30 nM biotin-labeled phenanthrene-BSA (FIG. 70C). Because the cell population was split after induction of cell surface scFvs, there was no change in the expression level of scFv fragments and the x axis signal can remain the same for the two groups. However, those cell-surface antibodies that recognized soluble hapten can be competitively inhibited from binding to the biotinylated hapten-protein conjugate, and cells carrying antibodies with these binding characteristics can show a decreased signal on they axis of the flow plot. Thus, by selecting the cell population that shifted down in the presence of soluble competitor (FIG. 70C), those rare surface-displayed antibodies that were specifically inhibited by the soluble haptens were enriched. The total cells selected in this gate was ~0.6% of the total cells in the absence of soluble hapten (FIG. 70B) and ~1% of cells in the presence of soluble hapten (FIG. 70C). Thus, without being bound by theory, ~40% of the yeast clones in this very small population can contain antibodies that can recognize soluble hapten.

When the yeast cells derived from Protocol 2 were examined, the first FACS analysis showed very different characteristics than the Protocol 1 cells, as shown in FIG. 71A. The Q2 quadrant of Pool 2 was relatively clean in the presence of BSA-Biotin (FIG. 71A), so a negative sort was not required. However, relatively few cells in this population bound to the antigen (biotin-BSA-2-methylphenanthrene-BSA) and the scattered populations in Q2 and Q4 can overwhelm the small population that can be inhibited by soluble hapten in the subsequent competitive FACS selection. Therefore, the cells derived from Protocol 2 were first selected for those clones that bound tightly to the biotin labeled 2-methylphenanthrene-BSA, as shown in P5 gate of FIG. 71B. After this selection, a competitive FACS strategy was employed. In this competitive selection, 200 µM soluble 2-methylphenanthrene as the soluble competitor and 10 nM biotinylated 2-methylphenanthrene-BSA as the protein conjugate. In the absence of soluble hapten, the cells selected in P4 gate comprised ~0.7% of total cells (FIG. 71C), cells in this gate population increased to ~1% when soluble hapten was added (FIG. 71D). Similarly to Pool 1, these results indicate that roughly 30% yeast clones from this population can recognize the soluble hapten.

Yeast cells derived from Protocol 2 were examined, the first FACS analysis showed very different characteristics than the Protocol 1 cells, as shown in FIG. 71A. The Q2 quadrant of Pool 2 was relatively clean in the presence of BSA-Biotin (FIG. 71A), so a negative sort was not required. However, relatively few cells in this population bound to the antigen (biotin-BSA-2-methylphenanthrene-BSA) and the scattered populations in Q2 and Q4 can overwhelm the small population that can be inhibited by soluble hapten in the subsequent competitive FACS selection. Therefore, the cells derived from Protocol 2 were first selected for clones that bound tightly to the biotin labeled 2-methylphenanthrene-BSA, as shown by circled cells of FIG. 71B. After this selection, a competitive FACS strategy was employed. In this competitive selection, 200 µM soluble 2-methylphenanthrene as the soluble competitor and 10 nM biotinylated 2-methylphenanthrene-BSA as the protein conjugate. In the absence of soluble hapten, the cells selected in circled gate comprised ~0.7% of total cells (FIG. 71C), while cells in this gated population increased to ~1% when soluble hapten was added (FIG. 71D). Similarly to Pool 1, these results indicate that roughly 30% yeast clones from this population can recognize the soluble hapten.

Competitive FACS of Monoclonal Yeast Cells, Sequence Analysis and Competitive ELISA of Periplasmic Extracts.

Single clones were induced individually from the cells collected in the gates shown in FIG. 70C and FIG. 71D. 184 individual clones were picked from cells gated as shown in FIG. 70C and analyzed their binding to biotinylated phenanthrene-BSA in the presence of soluble phenanthrene or 2-methyphenanthrene. In 70 of 184 clones (~38%) the presence of the soluble inhibitor changed the monoclonal yeast cells' migration in flow cytometry. FACS of three representative clones (D7, G8 and A10) are shown in FIG. 51. Clones D7 and G8 appeared unable to distinguish between the 2 soluble competitors, while the clone A10 appeared to show preference for the 2-methyl derivative. The 70 clones identified via FACS were subsequently cloned into an expression vector to produce soluble scFv protein, and the crude periplasmic extracts were used to confirm binding of scFv to soluble hapten by competitive ELISA without the avidity or other interferences that can arise from the yeast display system. Of the 70 clones identified by competitive flow cytometry, 65 also showed activity in the competitive ELISA format. When these 65 clones were sequenced, 7 distinct scFv sequences were found. Such duplication is expected in immune libraries, where significant in vivo selection has already occurred. The fact that the inventors have independently isolated duplicate clones with similar binding properties demonstrates the selectivity of the method.

Competitive ELISA with Purified scFvs.

The binding characteristics of the three clones were investigated as models of the antibodies present in the immune library. Purified scFvs were analyzed by competitive ELISA for their abilities to recognize as unsubstituted phenanthrene or methylated phenanthrenes (FIG. 72). Clone D7 bound to the phenanthrenes tested with no significant difference, while G8 and A10 were able to differentiate among various methylated phenanthrenes. G8 scFv bound to 4-methylphenanthrene most tightly, and A10 preferred 2-methylphenanthrene over other isomers.

CONCLUSIONS

In this study, the inventors demonstrate that the FACS selections described herein provide a powerful new tool for the isolation of rare hapten-specific scFvs. Two FACS procedures were required after transfer of the phage-selected library to the yeast display system. The first selection removed clones that bound non-specifically to our antigen (Protocol 1) or enriched the library for those clones that bound efficiently to our protein antigen (Protocol 2). In both cases, ~50% of the total phage-selected clones were eliminated. The second, competitive FACS allowed us to isolate a very small pool of clones (~1% total sorted cells) that were highly enriched (13-35%) in clones that bound to soluble hapten. Thus, after the two FACS selections, sequence analysis and competitive ELISA of periplasmic extracts can be limited to ~0.5% of the original phage-selected population. When combined with the 20-100-fold enrichment achieved during the panning steps, these methods increased the chances of finding hapten-specific scFvs in from 0.025-0.005% in the original immune library to 13-35% in the final selected pool. Such enrichment will greatly reduce the workload of investigators who wish to utilize recombinant technology to generate hapten-specific antibodies, and hopefully will increase the total hapten-specific scFvs available to the general public in the future.

Experiments are currently in progress to further study the binding properties of the 10 distinct PAH-specific scFvs isolated in these experiments and to utilize these unique reagents in new sensors to distinguish the sources of environmental polycyclic aromatic hydrocarbon contamination.

REFERENCES CITED IN THIS EXAMPLE

P1. Dinis-Oliveira, R. J., Heterogeneous and homogeneous immunoassays for drug analysis. *Bioanalysis* 2014, 6, (21), 2877-2896.
P2. Ronkainen, N. J.; Okon, S. L. In *The role of immunoassays in urine drug screening*, 2014; Scrivener Publishing LLC: 2014; pp 493-524.
P3. Batrla, R.; Jordan, B. W. M., Personalized health care beyond oncology: new indications for immunoassay-based companion diagnostics. *Ann. N.Y. Acad. Sci.* 2015, 1346, (Companion Diagnostics), 71-80.
P4. Liang, H. C.; Bilon, N.; Hay, M. T., Analytical methods for pesticide residues in the water environment. *Water Environ. Res.* 2015, 87, (10), 1923-1937.
P5. Castro-Jimenez, J.; Gonzalez, C., Immunoassay-based screening of polychlorinated biphenyls (PCB) in sediments—Requirements for a new generation of test kits. *J. Environ. Monit.* 2011, 13, (4), 894-900.
P6. Kavanagh, O.; Elliott, C. T.; Campbell, K., Progress in the development of immunoanalytical methods incorporating recombinant antibodies to small molecular weight biotoxins. *Anal. Bioanal. Chem.* 2015, 407, (10), 2749-2770.
P7. Ahmad, A.; Moore, E. J., Comparison of Cell-Based Biosensors with Traditional Analytical Techniques for Cytotoxicity Monitoring and Screening of Polycyclic Aromatic Hydrocarbons in the Environment. *Anal. Lett.* 2009, 42, (1), 1-28.
P8. Beloglazova, N. V.; Goryacheva, I. Y.; Mikhirev, D. A.; de Saeger, S.; Niessner, R.; Knopp, D., New immunochemically-based field test for monitoring benzo[a]pyrene in aqueous samples. *Anal Sci* 2008, 24, (12), 1613-7.
P9. Beloglazova, N. V.; Goryacheva, I. Y.; de Saeger, S.; Scippo, M. L.; Niessner, R.; Knopp, D., New approach to quantitative analysis of benzo[a]pyrene in food supplements by an immunochemical column test. *Talanta* 2011, 85, (1), 151-6.
P10. Blake, D. A.; Blake, R. C., 2nd; Abboud, E. R.; Li, X.; Yu, H.; Kriegel, A. M.; Khosraviani, M.; Darwish, I. A., Antibodies to heavy metals: Isolation, characterization and incorporation into microplate-based assays and immunosensors. In Immunoassay and Other Bioanalytical Techniques, Van Emon, J. M., Ed. Taylor and Francis: Boca Ratan, Fla., 2007; pp 93-111.
P11. Melton, S. J.; Yu, H.; Williams, K. H.; Morris, S. A.; Long, P. E.; Blake, D. A., Field-based detection and monitoring of uranium in contaminated groundwater using two immunosensors. *Environ. Sci. Technol.* 2009, 43, (17), 6703-6709.
P12. Darwish, I. A.; Blake, D. A., One-step competitive immunoassay for cadmium ions: development and validation for environmental water samples. *Analytical chemistry* 2001, 73, (8), 1889-95.
P13. Blake, D. A.; Chakrabarti, P.; Khosraviani, M.; Hatcher, F. M.; Westhoff, C. M.; Goebel, P.; Wylie, D. E.; Blake, R. C., 2nd, Metal binding properties of a monoclonal antibody directed toward metal-chelate complexes. *Journal of Biological Chemistry* 1996, 271, (44), 27677-85.
P14. Reardan, D. T.; Meares, C. F.; Goodwin, D. A.; McTigue, M.; David, G. S.; Stone, M. R.; Leung, J. P.; Bartholomew, R. M.; Frincke, J. M., Antibodies against metal chelates. *Nature* 1985, 316, (6025), 265-8.
P15. Baker, M., Reproducibility crisis: Blame it on the antibodies. In *Nature*, England, 2015; Vol. 521, pp 274-6.
P16. Yang, W. P.; Green, K.; Pinz-Sweeney, S.; Briones, A. T.; Burton, D. R.; Barbas, C. F., 3rd, CDR walking mutagenesis for the affinity maturation of a potent human anti-HIV-1 antibody into the picomolar range. *J Mol Biol* 1995, 254, (3), 392-403.
P17. Boder, E. T.; Midelfort, K. S.; Wittrup, K. D., Directed evolution of antibody fragments with monovalent femtomolar antigen-binding affinity. *Proc Natl Acad Sci USA* 2000, 97, (20), 10701-5.
P18. Ferrara, F.; Naranjo, L. A.; Kumar, S.; Gaiotto, T.; Mukundan, H.; Swanson, B.; Bradbury, A. R., Using phage and yeast display to select hundreds of monoclonal antibodies. *PLoS One* 2012, 7, (11), e49535.
P19. Begley, C. G.; Ellis, L. M., Raise standards for preclinical cancer research. *Nature (London, U.K.)* 2012, 483, (7391), 531-533.
P20. Bradbury, A.; Pluckthun, A., Reproducibility: Standardize antibodies used in research. *Nature (London, U.K.)* 2015, 518, (7537), 27-29.
P21. Sblattero, D.; Bradbury, A., Exploiting recombination in single bacteria to make large phage antibody libraries. *Nat Biotechnol* 2000, 18, (1), 75-80.
P22. Allan, S. E.; Smith, B. W.; Anderson, K. A., Impact of the deepwater horizon oil spill on bioavailable polycyclic aromatic hydrocarbons in Gulf of Mexico coastal waters. *Environ Sci Technol* 2012, 46, (4), 2033-9.
P23. Saha, M.; Togo, A.; Mizukawa, K.; Murakami, M.; Takada, H.; Zakaria, M. P.; Chiem, N. H.; Tuyen, B. C.; Prudente, M.; Boonyatumanond, R.; Sarkar, S. K.; Bhattacharya, B.; Mishra, P.; Tana, T. S., Sources of sedimentary PAHs in tropical Asian waters: differentiation between pyrogenic and petrogenic sources by alkyl homolog abundance. *Mar Pollut Bull* 2009, 58, (2), 189-200.
P24. Feldhaus, M. J.; Siegel, R. W.; Opresko, L. K.; Coleman, J. R.; Feldhaus, J. M.; Yeung, Y. A.; Cochran, J. R.; Heinzelman, P.; Colby, D.; Swers, J.; Graff, C.; Wiley, H. S.; Wittrup, K. D., Flow-cytometric isolation of human antibodies from a nonimmune *Saccharomyces cerevisiae* surface display library. In *Nat Biotechnol*, United States, 2003; Vol. 21, pp 163-70.
P25. Ayriss, J.; Woods, T.; Bradbury, A.; Pavlik, P., High-throughput screening of single-chain antibodies using multiplexed flow cytometry. *J Proteome Res* 2007, 6, (3), 1072-82.
P26. Matschulat, D.; Deng, A.; Niessner, R.; Knopp, D., Development of a highly sensitive monoclonal antibody based ELISA for detection of benzo[a]pyrene in potable water. *Analyst* 2005, 130, (7), 1078-86.

P27. Oldenburg, K. R.; Vo, K. T.; Michaelis, S.; Paddon, C., Recombination-mediated PCR-directed plasmid construction in vivo in yeast. In *Nucleic Acids Res*, England, 1997; Vol. 25, pp 451-2.

P28. Hua, S. B.; Qiu, M.; Chan, E.; Zhu, L.; Luo, Y., Minimum length of sequence homology required for in vivo cloning by homologous recombination in yeast. In *Plasmid*, United States, 1997; Vol. 38, pp 91-6.

P29. Schwemmlein, M.; Peipp, M.; Barbin, K.; Saul, D.; Stockmeyer, B.; Repp, R.; Birkmann, J.; Oduncu, F.; Emmerich, B.; Fey, G., A CD33-specific single-chain immunotoxin mediates potent apoptosis of cultured human myeloid leukaemia cells. *Br J Haematol* 2006, 133, (2), 141-51.

P30. Peipp, M.; Simon, N.; Loichinger, A.; Baum, W.; Mahr, K.; Zunino, S.; Fey, G., An improved procedure for the generation of recombinant single-chain Fv antibody fragments reacting with human CD13 on intact cells. *J Immunol Methods* 2001, 251, (1-2), 161-76.

P31. Schaefer, J.; Honegger, A.; Plückthun, A., Construction of scFv Fragments from Hybridoma or Spleen Cells by PCR Assembly. In *Antibody Engineering*, Kontermann, R.; Dübel, S., Eds. Springer Berlin Heidelberg: 2010; pp 21-44.

P32. Moghaddam, A.; Borgen, T.; Stacy, J.; Kausmally, L.; Simonsen, B.; Marvik, O.; Brekke, O.; Braunagel, M., Identification of scFv antibody fragments that specifically recognise the heroin metabolite 6-monoacetylmorphine but not morphine. *J Immunol Methods* 2003, 280, (1-2), 139-55.

P33. Fernando, H.; Rodriguez, R.; Balasubramanian, S., Selective recognition of a DNA G-quadruplex by an engineered antibody. *Biochemistry* 2008, 47, (36), 9365-71.

P34. Gai, S.; Wittrup, K., Yeast surface display for protein engineering and characterization. *Curr Opin Struct Biol* 2007, 17, (4), 467-73.

P35. Weaver-Feldhaus, J.; Miller, K.; Feldhaus, M.; Siegel, R., Directed evolution for the development of conformation-specific affinity reagents using yeast display. *Protein Eng Des Sel* 2005, 18, (11), 527-36.

36. Hoen, P. A.; Jirka, S. M.; Ten Broeke, B. R.; Schultes, E. A.; Aguilera, B.; Pang, K. H.; Heemskerk, H.; Aartsma-Rus, A.; van Ommen, G. J.; den Dunnen, J. T., Phage display screening without repetitious selection rounds. In *Anal Biochem*, 2011 Elsevier Inc: United States, 2012; Vol. 421, pp 622-31.

REFERENCES

US)., I.o.M. (2010). Short- and Long-Term Effects on Human Health. In Assessing the Effects of the Gulf of Mexico Oil Spill on Human Health: A Summary of the June 2010 Workshop (Washington (DC): National Academies Press (US)), pp. 43-74.

Abel, J., and Haarmann-Stemmann, T. (2010). An introduction to the molecular basics of aryl hydrocarbon receptor biology. Biol Chem 391, 1235-1248.

Allan, S. E., Smith, B. W., and Anderson, K. A. (2012). Impact of the deepwater horizon oil spill on bioavailable polycyclic aromatic hydrocarbons in Gulf of Mexico coastal waters. Environ Sci Technol 46, 2033-2039.

Alnafisi, A., Hughes, J., Wang, G., and Miller, C. A. (2007). Evaluating polycyclic aromatic hydrocarbons using a yeast bioassay. Environ Toxicol Chem 26, 1333-1339.

Amorim, M. J., Oliveira, E., Teixeira, A. S., Gravato, C. S., Loureiro, S., Guilhermino, L. C., Van Gestel, C. A., and Soares, A. M. (2011). Toxicity and bioaccumulation of phenanthrene in *Enchytraeus albidus* (Oligochaeta: Enchytraeidae). Environ Toxicol Chem 30, 967-972.

Ayriss, J., Woods, T., Bradbury, A., and Pavlik, P. (2007). High-throughput screening of single-chain antibodies using multiplexed flow cytometry. J Proteome Res 6, 1072-1082.

Baba, T., Mimura, J., Nakamura, N., Harada, N., Yamamoto, M., Morohashi, K., and Fujii-Kuriyama, Y. (2005). Intrinsic function of the aryl hydrocarbon (dioxin) receptor as a key factor in female reproduction. Mol Cell Biol 25, 10040-10051.

Baker, M. (2015). Reproducibility crisis: Blame it on the antibodies. In Nature (England), pp. 274-276.

Barron, M. G., and Holder, E. (2003). Are Exposure and Ecological Risks of PAHs Underestimated at Petroleum Contaminated Sites? Human and Ecological Risk Assessment: An International Journal 9, 1533-1545.

Bednar, A. J., Jones, W. T., Parker, L. V., U.S. Army Corps of Engineers, Engineer Research and Development Center. (2011). Field-portable Gas Chromatograph Mass Spectrometer (GC-MS) unit for semi-volatile compound analysis in groundwater.

Blake, D. A., Chakrabarti, P., Khosraviani, M., Hatcher, F. M., Westhoff, C. M., Goebel, P., Wylie, D. E., and Blake, R. C., 2nd (1996). Metal binding properties of a monoclonal antibody directed toward metal-chelate complexes. Journal of Biological Chemistry 271, 27677-27685.

Blake, R. C., 2nd, Pavlov, A. R., and Blake, D. A. (1999). Automated kinetic exclusion assays to quantify protein binding interactions in homogeneous solution. Anal Biochem 272, 123-134.

Blumer, M. (1976). Polycyclic aromatic compounds in nature. Sci Am 234, 35-45.

Boder, E. T., Midelfort, K S., and Wittrup, K. D. (2000). Directed evolution of antibody fragments with monovalent femtomolar antigen-binding affinity. Proc Natl Acad Sci USA 97, 10701-10705.

Boder, E. T., and Wittrup, K. D. (1997). Yeast surface display for screening combinatorial polypeptide libraries. Nat Biotechnol 15, 553-557.

Boder, E. T., and Wittrup, K. D. (2000). Yeast surface display for directed evolution of protein expression, affinity, and stability. Methods Enzymol 328, 430-444.

Boonyatumanond, R., Wattayakorn, G., Togo, A., and Takada, H. (2006). Distribution and origins of polycyclic aromatic hydrocarbons (PAHs) in riverine, estuarine, and marine sediments in Thailand. Mar Pollut Bull 52, 942-956.

Bostrom, J., Lee, C. V., Haber, L., and Fuh, G. (2009). Improving antibody binding affinity and specificity for therapeutic development. Methods Mol Biol 525, 353-376, xiii.

Boutros, P. C., Yao, C. Q., Watson, J. D., Wu, A. H., Moffat, I. D., Prokopec, S. D., Smith, A. B., Okey, A. B., and Pohjanvirta, R. (2011). Hepatic transcriptomic responses to TCDD in dioxin-sensitive and dioxin-resistant rats during the onset of toxicity. Toxicol Appl Pharmacol 251, 119-129.

Bunger, M. K., Moran, S. M., Glover, E., Thomae, T. L., Lahvis, G. P., Lin, B. C., and Bradfield, C. A. (2003). Resistance to 2,3,7,8-tetrachlorodibenzo-p-dioxin toxicity and abnormal liver development in mice carrying a mutation in the nuclear localization sequence of the aryl hydrocarbon receptor. J Biol Chem 278, 17767-17774.

Cerniglia, C. (1992). Biodegradation of polycyclic aromatic hydrocarbons. Biodegradation 3, 351-368.

Chames, P., Coulon, S., and Baty, D. (1998). Improving the affinity and the fine specificity of an anti-cortisol antibody by parsimonious mutagenesis and phage display. J Immunol 161, 5421-5429.

Chernova, T. G., Rao, P. S., Pikovskii, Y. I., Alekseeva, T. A., Nagender Nath, B., Ramalingeswara Rao, B., and Rao, C. M. (2001). The composition and the source of hydrocarbons in sediments taken from the tectonically active Andaman Backarc Basin, Indian Ocean. Marine Chemistry 75, 1-15.

Darling, R. J., and Brault, P. A. (2004). Kinetic exclusion assay technology: characterization of molecular interactions. Assay Drug Dev Technol 2, 647-657.

Darwish, I. A. (2006). Immunoassay Methods and their Applications in Pharmaceutical Analysis: Basic Methodology and Recent Advances. International Journal of Biomedical Science: IJBS 2, 217-235.

De Nobel, J. G., and Barnett, J. A. (1991). Passage of molecules through yeast cell walls: a brief essay-review. Yeast 7, 313-323.

Diana, S. A., and Thurman, E. M. (1997). Environmental Immunoassays: Alternative Techniques for Soil and Water Analysis. In Immunochemical Technology for Environmental Applications (American Chemical Society), pp. 1-20.

EPA, U. (2012). Estimation Programs Interface Suite™ for Microsoft® Windows, v 4.11 (Washington, D.C.: United States Environmental Protection Agency).

Feldhaus, M. J., Siegel, R. W., Opresko, L. K., Coleman, J. R., Feldhaus, J. M., Yeung, Y. A., Cochran, J. R., Heinzelman, P., Colby, D., Swers, J., et al. (2003). Flow-cytometric isolation of human antibodies from a nonimmune Saccharomyces cerevisiae surface display library. In Nat Biotechnol (United States), pp. 163-170.

Feng, S., Cao, Z., and Wang, X. (2013). Role of aryl hydrocarbon receptor in cancer. Biochim Biophys Acta, Rev Cancer 1836, 197-210.

Fernandez-Salguero, P. M., Hilbert, D. M., Rudikoff, S., Ward, J. M., and Gonzalez, F. J. (1996). Aryl-hydrocarbon receptor-deficient mice are resistant to 2,3,7,8-tetrachlorodibenzo-p-dioxin-induced toxicity. Toxicol Appl Pharmacol 140, 173-179.

Fernando, H., Rodriguez, R., and Balasubramanian, S. (2008). Selective recognition of a DNA G-quadruplex by an engineered antibody. Biochemistry 47, 9365-9371.

Ferrara, F., Naranjo, L. A., Kumar, S., Gaiotto, T., Mukundan, H., Swanson, B., and Bradbury, A. R. (2012). Using phage and yeast display to select hundreds of monoclonal antibodies. PLoS One 7, e49535.

Fox, J. E., Burow, M. E., McLachlan, J. A., and Miller, C. A., 3rd (2008). Detecting ligands and dissecting nuclear receptor-signaling pathways using recombinant strains of the yeast Saccharomyces cerevisiae. Nat Protoc 3, 637-645.

Gai, S., and Wittrup, K. (2007). Yeast surface display for protein engineering and characterization. Curr Opin Struct Biol 17, 467-473.

Gendloff, E. H., Casale, W. L., Ram, B. P., Tai, J. H., Pestka, J. J., and Hart, L. P. (1986). Hapten-protein conjugates prepared by the mixed anhydride method. Cross-reactive antibodies in heterologous antisera. J Immunol Methods 92, 15-20.

Georgieva, Y., and Konthur, Z. (2011). Design and screening of M13 phage display cDNA libraries. Molecules 16, 1667-1681.

Glanville, J., Zhai, W., Berka, J., Telman, D., Huerta, G., Mehta, G. R., Ni, I., Mei, L., Sundar, P. D., Day, G. M., et al. (2009). Precise determination of the diversity of a combinatorial antibody library gives insight into the human immunoglobulin repertoire. Proc Natl Acad Sci USA 106, 20216-20221.

Gust, K. A. (2006). Joint Toxicity of Cadmium and Phenanthrene in the Freshwater Amphipod Hyalella azteca. Archives of Environmental Contamination and Toxicology 50, 7-13.

Haritash, A. K., and Kaushik, C. P. (2009). Biodegradation aspects of polycyclic aromatic hydrocarbons (PAHs): a review. J Hazard Mater 169, 1-15.

Hecht, S. S., Bondinell, W. E., and Hoffmann, D. (1974). Chrysene and methylchrysenes: presence in tobacco smoke and carcinogenicity. J Natl Cancer Inst 53, 1121-1133.

Heitkamp, M. A., Franklin, W., and Cerniglia, C. E. (1988). Microbial metabolism of polycyclic aromatic hydrocarbons: isolation and characterization of a pyrene-degrading bacterium. Applied and Environmental Microbiology 54, 2549-2555.

Hollender, J., Koch, B., Lutermann, C., and Dott, W. (2003). Efficiency of Different Methods and Solvents for the Extraction of Polycyclic Aromatic Hydrocarbons from Soils. International Journal of Environmental Analytical Chemistry 83, 21-32.

Hua, S. B., Qiu, M., Chan, E., Zhu, L., and Luo, Y. (1997). Minimum length of sequence homology required for in vivo cloning by homologous recombination in yeast. In Plasmid (United States), pp. 91-96.

Inkley, D. B., Kronenthal, S. G.-R., and McCormick, L. (2013). Restoring A Degraded Gulf of Mexico: Wildlife and Wetlands Three Years into the Gulf Oil Disaster (national wildlife federation).

Jenner, W. N., and Law, B. (1996). Immunogen preparation and purification. In Immunoassay: a practical guide, B. Law, ed. (London; Bristol, Pa.: Taylor & Francis), pp. 11-31.

Jin, G.-B., Winans, B., Martin, K. C., and Lawrence, B. P. (2014). New insights into the role of the aryl hydrocarbon receptor in the function of CD11c+ cells during respiratory viral infection. European Journal of Immunology 44, 1685-1698.

Juhascik, M. P., and Jenkins, A. J. (2009). Comparison of liquid/liquid and solid-phase extraction for alkaline drugs. J Chromatogr Sci 47, 553-557.

Keith, L. H. (2014). The Source of U.S. EPA's Sixteen PAH Priority Pollutants. Polycyclic Aromatic Compounds 35, 147-160.

Kerley-Hamilton, J. S., Trask, H. W., Ridley, C. J. A., DuFour, E., Lesseur, C., Ringelberg, C. S., Moodie, K. L., Shipman, S. L., Korc, M., Gui, J., et al. (2012). Inherent and Benzo[a]pyrene-Induced Differential Aryl Hydrocarbon Receptor Signaling Greatly Affects Life Span, Atherosclerosis, Cardiac Gene Expression, and Body and Heart Growth in Mice. Toxicological Sciences 126, 391-404.

Knopp, D. (2006). Immunoassay development for environmental analysis. Analytical and Bioanalytical Chemistry 385, 425-427.

Kohler, G., and Milstein, C. (1975). Continuous cultures of fused cells secreting antibody of predefined specificity. Nature 256, 495-497.

Lau, E. V., Gan, S., and Ng, H. K. (2010). Extraction techniques for polycyclic aromatic hydrocarbons in soils. Int J Anal Chem 2010, 398381.

LaVoie, E. J., Bedenko, V., Tulley-Freiler, L., and Hoffmann, D. (1982). Tumor-initiating activity and metabolism of polymethylated phenanthrenes. Cancer Res 42, 4045-4049.

LaVoie, E. J., Tulley-Freiler, L., Bedenko, V., and Hoffmann, D. (1981). Mutagenicity, tumor-initiating activity, and metabolism of methylphenanthrenes. Cancer Res 41, 3441-3447.

Lee, C. M., Iorno, N., Sierro, F., and Christ, D. (2007). Selection of human antibody fragments by phage display. Nat Protoc 2, 3001-3008.

Lesnik, B. (2006). Immunoassay Techniques in Environmental Analyses. In Encyclopedia of Analytical Chemistry (John Wiley & Sons, Ltd).

Li, N., and Lee, H. K. (2001). Solid-phase extraction of polycyclic aromatic hydrocarbons in surface water. Negative effect of humic acid. J Chromatogr A 921, 255-263.

Lynge, E., Andersen, A., Nilsson, R., Barlow, L., Pukkala, E., Nordlinder, R., Boffetta, P., Grandjean, P., Heikkila, P., Horte, L. G., et al. (1997). Risk of cancer and exposure to gasoline vapors. Am J Epidemiol 145, 449-458.

Machala, M., Svihalkova-Sindlerova, L., Pencikova, K., Kremar, P., Topinka, J., Milcova, A., Novakova, Z., Kozubik, A., and Vondracek, J. (2008). Effects of methylated chrysenes on AhR-dependent and -independent toxic events in rat liver epithelial cells. Toxicology 247, 93-101.

Mallett, M. J., Grandy, N.J., and Lacey, R. F. (1997). Interlaboratory comparison of a method to evaluate the effects of chemicals on fish growth. Environ Toxicol Chem 16, 528-533.

Martin H, Patterson B M, Davis G B. Field trial of contaminant groundwater monitoring: comparing time-integrating ceramic dosimeters and conventional water Sampling Environ. Sci. Technol. 2003; 37:1360-1364.

Matschulat, D., Deng, A., Niessner, R., and Knopp, D. (2005). Development of a highly sensitive monoclonal antibody based ELISA for detection of benzo[a]pyrene in potable water. Analyst 130, 1078-1086.

Melton, S. J. (2010). Transitioning from the bench to the real world: Adaptation of uranyl specific antibodies for use in field-based environmental analysis (Tulane University Tulane University).

Melton, S. J., Yu, H., Williams, K. H., Morris, S. A., Long, P. E., and Blake, D. A. (2009). Field-based detection and monitoring of uranium in contaminated groundwater using two immunosensors. Environ Sci Technol 43, 6703-6709.

Mimura, J., Yamashita, K., Nakamura, K., Morita, M., Takagi, T. N., Nakao, K., Ema, M., Sogawa, K., Yasuda, M., Katsuki, M., et al. (1997). Loss of teratogenic response to 2,3,7,8-tetrachlorodibenzo-p-dioxin (TCDD) in mice lacking the Ah (dioxin) receptor. Genes Cells 2, 645-654.

Moghaddam, A., Borgen, T., Stacy, J., Kausmally, L., Simonsen, B., Marvik, O., Brekke, O., and Braunagel, M. (2003a). Identification of scFv antibody fragments that specifically recognise the heroin metabolite 6-monoacetylmorphine but not morphine. J Immunol Methods 280, 139-155.

Moghaddam, A., Borgen, T., Stacy, J., Kausmally, L., Simonsen, B., Marvik, O. J., Brekke, O. H., and Braunagel, M. (2003b). Identification of scFv antibody fragments that specifically recognise the heroin metabolite 6-monoacetylmorphine but not morphine. J Immunol Methods 280, 139-155.

Mu, J., Wang, J., Jin, F., Wang, X., and Hong, H. (2014). Comparative embryotoxicity of phenanthrene and alkylphenanthrene to marine medaka (Oryzias melastigma). Mar Pollut Bull 85, 505-515.

National Research Council Committee on Oil in the Sea: Inputs, F.a.E. (2003). Input of Oil to the Sea. In Oil in the Sea III: Inputs, Fates, and Effects (Washington (DC): National Academies Press (US) Copyright 2003 by the National Academy of Sciences).

Oldenburg, KR., Vo, K. T., Michaelis, S., and Paddon, C. (1997). Recombination-mediated PCR-directed plasmid construction in vivo in yeast. In Nucleic Acids Res (England), pp. 451-452.

Patel, A. S., Talbott, E. O., Zborowski, J. V., Rycheck, J. A., Dell, D., Xu, X., and Schwerha, J. (2004). Risk of cancer as a result of community exposure to gasoline vapors. Arch Environ Health 59, 497-503.

Peipp, M., Simon, N., Loichinger, A., Baum, W., Mahr, K., Zunino, S., and Fey, G. (2001). An improved procedure for the generation of recombinant single-chain Fv antibody fragments reacting with human CD13 on intact cells. J Immunol Methods 251, 161-176.

Pepper, L. R., Cho, Y. K., Boder, E. T., and Shusta, E. V. (2008). A decade of yeast surface display technology: Where are we now? Combinatorial chemistry & high throughput screening 11, 127-134.

Pfeifer, G. P., Denissenko, M. F., Olivier, M., Tretyakova, N., Hecht, S. S., and Hainaut, P. (2002). Tobacco smoke carcinogens, DNA damage and p53 mutations in smoking-associated cancers. Oncogene 21, 7435-7451.

Phillips, D. H., Grover, P. L., and Sims, P. (1979). A quantitative determination of the covalent binding of a series of polycylic hydrocarbons to DNA in mouse skin. Int J Cancer 23, 201-208.

Plaza, G., Ulfig, K., and Tien, A. (2000). Immunoassays and Environmental Studies. Journal of Environmental Studies 9, 231-236.

Rajpal, A., Beyaz, N., Haber, L., Cappuccilli, G., Yee, H., Bhatt, R. R., Takeuchi, T., Lerner, R. A., and Crea, R. (2005). A general method for greatly improving the affinity of antibodies by using combinatorial libraries. Proceedings of the National Academy of Sciences of the United States of America 102, 8466-8471.

Saha, M., Togo, A., Mizukawa, K., Murakami, M., Takada, H., Zakaria, M. P., Chiem, N. H., Tuyen, B. C., Prudente, M., Boonyatumanond, R., et al. (2009). Sources of sedimentary PAHs in tropical Asian waters: differentiation between pyrogenic and petrogenic sources by alkyl homolog abundance. Mar Pollut Bull 58, 189-200.

Samarajeewa, U., Wei, C. I., Huang, T. S., and Marshall, M. R. (1991). Application of immunoassay in the food industry. Critical Reviews in Food Science and Nutrition 29, 403-434.

Sblattero, D., and Bradbury, A. (2000a). Exploiting recombination in single bacteria to make large phage antibody. Nat Biotechnol 18, 75-80.

Sblattero, D., and Bradbury, A. (2000b). Exploiting recombination in single bacteria to make large phage antibody libraries. Nat Biotechnol 18, 75-80.

Schaefer, J., Honegger, A., and Plückthun, A. (2010). Construction of scFv Fragments from Hybridoma or Spleen Cells by PCR Assembly. In Antibody Engineering, R. Kontermann, and S. Dübel, eds. (Springer Berlin Heidelberg), pp. 21-44.

Scharnweber, T., Fisher, M., Suchanek, M., Knopp, D., and Niessner, R. (2001). Monoclonal antibody to polycyclic aromatic hydrocarbons based on a new benzo[a]pyrene immunogen. Fresenius J Anal Chem 371, 578-585.

Schwacke, L. H., Smith, C. R., Townsend, F. I., Wells, R. S., Hart, L. B., Balmer, B. C., Collier, T. K., De Guise, S., Fry, M. M., Guillette, L. J., Jr., et al. (2014). Health of common bottlenose dolphins (Tursiops truncatus) in Barataria Bay, La., following the deepwater horizon oil spill. Environ Sci Technol 48, 93-103.

Schwemmlein, M., Peipp, M., Barbin, K., Saul, D., Stockmeyer, B., Repp, R., Birkmann, J., Oduncu, F., Emmerich, B., and Fey, G. (2006). A CD33-specific single-chain immunotoxin mediates potent apoptosis of cultured human myeloid leukaemia cells. Br J Haematol 133, 141-151.

Sherry, J. (1997). Environmental immunoassays and other bioanalytical methods: overview and update. Chemosphere 34, 1011-1025.

Shimada, T. (2006). Xenobiotic-metabolizing enzymes involved in activation and detoxification of carcinogenic polycyclic aromatic hydrocarbons. Drug Metab Pharmacokinet 21, 257-276.

Shimizu, Y., Nakatsuru, Y., Ichinose, M., Takahashi, Y., Kume, H., Mimura, J., Fujii-Kuriyama, Y., and Ishikawa, T. (2000). Benzo[a]pyrene carcinogenicity is lost in mice lacking the aryl hydrocarbon receptor. Proceedings of the National Academy of Sciences 97, 779-782.

Sidhu, S. S. (2001). Engineering M13 for phage display. Biomol Eng 18, 57-63.

Spier, C. R., Vadas, G. G., Kaattari, S. L., and Unger, M. A. (2011). Near real-time, on-site, quantitative analysis of PAHs in the aqueous environment using an antibody-based biosensor. Environ Toxicol Chem 30, 1557-1563.

Su, F. Y., Endo, Y., Saiki, H., Xing, X. H., and Ohmura, N. (2007). Simple and sensitive bacterial quantification by a flow-based kinetic exclusion fluorescence immunoassay. Biosens Bioelectron 22, 2500-2507.

Sun, Y., Miller Iii, C. A., Wiese, T. E., and Blake, D. A. (2014). Methylated phenanthrenes are more potent than phenanthrene in a bioassay of human aryl hydrocarbon receptor (AhR) signaling. Environmental Toxicology and Chemistry, n/a-n/a.

Szurdoki, F., Jaeger, L., Harris, A., Kido, H., Wengatz, I., Goodrow, M. H., Szekacs, A., Wortberg, M., Zheng, J., Stoutamire, D. W., et al. (1996). Rapid assays for environmental and biological monitoring. J Environ Sci Health B 31, 451-458.

t Hoen, P. A., Jirka, S. M., Ten Broeke, B. R., Schultes, E. A., Aguilera, B., Pang, K. H., Heemskerk, H., Aartsma-Rus, A., van Ommen, G. J., and den Dunnen, J. T. (2012). Phage display screening without repetitious selection rounds. In Anal Biochem (United States: 2011 Elsevier Inc), pp. 622-631.

Tijet, N., Boutros, P. C., Moffat, I. D., Okey, A. B., Tuomisto, J., and Pohjanvirta, R. (2006). Aryl hydrocarbon receptor regulates distinct dioxin-dependent and dioxin-independent gene batteries. Mol Pharmacol 69, 140-153.

Uno, S., Dalton, T. P., Shertzer, H. G., Genter, M. B., Warshawsky, D., Talaska, G., and Nebert, D. W. (2001). Benzo[a]pyrene-induced toxicity: paradoxical protection in Cyp1a1(-/-) knockout mice having increased hepatic BaP-DNA adduct levels. Biochem Biophys Res Commun 289, 1049-1056.

Veglia, F., Matullo, G., and Vineis, P. (2003). Bulky DNA adducts and risk of cancer: a meta-analysis. Cancer Epidemiol Biomarkers Prev 12, 157-160.

Vendrame, R., Braga, R. S., Takahata, Y., and Galvao, D. S. (1999). Structure-activity relationship studies of carcinogenic activity of polycyclic aromatic hydrocarbons using calculated molecular descriptors with principal component analysis and neural network methods. J Chem Inf Comput Sci 39, 1094-1104.

Volkering, F., Breure, A. M., Sterkenburg, A., and van Andel, J. G. (1992). Microbial degradation of polycyclic aromatic hydrocarbons: effect of substrate availability on bacterial growth kinetics. Applied Microbiology and Biotechnology 36, 548-552.

Vondracek, J., Svihalkova-Sindlerova, L., Pencikova, K., Marvanova, S., Krcmar, P., Ciganek, M., Neca, J., Trosko, J. E., Upham, B., Kozubik, A., et al. (2007). Concentrations of methylated naphthalenes, anthracenes, and phenanthrenes occurring in Czech river sediments and their effects on toxic events associated with carcinogenesis in rat liver cell lines. Environ Toxicol Chem 26, 2308-2316.

Wandinger, S. K., Richter, K., and Buchner, J. (2008). The Hsp90 chaperone machinery. J Biol Chem 283, 18473-18477.

Wang, C., Sun, H., Chang, Y., Song, Z., and Qin, X. (2011). PAHs distribution in sediments associated with gas hydrate and oil seepage from the Gulf of Mexico. Marine Pollution Bulletin 62, 2714-2723.

Wang, W., Meng, B., Lu, X., Liu, Y., and Tao, S. (2007). Extraction of polycyclic aromatic hydrocarbons and organochlorine pesticides from soils: A comparison between Soxhlet extraction, microwave-assisted extraction and accelerated solvent extraction techniques. Analytica Chimica Acta 602, 211-222.

Watson, J. D., Prokopec, S. D., Smith, A. B., Okey, A. B., Pohjanvirta, R., and Boutros, P. C. (2014). TCDD dysregulation of 13 AHR-target genes in rat liver. Toxicol Appl Pharmacol 274, 445-454.

Weaver-Feldhaus, J., Miller, K., Feldhaus, M., and Siegel, R. (2005). Directed evolution for the development of conformation-specific affinity reagents using yeast display. Protein Eng Des Sel 18, 527-536.

Wise, S. A., Sander, L. C., and Schantz, M. M. (2015). Analytical Methods for Determination of Polycyclic Aromatic Hydrocarbons (PAHs)—A Historical Perspective on the 16 U.S. EPA Priority Pollutant PAHs. Polycyclic Aromatic Compounds 35, 187-247.

Yalow, R. S., and Berson, S. A. (1959). Assay of plasma insulin in human subjects by immunological methods. Nature 184 (Suppl 21), 1648-1649.

Zhang, N. (2011). The role of endogenous aryl hydrocarbon receptor signaling in cardiovascular physiology. Journal of Cardiovascular Disease Research 2, 91-95.

Zhu, X., Kriegel, A. M., Boustany, C. A., and Blake, D. A. (2011). Single-chain variable fragment (scFv) antibodies optimized for environmental. Anal Chem 83, 3717-3724.

Example 6—D7 Antibody Detects Degradation of PAHs by Marine Bacteria in Synthetic Seawater The D7 antibody is active in an artificial seawater matrix (ONR7a) (see FIG. 74).

The D7 Antibody has been used to monitor the degradation of phenanthrene, fluorene, pyrene and fluoranthrene by Cycloclasticus pugetii, a bacteria that is important in degrading PAHs after crude oil spills. (see FIG. 75).

The data generated by competitive ELISA using the D7 antibody, a rapid, inexpensive assay is comparable to that generated using gas chromatography, a test that requires extensive sample pretreatment and expensive instrumentation. (see FIG. 76).

The D7 antibody can detect phenanthrene in the presence of crude oil at concentrations similar to those found in oil spills (0.8-4 mL per liter of seawater). At both concentrations tested (0.8 and 4 mL crude oil/L of synthetic seawater), the D7 antibody was able to detect phenanthrene, as shown by the 30% decrease in absorbance in the competitive ELISA. This will form the basis for an ELISA to determine the measurement and degradation of PAHs in crude oil. (see FIG. 77).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A recombinant antibody or fragment thereof that specifically binds to a polycyclic aromatic hydrocarbon (PAH), wherein the PAH is selected from the group consisting of naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene, wherein the recombinant antibody or fragment thereof comprises a) a heavy chain with three CDRs comprising the amino acid sequences GYTFTSYWMH (SEQ ID NO: 60), EINPRNGRSNYNEKFKN (SEQ ID NO: 61), and DGGDY (SEQ ID NO: 62), respectively, and a light chain with three CDRs comprising the amino acid sequences KASQDVGTAVA (SEQ ID NO: 63), WASTRHT (SEQ ID NO: 64), and QQYSSYPLT (SEQ ID NO: 65), respectively;

b) a heavy chain with three CDRs comprising the amino acid sequences GNTFTSYTMH (SEQ ID NO: 69), YINPSSGYTEYNQKFKD (SEQ ID NO: 70), and GPRY (SEQ ID NO: 71), respectively, and a light chain with three CDRs comprising the amino acid sequences KASQNVGTNVA (SEQ ID NO: 72), SASYRYS (SEQ ID NO: 73), and QQYNSYPYT (SEQ ID NO: 74), respectively;

c) a heavy chain with three CDRs comprising the amino acid sequences GYTFTSYWMH (SEQ ID NO: 145), EINPSNGRTNYNEKFKS (SEQ ID NO: 77), and DGGDY (SEQ ID NO: 78), respectively, and a light chain with three CDRs comprising the amino acid sequences KASQDVGTAVA (SEQ ID NO: 79), WASTRHT (SEQ ID NO: 80), and QQYSSYPLT (SEQ ID NO: 81), respectively;

d) a heavy chain with three CDRs comprising the amino acid sequences GYTFTSYWIVH (SEQ ID NO: 85), EINPRNGRSNYNEKFKN (SEQ ID NO: 86), and DGGDY (SEQ ID NO: 87), respectively, and a light chain with three CDRs comprising the amino acid sequences KASQNVGTNVA (SEQ ID NO: 88), SASYRYS (SEQ ID NO: 89), and QQYNSYPLT (SEQ ID NO: 90), respectively;

e) a heavy chain with three CDRs comprising the amino acid sequences GYTFTSYWIVH (SEQ ID NO: 94), EINPRNGRSNYNEKFKN (SEQ ID NO: 95), and DGGDY (SEQ ID NO: 96), respectively, and a light chain with three CDRs comprising the amino acid sequences KASQDVGTAVA (SEQ ID NO: 97), WASTRHT (SEQ ID NO: 98), and XQYXXYPLT (SEQ ID NO: 99), respectively;

f) a heavy chain with three CDRs comprising the amino acid sequences GYAFTKYLIE (SEQ ID NO: 103), VINPGSGSTSYNEKFRY (SEQ ID NO: 104), and IPASYRSDSLDC (SEQ ID NO: 105), respectively, and a light chain with three CDRs comprising the amino acid sequences KASQDVGTAVA (SEQ ID NO: 106), WASTRHT (SEQ ID NO: 107), and QQYSSYPWT (SEQ ID NO: 108), respectively;

g) a heavy chain with three CDRs comprising the amino acid sequences GYTFTKYLIE (SEQ ID NO: 112), VINPGSGSTSYNEKFRYK (SEQ ID NO: 113), and IPASYRSDSLDC (SEQ ID NO: 114), respectively, and a light chain with three CDRs comprising the amino acid sequences KASQDVGTAVA (SEQ ID NO: 115), WASTRHT (SEQ ID NO: 116), and QQYSSYPWT (SEQ ID NO: 117), respectively;

h) a heavy chain with three CDRs comprising the amino acid sequences GYAFTKYLIE (SEQ ID NO: 121), VINPGSGSTSYNEKFRY (SEQ ID NO: 122), and IPASYRSDSLDC (SEQ ID NO: 123), respectively, and a light chain with three CDRs comprising the amino acid sequences KASQDVGTAVA (SEQ ID NO: 124), WASTRHT (SEQ ID NO: 125), and QQYKSYPLT (SEQ ID NO: 126), respectively;

i) a heavy chain with three CDRs comprising the amino acid sequences GYVFTNFLIE (SEQ ID NO: 130), VINPGNGGAAYNEKFKG (SEQ ID NO: 131), and LPPSYDYDGDIDY (SEQ ID NO: 132), respectively, and a light chain with three CDRs comprising the amino acid sequences RASKSVTTSGYSLMH (SEQ ID NO: 133), PASNLES (SEQ ID NO: 134), and QHSRELPWT (SEQ ID NO: 135), respectively; or j) a heavy chain with three CDRs comprising the amino acid sequences GYAFTNFLIE (SEQ ID NO: 139), VINPGSGGTGYNEKFKG (SEQ ID NO: 140), and LPPSYDYDGDIDY (SEQ ID NO: 141), respectively, and a light chain with three CDRs comprising the amino acid sequences RASKSVSSSGYSLIH (SEQ ID NO: 142), LASNLXS (SEQ ID NO: 143), and XHSXXLPWX (SEQ ID NO: 144), respectively.

2. The recombinant antibody or fragment thereof of claim 1, wherein the PAH is petrogenic.

3. The recombinant antibody or fragment thereof of claim 1, wherein the antibody specifically binds to phenanthrene, and wherein the antibody does not show substantial cross-reactivity against a PAH selected from the group consisting of naphthalene, acenapthene, acenapthylene, fluorene, anthracene, benz[a]anthracene, chrysene, benzo[b]fluoranthene, benzo[k]fluoranthene, benzo[a]pyrene, benzol[ghi]perylene, and dibenz[a,h]anthracene.

4. The recombinant antibody or fragment thereof of claim 1, wherein phenanthrene is methylated.

5. The recombinant antibody or fragment thereof of claim 1, wherein the antibody or fragment thereof comprises a variable domain having a variable light chain ($V_L$) amino acid sequence comprising SEQ ID NO: 58, 67, 76, 83, 92, 101, 110, 119, 128, or 137, or having a variable heavy chain ($V_H$) amino acid sequence comprising SEQ ID NO: 57, 66, 75, 82, 91, 100, 109, 118, 127, or 136.

6. The recombinant antibody or fragment thereof of claim 1, wherein the antibody or fragment thereof has an $IC_{50}$ less than or equal to 8.3 µM.

7. The recombinant antibody or fragment thereof of claim 1, wherein phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-dimethylphenanthrene (3,6-DMP).

8. The recombinant antibody or fragment thereof of claim 1, wherein the antibody or fragment thereof comprises the amino acid sequence of any one of SEQ ID NOS: 37-46.

9. The recombinant antibody or fragment thereof of claim 1 encoded by a nucleic acid comprising any one of SEQ ID NOS: 47-56.

10. A method of detecting the presence of a methylated PAH, the method comprising:
a) obtaining a sample;
b) contacting the sample with the recombinant antibody or fragment thereof of claim 1 for at least a period of time sufficient for the antibody or fragment thereof to bind its target; and
c) determining whether a methylated PAH is present in the sample.

11. The method of claim 10, wherein the PAH is selected from the group consisting of naphthalene, acenapthene, acenapthylene, phenanthrene, fluorene, anthracene, benz[a]anthracene, chrysene, pyrene, fluoranthene, benzo[b]fluoranthene, benzo[k]fluoranthene, benzo[a]pyrene, indeno[1,2,3-cd]pyrene, benzol[ghi]perylene, and dibenz[a,h]anthracene.

12. The method of claim 11, wherein phenanthrene is 1-methylphenanthrene (1-MP), 2-methylphenanthrene (2-MP), 3-methylphenanthrene (3-MP), 4-methylphenanthrene (4-MP), 9-methylphenanthrene (9-MP), or 3,6-dimethylphenanthrene (3,6-DMP).

* * * * *

SEQUENCE LISTING

```
<160> NUMBER OF SEQ ID NOS: 241

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctaccgtgg cccaggcggc catggccaga agcgcgcatg ccsa                44

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctagagcgcg catgccgagg ttcdsctgca acagty                         36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctagagcgcg catgcccagg tgcaamtgma gsagtc                         36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctagagcgcg catgccgavg tgmwgctggt ggagtc                         36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctagagcgcg catgcccagg ttaytctgaa agagtc                         36
```

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctagagcgcg catgccgakg tgcagcttca gsagtc                                 36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctagagcgcg catgcccaga tccagttsgy gcagtc                                 36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctagagcgcg catgcccagr tccaactgca gcagyc                                 36

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctagagcgcg catgccgagg tgmagctast tgagwc                                 36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctagagcgcg catgccgaag tgaagmttga ggagtc                                 36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctagagcgcg catgccgatg tgaacctgga agtgtc                                 36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
ctagagcgcg catgcccaga tkcagcttma ggagtc         36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ctagagcgcg catgcccagg cttatctgca gcagtc         36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ctagagcgcg catgcccagg ttcacctaca acagtc         36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ctagagcgcg catgcccagg tgcagcttgt agagac         36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ctagagcgcg catgccgarg tgmagctgkt ggagac         36

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ccgcctcgag cacctccgcc ggagccgccg ccgccagaac caccaccacc cgaggagacg    60 gtgacmgtgg                                                          70

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccgcctcgag cacctccgcc ggagccgccg ccgccagaac caccaccacc cgcagagaca      60
gtgaccagag                                                             70

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccgcctcgag cacctccgcc ggagccgccg ccgccagaac caccaccacc cgaggagact      60 gtgagastgg                                                             70

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcggaggtg ctcgaggcgg tggcggatcg gacawtgttc tcacccagtc                 50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcggaggtg ctcgaggcgg tggcggatcg gacatccaga tgacacagwc                 50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggcggaggtg ctcgaggcgg tggcggatcg gatrttgtga tgacccagwc                 50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggcggaggtg ctcgaggcgg tggcggatcg gacattstgm tgacccagtc       50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcggaggtg ctcgaggcgg tggcggatcg gatgttgtgv tgacccaaac       50

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggcggaggtg ctcgaggcgg tggcggatcg gacacaactg tgacccagtc       50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcggaggtg ctcgaggcgg tggcggatcg gayattktgc tcactcagtc       50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcggaggtg ctcgaggcgg tggcggatcg gatattgtga tracccaggm       50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggcggaggtg ctcgaggcgg tggcggatcg gacattgtaa tgacccaatc       50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggcggaggtg ctcgaggcgg tggcggatcg gacattgtga tgwcacagtc          50

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggcggaggtg ctcgaggcgg tggcggatcg gatrtccaga tgamccagtc          50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggcggaggtg ctcgaggcgg tggcggatcg gatggagaaa caacacaggc          50

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgatggtgc tggccggcct ggcctgagct agcgcgttt                      39

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtgagctag cgcgtttbat ttccagcttg g                              31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggtgagctag cgcgttttat ttccaatttt g                              31

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctggtggtg gtggttctgg tggtggtggt tctgctagaa gcgcgcatgc c        51

<210> SEQ ID NO 36
<211> LENGTH: 55
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 36
cgttcaggtc ttcttcagag atcagtttct gttcagcacc tgagctagcg cgttt        55

<210> SEQ ID NO 37
<211> LENGTH: 248
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 37

```
Ser Ala His Ala Glu Ala Tyr Leu Gln Gln Ser Gly Ala Glu Leu Val
1               5                   10                  15

Lys Pro Gly Ala Ser Val Lys Leu Ser Cys Lys Ala Ser Gly Tyr Thr
            20                  25                  30

Phe Thr Ser Tyr Trp Met His Trp Val Lys Gln Arg Pro Gly Gln Gly
        35                  40                  45

Leu Glu Trp Ile Gly Glu Ile Asn Pro Arg Asn Gly Arg Ser Asn Tyr
    50                  55                  60

Asn Glu Lys Phe Lys Asn Lys Ala Thr Val Thr Val Asp Lys Tyr Ser
65                  70                  75                  80

Asn Thr Ala Tyr Met Gln Leu Ser Ser Leu Thr Ser Asp Asp Ser Ala
                85                  90                  95

Val Tyr Tyr Cys Thr Arg Asp Gly Gly Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Ala Arg Gly Gly Gly Ser Asp Ile Val Leu Thr Gln
    130                 135                 140

Ser His Lys Phe Met Ser Thr Ser Val Gly Asp Arg Val Ser Ile Thr
145                 150                 155                 160

Cys Lys Ala Ser Gln Asp Val Gly Thr Ala Val Ala Trp Tyr Gln Gln
                165                 170                 175

Lys Pro Gly Gln Ser Pro Lys Leu Leu Ile Tyr Trp Ala Ser Thr Arg
            180                 185                 190

His Thr Gly Val Pro Asp Arg Phe Thr Gly Ser Gly Ser Gly Thr Asp
        195                 200                 205

Phe Thr Leu Thr Ile Ser Asn Val Gln Ser Glu Asp Leu Ala Asp Tyr
    210                 215                 220

Phe Cys Gln Gln Tyr Ser Ser Tyr Pro Leu Thr Phe Gly Gly Gly Thr
225                 230                 235                 240

Lys Leu Glu Met Lys Arg Ala Ser
                245
```

<210> SEQ ID NO 38
<211> LENGTH: 247
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 38

Ser Ala His Ala Glu Ala Tyr Leu Gln Gln Ser Ala Ala Glu Leu Ala
1               5                   10                  15

Arg Pro Gly Ala Ser Val Lys Met Ser Cys Lys Ala Ser Gly Asn Thr
            20                  25                  30

Phe Thr Ser Tyr Thr Met His Trp Val Lys Gln Arg Pro Gly Gln Gly
        35                  40                  45

Leu Glu Trp Ile Gly Tyr Ile Asn Pro Ser Ser Gly Tyr Thr Glu Tyr
    50                  55                  60

Asn Gln Lys Phe Lys Asp Lys Thr Thr Leu Thr Ala Asp Thr Ser Ser
65                  70                  75                  80

Ser Thr Ala Tyr Met Gln Leu Ser Ser Leu Thr Pro Glu Asp Ser Ala
                85                  90                  95

Val Tyr Tyr Cys Ala Arg Gly Pro Arg Tyr Trp Gly Gln Gly Thr Leu
            100                 105                 110

Val Thr Val Ser Ala Gly Gly Gly Gly Ser Gly Gly Gly Gly Ser Gly
        115                 120                 125

Gly Gly Ala Arg Gly Gly Gly Ser Asp Thr Thr Val Thr Gln Ser
    130                 135                 140

Gln Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Ala Leu Ile Tyr Ser Ala Ser Tyr Arg Tyr
            180                 185                 190

Ser Gly Val Pro Asp Arg Phe Thr Gly Ser Gly Ser Gly Thr Asp Phe
        195                 200                 205

Thr Leu Thr Ile Ser Asn Val Gln Ser Glu Asp Leu Ala Glu Tyr Phe
    210                 215                 220

Cys Gln Gln Tyr Asn Ser Tyr Pro Tyr Thr Phe Gly Gly Gly Thr Lys
225                 230                 235                 240

Leu Glu Ile Lys Arg Ala Ser
                245

<210> SEQ ID NO 39
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala His Ala Gln Ile Gln Leu Gln Gln Pro Gly Ala Glu Leu Val Lys
1               5                   10                  15

Pro Gly Ala Ser Val Lys Leu Ser Cys Lys Ala Ser Gly Tyr Thr Phe
            20                  25                  30

Thr Ser Tyr Trp Met His Trp Val Lys Gln Arg Pro Gly Gln Gly Leu
        35                  40                  45

Glu Trp Ile Gly Glu Ile Asn Pro Ser Asn Gly Arg Thr Asn Tyr Asn
    50                  55                  60

Glu Lys Phe Lys Ser Lys Ala Thr Leu Thr Val Asp Lys Ser Ser Ser
65                  70                  75                  80

```
Thr Ala Tyr Met Gln Leu Ser Ser Leu Thr Ser Glu Asp Ser Ala Val
                85                  90                  95

Tyr Tyr Cys Ala Arg Asp Gly Asp Tyr Trp Gly Gln Gly Thr Thr
            100                 105                 110

Leu Thr Val Ser Ser Gly Gly Gly Ser Gly Gly Gly Ser Gly
            115                 120                 125

Gly Gly Ala Arg Gly Gly Gly Ser Asp Ile Val Met Ser Gln Ser
130             135                 140

His Lys Phe Met Ser Thr Ser Val Gly Asp Arg Val Ser Ile Thr Cys
145                 150                 155                 160

Lys Ala Ser Gln Asp Val Gly Thr Ala Val Ala Trp Tyr Gln Gln Lys
                165                 170                 175

Pro Gly Gln Ser Pro Lys Leu Leu Ile Tyr Trp Ala Ser Thr Arg His
                180                 185                 190

Thr Gly Val Pro Asp Arg Phe Thr Gly Ser Gly Ser Gly Thr Asp Phe
            195                 200                 205

Thr Leu Thr Ile Ser Asn Val Gln Ser Gly Asp Leu Ala Asp Tyr Phe
    210                 215                 220

Cys Gln Gln Tyr Ser Ser Tyr Pro Leu Thr Phe Gly Gly Gly Thr Lys
225                 230                 235                 240

Leu Glu Ile Lys Arg Ala Ser
                245

<210> SEQ ID NO 40
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Ala His Ala Glu Ile Gln Leu Gln Gln Ser Gly Ala Glu Leu Val
1               5                   10                  15

Lys Pro Gly Ala Ser Val Lys Leu Ser Cys Lys Ala Ser Gly Tyr Thr
                20                  25                  30

Phe Thr Ser Tyr Trp Met His Trp Val Lys Gln Arg Pro Ala Gln Gly
            35                  40                  45

Leu Glu Trp Ile Gly Glu Ile Asn Pro Arg Asn Gly Arg Ser Asn Tyr
        50                  55                  60

Asn Glu Lys Phe Lys Asn Lys Ala Thr Val Thr Val Asp Lys Tyr Ser
65                  70                  75                  80

Asn Thr Ala Tyr Met Gln Leu Ser Ser Leu Thr Ser Asp Asp Ser Ala
                85                  90                  95

Val Tyr Tyr Cys Thr Arg Asp Gly Asp Tyr Trp Gly Gln Gly Thr
                100                 105                 110

Thr Leu Thr Val Ser Ser Gly Gly Gly Gly Ser Gly Gly Gly Gly Ser
            115                 120                 125

Gly Gly Gly Ala Arg Gly Gly Gly Ser Asp Ile Val Leu Thr Gln
130                 135                 140

Ser Gln Lys Phe Met Ser Thr Ser Val Gly Asp Arg Val Ser Val Thr
145                 150                 155                 160

Cys Lys Ala Ser Gln Asn Val Gly Thr Asn Val Ala Trp Tyr Gln Gln
                165                 170                 175

Lys Pro Gly Gln Ser Pro Lys Ala Leu Ile Tyr Ser Ala Ser Tyr Arg
                180                 185                 190
```

-continued

```
Tyr Ser Gly Val Pro Asp Arg Phe Thr Gly Ser Gly Ser Gly Thr Asp
        195                 200                 205

Phe Thr Leu Thr Ile Ser Asn Val Gln Ser Glu Asp Leu Ala Asp Tyr
    210                 215                 220

Phe Cys Gln Gln Tyr Asn Ser Tyr Pro Leu Thr Phe Gly Gly Gly Thr
225                 230                 235                 240

Lys Leu Glu Met Lys Arg Ala Ser
                245
```

<210> SEQ ID NO 41
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (220)..(220)
<223> OTHER INFORMATION: Any amino acid
<220> FEATURE:
<221> NAME/KEY: MOD_RES
<222> LOCATION: (222)..(223)
<223> OTHER INFORMATION: Any amino acid
<220> FEATURE:
<221> NAME/KEY: MOD_RES
<222> LOCATION: (227)..(227)
<223> OTHER INFORMATION: Any amino acid
<220> FEATURE:
<221> NAME/KEY: MOD_RES
<222> LOCATION: (230)..(231)
<223> OTHER INFORMATION: Any amino acid
<220> FEATURE:
<221> NAME/KEY: MOD_RES
<222> LOCATION: (241)..(241)
<223> OTHER INFORMATION: Any amino acid
<220> FEATURE:
<221> NAME/KEY: MOD_RES
<222> LOCATION: (244)..(244)
<223> OTHER INFORMATION: Any amino acid
<220> FEATURE:
<221> NAME/KEY: MOD_RES
<222> LOCATION: (247)..(248)
<223> OTHER INFORMATION: Any amino acid
<220> FEATURE:
<221> NAME/KEY: MOD_RES
<222> LOCATION: (253)..(254)
<223> OTHER INFORMATION: Any amino acid

<400> SEQUENCE: 41

```
Ser Ala His Ala Glu Ala Tyr Leu Gln Gln Ser Gly Ala Glu Leu Val
1               5                   10                  15

Lys Pro Gly Ala Ser Val Lys Leu Ser Cys Lys Ala Ser Gly Tyr Thr
            20                  25                  30

Phe Thr Ser Tyr Trp Met His Trp Val Lys Gln Arg Pro Gly Gln Gly
        35                  40                  45

Leu Glu Trp Ile Gly Glu Ile Asn Pro Arg Asn Gly Arg Ser Asn Tyr
    50                  55                  60

Asn Glu Lys Phe Lys Asn Lys Ala Thr Val Thr Val Asp Lys Tyr Ser
65                  70                  75                  80
```

```
Asn Thr Ala Tyr Met Gln Leu Ser Ser Leu Thr Ser Asp Asp Ser Ala
                85                  90                  95

Val Tyr Tyr Cys Thr Arg Asp Gly Gly Asp Tyr Trp Gly Gln Gly Thr
            100                 105                 110

Thr Val Thr Val Ser Ser Gly Gly Gly Ser Gly Gly Gly Gly Ser
        115                 120                 125

Gly Gly Gly Ala Arg Gly Gly Gly Ser Asp Ile Val Leu Thr Gln
    130                 135                 140

Ser His Lys Phe Met Ser Thr Ser Val Gly Asp Arg Val Ser Ile Thr
145                 150                 155                 160

Cys Lys Ala Ser Gln Asp Val Gly Thr Ala Val Ala Trp Tyr Gln Gln
                165                 170                 175

Lys Pro Gly Gln Ser Pro Lys Leu Leu Ile Tyr Trp Ala Ser Thr Arg
            180                 185                 190

His Thr Gly Xaa Pro Asp Arg Phe Thr Gly Ser Gly Ser Gly Thr Asp
        195                 200                 205

Phe Thr Leu Thr Ile Xaa Asn Val Gln Ser Glu Xaa Leu Xaa Xaa Tyr
    210                 215                 220

Phe Cys Xaa Gln Tyr Xaa Xaa Tyr Pro Leu Thr Phe Gly Gly Gly Thr
225                 230                 235                 240

Xaa Trp Lys Xaa Asn Ala Xaa Xaa Gln Val Leu Asn Xaa Xaa
                245                 250

<210> SEQ ID NO 42
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Ala
            20                  25                  30

Phe Thr Lys Tyr Leu Ile Glu Trp Val Lys Gln Arg Pro Gly Gln Gly
        35                  40                  45

Leu Glu Trp Ile Gly Val Ile Asn Pro Gly Ser Gly Ser Thr Ser Tyr
    50                  55                  60

Asn Glu Lys Phe Arg Tyr Lys Ala Ile Leu Thr Ala Asp Thr Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser Gly Gly Gly
        115                 120                 125

Gly Ser Gly Gly Gly Gly Ser Gly Gly Gly Ala Arg Gly Gly Gly Gly
    130                 135                 140

Ser Asp Thr Thr Val Thr Gln Ser His Lys Phe Met Ser Thr Ser Val
145                 150                 155                 160

Gly Asp Arg Val Ser Ile Thr Cys Lys Ala Ser Gln Asp Val Gly Thr
                165                 170                 175

Ala Val Ala Trp Tyr Gln Gln Lys Pro Gly Gln Ser Pro Lys Leu Leu
            180                 185                 190
```

Ile Tyr Trp Ala Ser Thr Arg His Thr Gly Val Pro Asp Arg Phe Thr
            195                 200                 205

Gly Ser Gly Ser Gly Thr Asp Phe Thr Leu Thr Ile Ser Asn Val Gln
        210                 215                 220

Ser Glu Asp Leu Ala Asp Tyr Phe Cys Gln Gln Tyr Ser Ser Tyr Pro
225                 230                 235                 240

Trp Thr Phe Gly Gly Gly Thr Lys Leu Glu Met Lys Arg Ala Ser
                245                 250                 255

<210> SEQ ID NO 43
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Ala His Ala Glu Val Gln Leu Gln Gln Ser Gly Thr Glu Leu Val
1               5                   10                  15

Lys Pro Gly Ala Ser Val Lys Leu Ser Cys Lys Thr Ser Gly Tyr Thr
            20                  25                  30

Phe Thr Lys Tyr Leu Ile Glu Trp Val Lys Gln Arg Pro Gly Gln Gly
        35                  40                  45

Leu Glu Trp Ile Gly Val Ile Asn Pro Gly Ser Gly Ser Thr Ser Tyr
    50                  55                  60

Asn Glu Lys Phe Arg Tyr Lys Ala Ile Leu Thr Ala Asp Thr Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser Gly Gly Gly
        115                 120                 125

Gly Ser Gly Gly Gly Gly Ser Gly Gly Gly Ala Arg Gly Gly Gly Gly
    130                 135                 140

Ser Asp Thr Thr Val Thr Gln Ser His Lys Phe Met Ser Thr Ser Val
145                 150                 155                 160

Gly Asp Arg Val Ser Ile Thr Cys Lys Ala Ser Gln Asp Val Gly Thr
                165                 170                 175

Ala Val Ala Trp Tyr Gln Gln Lys Pro Gly Gln Ser Pro Lys Leu Leu
            180                 185                 190

Ile Tyr Trp Ala Ser Thr Arg His Thr Gly Val Pro Asp Arg Phe Thr
        195                 200                 205

Gly Ser Gly Ser Gly Thr Asp Phe Thr Leu Thr Ile Ser Asn Val Gln
    210                 215                 220

Ser Glu Asp Leu Ala Asp Tyr Phe Cys Gln Gln Tyr Ser Ser Tyr Pro
225                 230                 235                 240

Trp Thr Phe Gly Gly Gly Thr Lys Leu Glu Met Lys Arg Ala Ser
                245                 250                 255

<210> SEQ ID NO 44
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Ala
            20                  25                  30

Phe Thr Lys Tyr Leu Ile Glu Trp Val Lys Gln Arg Pro Gly Gln Gly
        35                  40                  45

Leu Glu Trp Ile Gly Val Ile Asn Pro Gly Ser Gly Ser Thr Ser Tyr
    50                  55                  60

Asn Glu Lys Phe Arg Tyr Lys Ala Ile Leu Thr Ala Asp Thr Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser Gly Gly Gly
        115                 120                 125

Gly Ser Gly Gly Gly Gly Ser Gly Gly Gly Ala Arg Gly Gly Gly Gly
    130                 135                 140

Ser Asp Thr Thr Val Thr Gln Ser His Lys Phe Met Ser Thr Ser Val
145                 150                 155                 160

Gly Asp Arg Val Ser Ile Thr Cys Lys Ala Ser Gln Asp Val Gly Thr
                165                 170                 175

Ala Val Ala Trp Tyr Gln Gln Arg Pro Gly Gln Ser Pro Lys Leu Leu
            180                 185                 190

Ile Tyr Trp Ala Ser Thr Arg His Thr Gly Val Pro Asp Arg Phe Thr
        195                 200                 205

Gly Ser Gly Ser Gly Thr Asp Phe Thr Leu Thr Ile Ser Asn Val Gln
    210                 215                 220

Ser Glu Asp Leu Ala Asp Tyr Phe Cys Gln Gln Tyr Lys Ser Tyr Pro
225                 230                 235                 240

Leu Thr Phe Gly Gly Gly Thr Lys Leu Glu Ile Lys Arg Ala Ser
                245                 250                 255

<210> SEQ ID NO 45
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Val
            20                  25                  30

Phe Thr Asn Phe Leu Ile Glu Trp Val Lys Gln Arg Pro Gly Gln Gly
        35                  40                  45

Leu Glu Trp Ile Gly Val Ile Asn Pro Gly Asn Gly Gly Ala Ala Tyr
    50                  55                  60

Asn Glu Lys Phe Lys Gly Lys Ala Ile Leu Thr Ala Asp Lys Ser Ser
65                  70                  75                  80

Ser Thr Ala Tyr Met Gln Leu Ser Ser Leu Thr Ser Asp Asp Ser Ala

```
                    85                  90                  95
Val Tyr Phe Cys Ala Arg Leu Pro Pro Ser Tyr Asp Tyr Asp Gly Asp
                100                 105                 110

Ile Asp Tyr Trp Gly Gln Gly Thr Thr Val Thr Val Ser Ser Gly Gly
            115                 120                 125

Gly Gly Ser Gly Gly Gly Gly Ser Gly Gly Gly Ala Arg Gly Gly Gly
        130                 135                 140

Gly Ser Asp Leu Val Leu Thr Gln Ser Pro Ala Ser Leu Ala Val Ala
145                 150                 155                 160

Leu Gly Gln Arg Ala Thr Ile Ser Cys Arg Ala Ser Lys Ser Val Thr
                165                 170                 175

Thr Ser Gly Tyr Ser Leu Met His Trp Tyr Arg Gln Lys Pro Gly Gln
                180                 185                 190

Pro Pro Lys Leu Leu Ile Tyr Pro Ala Ser Asn Leu Glu Ser Gly Val
                195                 200                 205

Pro Ala Arg Phe Ser Gly Ser Gly Ser Gly Thr Asp Phe Thr Leu Asn
            210                 215                 220

Ile His Pro Val Glu Glu Glu Asp Ala Ala Thr Tyr Tyr Cys Gln His
225                 230                 235                 240

Ser Arg Glu Leu Pro Trp Thr Phe Gly Gly Gly Thr Lys Leu Glu Ile
                245                 250                 255

Lys Arg Ala Ser
            260

<210> SEQ ID NO 46
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (205)..(205)
<223> OTHER INFORMATION: Any amino acid
<220> FEATURE:
<221> NAME/KEY: MOD_RES
<222> LOCATION: (211)..(211)
<223> OTHER INFORMATION: Any amino acid
<220> FEATURE:
<221> NAME/KEY: MOD_RES
<222> LOCATION: (218)..(218)
<223> OTHER INFORMATION: Any amino acid
<220> FEATURE:
<221> NAME/KEY: MOD_RES
<222> LOCATION: (229)..(230)
<223> OTHER INFORMATION: Any amino acid
<220> FEATURE:
<221> NAME/KEY: MOD_RES
<222> LOCATION: (239)..(239)
<223> OTHER INFORMATION: Any amino acid
<220> FEATURE:
<221> NAME/KEY: MOD_RES
<222> LOCATION: (242)..(243)
<223> OTHER INFORMATION: Any amino acid
<220> FEATURE:
<221> NAME/KEY: MOD_RES
<222> LOCATION: (247)..(251)
<223> OTHER INFORMATION: Any amino acid
<220> FEATURE:
<221> NAME/KEY: MOD_RES
<222> LOCATION: (257)..(261)
<223> OTHER INFORMATION: Any amino acid
<220> FEATURE:
<221> NAME/KEY: MOD_RES
<222> LOCATION: (263)..(266)
<223> OTHER INFORMATION: Any amino acid
```

-continued

```
<220> FEATURE:
<221> NAME/KEY: MOD_RES
<222> LOCATION: (268)..(277)
<223> OTHER INFORMATION: Any amino acid

<400> SEQUENCE: 46

Ser Ala His Ala Gln Val Gln Leu Gln Gln Ser Gly Ala Glu Leu Val
1               5                   10                  15

Arg Pro Gly Thr Ser Val Lys Val Ser Cys Lys Ala Ser Gly Tyr Ala
            20                  25                  30

Phe Thr Asn Phe Leu Ile Glu Trp Val Lys Gln Arg Pro Gly Gln Gly
        35                  40                  45

Leu Glu Trp Ile Gly Val Ile Asn Pro Gly Ser Gly Gly Thr Gly Tyr
    50                  55                  60

Asn Glu Lys Phe Lys Gly Lys Ala Thr Leu Thr Ala Asp Lys Ser Ser
65                  70                  75                  80

Ser Thr Ala Tyr Met Gln Leu Asn Ser Leu Thr Ser Asp Asp Ser Ala
                85                  90                  95

Val Tyr Phe Cys Ala Arg Leu Pro Pro Ser Tyr Asp Tyr Asp Gly Asp
            100                 105                 110

Ile Asp Tyr Trp Gly Gln Gly Thr Thr Val Thr Val Ser Ser Gly Gly
        115                 120                 125

Gly Gly Ser Gly Gly Gly Gly Ser Gly Gly Gly Ala Arg Gly Gly Gly
    130                 135                 140

Gly Ser Asp Ile Val Met Ser Gln Ser Pro Ala Ser Leu Ala Val Ser
145                 150                 155                 160

Leu Gly Gln Arg Ala Thr Ile Ser Cys Arg Ala Ser Lys Ser Val Ser
                165                 170                 175

Ser Ser Gly Tyr Ser Leu Ile His Trp Tyr Gln Gln Lys Pro Gly Gln
            180                 185                 190

Pro Pro Lys Leu Val Ile Tyr Leu Ala Ser Asn Leu Xaa Ser Gly Val
        195                 200                 205

Pro Ala Xaa Phe Ser Gly Ser Gly Ser Xaa Thr Asp Phe Thr Leu Asn
    210                 215                 220

Ile His Pro Val Xaa Xaa Glu Asp Ala Ala Thr Tyr Tyr Cys Xaa His
225                 230                 235                 240

Ser Xaa Xaa Leu Pro Trp Xaa Xaa Xaa Xaa Xaa Gln Ala Gly Asn Gln
                245                 250                 255

Xaa Xaa Xaa Xaa Xaa Pro Xaa Xaa Xaa Xaa Asp Xaa Xaa Xaa Xaa Xaa
            260                 265                 270

Xaa Xaa Xaa Xaa Xaa Thr
        275

<210> SEQ ID NO 47
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
agcgcgcatg ccgaggctta tctgcagcag tctggggctg aactggtgaa gcctggggct      60
tcagtgaagc tgtcctgcaa ggcttctggc tacaccttca ccagctactg gatgcacgag     120
tgggtgaagc agaggcctgg acaaggcctt gagtggattg gagagattaa tcctagaaac     180
ggtcgtagta actacaatga gaagttcaag aacaaggcca cagtgactgt agacaaatat     240
```

| | |
|---|---|
| tccaacacag cctacatgca actcagcagc ctgacatctg acgactctgc ggtctattac | 300 |
| tgtacaagag atgggggtga ctactggggc caaggcacca ctgtcaccgt ctcctcgggt | 360 |
| ggtggtggtt ctggcggcgg cggctccggc ggaggtgctc gaggcggtgg cggatcggac | 420 |
| attgtgctga cccagtctca caattcatg tccacatcag taggagacag ggtcagcatc | 480 |
| acctgcaagg ccagtcagga tgtgggtact gctgtagcct ggtatcaaca gaaaccaggg | 540 |
| caatctccta aactactgat ttactgggca tccacccggc acactggagt ccctgatcgc | 600 |
| ttcacaggca gtggatctgg gacagatttc actctcacca ttagcaatgt gcagtctgaa | 660 |
| gacttggcag attatttctg tcagcaatat agcagctatc ctctcacgtt cggagggggg | 720 |
| accaagctgg aaatgaaacg cgctagc | 747 |

<210> SEQ ID NO 48
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

| | |
|---|---|
| agcgcgcatg ccgaggctta tctgcagcag tctgcagctg aactggcaag acctggggcc | 60 |
| tcagtgaaga tgtcctgcaa ggcttctggc aacaccttca ctagctacac gatgcactgg | 120 |
| gtaaaacaga ggcctggaca gggtctggaa tggattggat acattaatcc tagcagtgga | 180 |
| tatactgaat acaatcagaa gttcaaggac aagaccacat tgactgcaga cacatcctcc | 240 |
| agcacagcct acatgcaact gagcagcctg acacctgagg actctgcggt ctattattgt | 300 |
| gcaagaggcc ccaggtactg gggccaaggg actctggtca ctgtctctgc gggtggtggt | 360 |
| ggttctggcg gcggcggctc cggcggaggt gctcgaggcg gtggcggatc ggacacaact | 420 |
| gtgacccagt ctcaaaaatt catgtccaca tcagtaggag acagggtcag cgtcacctgc | 480 |
| aaggccagtc agaatgtggg tactaatgtt gcctggtatc aacagaaacc agggcaatct | 540 |
| cctaaagcac tgatttactc ggcatcctac cggtacagtg gagtccctga tcgcttcaca | 600 |
| ggcagtggat ctgggacaga tttcactctc accatcagca atgtgcagtc tgaagacttg | 660 |
| gcagagtatt tctgtcagca atataacagc tatccgtaca cgttcggagg ggggaccaag | 720 |
| ctggaaatca aacgcgctag c | 741 |

<210> SEQ ID NO 49
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

| | |
|---|---|
| agcgcgcatg cccagatcca actgcagcag cctggggctg aactggtgaa gcctggggct | 60 |
| tcagtgaagc tgtcctgcaa ggcttctggc tacaccttca ccagctactg gatgcactgg | 120 |
| gtgaagcaga ggcctggaca aggccttgag tggattggaa gattaatcc tagcaacggt | 180 |
| cgtactaact acaatgagaa gttcaagagc aaggccacac tgactgtaga caaatcctcc | 240 |
| agcacagcct acatgcaact cagcagcctg acatctgagg actctgcggt ctattactgt | 300 |
| gcaagagatg ggggtgacta ctgggggccaa ggcaccactc tcacagtctc ctcgggtggt | 360 |

```
ggtggttctg gcggcggcgg ctccggcgga ggtgctcgag gcggtggcgg atcggacatt      420
gtgatgtcac agtctcacaa attcatgtcc acatcagtag gagacagggt cagcatcacc      480
tgcaaggcca gtcaggatgt gggtactgct gtagcctggt atcaacagaa accagggcaa      540
tctcctaaac tactgattta ctgggcatcc acccggcaca ctggagtccc tgatcgcttc      600
acaggcagtg gatctgggac agatttcact ctcaccatta gcaatgtgca gtctggagac      660
ttggcagatt atttctgtca gcaatatagc agctatcctc tcacgttcgg agggggacc      720 aagctggaaa tcaaacgcgc tagc                                              744

<210> SEQ ID NO 50
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
agcgcgcatg ccgagatcca actgcagcag tctggggctg aactggtgaa gcctggggcc      60
tcagtgaagc tgtcctgcaa ggcttctggc tacaccttca ccagctactg gatgcactgg     120
gtgaagcaga ggcctgcaca aggccttgag tggattggag agattaatcc tagaaacggt     180
cgtagtaact acaatgagaa gttcaagaat aaggccacag tgactgtaga caaatattcc     240
aacacagcct acatgcaact cagcagcctg acatctgacg actctgcggt ctattactgt     300
acaagagatg ggggtgacta ctggggccaa ggcaccactc tcacagtctc ctcgggtggt     360
ggtggttctg gcggcggcgg ctccggcgga ggtgctcgag gcggtggcgg atcggacatt     420
gtgctgaccc agtctcaaaa attcatgtcc acatcagtag gagacagggt cagcgtcacc      480
tgcaaggcca gtcagaatgt gggtactaat gtagcctggt atcaacagaa accagggcaa     540
tctcctaaag cactgattta ctcggcatcc taccggtaca gtggagtccc tgatcgcttc     600
acaggcagtg gatctgggac agatttcact ctcaccatta gcaatgtgca gtctgaagac     660
ttggcagatt atttctgtca gcaatataac agctatcctc tcacgttcgg agggggacc      720 aagctggaaa tgaaacgcgc tagc                                             744

<210> SEQ ID NO 51
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (586)..(586)
<223> OTHER INFORMATION: a, c, t, g, unknown or other
<220> FEATURE:
<221> NAME/KEY: modified_base
<222> LOCATION: (641)..(641)
<223> OTHER INFORMATION: a, c, t, g, unknown or other
<220> FEATURE:
<221> NAME/KEY: modified_base
<222> LOCATION: (658)..(658)
<223> OTHER INFORMATION: a, c, t, g, unknown or other
<220> FEATURE:
<221> NAME/KEY: modified_base
<222> LOCATION: (664)..(665)
<223> OTHER INFORMATION: a, c, t, g, unknown or other
<220> FEATURE:
<221> NAME/KEY: modified_base
<222> LOCATION: (667)..(667)
<223> OTHER INFORMATION: a, c, t, g, unknown or other
```

```
<220> FEATURE:
<221> NAME/KEY: modified_base
<222> LOCATION: (681)..(681)
<223> OTHER INFORMATION: a, c, t, g, unknown or other
<220> FEATURE:
<221> NAME/KEY: modified_base
<222> LOCATION: (689)..(689)
<223> OTHER INFORMATION: a, c, t, g, unknown or other
<220> FEATURE:
<221> NAME/KEY: modified_base
<222> LOCATION: (692)..(692)
<223> OTHER INFORMATION: a, c, t, g, unknown or other
<220> FEATURE:
<221> NAME/KEY: modified_base
<222> LOCATION: (722)..(722)
<223> OTHER INFORMATION: a, c, t, g, unknown or other
<220> FEATURE:
<221> NAME/KEY: modified_base
<222> LOCATION: (741)..(742)
<223> OTHER INFORMATION: a, c, t, g, unknown or other
<220> FEATURE:
<221> NAME/KEY: modified_base
<222> LOCATION: (757)..(758)
<223> OTHER INFORMATION: a, c, t, g, unknown or other
<220> FEATURE:
<221> NAME/KEY: modified_base
<222> LOCATION: (761)..(762)
<223> OTHER INFORMATION: a, c, t, g, unknown or other

<400> SEQUENCE: 51
agcgcgcatg ccgaggctta tctgcagcag tctggggctg aactggtgaa gcctgggct      60 tcagtgaagc tgtcctgcaa ggcttctggc tacaccttca ccagctactg gatgcactgg    120
gtgaagcaga ggcctggaca aggccttgag tggattggag agattaatcc tagaaacggt    180
cgtagtaact acaatgagaa gttcaagaac aaggccacag tgactgtaga caaatattcc    240
aacacagcct acatgcaact cagcagcctg acatctgacg actctgcggt ctattactgt    300
acaagagatg ggggtgacta ctggggccaa ggcaccactg tcaccgtctc ctcgggtggt    360
ggtggttctg gcggcggcgg ctccggcgga ggtgctcgag gcggtggcgg atcggacatt    420
gtgctgaccc agtctcacaa attcatgtcc acatcagtag gagacagggt cagcatcacc    480
tgcaaggcca gtcaggatgt gggtactgct gtagcctggt atcaacagaa accagggcaa    540
tctcctaaac tactgattta ctgggcatcc acccggcaca ctggantccc tgatcgcttc    600
acaggcagtg gatctgggac agatttcact ctcaccatta ncaatgtgca gtctgaanac    660
ttgnnanatt atttctgtca ncaatatanc anctatcctc tcacgttcgg aggggggacc    720
anctggaaat gaaacgcgct nnctcaggtg ctgaacnnaa nn                       762

<210> SEQ ID NO 52
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
agcgcgcatg ccgaggctta tctgcagcag tctggagctg agttggtaag gcctgggact     60
tcagtgaagg tgtcctgcaa ggcctctgga tacgccttca ctaaatactt gattgagtgg    120
gtaaagcaga ggcctggaca gggccttgag tggattggag tgattaatcc tggaagtggt    180
agtactagtt acaatgagaa gttcaggtac aaggcaatat tgactgcaga cacatcctcc    240
agcactgcct acatgcaact cagcagcctg acatctgatg actctgcggt ttatttctgt    300
gcaacaatac cggcctccta tcggtccgat tcccttgact gctgggccaa aggcaccacg    360
```

```
gtcaccgtct cctcgggtgg tggtggttct ggcggcggcg gctccggcgg aggtgctcga    420
ggcggtggcg gatcggacac aactgtgacc cagtctcaca aattcatgtc cacatcagta    480
ggagacaggg tcagcatcac ctgcaaggcc agtcaggatg tgggtactgc tgtagcctgg    540
tatcaacaga aaccagggca atctcctaaa ctactgattt actgggcatc cacccggcac    600
actggagtcc ctgatcgctt cacaggcagt ggatctggga cagatttcac tctcaccatt    660
agcaatgtgc agtctgaaga cttggcagat tatttctgtc agcaatatag cagctatccg    720
tggacgttcg gtggaggcac caagctggaa atgaaacgcg ctagc                    765
```

<210> SEQ ID NO 53
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
agcgcgcatg ccgaggtgca actgcagcag tctgggactg aactggtgaa gcctggggct     60
tcagtgaagc tgtcctgcaa gacttctggc tacacccttc ctaaatactt gattgagtgg    120
gtaaagcaga ggcctggaca gggccttgag tggattggag tgattaatcc tggaagtggt    180
agtactagtt acaatgagaa gttcaggtac aaggcaatat tgactgcaga cacatcctcc    240
agcactgcct acatgcaact cagcagcctg acatctgatg actctgcggt ttatttctgt    300
gcaacaatac cggcctccta tcggtccgat tcccttgact gctggggcca aggcaccacg    360
gtcaccgtct cctcgggtgg tggtggttct ggcggcggcg gctccggcgg aggtgctcga    420
ggcggtggcg gatcggacac aactgtgacc cagtctcaca aattcatgtc cacatcagta    480
ggagacaggg tcagcatcac ctgcaaggcc agtcaggatg tgggtactgc tgtagcctgg    540
tatcaacaga aaccagggca atctcctaaa ctactgattt actgggcatc cacccggcac    600
actggagtcc ctgatcgctt cacaggcagt ggatctggga cagatttcac tctcaccatt    660
agcaatgtgc agtctgaaga cttggcagat tatttctgtc agcaatatag cagctatccg    720
tggacgttcg gtggaggcac caagctggaa atgaaacgcg ctagc                    765
```

<210> SEQ ID NO 54
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
agcgcgcatg ccgaggctta tctgcagcag tctggagctg agttggtaag gcctgggact     60
tcagtgaagg tgtcctgcaa ggcctctgga tacgccttca ctaaatactt gattgagtgg    120
gtaaagcaga ggcctggaca gggccttgag tggattggag tgattaatcc tggaagtggt    180
agtactagtt acaatgagaa gttcaggtac aaggcaatat tgactgcaga cacatcctcc    240
agcactgcct acatgcaact cagcagcctg acatctgatg actctgcggt ttatttctgt    300
gcaacaatac cggcctccta tcggtccgat tcccttgact gctggggcca aggcaccacg    360
gtcaccgtct cctcgggtgg tggtggttct ggcggcggcg gctccggcgg aggtgctcga    420
ggcggtggcg gatcggacac aactgtgacc cagtctcaca aattcatgtc cacatcagta    480
```

| | |
|---|---|
| ggagacaggg tcagcatcac ctgcaaggcc agtcaggatg tgggtactgc tgtagcctgg | 540 |
| tatcaacaga gaccagggca atctcctaaa ctactgattt actgggcatc cacccggcac | 600 |
| actggagtcc ctgatcgctt cacaggcagt ggatctggga cagatttcac tctcaccatc | 660 |
| agcaatgtgc agtctgaaga cttggcagac tatttctgtc agcaatataa aagctatcct | 720 |
| ctcactttcg gaggggggac caagctggaa atcaaacgcg ctagc | 765 |

<210> SEQ ID NO 55
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

| | |
|---|---|
| agcgcgcatg ccgaggctta tctgcagcag tctggagctg agctggtaag gcctgggact | 60 |
| tcagtgaagg tgtcctgcaa ggcttctgga tacgtcttca ccaatttctt gatagagtgg | 120 |
| gtaaaacaga ggcctggaca gggccttgag tggattgggg tgattaatcc tggaaatggt | 180 |
| ggtgctgcct ataatgagaa gttcaagggc aaggcgatac ttactgcaga caaatcctcc | 240 |
| agtactgcct atatgcagct tagcagtctg acatctgatg actctgcggt ctatttctgt | 300 |
| gcaagattgc cccctcgta tgattacgac ggcgacatcg actactgggg ccaaggcacc | 360 |
| acggtcaccg tctcctcggg tggtggtggt tctggcggcg gcggctccgg cggaggtgct | 420 |
| cgaggcggtg gcggatcgga ccttgtgctc actcagtctc ctgcttcctt agctgtggct | 480 |
| ctgggacaga gggccaccat tcatgcagg gccagcaaaa gtgtcactac atctggctat | 540 |
| agtttaatgc actggtaccg acagaaacca ggacagccac ccaaactcct catctatcct | 600 |
| gcatccaacc tagaatctgg ggtccctgcc agattcagtg gcagtgggtc tgggacagac | 660 |
| ttcacccctca acatccatcc tgtggaggag gaggatgctg caacctatta ctgtcagcac | 720 |
| agtagggagc ttccgtggac gttcggtgga ggcaccaagc tggaaatcaa acgcgctagc | 780 |

<210> SEQ ID NO 56
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (613)..(613)
<223> OTHER INFORMATION: a, c, t, g, unknown or other
<220> FEATURE:
<221> NAME/KEY: modified_base
<222> LOCATION: (631)..(633)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (685)..(685)
<223> OTHER INFORMATION: a, c, t, g, unknown or other
<220> FEATURE:
<221> NAME/KEY: modified_base
<222> LOCATION: (690)..(690)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other -continued

```
<220> FEATURE:
<221> NAME/KEY: modified_base
<222> LOCATION: (724)..(725)
<223> OTHER INFORMATION: a, c, t, g, unknown or other
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (739)..(743)
<223> OTHER INFORMATION: a, c, t, g, unknown or other
<220> FEATURE:
<221> NAME/KEY: modified_base
<222> LOCATION: (746)..(746)
<223> OTHER INFORMATION: a, c, t, g, unknown or other
<220> FEATURE:
<221> NAME/KEY: modified_base
<222> LOCATION: (749)..(752)
<223> OTHER INFORMATION: a, c, t, g, unknown or other
<220> FEATURE:
<221> NAME/KEY: modified_base
<222> LOCATION: (769)..(769)
<223> OTHER INFORMATION: a, c, t, g, unknown or other
<220> FEATURE:
<221> NAME/KEY: modified_base
<222> LOCATION: (772)..(772)
<223> OTHER INFORMATION: a, c, t, g, unknown or other
<220> FEATURE:
<221> NAME/KEY: modified_base
<222> LOCATION: (776)..(776)
<223> OTHER INFORMATION: a, c, t, g, unknown or other
<220> FEATURE:
<221> NAME/KEY: modified_base
<222> LOCATION: (780)..(783)
<223> OTHER INFORMATION: a, c, t, g, unknown or other
<220> FEATURE:
<221> NAME/KEY: modified_base
<222> LOCATION: (787)..(787)
<223> OTHER INFORMATION: a, c, t, g, unknown or other
<220> FEATURE:
<221> NAME/KEY: modified_base
<222> LOCATION: (792)..(793)
<223> OTHER INFORMATION: a, c, t, g, unknown or other
<220> FEATURE:
<221> NAME/KEY: modified_base
<222> LOCATION: (796)..(797)
<223> OTHER INFORMATION: a, c, t, g, unknown or other
<220> FEATURE:
<221> NAME/KEY: modified_base
<222> LOCATION: (803)..(803)
<223> OTHER INFORMATION: a, c, t, g, unknown or other
<220> FEATURE:
<221> NAME/KEY: modified_base
<222> LOCATION: (807)..(810)
<223> OTHER INFORMATION: a, c, t, g, unknown or other
<220> FEATURE:
<221> NAME/KEY: modified_base
<222> LOCATION: (813)..(813)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (821)..(822)
<223> OTHER INFORMATION: a, c, t, g, unknown or other
<220> FEATURE:
<221> NAME/KEY: modified_base
<222> LOCATION: (824)..(824)
<223> OTHER INFORMATION: a, c, t, g, unknown or other
<220> FEATURE:
<221> NAME/KEY: modified_base
<222> LOCATION: (827)..(827)
<223> OTHER INFORMATION: a, c, t, g, unknown or other
<220> FEATURE:
<221> NAME/KEY: modified_base
<222> LOCATION: (830)..(831)
```

<223> OTHER INFORMATION: a, c, t, g, unknown or other

<400> SEQUENCE: 56

```
agcgcgcatg cccaggtcca actgcagcag tctggagctg agctggtaag gcctgggact    60
tcagtgaagg tgtcctgcaa ggcttctgga tacgccttca ctaatttctt gatagagtgg   120
gtaaaacaga ggcctggaca gggccttgag tggattgggg tgattaatcc tggaagtggt   180
ggtactggtt acaatgagaa gttcaagggc aaggcaacac tgactgcaga caaatcctcc   240
agcactgcct acatgcagct caatagtcta acatctgatg actctgcggt ctatttctgt   300
gcaagattgc cccctcata tgattacgac ggcgacatcg actactgggg ccaaggcacc   360
actgtcaccg tctcctcggg tggtggtggt tctggcggcg gcggctccgg cggaggtgct   420
cgaggcggtg gcggatcgga cattgtgatg tcacagtctc ctgcttcctt agctgtatct   480
ctggggcaga gggccaccat ctcatgcagg gccagcaaaa gtgtcagttc atctggctat   540
agtttaatac actggtacca acagaaacca ggacagccac ccaaactcgt catctatctt   600
gcatctaacc tanattctgg ggtccctgcc nnnttcagtg gcagtggatc tggnacagac   660
ttcaccctca acatccatcc tgtgnaggan gaggatgctg caacctatta ctgtcancac   720
agtnngganc ttccgtggnn nnncgnggnn nnccaagctg gaaatcaang cnctanctcn   780
nnncctnaac annaanntga tcntctnnnn aananctgaa nngntgnctn nacc         834
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Ser Ala His Ala Glu Ala Tyr Leu Gln Gln Ser Gly Ala Glu Leu Val
1               5                   10                  15
Lys Pro Gly Ala Ser Val Lys Leu Ser Cys Lys Ala Ser Gly Tyr Thr
            20                  25                  30
Phe Thr Ser Tyr Trp Met His Trp Val Lys Gln Arg Pro Gly Gln Gly
        35                  40                  45
Leu Glu Trp Ile Gly Glu Ile Asn Pro Arg Asn Gly Arg Ser Asn Tyr
    50                  55                  60
Asn Glu Lys Phe Lys Asn Lys Ala Thr Val Thr Val Asp Lys Tyr Ser
65                  70                  75                  80
Asn Thr Ala Tyr Met Gln Leu Ser Ser Leu Thr Ser Asp Asp Ser Ala
                85                  90                  95
Val Tyr Tyr Cys Thr Arg Asp Gly Gly Asp Tyr Trp Gly Gln Gly Thr
            100                 105                 110
Thr Val Thr Val Ser Ser
        115
```

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Asp Ile Val Leu Thr Gln Ser His Lys Phe Met Ser Thr Ser Val Gly

```
                1               5                  10                  15
    Asp Arg Val Ser Ile Thr Cys Lys Ala Ser Gln Asp Val Gly Thr Ala
                    20                  25                  30

Val Ala Trp Tyr Gln Gln Lys Pro Gly Gln Ser Pro Lys Leu Leu Ile
                    35                  40                  45

Tyr Trp Ala Ser Thr Arg His Thr Gly Val Pro Asp Arg Phe Thr Gly
            50                  55                  60

Ser Gly Ser Gly Thr Asp Phe Thr Leu Thr Ile Ser Asn Val Gln Ser
    65                  70                  75                  80

Glu Asp Leu Ala Asp Tyr Phe Cys Gln Gln Tyr Ser Ser Tyr Pro Leu
                    85                  90                  95

Thr Phe Gly Gly Gly Thr Lys Leu Glu Met Lys Arg Ala Ser
                    100                 105                 110

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Gly Gly Ser Gly Gly Gly Ser Gly Gly Gly Ala Arg Gly
1               5                   10                  15

Gly Gly Gly Ser
            20

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Tyr Thr Phe Thr Ser Tyr Trp Met His
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Ile Asn Pro Arg Asn Gly Arg Ser Asn Tyr Asn Glu Lys Phe Lys
1               5                   10                  15

Asn

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Gly Gly Asp Tyr
```

```
<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Ala Ser Gln Asp Val Gly Thr Ala Val Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Ala Ser Thr Arg His Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Tyr Ser Ser Tyr Pro Leu Thr
1               5

<210> SEQ ID NO 66
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ser Ala His Ala Glu Ala Tyr Leu Gln Gln Ser Ala Ala Glu Leu Ala
1               5                   10                  15

Arg Pro Gly Ala Ser Val Lys Met Ser Cys Lys Ala Ser Gly Asn Thr
            20                  25                  30

Phe Thr Ser Tyr Thr Met His Trp Val Lys Gln Arg Pro Gly Gln Gly
        35                  40                  45

Leu Glu Trp Ile Gly Tyr Ile Asn Pro Ser Ser Gly Tyr Thr Glu Tyr
    50                  55                  60

Asn Gln Lys Phe Lys Asp Lys Thr Thr Leu Thr Ala Asp Thr Ser Ser
65                  70                  75                  80

Ser Thr Ala Tyr Met Gln Leu Ser Ser Leu Thr Pro Glu Asp Ser Ala
                85                  90                  95

Val Tyr Tyr Cys Ala Arg Gly Pro Arg Tyr Trp Gly Gln Gly Thr Leu
            100                 105                 110

Val Thr Val Ser Ala
        115
```

```
<210> SEQ ID NO 67
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Thr Thr Val Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys Arg Ala Ser
            100                 105                 110

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Gly Gly Ser Gly Gly Gly Ser Gly Gly Gly Ala Arg Gly
1               5                   10                  15

Gly Gly Gly Ser
            20

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Asn Thr Phe Thr Ser Tyr Thr Met His
1               5                   10

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile Asn Pro Ser Ser Gly Tyr Thr Glu Tyr Asn Gln Lys Phe Lys
1               5                   10                  15

Asp
```

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Pro Arg Tyr
1

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ala Ser Gln Asn Val Gly Thr Asn Val Ala
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Ala Ser Tyr Arg Tyr Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Asn Ser Tyr Pro Tyr Thr
1               5

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala His Ala Gln Ile Gln Leu Gln Gln Pro Gly Ala Glu Leu Val Lys
1               5                   10                  15

Pro Gly Ala Ser Val Lys Leu Ser Cys Lys Ala Ser Gly Tyr Thr Phe
            20                  25                  30

Thr Ser Tyr Trp Met His Trp Val Lys Gln Arg Pro Gly Gln Gly Leu
        35                  40                  45

Glu Trp Ile Gly Glu Ile Asn Pro Ser Asn Gly Arg Thr Asn Tyr Asn
    50                  55                  60

```
Glu Lys Phe Lys Ser Lys Ala Thr Leu Thr Val Asp Lys Ser Ser
 65                  70                  75                  80

Thr Ala Tyr Met Gln Leu Ser Ser Leu Thr Ser Glu Asp Ser Ala Val
                 85                  90                  95

Tyr Tyr Cys Ala Arg Asp Gly Gly Asp Tyr Trp Gly Gln Gly Thr Thr
            100                 105                 110

Leu Thr Val Ser Ser
            115

<210> SEQ ID NO 76
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Ser Gln Ser His Lys Phe Met Ser Thr Ser Val Gly
  1               5                  10                  15

Asp Arg Val Ser Ile Thr Cys Lys Ala Ser Gln Asp Val Gly Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Gly Asp Leu Ala Asp Tyr Phe Cys Gln Gln Tyr Ser Ser Tyr Pro Leu
                 85                  90                  95

Thr Phe Gly Gly Gly Thr Lys Leu Glu Ile Lys Arg Ala Ser
            100                 105                 110

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Ile Asn Pro Ser Asn Gly Arg Thr Asn Tyr Asn Glu Lys Phe Lys
  1               5                  10                  15

Ser

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Gly Gly Asp Tyr
  1               5

<210> SEQ ID NO 79
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 79

Lys Ala Ser Gln Asp Val Gly Thr Ala Val Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Trp Ala Ser Thr Arg His Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Tyr Ser Ser Tyr Pro Leu Thr
1               5

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ser Ala His Ala Glu Ile Gln Leu Gln Gln Ser Gly Ala Glu Leu Val
1               5                   10                  15

Lys Pro Gly Ala Ser Val Lys Leu Ser Cys Lys Ala Ser Gly Tyr Thr
            20                  25                  30

Phe Thr Ser Tyr Trp Met His Trp Val Lys Gln Arg Pro Ala Gln Gly
        35                  40                  45

Leu Glu Trp Ile Gly Glu Ile Asn Pro Arg Asn Gly Arg Ser Asn Tyr
    50                  55                  60

Asn Glu Lys Phe Lys Asn Lys Ala Thr Val Thr Val Asp Lys Tyr Ser
65                  70                  75                  80

Asn Thr Ala Tyr Met Gln Leu Ser Ser Leu Thr Ser Asp Ser Ala
                85                  90                  95

Val Tyr Tyr Cys Thr Arg Asp Gly Gly Asp Tyr Trp Gly Gln Gly Thr
            100                 105                 110

Thr Leu Thr Val Ser Ser
        115

<210> SEQ ID NO 83
<211> LENGTH: 110
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 83

Asp Ile Val Leu Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Gly Gly Thr Lys Leu Glu Met Lys Arg Ala Ser
            100                 105                 110

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Gly Gly Ser Gly Gly Gly Gly Ser Gly Gly Gly Ala Arg Gly
1               5                   10                  15

Gly Gly Gly Ser
            20

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Tyr Thr Phe Thr Ser Tyr Trp Met His
1               5                   10

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Ile Asn Pro Arg Asn Gly Arg Ser Asn Tyr Asn Glu Lys Phe Lys
1               5                   10                  15

Asn

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Asp Gly Gly Asp Tyr
1               5

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Ala Ser Gln Asn Val Gly Thr Asn Val Ala
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Ala Ser Tyr Arg Tyr Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Gln Tyr Asn Ser Tyr Pro Leu Thr
1               5

<210> SEQ ID NO 91
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ser Ala His Ala Glu Ala Tyr Leu Gln Gln Ser Gly Ala Glu Leu Val
1               5                   10                  15

Lys Pro Gly Ala Ser Val Lys Leu Ser Cys Lys Ala Ser Gly Tyr Thr
            20                  25                  30

Phe Thr Ser Tyr Trp Met His Trp Val Lys Gln Arg Pro Gly Gln Gly
        35                  40                  45

Leu Glu Trp Ile Gly Glu Ile Asn Pro Arg Asn Gly Arg Ser Asn Tyr
    50                  55                  60

Asn Glu Lys Phe Lys Asn Lys Ala Thr Val Thr Val Asp Lys Tyr Ser
65                  70                  75                  80

Asn Thr Ala Tyr Met Gln Leu Ser Ser Leu Thr Ser Asp Asp Ser Ala
                85                  90                  95

Val Tyr Tyr Cys Thr Arg Asp Gly Gly Asp Tyr Trp Gly Gln Gly Thr

-continued

```
                   100                 105                 110

Thr Val Thr Val Ser Ser
            115

<210> SEQ ID NO 92
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (82)..(82)
<223> OTHER INFORMATION: Any amino acid
<220> FEATURE:
<221> NAME/KEY: MOD_RES
<222> LOCATION: (84)..(85)
<223> OTHER INFORMATION: Any amino acid
<220> FEATURE:
<221> NAME/KEY: MOD_RES
<222> LOCATION: (89)..(89)
<223> OTHER INFORMATION: Any amino acid
<220> FEATURE:
<221> NAME/KEY: MOD_RES
<222> LOCATION: (92)..(93)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (109)..(110)
<223> OTHER INFORMATION: Any amino acid
<220> FEATURE:
<221> NAME/KEY: MOD_RES
<222> LOCATION: (115)..(116)
<223> OTHER INFORMATION: Any amino acid

<400> SEQUENCE: 92

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Xaa Pro Asp Arg Phe Thr Gly
    50                  55                  60

Ser Gly Ser Gly Thr Asp Phe Thr Leu Thr Ile Xaa Asn Val Gln Ser
65                  70                  75                  80

Glu Xaa Leu Xaa Xaa Tyr Phe Cys Xaa Gln Tyr Xaa Xaa Tyr Pro Leu
                85                  90                  95

Thr Phe Gly Gly Gly Thr Xaa Trp Lys Xaa Asn Ala Xaa Xaa Gln Val
            100                 105                 110

Leu Asn Xaa Xaa
        115
```

```
<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Gly Gly Ser Gly Gly Gly Ser Gly Gly Gly Ala Arg Gly
1               5                   10                  15

Gly Gly Gly Ser
            20

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Tyr Thr Phe Thr Ser Tyr Trp Met His
1               5                   10

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Ile Asn Pro Arg Asn Gly Arg Ser Asn Tyr Asn Glu Lys Phe Lys
1               5                   10                  15

Asn

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Gly Gly Asp Tyr
1               5

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Ala Ser Gln Asp Val Gly Thr Ala Val Ala
1               5                   10

<210> SEQ ID NO 98
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Ala Ser Thr Arg His Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid

<400> SEQUENCE: 99

Xaa Gln Tyr Xaa Xaa Tyr Pro Leu Thr
1               5

<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Ala
                20                  25                  30

Phe Thr Lys Tyr Leu Ile Glu Trp Val Lys Gln Arg Pro Gly Gln Gly
            35                  40                  45

Leu Glu Trp Ile Gly Val Ile Asn Pro Gly Ser Gly Ser Thr Ser Tyr
        50                  55                  60

Asn Glu Lys Phe Arg Tyr Lys Ala Ile Leu Thr Ala Asp Thr Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser
        115                 120                 125

<210> SEQ ID NO 101
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Asp Thr Thr Val Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Lys Leu Glu Met Lys Arg Ala Ser
            100                 105                 110
```

<210> SEQ ID NO 102
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Gly Gly Gly Gly Ser Gly Gly Gly Ser Gly Gly Gly Ala Arg Gly
1               5                   10                  15

Gly Gly Gly Ser
            20
```

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Gly Tyr Ala Phe Thr Lys Tyr Leu Ile Glu
1               5                   10
```

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Val Ile Asn Pro Gly Ser Gly Ser Thr Ser Tyr Asn Glu Lys Phe Arg
1               5                   10                  15

Tyr
```

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Ile Pro Ala Ser Tyr Arg Ser Asp Ser Leu Asp Cys
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Lys Ala Ser Gln Asp Val Gly Thr Ala Val Ala
1               5                   10
```

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Trp Ala Ser Thr Arg His Thr
1               5
```

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Gln Gln Tyr Ser Ser Tyr Pro Trp Thr
1               5
```

<210> SEQ ID NO 109
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Ser Ala His Ala Glu Val Gln Leu Gln Gln Ser Gly Thr Glu Leu Val
1               5                   10                  15

Lys Pro Gly Ala Ser Val Lys Leu Ser Cys Lys Thr Ser Gly Tyr Thr
            20                  25                  30

Phe Thr Lys Tyr Leu Ile Glu Trp Val Lys Gln Arg Pro Gly Gln Gly
        35                  40                  45

Leu Glu Trp Ile Gly Val Ile Asn Pro Gly Ser Gly Ser Thr Ser Tyr
    50                  55                  60

Asn Glu Lys Phe Arg Tyr Lys Ala Ile Leu Thr Ala Asp Thr Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser
        115                 120                 125
```

<210> SEQ ID NO 110
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Thr Thr Val Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Lys Leu Glu Met Lys Arg Ala Ser
            100                 105                 110

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Gly Gly Ser Gly Gly Gly Ser Gly Gly Gly Ala Arg Gly
1               5                   10                  15

Gly Gly Gly Ser
            20

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Tyr Thr Phe Thr Lys Tyr Leu Ile Glu
1               5                   10

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Ile Asn Pro Gly Ser Gly Ser Thr Ser Tyr Asn Glu Lys Phe Arg
1               5                   10                  15

Tyr Lys

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Pro Ala Ser Tyr Arg Ser Asp Ser Leu Asp Cys
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ala Ser Gln Asp Val Gly Thr Ala Val Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Trp Ala Ser Thr Arg His Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Tyr Ser Ser Tyr Pro Trp Thr
1               5

<210> SEQ ID NO 118
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Ala
                20                  25                  30

Phe Thr Lys Tyr Leu Ile Glu Trp Val Lys Gln Arg Pro Gly Gln Gly
            35                  40                  45

Leu Glu Trp Ile Gly Val Ile Asn Pro Gly Ser Gly Ser Thr Ser Tyr
        50                  55                  60

```
Asn Glu Lys Phe Arg Tyr Lys Ala Ile Leu Thr Ala Asp Thr Ser Ser
 65                  70                  75                  80

Ser Thr Ala Tyr Met Gln Leu Ser Ser Leu Thr Ser Asp Asp Ser Ala
                 85                  90                  95

Val Tyr Phe Cys Ala Thr Ile Pro Ala Ser Tyr Arg Ser Asp Ser Leu
            100                 105                 110

Asp Cys Trp Gly Gln Gly Thr Thr Val Thr Val Ser Ser
        115                 120                 125

<210> SEQ ID NO 119
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Thr Thr Val Thr Gln Ser His Lys Phe Met Ser Thr Ser Val Gly
 1               5                  10                  15

Asp Arg Val Ser Ile Thr Cys Lys Ala Ser Gln Asp Val Gly Thr Ala
             20                  25                  30

Val Ala Trp Tyr Gln Gln Arg Pro Gly Gln Ser Pro Lys Leu Leu Ile
         35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Lys Ser Tyr Pro Leu
                 85                  90                  95

Thr Phe Gly Gly Gly Thr Lys Leu Glu Ile Lys Arg Ala Ser
            100                 105                 110

<210> SEQ ID NO 120
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Gly Gly Ser Gly Gly Gly Ser Gly Gly Gly Ala Arg Gly
 1               5                  10                  15

Gly Gly Gly Ser
            20

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Tyr Ala Phe Thr Lys Tyr Leu Ile Glu
 1               5                  10

<210> SEQ ID NO 122
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Ile Asn Pro Gly Ser Gly Ser Thr Ser Tyr Asn Glu Lys Phe Arg
1               5                   10                  15

Tyr

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Pro Ala Ser Tyr Arg Ser Asp Ser Leu Asp Cys
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Ala Ser Gln Asp Val Gly Thr Ala Val Ala
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Ala Ser Thr Arg His Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Gln Tyr Lys Ser Tyr Pro Leu Thr
1               5

<210> SEQ ID NO 127
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127
```

```
Ser Ala His Ala Glu Ala Tyr Leu Gln Gln Ser Gly Ala Glu Leu Val
1               5                   10                  15

Arg Pro Gly Thr Ser Val Lys Val Ser Cys Lys Ala Ser Gly Tyr Val
                20                  25                  30

Phe Thr Asn Phe Leu Ile Glu Trp Val Lys Gln Arg Pro Gly Gln Gly
            35                  40                  45

Leu Glu Trp Ile Gly Val Ile Asn Pro Gly Asn Gly Gly Ala Ala Tyr
        50                  55                  60

Asn Glu Lys Phe Lys Gly Lys Ala Ile Leu Thr Ala Asp Lys Ser Ser
65                  70                  75                  80

Ser Thr Ala Tyr Met Gln Leu Ser Ser Leu Thr Ser Asp Asp Ser Ala
                85                  90                  95

Val Tyr Phe Cys Ala Arg Leu Pro Pro Ser Tyr Asp Tyr Asp Gly Asp
            100                 105                 110

Ile Asp Tyr Trp Gly Gln Gly Thr Thr Val Thr Val Ser Ser
        115                 120                 125
```

<210> SEQ ID NO 128
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Asp Leu Val Leu Thr Gln Ser Pro Ala Ser Leu Ala Val Ala Leu Gly
1               5                   10                  15

Gln Arg Ala Thr Ile Ser Cys Arg Ala Ser Lys Ser Val Thr Thr Ser
                20                  25                  30

Gly Tyr Ser Leu Met His Trp Tyr Arg Gln Lys Pro Gly Gln Pro Pro
            35                  40                  45

Lys Leu Leu Ile Tyr Pro Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala Ser
```

<210> SEQ ID NO 129
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Gly Gly Gly Gly Ser Gly Gly Gly Gly Ser Gly Gly Gly Ala Arg Gly
1               5                   10                  15

Gly Gly Gly Ser
                20
```

<210> SEQ ID NO 130
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Val Phe Thr Asn Phe Leu Ile Glu
1               5                   10

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Val Ile Asn Pro Gly Asn Gly Gly Ala Ala Tyr Asn Glu Lys Phe Lys
1               5                   10                  15

Gly

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Leu Pro Pro Ser Tyr Asp Tyr Asp Gly Asp Ile Asp Tyr
1               5                   10

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Arg Ala Ser Lys Ser Val Thr Thr Ser Gly Tyr Ser Leu Met His
1               5                   10                  15

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Pro Ala Ser Asn Leu Glu Ser
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135
```

```
Gln His Ser Arg Glu Leu Pro Trp Thr
1               5

<210> SEQ ID NO 136
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ser Ala His Ala Gln Val Gln Leu Gln Gln Ser Gly Ala Glu Leu Val
1               5                   10                  15

Arg Pro Gly Thr Ser Val Lys Val Ser Cys Lys Ala Ser Gly Tyr Ala
            20                  25                  30

Phe Thr Asn Phe Leu Ile Glu Trp Val Lys Gln Arg Pro Gly Gln Gly
        35                  40                  45

Leu Glu Trp Ile Gly Val Ile Asn Pro Gly Ser Gly Gly Thr Gly Tyr
    50                  55                  60

Asn Glu Lys Phe Lys Gly Lys Ala Thr Leu Thr Ala Asp Lys Ser Ser
65                  70                  75                  80

Ser Thr Ala Tyr Met Gln Leu Asn Ser Leu Thr Ser Asp Asp Ser Ala
                85                  90                  95

Val Tyr Phe Cys Ala Arg Leu Pro Pro Ser Tyr Asp Tyr Asp Gly Asp
            100                 105                 110

Ile Asp Tyr Trp Gly Gln Gly Thr Thr Val Thr Val Ser Ser
        115                 120                 125

<210> SEQ ID NO 137
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (65)..(65)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (83)..(84)
<223> OTHER INFORMATION: Any amino acid
<220> FEATURE:
<221> NAME/KEY: MOD_RES
<222> LOCATION: (93)..(93)
<223> OTHER INFORMATION: Any amino acid
<220> FEATURE:
<221> NAME/KEY: MOD_RES
<222> LOCATION: (96)..(97)
<223> OTHER INFORMATION: Any amino acid
<220> FEATURE:
<221> NAME/KEY: MOD_RES
<222> LOCATION: (101)..(105)
<223> OTHER INFORMATION: Any amino acid
<220> FEATURE:
<221> NAME/KEY: MOD_RES
<222> LOCATION: (111)..(115)
<223> OTHER INFORMATION: Any amino acid
```

```
<220> FEATURE:
<221> NAME/KEY: MOD_RES
<222> LOCATION: (117)..(120)
<223> OTHER INFORMATION: Any amino acid
<220> FEATURE:
<221> NAME/KEY: MOD_RES
<222> LOCATION: (122)..(131)
<223> OTHER INFORMATION: Any amino acid

<400> SEQUENCE: 137

Asp Ile Val Met Ser Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Leu Ile His Trp Tyr Gln Gln Lys Pro Gly Gln Pro Pro
        35                  40                  45

Lys Leu Val Ile Tyr Leu Ala Ser Asn Leu Xaa Ser Gly Val Pro Ala
    50                  55                  60

Xaa Phe Ser Gly Ser Gly Ser Xaa Thr Asp Phe Thr Leu Asn Ile His
65                  70                  75                  80

Pro Val Xaa Xaa Glu Asp Ala Ala Thr Tyr Tyr Cys Xaa His Ser Xaa
                85                  90                  95

Xaa Leu Pro Trp Xaa Xaa Xaa Xaa Gln Ala Gly Asn Gln Xaa Xaa
            100                 105                 110

Xaa Xaa Xaa Pro Xaa Xaa Xaa Xaa Asp Xaa Xaa Xaa Xaa Xaa Xaa
        115                 120                 125

Xaa Xaa Xaa Thr
        130

<210> SEQ ID NO 138
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Gly Ser Gly Gly Gly Ser Gly Gly Gly Ala Arg Gly
1               5                   10                  15

Gly Gly Gly Ser
            20

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Tyr Ala Phe Thr Asn Phe Leu Ile Glu
1               5                   10

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140
```

```
Val Ile Asn Pro Gly Ser Gly Gly Thr Gly Tyr Asn Glu Lys Phe Lys
1               5                   10                  15

Gly

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Pro Pro Ser Tyr Asp Tyr Asp Gly Asp Ile Asp Tyr
1               5                   10

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Ala Ser Lys Ser Val Ser Ser Ser Gly Tyr Ser Leu Ile His
1               5                   10                  15

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 143

Leu Ala Ser Asn Leu Xaa Ser
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 144

Xaa His Ser Xaa Xaa Leu Pro Trp Xaa
1               5
```

```
<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Tyr Thr Phe Thr Ser Tyr Trp Met His
1               5                   10

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Glu Ser Gly Ser Val Ser Ser Glu Gln Leu Ala Gln Phe Arg Ser
1               5                   10                  15

Leu Asp

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Gly Lys Ser Ser Gly Ser Gly Ser Glu Ser Lys Ser Thr
1               5                   10

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Gly Gly Ser
1               5

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

His His Met His Gly Lys Thr Gln Ala Thr Ser Gly Thr Ile Gln Ser
1               5                   10                  15

Met His Gly Lys Thr Gln Ala Thr Ser Gly Thr Ile Gln Ser Ser Arg
            20                  25                  30

<210> SEQ ID NO 150
<211> LENGTH: 357
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 150
agcgcgcatg ccgaggctta tctgcagcag tctggggctg aactggtgaa gcctggggct      60
tcagtgaagc tgtcctgcaa ggcttctggc tacaccttca ccagctactg gatgcacgag     120
tgggtgaagc agaggcctgg acaaggcctt gagtggattg gagagattaa tcctagaaac     180
ggtcgtagta actacaatga gaagttcaag aacaaggcca cagtgactgt agacaaatat     240
tccaacacag cctacatgca actcagcagc ctgacatctg acgactctgc ggtctattac     300
tgtacaagag atgggggtga ctactgggc caaggcacca ctgtcaccgt ctcctcg        357

<210> SEQ ID NO 151
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gacattgtgc tgacccagtc tcacaaattc atgtccacat cagtaggaga cagggtcagc      60
atcacctgca aggccagtca ggatgtgggt actgctgtag cctggtatca acagaaacca     120
gggcaatctc ctaaactact gatttactgg gcatccaccc ggcacactgg agtccctgat     180
cgcttcacag gcagtggatc tgggacagat ttcactctca ccattagcaa tgtgcagtct     240
gaagacttgg cagattattt ctgtcagcaa tatagcagct atcctctcac gttcggaggg     300
gggaccaagc tggaaatgaa acgcgctagc                                      330

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggtggtggtg gttctggcgg cggcggctcc ggcggaggtg ctcgaggcgg tggcggatcg      60

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggctacacct tcaccagcta ctggatgcac                                       30

<210> SEQ ID NO 154
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gagattaatc ctagaaacgg tcgtagtaac tacaatgaga agttcaagaa c                51
```

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155 gatggggtg actac                                                        15

<210> SEQ ID NO 156
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aaggccagtc aggatgtggg tactgctgta gcc                                   33

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgggcatcca cccggcacac t                                                21

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cagcaatata gcagctatcc tctcacg                                          27

<210> SEQ ID NO 159
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
agcgcgcatg ccgaggctta tctgcagcag tctgcagctg aactggcaag acctggggcc      60
tcagtgaaga tgtcctgcaa ggcttctggc aacaccttca ctagctacac gatgcactgg     120
gtaaaacaga ggcctggaca gggtctggaa tggattggat acattaatcc tagcagtgga     180
tatactgaat acaatcagaa gttcaaggac aagaccacat tgactgcaga cacatcctcc     240
agcacagcct acatgcaact gagcagcctg acacctgagg actctgcggt ctattattgt     300
gcaagaggcc ccaggtactg gggccaaggg actctggtca ctgtctctgc g              351

<210> SEQ ID NO 160
<211> LENGTH: 330

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
gacacaactg tgacccagtc tcaaaaattc atgtccacat cagtaggaga cagggtcagc      60
gtcacctgca aggccagtca gaatgtgggt actaatgttg cctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgtacac gttcggaggg     300
gggaccaagc tggaaatcaa acgcgctagc                                      330

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ggtggtggtg gttctggcgg cggcggctcc ggcggaggtg ctcgaggcgg tggcggatcg      60

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggcaacacct tcactagcta cacgatgcac                                       30

<210> SEQ ID NO 163
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tacattaatc ctagcagtgg atatactgaa tacaatcaga gttcaagga c                51

<210> SEQ ID NO 164
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggccccaggt ac                                                          12

<210> SEQ ID NO 165
<211> LENGTH: 33
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 165
aaggccagtc agaatgtggg tactaatgtt gcc    33

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tcggcatcct accggtacag t    21

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cagcaatata acagctatcc gtacacg    27

<210> SEQ ID NO 168
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
agcgcgcatg cccagatcca actgcagcag cctggggctg aactggtgaa gcctggggct    60
tcagtgaagc tgtcctgcaa ggcttctggc tacaccttca ccagctactg gatgcactgg    120
gtgaagcaga ggcctggaca aggccttgag tggattggag agattaatcc tagcaacggt    180
cgtactaact acaatgagaa gttcaagagc aaggccacac tgactgtaga caaatcctcc    240
agcacagcct acatgcaact cagcagcctg acatctgagg actctgcggt ctattactgt    300
gcaagagatg ggggtgacta ctggggccaa ggcaccactc tcacagtctc ctcg    354

<210> SEQ ID NO 169
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacattgtga tgtcacagtc tcacaaattc atgtccacat cagtaggaga cagggtcagc    60
atcacctgca aggccagtca ggatgtgggt actgctgtag cctggtatca acagaaacca    120
gggcaatctc ctaaactact gatttactgg gcatccaccc ggcacactgg agtccctgat    180
cgcttcacag gcagtggatc tgggacagat ttcactctca ccattagcaa tgtgcagtct    240
ggagacttgg cagattattt ctgtcagcaa tatagcagct atcctctcac gttcggaggg    300
gggaccaagc tggaaatcaa acgcgctagc    330

```
<210> SEQ ID NO 170
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggtggtggtg gttctggcgg cggcggctcc ggcggaggtg ctcgaggcgg tggcggatcg      60

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggctacacct tcaccagcta ctggatgcac                                       30

<210> SEQ ID NO 172
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gagattaatc ctagcaacgg tcgtactaac tacaatgaga agttcaagag c                51

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173 gatggggtg actac                                                        15

<210> SEQ ID NO 174
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
aaggccagtc aggatgtggg tactgctgta gcc                                   33

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tgggcatcca cccggcacac t                                                21

<210> SEQ ID NO 176
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cagcaatata gcagctatcc tctcacg                                          27

<210> SEQ ID NO 177
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
agcgcgcatg ccgagatcca actgcagcag tctggggctg aactggtgaa gcctggggcc      60
tcagtgaagc tgtcctgcaa ggcttctggc tacaccttca ccagctactg gatgcactgg     120
gtgaagcaga ggcctgcaca aggccttgag tggattggag agattaatcc tagaaacggt     180
cgtagtaact acaatgagaa gttcaagaat aaggccacag tgactgtaga caaatattcc     240
aacacagcct acatgcaact cagcagcctg acatctgacg actctgcggt ctattactgt     300
acaagagatg ggggtgacta ctggggccaa ggcaccactc tcacagtctc ctcg           354

<210> SEQ ID NO 178
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gacattgtgc tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccattagcaa tgtgcagtct     240
gaagacttgg cagattattt ctgtcagcaa tataacagct atcctctcac gttcggaggg     300
gggaccaagc tggaaatgaa acgcgctagc                                     330

<210> SEQ ID NO 179
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
ggtggtggtg gttctggcgg cggcggctcc ggcggaggtg ctcgaggcgg tggcggatcg      60

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 180
ggctacacct tcaccagcta ctggatgcac                                           30

<210> SEQ ID NO 181
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gagattaatc ctagaaacgg tcgtagtaac tacaatgaga agttcaagaa t                   51

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182 gatggggtg actac                                                            15

<210> SEQ ID NO 183
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aaggccagtc agaatgtggg tactaatgta gcc                                       33

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcggcatcct accggtacag t                                                    21

<210> SEQ ID NO 185
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cagcaatata acagctatcc tctcacg                                              27

<210> SEQ ID NO 186
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186

```
agcgcgcatg ccgaggctta tctgcagcag tctggggctg aactggtgaa gcctggggct      60
tcagtgaagc tgtcctgcaa ggcttctggc tacaccttca ccagctactg gatgcactgg     120
gtgaagcaga ggcctggaca aggccttgag tggattggag agattaatcc tagaaacggt     180
cgtagtaact acaatgagaa gttcaagaac aaggccacag tgactgtaga caaatattcc     240
aacacagcct acatgcaact cagcagcctg acatctgacg actctgcggt ctattactgt     300
acaagagatg ggggtgacta ctggggccaa ggcaccactg tcaccgtctc ctcg           354
```

<210> SEQ ID NO 187
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (172)..(172)
<223> OTHER INFORMATION: a, c, t, g, unknown or other
<220> FEATURE:
<221> NAME/KEY: modified_base
<222> LOCATION: (227)..(227)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (250)..(251)
<223> OTHER INFORMATION: a, c, t, g, unknown or other
<220> FEATURE:
<221> NAME/KEY: modified_base
<222> LOCATION: (253)..(253)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (275)..(275)
<223> OTHER INFORMATION: a, c, t, g, unknown or other
<220> FEATURE:
<221> NAME/KEY: modified_base
<222> LOCATION: (278)..(278)
<223> OTHER INFORMATION: a, c, t, g, unknown or other
<220> FEATURE:
<221> NAME/KEY: modified_base
<222> LOCATION: (308)..(308)
<223> OTHER INFORMATION: a, c, t, g, unknown or other
<220> FEATURE:
<221> NAME/KEY: modified_base
<222> LOCATION: (327)..(328)
<223> OTHER INFORMATION: a, c, t, g, unknown or other
<220> FEATURE:
<221> NAME/KEY: modified_base
<222> LOCATION: (343)..(344)
<223> OTHER INFORMATION: a, c, t, g, unknown or other
<220> FEATURE:
<221> NAME/KEY: modified_base
<222> LOCATION: (347)..(348)
<223> OTHER INFORMATION: a, c, t, g, unknown or other

<400> SEQUENCE: 187

```
gacattgtgc tgacccagtc tcacaaattc atgtccacat cagtaggaga cagggtcagc      60
atcacctgca aggccagtca ggatgtgggt actgctgtag cctggtatca acagaaacca     120
gggcaatctc ctaaaactac tgatttactgg gcatccaccc ggcacactgg antccctgat    180
cgcttcacag gcagtggatc tgggacagat ttcactctca ccattancaa tgtgcagtct     240
```

```
gaanacttgn nanattattt ctgtcancaa tatancanct atcctctcac gttcggaggg    300
gggaccanct ggaaatgaaa cgcgctnnct caggtgctga acnnaann               348
```

<210> SEQ ID NO 188
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188

```
ggtggtggtg gttctggcgg cggcggctcc ggcggaggtg ctcgaggcgg tggcggatcg    60
```

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

```
ggctacacct tcaccagcta ctggatgcac                                    30
```

<210> SEQ ID NO 190
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

```
gagattaatc ctagaaacgg tcgtagtaac tacaatgaga agttcaagaa c             51
```

<210> SEQ ID NO 191
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191

```
gatggggtg actac                                                     15
```

<210> SEQ ID NO 192
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192

```
aaggccagtc aggatgtggg tactgctgta gcc                                33
```

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgggcatcca cccggcacac t                                            21

<210> SEQ ID NO 194
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other

<400> SEQUENCE: 194
cancaatata ncanctatcc tctcacg                                      27

<210> SEQ ID NO 195
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
agcgcgcatg ccgaggctta tctgcagcag tctggagctg agttggtaag gcctgggact    60
tcagtgaagg tgtcctgcaa ggcctctgga tacgccttca ctaaatactt gattgagtgg   120
gtaaagcaga ggcctggaca gggccttgag tggattggag tgattaatcc tggaagtggt   180
agtactagtt acaatgagaa gttcaggtac aaggcaatat tgactgcaga cacatcctcc   240
agcactgcct acatgcaact cagcagcctg acatctgatg actctgcggt ttatttctgt   300
gcaacaatac cggcctccta tcggtccgat tcccttgact gctggggcca aggcaccacg   360
gtcaccgtct cctcg                                                   375

<210> SEQ ID NO 196
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gacacaactg tgacccagtc tcacaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atccgtggac gttcggtgga   300
ggcaccaagc tggaaatgaa acgcgctagc                                   330

<210> SEQ ID NO 197

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ggtggtggtg gttctggcgg cggcggctcc ggcggaggtg ctcgaggcgg tggcggatcg     60

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggatacgcct tcactaaata cttgattgag                                      30

<210> SEQ ID NO 199
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gtgattaatc ctggaagtgg tagtactagt tacaatgaga agttcaggta c              51

<210> SEQ ID NO 200
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ataccggcct cctatcggtc cgattccctt gactgc                               36

<210> SEQ ID NO 201
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
aaggccagtc aggatgtggg tactgctgta gcc                                  33

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tgggcatcca cccggcacac t                                               21

<210> SEQ ID NO 203
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cagcaatata gcagctatcc gtggacg                                            27

<210> SEQ ID NO 204
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
agcgcgcatg ccgaggtgca actgcagcag tctgggactg aactggtgaa gcctggggct        60
tcagtgaagc tgtcctgcaa gacttctggc tacaccttca ctaaatactt gattgagtgg       120
gtaaagcaga ggcctggaca gggccttgag tggattggag tgattaatcc tggaagtggt       180
agtactagtt acaatgagaa gttcaggtac aaggcaatat tgactgcaga cacatcctcc       240
agcactgcct acatgcaact cagcagcctg acatctgatg actctgcggt ttatttctgt       300
gcaacaatac cggcctccta tcggtccgat tcccttgact gctggggcca aggcaccacg       360
gtcaccgtct cctcg                                                        375

<210> SEQ ID NO 205
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
gacacaactg tgacccagtc tcacaaattc atgtccacat cagtaggaga cagggtcagc        60
atcacctgca aggccagtca ggatgtgggt actgctgtag cctggtatca acagaaacca       120
gggcaatctc ctaaactact gatttactgg gcatccaccc ggcacactgg agtccctgat       180
cgcttcacag gcagtggatc tgggacagat ttcactctca ccattagcaa tgtgcagtct       240
gaagacttgg cagattattt ctgtcagcaa tatagcagct atccgtggac gttcggtgga       300
ggcaccaagc tggaaatgaa acgcgctagc                                        330

<210> SEQ ID NO 206
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ggtggtggtg gttctggcgg cggcggctcc ggcggaggtg ctcgaggcgg tggcggatcg        60

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 207
ggctacacct tcactaaata cttgattgag        30

<210> SEQ ID NO 208
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gtgattaatc ctggaagtgg tagtactagt tacaatgaga agttcaggta caag        54

<210> SEQ ID NO 209
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ataccggcct cctatcggtc cgattccctt gactgc        36

<210> SEQ ID NO 210
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
aaggccagtc aggatgtggg tactgctgta gcc        33

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tgggcatcca cccggcacac t        21

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
cagcaatata gcagctatcc gtggacg        27

<210> SEQ ID NO 213
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213

```
agcgcgcatg ccgaggctta tctgcagcag tctggagctg agttggtaag gcctgggact        60
tcagtgaagg tgtcctgcaa ggcctctgga tacgccttca ctaaatactt gattgagtgg       120
gtaaagcaga ggcctggaca gggccttgag tggattggag tgattaatcc tggaagtggt       180
agtactagtt acaatgagaa gttcaggtac aaggcaatat tgactgcaga cacatcctcc       240
agcactgcct acatgcaact cagcagcctg acatctgatg actctgcggt ttatttctgt       300
gcaacaatac cggcctccta tcggtccgat tcccttgact gctggggcca aggcaccacg       360
gtcaccgtct cctcg                                                         375
```

<210> SEQ ID NO 214
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214

```
gacacaactg tgacccagtc tcacaaattc atgtccacat cagtaggaga cagggtcagc        60
atcacctgca aggccagtca ggatgtgggt actgctgtag cctggtatca acagagacca       120
gggcaatctc ctaaactact gatttactgg gcatccaccc ggcacactgg agtccctgat       180
cgcttcacag gcagtggatc tgggacagat ttcactctca ccatcagcaa tgtgcagtct       240
gaagacttgg cagactattt ctgtcagcaa tataaaagct atcctctcac tttcggaggg       300
gggaccaagc tggaaatcaa acgcgctagc                                         330
```

<210> SEQ ID NO 215
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215

```
ggtggtggtg gttctggcgg cggcggctcc ggcggaggtg ctcgaggcgg tggcggatcg        60
```

<210> SEQ ID NO 216
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216

```
ggatacgcct tcactaaata cttgattgag                                          30
```

<210> SEQ ID NO 217
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217

```
gtgattaatc ctggaagtgg tagtactagt tacaatgaga agttcaggta c                  51
```

```
<210> SEQ ID NO 218
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ataccggcct cctatcggtc cgattccctt gactgc                              36

<210> SEQ ID NO 219
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aaggccagtc aggatgtggg tactgctgta gcc                                 33

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tgggcatcca cccggcacac t                                              21

<210> SEQ ID NO 221
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cagcaatata aaagctatcc tctcact                                        27

<210> SEQ ID NO 222
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
agcgcgcatg ccgaggctta tctgcagcag tctggagctg agctggtaag gcctgggact    60
tcagtgaagg tgtcctgcaa ggcttctgga tacgtcttca ccaatttctt gatagagtgg   120
gtaaaacaga ggcctggaca gggccttgag tggattgggg tgattaatcc tggaaatggt   180
ggtgctgcct ataatgagaa gttcaagggc aaggcgatac ttactgcaga caaatcctcc   240
agtactgcct atatgcagct tagcagtctg acatctgatg actctgcggt ctatttctgt   300
gcaagattgc cccctcgta tgattacgac ggcgacatcg actactgggg ccaaggcacc   360
acggtcaccg tctcctcg                                                 378

<210> SEQ ID NO 223
<211> LENGTH: 342
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gaccttgtgc tcactcagtc tcctgcttcc ttagctgtgg ctctgggaca gagggccacc    60
atctcatgca gggccagcaa aagtgtcact acatctggct atagtttaat gcactggtac   120
cgacagaaac caggacagcc acccaaactc ctcatctatc ctgcatccaa cctagaatct   180
ggggtccctg ccagattcag tggcagtggg tctgggacag acttcaccct caacatccat   240
cctgtggagg aggaggatgc tgcaacctat tactgtcagc acagtaggga gcttccgtgg   300
acgttcggtg gaggcaccaa gctggaaatc aaacgcgcta gc                     342

<210> SEQ ID NO 224
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggtggtggtg gttctggcgg cggcggctcc ggcggaggtg ctcgaggcgg tggcggatcg    60

<210> SEQ ID NO 225
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggatacgtct tcaccaattt cttgatagag                                    30

<210> SEQ ID NO 226
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gtgattaatc ctggaaatgg tggtgctgcc tataatgaga agttcaaggg c             51

<210> SEQ ID NO 227
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227 ttgccccct cgtatgatta cgacggcgac atcgactac                           39

<210> SEQ ID NO 228
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
agggccagca aaagtgtcac tacatctggc tatagtttaa tgcac        45

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cctgcatcca acctagaatc t        21

<210> SEQ ID NO 230
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
cagcacagta gggagcttcc gtggacg        27

<210> SEQ ID NO 231
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
agcgcgcatg cccaggtcca actgcagcag tctggagctg agctggtaag gcctgggact        60
tcagtgaagg tgtcctgcaa ggcttctgga tacgccttca ctaatttctt gatagagtgg       120
gtaaaacaga ggcctggaca gggccttgag tggattgggg tgattaatcc tggaagtggt       180
ggtactggtt acaatgagaa gttcaagggc aaggcaacac tgactgcaga caaatcctcc       240
agcactgcct acatgcagct caatagtcta acatctgatg actctgcggt ctatttctgt       300
gcaagattgc ccccctcata tgattacgac ggcgacatcg actactgggg ccaaggcacc       360
actgtcaccg tctcctcg       378

<210> SEQ ID NO 232
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (175)..(175)
<223> OTHER INFORMATION: a, c, t, g, unknown or other
<220> FEATURE:
<221> NAME/KEY: modified_base
<222> LOCATION: (193)..(195)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base

```
<222> LOCATION: (247)..(247)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (286)..(287)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (301)..(305)
<223> OTHER INFORMATION: a, c, t, g, unknown or other
<220> FEATURE:
<221> NAME/KEY: modified_base
<222> LOCATION: (308)..(308)
<223> OTHER INFORMATION: a, c, t, g, unknown or other
<220> FEATURE:
<221> NAME/KEY: modified_base
<222> LOCATION: (311)..(314)
<223> OTHER INFORMATION: a, c, t, g, unknown or other
<220> FEATURE:
<221> NAME/KEY: modified_base
<222> LOCATION: (331)..(331)
<223> OTHER INFORMATION: a, c, t, g, unknown or other
<220> FEATURE:
<221> NAME/KEY: modified_base
<222> LOCATION: (334)..(334)
<223> OTHER INFORMATION: a, c, t, g, unknown or other
<220> FEATURE:
<221> NAME/KEY: modified_base
<222> LOCATION: (338)..(338)
<223> OTHER INFORMATION: a, c, t, g, unknown or other
<220> FEATURE:
<221> NAME/KEY: modified_base
<222> LOCATION: (342)..(345)
<223> OTHER INFORMATION: a, c, t, g, unknown or other
<220> FEATURE:
<221> NAME/KEY: modified_base
<222> LOCATION: (349)..(349)
<223> OTHER INFORMATION: a, c, t, g, unknown or other
<220> FEATURE:
<221> NAME/KEY: modified_base
<222> LOCATION: (354)..(355)
<223> OTHER INFORMATION: a, c, t, g, unknown or other
<220> FEATURE:
<221> NAME/KEY: modified_base
<222> LOCATION: (358)..(359)
<223> OTHER INFORMATION: a, c, t, g, unknown or other
<220> FEATURE:
<221> NAME/KEY: modified_base
<222> LOCATION: (365)..(365)
<223> OTHER INFORMATION: a, c, t, g, unknown or other
<220> FEATURE:
<221> NAME/KEY: modified_base
<222> LOCATION: (369)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (377)..(377)
<223> OTHER INFORMATION: a, c, t, g, unknown or other
<220> FEATURE:
<221> NAME/KEY: modified_base
<222> LOCATION: (383)..(384)
<223> OTHER INFORMATION: a, c, t, g, unknown or other
<220> FEATURE:
```

<221> NAME/KEY: modified_base
<222> LOCATION: (386)..(386)
<223> OTHER INFORMATION: a, c, t, g, unknown or other
<220> FEATURE:
<221> NAME/KEY: modified_base
<222> LOCATION: (389)..(389)
<223> OTHER INFORMATION: a, c, t, g, unknown or other
<220> FEATURE:
<221> NAME/KEY: modified_base
<222> LOCATION: (392)..(393)
<223> OTHER INFORMATION: a, c, t, g, unknown or other

<400> SEQUENCE: 232
gacattgtga tgtcacagtc tcctgcttcc ttagctgtat ctctggggca gagggccacc        60
atctcatgca gggccagcaa aagtgtcagt tcatctggct atagtttaat acactggtac       120
caacagaaac caggacagcc acccaaactc gtcatctatc ttgcatctaa cctanattct       180
ggggtccctg ccnnnttcag tggcagtgga tctggnacag acttcaccct caacatccat       240
cctgtgnagg angaggatgc tgcaacctat tactgtcanc acagtnngga ncttccgtgg       300
nnnnncgngg nnnnccaagc tggaaatcaa ngcnctanct cnnnnccnta acannaannt       360
gatcntctnn nnaananctg aanngntgnc tnnacc                                 396

<210> SEQ ID NO 233
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ggtggtggtg gttctggcgg cggcggctcc ggcggaggtg ctcgaggcgg tggcggatcg        60

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ggatacgcct tcactaattt cttgatagag                                         30

<210> SEQ ID NO 235
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gtgattaatc ctggaagtgg tggtactggt tacaatgaga agttcaaggg c                 51

<210> SEQ ID NO 236
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
ttgcccccct catatgatta cgacggcgac atcgactac                               39

<210> SEQ ID NO 237
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
agggccagca aaagtgtcag ttcatctggc tatagtttaa tacac            45

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 238
cttgcatcta acctanattc t            21

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (16)..(18)
<223> OTHER INFORMATION: a, c, t, g, unknown or other

<400> SEQUENCE: 239
nnggancttc cgtggnnn            18

<210> SEQ ID NO 240
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Gly Gly Gly Ser Gly Gly Gly Ser Gly Gly Gly Ala Arg Gly
1               5                   10                  15

Gly Gly Gly Ser
            20

<210> SEQ ID NO 241
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 241
tttttttttt tttttttttt                                              20
```